(12) United States Patent
Evarts et al.

(10) Patent No.: US 9,221,795 B2
(45) Date of Patent: Dec. 29, 2015

(54) PHOSPHATIDYLINOSITOL 3-KINASE INHIBITORS

(71) Applicant: Gilead Sciences, Inc., Foster City, CA (US)

(72) Inventors: Jerry Evarts, Redmond, WA (US);
Joshua Kaplan, Foster City, CA (US);
Musong Kim, Bothell, WA (US); Leena Patel, Mercer Island, WA (US);
Stephane Perreault, Brier, WA (US);
Gary Phillips, Issaquah, WA (US);
Jennifer A. Treiberg, Redmond, WA (US); Joshua Van Veldhuizen, Seattle, WA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 14/304,539

(22) Filed: Jun. 13, 2014

(65) Prior Publication Data
US 2014/0371246 A1    Dec. 18, 2014

Related U.S. Application Data

(60) Provisional application No. 61/835,333, filed on Jun. 14, 2013.

(51) Int. Cl.
| C07D 401/14 | (2006.01) |
| A61K 31/57 | (2006.01) |
| A61K 31/517 | (2006.01) |
| A61P 35/00 | (2006.01) |

(52) U.S. Cl.
CPC .......... *C07D 401/14* (2013.01); *A61K 31/517* (2013.01)

(58) Field of Classification Search
CPC .......................... C07D 401/14; A61K 31/517
USPC ....................................... 544/284; 514/266.2
See application file for complete search history.

(56) References Cited

U.S. PATENT DOCUMENTS

| 3,845,770 A | 11/1974 | Theeuwes et al. |
| 4,326,525 A | 4/1982 | Swanson et al. |
| 4,902,514 A | 2/1990 | Barclay et al. |
| 4,943,593 A | 7/1990 | Palfreyman et al. |
| 4,965,288 A | 10/1990 | Palfreyman et al. |
| 4,992,445 A | 2/1991 | Lawter et al. |
| 4,997,854 A | 3/1991 | Kagan et al. |
| 5,001,139 A | 3/1991 | Lawter et al. |
| 5,021,456 A | 6/1991 | Palfreyman et al. |
| 5,023,252 A | 6/1991 | Hseih |
| 5,059,714 A | 10/1991 | Palfreyman et al. |
| 5,120,764 A | 6/1992 | McCarthy et al. |
| 5,182,297 A | 1/1993 | Palfreyman et al. |
| 5,252,608 A | 10/1993 | Palfreyman et al. |
| 5,616,345 A | 4/1997 | Geoghegan et al. |
| 5,858,753 A | 1/1999 | Chantry et al. |
| 5,882,910 A | 3/1999 | Chantry et al. |
| 5,985,589 A | 11/1999 | Chantry et al. |
| 6,518,277 B1 | 2/2003 | Sadhu et al. |
| 6,667,300 B2 | 12/2003 | Sadhu et al. |
| 6,800,620 B2 | 10/2004 | Sadhu et al. |
| 6,949,535 B2 | 9/2005 | Sadhu et al. |
| 7,932,260 B2 | 4/2011 | Fowler et al. |
| 8,138,195 B2 | 3/2012 | Sadhu et al. |

(Continued)

FOREIGN PATENT DOCUMENTS

| EP | 0884310 B1 | 9/2005 |
| WO | WO-9746688 A1 | 12/1997 |

(Continued)

OTHER PUBLICATIONS

Klempner et al.Cancer Discov. Dec. 2013;3(12):1345-54.*
Massacesi et al. Ann. N.Y. Acad. Sci. 1280 (2013) 19-23.*
Gautschi et al., Clin. Cancer Res., 14(6), 1639-1648, 2008.*
Mountzios et al., Cancer Treatments Reviews, 34, 175-182, 2008.*
Mass, R. D., Int. J. Radiation Oncology Bio. Phys.vol. 58(3): 932-940, 2004.*
Fabbro et al. Pharmacology & therapeutics 93, 79-98, 2002.*
Cecil Textbook of Medicine, edited by Bennet, J.C., and Plum F., 20th edition,vol. 1, 1004-101 O, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*

(Continued)

*Primary Examiner* — Venkataraman Balasubramanian
(74) *Attorney, Agent, or Firm* — Yu-Ming Dammann

(57) ABSTRACT

The present disclosure provides phosphatidylinositol 3-kinase (PI3K) inhibitors of formula (I),

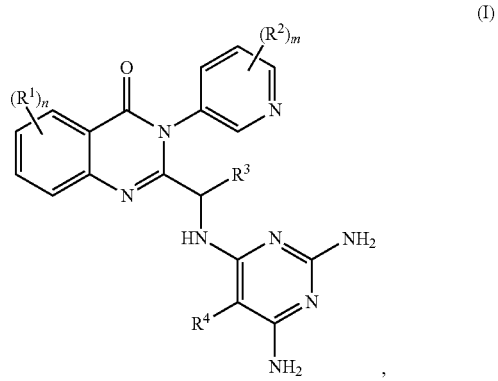

or pharmaceutically acceptable salts or isomers thereof, in which n, m, $R^1$, $R^2$, $R^4$, and $R^3$ are as defined herein. These compounds are useful for treatment of conditions mediated by one or more PI3K isoforms, such as PI3Kδ. The present disclosure further provides pharmaceutical compositions that include a compound of formula (I), or pharmaceutically acceptable salts or isomers thereof, and methods of using these compounds and compositions to treat conditions mediated by one or more PI3K isoforms, such as PI3Kδ.

59 Claims, No Drawings

(56) References Cited

U.S. PATENT DOCUMENTS

| | | | |
|---|---|---|---|
| 8,193,182 | B2 | 6/2012 | Ren et al. |
| 8,207,153 | B2 | 6/2012 | Fowler et al. |
| 8,492,389 | B2 | 7/2013 | Sadhu et al. |
| 8,569,323 | B2 | 10/2013 | Ren et al. |
| RE44,599 | E | 11/2013 | Fowler et al. |
| 8,586,597 | B2 | 11/2013 | Fowler et al. |
| RE44,638 | E | 12/2013 | Fowler et al. |
| 8,623,881 | B2 | 1/2014 | Sadhu et al. |
| 8,637,533 | B2 | 1/2014 | Sadhu et al. |
| 8,653,077 | B2 | 2/2014 | Sadhu et al. |
| 8,779,131 | B2 | 7/2014 | Kesicki et al. |
| 2002/0161014 | A1 | 10/2002 | Sadhu et al. |
| 2004/0248871 | A1 | 12/2004 | Farjanel et al. |
| 2008/0234299 | A1 | 9/2008 | Buchstaller et al. |
| 2010/0256167 | A1 | 10/2010 | Fowler et al. |
| 2011/0046165 | A1 | 2/2011 | Ren et al. |
| 2011/0152296 | A1 | 6/2011 | Cushing et al. |
| 2011/0217300 | A1 | 9/2011 | Liu et al. |
| 2011/0245257 | A1 | 10/2011 | Cushing et al. |
| 2011/0269779 | A1 | 11/2011 | Wilson et al. |
| 2011/0275653 | A1 | 11/2011 | Chen et al. |
| 2011/0281866 | A1 | 11/2011 | Ren et al. |
| 2011/0281897 | A1 | 11/2011 | Chen et al. |
| 2012/0015964 | A1 | 1/2012 | Fowler et al. |
| 2012/0059000 | A1 | 3/2012 | Ren et al. |
| 2012/0094997 | A1 | 4/2012 | England et al. |
| 2012/0122838 | A1 | 5/2012 | Ren et al. |
| 2012/0149701 | A1 | 6/2012 | Ren et al. |
| 2012/0202785 | A1 | 8/2012 | Heald et al. |
| 2012/0245169 | A1 | 9/2012 | Ren et al. |
| 2014/0121223 | A1 | 5/2014 | Fowler et al. |
| 2014/0121224 | A1 | 5/2014 | Fowler et al. |
| 2014/0153772 | A1 | 6/2014 | Guymon |
| 2014/0179718 | A1 | 6/2014 | Evarts et al. |

FOREIGN PATENT DOCUMENTS

| | | |
|---|---|---|
| WO | WO-01/19800 A2 | 3/2001 |
| WO | WO-01/30768 A1 | 5/2001 |
| WO | WO-01/81346 A2 | 11/2001 |
| WO | WO-01/98278 A1 | 12/2001 |
| WO | WO-2003/035075 A1 | 5/2003 |
| WO | WO-03/076418 A1 | 9/2003 |
| WO | WO-2004/037176 A2 | 5/2004 |
| WO | WO-2005/051922 A1 | 6/2005 |
| WO | WO-2005/113556 A1 | 12/2005 |
| WO | WO-2005/123696 A1 | 12/2005 |
| WO | WO-2006/004915 A1 | 1/2006 |
| WO | WO-2008/118455 A1 | 10/2008 |
| WO | WO-2009/088986 A1 | 7/2009 |
| WO | WO-2009/088990 A1 | 7/2009 |
| WO | WO-2010/059593 A1 | 5/2010 |
| WO | WO-2010/092340 A1 | 8/2010 |
| WO | WO-2010/129816 A2 | 11/2010 |
| WO | WO-2010/151735 A2 | 12/2010 |
| WO | WO-2010/151740 A2 | 12/2010 |
| WO | WO-2011/008302 A1 | 1/2011 |
| WO | WO-2011/031896 A2 | 3/2011 |
| WO | WO-2011/058113 A1 | 5/2011 |
| WO | WO-2011/075628 A1 | 6/2011 |
| WO | WO-2011/075699 A2 | 6/2011 |
| WO | WO-2011/123751 A2 | 10/2011 |
| WO | WO-2011/146882 A1 | 11/2011 |
| WO | WO-2011/150156 A2 | 12/2011 |
| WO | WO-2012/003271 A1 | 1/2012 |
| WO | WO-2012/003274 A1 | 1/2012 |
| WO | WO-2012/037204 A1 | 3/2012 |
| WO | WO-2012/061696 A1 | 5/2012 |
| WO | WO-2012/068343 A1 | 5/2012 |
| WO | WO-2012/087784 A1 | 6/2012 |
| WO | WO-2012/097000 A1 | 7/2012 |
| WO | WO-2012/125629 A1 | 9/2012 |
| WO | WO-2012/135009 A1 | 10/2012 |
| WO | WO-2012/146666 A1 | 11/2012 |
| WO | WO-2012/146667 A1 | 11/2012 |
| WO | WO-2013/032591 A1 | 3/2013 |
| WO | WO-2014/100765 A1 | 6/2014 |
| WO | WO-2014/100767 A1 | 6/2014 |

OTHER PUBLICATIONS

Dermer et al., Bio/Technology, 1994, 12:320.*

Golub et al., Science, 286, 531-537, 1999.*

Chantry, David et al.,(1997) "p110δ, a Novel Phosphatidylinositol 3-Kinase Catalystic Subunit That Associates with p85 and is Expressed Predominantly in Leukocytes", *J. Biol. Chem.*, 272:19236-41.

Hiles, Ian D. et al., (1992) "Phosphatidylinositol 3-Kinase: Structure and Expression of the 110 kd Catalytic Subunit", *Cell*, 70:419-29.

Otsu, Masayuki et al., (1991) "Characterization of Two 85 kd Proteins That Associate with Receptor Tyrosine Kinases, Middle-T/pp60c-src Complexes, and PI3-Kinase", *Cell*, 65:91-104.

Panayotou, George et al, (1992) "Phosphatidyl-inositol 3-kinase: a key enzyme in diverse signalling processes", Trends in Cell Biology, vol. 2, pp. 358-360.

Rameh, Lucia E. et al., (1999) "The Role of Phosphoinositide 3-Kinase Lipid Products in Cell Function", *J. Biol. Chem.*, 274:8347-8350.

Vanhaesebroeck, Bart et al., (1997) "p110d, a novel phosphoinositide 3-kinase in leukocytes", *Proc. Natl. Acad. Sci. USA*, vol. 94:4330-35.

Ameriks, M.K. et al. (May 1, 2009). "Small Molecule Inhibitors of Phosphoinositide 3-Kinase (PI3K) δ and γ," *Current Topics in Medicinal Chemistry* 9(8):738-753.

Cheson, B.D. et al. (Aug. 7, 2008). "Monoclonal Antibody Therapy for B-Cell Non-Hodgkin's Lymphoma," *The New England Journal of Medicine* 359(6):613-626.

Ferrara N. et al. (Dec. 1999). "Clinical Application of Angiogenic Growth Factors and Their Inhibitors," *Nature Medicine* 5(12):1359-1364.

Foster, A.B. (Dec. 1984). "Deuterium Isotope Effects in Studies of Drug Metabolism," Trends Pharmacol. Sci. 5(12):524-527.

International Search Report mailed on Feb. 19, 2014, for PCT Application No. PCT/US2013/077311, filed on Dec. 20, 2013, 3 pages.

International Search Report mailed on Feb. 19, 2014, for PCT Application No. PCT/US2013/077315, filed on Dec. 20, 2013, 5 pages.

International Search Report mailed on Jun. 26, 2014, for PCT Application No. PCT/US2013/077311, filed on Dec. 20, 2013, (3 pages).

International Search Report mailed on Jun. 26, 2014 for PCT Application No. PCT/US2013/077315, filed on Dec. 20, 2013, (5 pages).

McMahon, G., (2000), "VEGF Receptor Signaling in Tumor Angiogenesis", *The Oncologist*, 5 (suppl):3-10.

Morton, L.M., et al. (Jan. 1, 2006, e-published Sep. 8, 2005). "Lymphoma Incidence Patterns by WHO Subtype in the United States, 1992-2001," *Blood* 107(1):265-276.

Nicolaou, K.C. et al. (Feb. 1, 1994). "Calicheamicin θ: A Rationally Designed Molecule with Extremely Potent and Selective DNA Cleaving Properties and Apoptosis Inducing Activity," *Angewandte Chemie International Edition in English* 33(2):1983-186.

Non-Final Office Action dated Aug. 21, 2014 for U.S. Appl. No. 14/137,979, filed Dec. 20, 2013.

Non-Final Office Action dated Aug. 21, 2014 for U.S. Appl. No. 14/137,978, filed Dec. 20, 2013.

Norman, P. (Nov. 2011, e-published Sep. 23, 2011). "Novel 1, 5-Naphthyridine PI3Kδ Inhibitors, an Evaluation of WO2011075628," *Expert Opinion on Therapeutic Patents* 21(11):1805-1810.

Pinedo, H.M. et al., (2000). "Translational Research: The Role of VEGF in Tumor Angiogenesis", *The Oncologist*, 5 (suppl 1):1-2.

U.S. Appl. No. 14/284,331, filed May 21, 2014, by Kesicki et al. (copy not attached).

Vanhaesebroeck, B. et al. (Apr. 29, 1997) "P110δ, a Novel Phosphoinositide 3-Kinase in Leukocytes," *Proc. Natl. Acad. Sci. USA*, 94(9):4330-4335.

(56) References Cited

OTHER PUBLICATIONS

Verheijen, J.C. et al. (Jun. 1, 2007). "Phosphatidylinositol 3-Kinase (PI3K) Inhibitors as Anticancer Drugs," *Drugs of the Future* 32(6):537-547.

Wierda, W.G. (2006). "Current and Investigational Therapies for Patients with CLL," *Hematology Am. Soc. Hematol. Educ. Program* pp. 285-294.

Written Opinion mailed on Feb. 19, 2014, for PCT Application No. PCT/US2013/077311, filed on Dec. 20, 2013, 5 pages.

Written Opinion mailed on Feb. 19, 2014, for PCT Application No. PCT/US2013/077315, filed on Dec. 20, 2013, 9 pages.

Intl. Search Report and Written Opinion dated Sep. 17, 2014 for PCT/US2014/042392.

Intl. Search Report dated Feb. 24, 2003 for PCT/US2002/27240.

* cited by examiner

PHOSPHATIDYLINOSITOL 3-KINASE INHIBITORS

CROSS REFERENCE TO RELATED APPLICATIONS

This patent application claims the benefit of priority of U.S. Application Ser. No. 61/835,333, filed Jun. 14, 2013. The content of this provisional application is hereby incorporated herein in its entirety.

FIELD

The present disclosure relates generally to inhibitors of phosphatidylinositol 3-kinase (PI3K) activity and to novel compounds that are selective inhibitors of PI3K delta activity.

BACKGROUND

Cell signaling via 3'-phosphorylated phosphoinositides has been implicated in a variety of cellular processes, e.g., malignant transformation, growth factor signaling, inflammation, and immunity. See generally Rameh et al., *J. Biol. Chem.*, 274:8347-8350 (1999). Phosphatidylinositol 3-kinase (PI 3-kinase; PI3K) is responsible for generating these phosphorylated signaling products. PI3K originally was identified as a protein associated with viral oncoproteins and growth factor receptor tyrosine kinases that phosphorylate phosphatidylinositol (PI) and its phosphorylated derivatives at the 3'-hydroxyl of the inositol ring. See Panayotou et al., *Trends Cell Biol* 2:358-60 (1992).

Three classes of the PI 3-kinase (PI3K) are proposed, based on their substrate specificities. Class I PI3Ks phosphorylate phosphatidylinositol (PI), phosphatidylinositol-4-phosphate, and phosphatidylinositol-4,5-biphosphate (PIP$_2$) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, and Class III PI3Ks phosphorylate PI.

The initial purification and molecular cloning of PI 3-kinase revealed that it was a heterodimer consisting of p85 and p110 subunits. See Otsu et al., *Cell*, 65:91-104 (1991); Hiles et al., *Cell*, 70:419-29 (1992). Since then, four distinct Class I PI3Ks have been identified, designated as PI3K α, β, δ, and γ isomers, each consisting of a distinct 110 kDa catalytic subunit and a regulatory subunit. More specifically, three of the catalytic subunits, i.e., p110α, p110β, and p110δ, each interact with the same regulatory subunit, i.e., p85, whereas p110γ interacts with a distinct p101 regulatory subunit. As described below, the patterns of expression of each of these PI3Ks in human cells and tissues also are distinct.

Identification of the p110δ isoform of PI 3-kinase is described in Chantry et al., *J. Biol. Chem.*, 272:19236-41 (1997). It was observed that the human p110δ isoform is expressed in a tissue-restricted fashion. It is expressed at high levels in lymphocytes and lymphoid tissues, suggesting that the protein might play a role in PI 3-kinase-mediated signaling in the immune system. The p110δ isoform is described in U.S. Pat. Nos. 5,858,753; 5,882,910; and 5,985,589, each of which is incorporated herein by reference. See also Vanhaesebroeck et al., *Proc. Natl. Acad. Sci. USA*, 94:4330-5 (1997); and WO 97/46688.

Therefore, there is a need for therapeutic agents that inhibit PI3K isomers to treat disorders or diseases that are mediated by PI3K.

SUMMARY

The present application provides novel compounds that are inhibitors of PI3K isoforms, such as PI3Kδ. The application also provides compositions, including pharmaceutical compositions, kits that include the compounds, and methods of using and making the compounds. The compounds provided herein are useful in treating diseases, disorders, or conditions that are mediated by PI3K isoforms, such as PI3Kδ. The application also provides the compounds for use in therapy. The application further provides compounds for use in a method of treating a disease, disorder, or condition that is mediated by PI3K isoforms. Moreover, the application provides uses of the compounds in the manufacture of a medicament for the treatment of a disease, disorder or condition that is mediated by PI3K isoforms.

In one aspect, the PI3K inhibitor is a compound having the structure of formula (I):

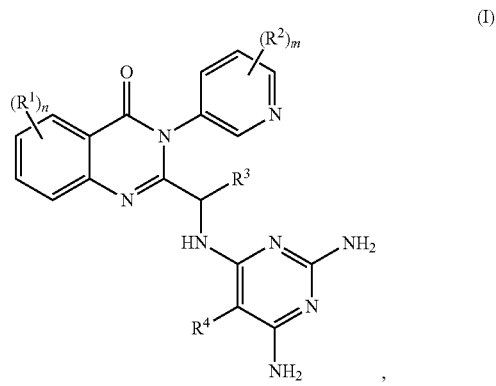

or a pharmaceutically acceptable salt, tautomer, isomer, a mixture of isomers, or prodrug thereof; wherein:

n is 0, 1, 2 or 3;

each $R^1$ is independently halo, cyano, optionally substituted alkylsulfonyl, optionally substituted alkyl, optionally substituted cycloalkyl, optionally substituted heterocycloalkyl, or optional substituted alkoxy;

m is 0, 1, 2, or 3;

each $R^2$ is independently halo, optionally substituted alkoxy, optionally substituted alkyl, optionally substituted cycloalkyl, or optionally substituted heterocycloalkyl;

$R^3$ is hydrogen, optionally substituted alkyl, optionally substituted cycloalkyl, optionally substituted alkoxy, or optionally substituted heterocycloalkyl; and $R^4$ is cyano.

In one aspect, the compounds having the structure of formula (I) wherein:

n is 0, 1, 2 or 3;

each $R^1$ is independently selected from halogen, cyano, alkyl, or alkylsulfonyl, wherein the alkyl moiety may be optionally substituted with 1 to 3 halogen;

m is 0, 1, 2 or 3;

each $R^2$ is independently selected from halogen, alkoxy, alkyl, or cycloalkyl, wherein the alkyl moiety may be optionally substituted with 1 to 3 halogen;

$R^3$ is hydrogen, alkyl, or cycloalkyl, wherein the alkyl moiety may be optionally substituted with cycloalkyl; and $R^4$ is cyano.

In some embodiments, the compounds have the structure of formula (I) wherein each $R^1$ is independently selected from halogen, cyano, $C_{1-4}$ alkyl, $C_{1-4}$ haloalkyl, or $C_{1-4}$ alkylsulfonyl. In certain embodiments, each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl.

In other embodiments, the compounds have the structure of formula (I) wherein each $R^2$ is independently selected from halogen, $C_{1-4}$ alkoxy, $C_{1-4}$ alkyl, $C_{1-4}$ haloalkyl, or $C_{3-6}$ cycloalkyl. In yet other embodiments, each $R^2$ is independently selected from fluoro, chloro, iodo, bromo, methoxy, ethoxy, propoxy, butoxy, pentoxy, hexoxy, methyl, ethyl, propyl, butyl, fluoromethyl, fluoroethyl, difluoromethyl, difluoroethyl, trifluoromethyl, cyclopropyl, cyclobutyl, cyclopentyl, or cyclohexyl.

In certain embodiments, the compounds have the structure of formula (I) wherein $R^3$ is selected from hydrogen, alkyl, cycloalkyl, or cycloalkylalkyl. In other embodiments, $R^3$ is selected from hydrogen, $C_{1-4}$ alkyl, $C_{3-6}$ cycloalkyl, or $C_{3-6}$ cycloalkyl$C_{1-4}$ alkyl. In yet other embodiments, $R^3$ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl.

In additional embodiments, the compound having the structure of formula (I) wherein n is 0, 1, 2, 3, or 4;

each $R^1$ is independently halo, cyano, optionally substituted alkyl, optionally substituted cycloalkyl, optionally substituted heterocycloalkyl, optional substituted alkoxy, or $SO_2R^{1x}$ wherein $R^{1x}$ is optionally substituted alkyl;

m is 0, 1, 2, or 3;

each $R^2$ is independently halo, —$NH_2$, optionally substituted alkoxyalkyl, optionally substituted alkyl, optionally substituted cycloalkyl, or optionally substituted heterocycloalkyl;

$R^3$ is hydrogen, optionally substituted alkyl, optionally substituted cycloalkyl, optionally substituted alkoxyalkyl, or optionally substituted heterocycloalkyl; and $R^4$ is selected from halo, cyano, and —$CONH_2$.

In one additional embodiment, the compound having the structure of formula (I), wherein:

n is 0, 1, 2, 3, or 4;

each $R^1$ is independently selected from halo, cyano, alkyl, or alkylsulfonyl, wherein the alkyl moiety may be optionally substituted with 1 to 3 halogen;

m is 0, 1, 2, or 3;

each $R^2$ is independently selected from halo, —$NH_2$, alkoxy, alkyl, or cycloalkyl, wherein the alkyl moiety may be optionally substituted with 1 to 3 halogen;

$R^3$ is hydrogen, alkyl, or cycloalkyl, wherein the alkyl moiety may be optionally substituted with cycloalkyl; and $R^4$ is cyano, halo, or —$CONH_2$.

In other additional embodiments, the compounds having the structure of formula (I) wherein $R^4$ is selected from the group consisting of fluoro, chloro, bromo, iodo, cyano, and —$CONH_2$.

In some embodiment, the compounds have the structure of formula (I) wherein n is 1 or 2. In another embodiment, n is 1. In yet another embodiment, n is 2.

In other embodiments, the compounds have the structure of formula (I) wherein m is 0, 1, or 2. In another embodiment, m is 0. In other embodiments, m is 1. In yet another embodiment, m is 2.

In certain embodiments, the compounds have the structure of formula (I), wherein:

n is 1 or 2;

each $R^1$ is independently selected from halogen, cyano, alkylsulfonyl, or alkyl, wherein the alkyl moiety is optionally substituted with halogen;

m is 0, 1, or 2;

each $R^2$ is independently selected from halo, alkoxy, alkyl, or cycloalkyl, wherein the alkoxy, alkyl or cycloalkyl moieties are optionally substituted with halogen, alkyl, or cycloalkyl;

$R^3$ is hydrogen, alkyl, or cycloalkyl, wherein the alkyl or cycloalkyl moieties are optionally substituted with halogen or cycloalkyl; and $R^4$ is cyano.

In other embodiments, the compounds have the structure of formula (I), wherein:

n is 1 or 2;

each $R^1$ is independently selected from halogen, cyano, $C_{1-4}$ haloalkyl, or $C_{1-4}$alkylsulfonyl;

m is 0, 1, or 2;

each $R^2$ is independently selected from halogen, $C_{1-4}$ alkoxy, $C_{1-4}$ haloalkyl, or $C_{3-6}$ cycloalkyl.

$R^3$ is selected from hydrogen, $C_{1-4}$ alkyl, $C_{3-6}$ cycloalkyl, or $C_{3-6}$cycloalkyl$C_{1-4}$alkyl; and $R^4$ is cyano.

In another embodiment, the compounds have the structure of formula (I), wherein:

n is 1 or 2;

each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl;

m is 0, 1, or 2;

each $R^2$ is independently selected from fluoro, chloro, iodo, bromo, methoxy, ethoxy, propoxy, butoxy, pentoxy, hexoxy, methyl, ethyl, propyl, butyl, fluoromethyl, fluoroethyl, difluoromethyl, difluoroethyl, trifluoromethyl, cyclopropyl, cyclobutyl, cyclopentyl, or cyclohexyl;

$R^3$ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl; and $R^4$ is cyano.

In some embodiments, the PI3K inhibitor is a compound having the structure of formula (I) or a pharmaceutically acceptable salt, tautomer, isomer, a mixture of isomers, prodrug, or solvate thereof, wherein:

n is 2 and m is 2;

each $R^1$ is independently selected from halogen, cyano, $C_{1-4}$ alkylsulfonyl, $C_{1-4}$ alkyl, or $C_{1-4}$haloalkyl;

each $R^2$ is independently selected from halogen, $C_{1-4}$ alkoxy, $C_{1-4}$ alkyl, $C_{1-4}$ haloalkyl, or $C_{3-6}$cycloalkyl;

$R^3$ is selected from hydrogen, $C_{1-4}$ alkyl, $C_{3-6}$ cycloalkyl, or $C_{1-4}$cycloalkyl$C_{1-4}$ alkyl; and $R^4$ is cyano.

In other embodiments, the PI3K inhibitor is a compound having the structure of formula (I) or a pharmaceutically acceptable salt, tautomer, isomer, a mixture of isomers, prodrug, or solvate thereof, wherein:

n is 1 and m is 2;

$R^1$ is independently selected from halogen, cyano, $C_{1-4}$ alkylsulfonyl, $C_{1-4}$ alkyl, or $C_{1-4}$ haloalkyl;

each $R^2$ is independently selected from halogen, $C_{1-4}$ alkoxy, $C_{1-4}$ alkyl, $C_{1-4}$haloalkyl, or $C_{3-6}$ cycloalkyl;

$R^3$ is selected from hydrogen, $C_{1-4}$ alkyl, $C_{3-6}$ cycloalkyl, or $C_{1-4}$ cycloalkyl$C_{1-4}$ alkyl; and $R^4$ is cyano.

In some embodiments, the PI3K inhibitor is a compound having the structure of formula (I) or a pharmaceutically acceptable salt, tautomer, isomer, a mixture of isomers, prodrug, or solvate thereof, wherein:

n is 2 and m is 1;
each $R^1$ is independently selected from halogen, cyano, $C_{1-4}$ alkylsulfonyl, $C_{1-4}$ alkyl, or $C_{1-4}$ haloalkyl;
$R^2$ is selected from halogen, $C_{1-4}$ alkoxy, $C_{1-4}$ alkyl, $C_{1-4}$ haloalkyl, or $C_{3-6}$ cycloalkyl;
$R^3$ is selected from hydrogen, $C_{1-4}$ alkyl, $C_{3-6}$ cycloalkyl, or $C_{1-4}$ cycloalkyl$C_{1-4}$ alkyl; and
$R^4$ is cyano.

In some embodiments, the PI3K inhibitor is a compound having the structure of formula (I) or a pharmaceutically acceptable salt, tautomer, isomer, a mixture of isomers, prodrug, or solvate thereof, wherein:

n is 1 and m is 1;
$R^1$ is selected from halogen, cyano, $C_{1-4}$ alkylsulfonyl, $C_{1-4}$ alkyl, or $C_{1-4}$ haloalkyl;
$R^2$ is selected from halogen, $C_{1-4}$ alkoxy, $C_{1-4}$ alkyl, $C_{1-4}$ haloalkyl, or $C_{3-6}$ cycloalkyl;
$R^3$ is selected from hydrogen, $C_{1-4}$ alkyl, $C_{3-6}$ cycloalkyl, or $C_{1-4}$ cycloalkyl$C_{1-4}$ alkyl; and
$R^4$ is cyano.

In some embodiments, the PI3K inhibitor is a compound having the structure of formula (I) or a pharmaceutically acceptable salt, tautomer, isomer, a mixture of isomers, prodrug, or solvate thereof, wherein:

n is 1 and m is 0;
$R^1$ is selected from halogen, cyano, $C_{1-4}$ alkylsulfonyl, $C_{1-4}$ alkyl, or $C_{1-4}$ haloalkyl;
$R^3$ is selected from hydrogen, $C_{1-4}$ alkyl, $C_{3-6}$ cycloalkyl, or $C_{1-4}$ cycloalkyl$C_{1-4}$ alkyl; and
$R^4$ is cyano.

In some embodiments, the PI3K inhibitor is a compound having the structure of formula (I) or a pharmaceutically acceptable salt, tautomer, isomer, a mixture of isomers, prodrug, or solvate thereof, wherein:

n is 2 and m is 0;
each $R^1$ is independently selected from halogen, cyano, $C_{1-4}$ alkylsulfonyl, $C_{1-4}$ alkyl, or $C_{1-4}$ haloalkyl;
$R^3$ is selected from hydrogen, $C_{1-4}$ alkyl, $C_{3-6}$ cycloalkyl, or $C_{1-4}$ cycloalkyl$C_{1-4}$ alkyl; and
$R^4$ is cyano.

In additional embodiments, the compounds have the structure of formula (I), wherein:

n is 1 or 2;
each $R^1$ is independently selected from halo, cyano, alkylsulfonyl, or alkyl, wherein the alkyl moiety is optionally substituted with halogen;
m is 0, 1, or 2;
each $R^2$ is independently selected from halo, —$NH_2$, alkoxyalkyl, alkyl, or cycloalkyl, wherein the alkyl or cycloalkyl moieties are optionally substituted with halogen, alkyl, or cycloalkyl;
$R^3$ is hydrogen, alkyl, or cycloalkyl, wherein the alkyl or cycloalkyl moieties are optionally substituted with halogen or cycloalkyl; and
$R^4$ is cyano, halo, or —$CONH_2$.

In other embodiments, the compounds have the structure of formula (I), wherein:

n is 1 or 2;
each $R^1$ is independently selected from halo, cyano, $C_{1-4}$alkyl, $C_{1-4}$ haloalkyl, or $C_{1-4}$alkylsulfonyl;
m is 0, 1, or 2;
each $R^2$ is independently selected from halo, —$NH_2$, $C_{1-4}$alkyl, $C_{1-4}$ haloalkyl, or $C_{3-6}$ cycloalkyl.

$R^3$ is selected from hydrogen, $C_{1-4}$ alkyl, $C_{3-6}$ cycloalkyl, or $C_{3-6}$cycloalkyl$C_{1-4}$alkyl; and
$R^4$ is cyano, halo, or —$CONH_2$.

In another embodiment, the compounds have the structure of formula (I), wherein:

n is 1 or 2;
each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl;
m is 0, 1, or 2;
each $R^2$ is independently selected from fluoro, chloro, iodo, —$NH_2$, bromo, methyl, ethyl, propyl, butyl, fluoromethyl, fluoroethyl, difluoromethyl, difluoroethyl, trifluoromethyl, cyclopropyl, cyclobutyl, cyclopentyl, or cyclohexyl;
$R^3$ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl; and
$R^4$ is cyano, halo, or —$CONH_2$.

In some embodiments, the PI3K inhibitor is a compound having the structure of formula (I) or a pharmaceutically acceptable salt, tautomer, isomer, a mixture of isomers, prodrug, or solvate thereof, wherein:

n is 2 and m is 2;
each $R^1$ is independently selected from halo, cyano, $C_{1-4}$ alkylsulfonyl, $C_{1-4}$ alkyl, or $C_{1-4}$ haloalkyl;
each $R^2$ is independently selected from halo, —$NH_2$, $C_{1-4}$ alkyl, $C_{1-4}$haloalkyl, or $C_{3-6}$ cycloalkyl;
$R^3$ is selected from hydrogen, $C_{1-4}$ alkyl, $C_{3-6}$ cycloalkyl, or $C_{1-4}$ cycloalkyl$C_{1-4}$ alkyl; and
$R^4$ is cyano, halo, or —$CONH_2$.

In other embodiments, the PI3K inhibitor is a compound having the structure of formula (I) or a pharmaceutically acceptable salt, tautomer, isomer, a mixture of isomers, prodrug, or solvate thereof, wherein:

n is 1 and m is 2;
$R^1$ is independently selected from halo, cyano, $C_{1-4}$ alkylsulfonyl, $C_{1-4}$ alkyl, or $C_{1-4}$ haloalkyl;
each $R^2$ is independently selected from halo, —$NH_2$, $C_{1-4}$alkoxy, $C_{1-4}$ alkyl, $C_{1-4}$haloalkyl, or $C_{3-6}$ cycloalkyl;
$R^3$ is selected from hydrogen, $C_{1-4}$ alkyl, $C_{3-6}$ cycloalkyl, or $C_{1-4}$cycloalkyl$C_{1-4}$ alkyl; and
$R^4$ is cyano, halo, or —$CONH_2$.

In some embodiments, the PI3K inhibitor is a compound having the structure of formula (I) or a pharmaceutically acceptable salt, tautomer, isomer, a mixture of isomers, prodrug, or solvate thereof, wherein:

n is 2 and m is 1;
each $R^1$ is independently selected from halo, cyano, $C_{1-4}$ alkylsulfonyl, $C_{1-4}$ alkyl, or $C_{1-4}$ haloalkyl;
$R^2$ is selected from halo, —$NH_2$, $C_{1-4}$ alkyl, $C_{1-4}$haloalkyl, or $C_{3-6}$ cycloalkyl;
$R^3$ is selected from hydrogen, $C_{1-4}$ alkyl, $C_{3-6}$ cycloalkyl, or $C_{1-4}$ cycloalkyl$C_{1-4}$ alkyl; and
$R^4$ is cyano, halo, or —$CONH_2$.

In some embodiments, the PI3K inhibitor is a compound having the structure of formula (I) or a pharmaceutically acceptable salt, tautomer, isomer, a mixture of isomers, prodrug, or solvate thereof, wherein:

n is 1 and m is 1;
$R^1$ is selected from halo, cyano, $C_{1-4}$ alkylsulfonyl, $C_{1-4}$ alkyl, or $C_{1-4}$ haloalkyl;
$R^2$ is selected from halo, —$NH_2$, $C_{1-4}$ alkyl, $C_{1-4}$ haloalkyl, or $C_{3-6}$ cycloalkyl;

R³ is selected from hydrogen, $C_{1-4}$ alkyl, $C_{3-6}$ cycloalkyl, or $C_{1-4}$ cycloalkyl$C_{1-4}$ alkyl; and R⁴ is cyano, halo, or —CONH₂.

In some embodiments, the PI3K inhibitor is a compound having the structure of formula (I) or a pharmaceutically acceptable salt, tautomer, isomer, a mixture of isomers, prodrug, or solvate thereof, wherein:

n is 1 and m is 0;

R¹ is selected from halo, cyano, $C_{1-4}$ alkylsulfonyl, $C_{1-4}$ alkyl, or $C_{1-4}$ haloalkyl;

R³ is selected from hydrogen, $C_{1-4}$ alkyl, $C_{3-6}$ cycloalkyl, or $C_{1-4}$ cycloalkyl$C_{1-4}$ alkyl; and R⁴ is cyano, halo, or —CONH₂.

In some embodiments, the PI3K inhibitor is a compound having the structure of formula (I) or a pharmaceutically acceptable salt, tautomer, isomer, a mixture of isomers, prodrug, or solvate thereof, wherein:

n is 2 and m is 0;

each R¹ is independently selected from halo, cyano, $C_{1-4}$ alkylsulfonyl, $C_{1-4}$ alkyl, or $C_{1-4}$ haloalkyl;

R³ is selected from hydrogen, $C_{1-4}$ alkyl, $C_{3-6}$ cycloalkyl, or $C_{1-4}$ cycloalkyl$C_{1-4}$ alkyl; and R⁴ is cyano, halo, or —CONH₂.

In some embodiments, the PI3K inhibitor is a compound having the structure of formula (I) or a pharmaceutically acceptable salt, tautomer, isomer, a mixture of isomers, prodrug, or solvate thereof, wherein:

n is 1;

m is 1;

R¹ is selected from halo, cyano, $C_{1-4}$ alkylsulfonyl, $C_{1-4}$ alkyl, or $C_{1-4}$ haloalkyl;

R² is —NH₂;

R³ is selected from hydrogen, $C_{1-4}$ alkyl, $C_{3-6}$ cycloalkyl, or $C_{1-4}$ cycloalkyl$C_{1-4}$ alkyl; and R⁴ is cyano, halo, or —CONH₂.

In some embodiments, the PI3K inhibitor is a compound having the structure of formula (I) or a pharmaceutically acceptable salt, tautomer, isomer, a mixture of isomers, prodrug, or solvate thereof, wherein:

n is 2;

m is 1;

each R¹ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl;

each R² is —NH₂;

R³ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl; and R⁴ is cyano, halo, or —CONH₂.

In certain embodiments, the PI3K inhibitors are the compounds selected from Table 1, or a pharmaceutically acceptable salt, tautomer, isomer, a mixture of isomers, or prodrug thereof. In some embodiments, the compounds are the atropisomers. In other embodiments, the compounds are the (S)-enantiomer. In some other embodiments, the compounds are the (R)-enantiomer. In other additional embodiments, the compounds are atropisomers.

The application also provides a pharmaceutical composition that includes a compound of formula (I) or a pharmaceutically acceptable salt, tautomer, isomer, a mixture of isomers, or prodrug thereof, together with at least one pharmaceutically acceptable vehicle. Examples of pharmaceutically acceptable vehicle may be selected from carriers, adjuvants, and excipients.

Also provided herein is a method of treating a disease or condition in a human in need thereof by administering to the human a therapeutically effective amount of a compound of formula (I) or a pharmaceutically acceptable salt, tautomer, isomer, a mixture of isomers, or prodrug thereof. Further provided is a compound of formula (I) for use in a method of treating a disease, disorder or condition that is mediated by PI3K isoforms. The application also provides the use of a compounds of formula (I) in the manufacture of a medicament for the treatment of a disease, disorder or condition that is mediated by PI3K isoforms. In certain embodiments, the disease or condition is associated or mediated by PI3K. In some embodiments, the disease or condition is an inflammatory disorder, an autoimmune disease, or a cancer. In certain other embodiments, the disease or condition is an inflammatory disorder. In other embodiments, the disease or condition is an autoimmune disease. In additional embodiments, the disease or condition is a cancer.

Also provided herein is a method of inhibiting kinase activity of a phosphatidylinositol 3-kinase delta polypeptide by contacting the polypeptide with a compound of formula (I) or a pharmaceutically acceptable salt, tautomer, isomer, a mixture of isomers, or prodrug thereof. Additionally provided herein is a method of inhibiting kinase activity of a phosphatidylinositol 3-kinase beta polypeptide by contacting the polypeptide with a compound of formula (I) or a pharmaceutically acceptable salt, tautomer, isomer, a mixture of isomers, or prodrug thereof.

Further provided is a method of inhibiting excessive or destructive immune reactions, comprising administering an effective amount of a compound of formula (I) described herein or a pharmaceutically acceptable salt, isomer, a mixture of isomers, or prodrug thereof such as asthma, rheumatoid arthritis, multiple sclerosis, and lupus. Moreover, provided is a method of inhibiting excess or destructive immune reactions, comprising administering an effective amount of a compound of formula (I) described herein or a pharmaceutically acceptable salt, isomer, a mixture of isomers, or prodrug thereof such as psoriasis, or chronic obstructive pulmonary disease (COPD).

Also provided is a method of disrupting leukocyte function comprising contacting the leukocytes with an effective amount of a compound of formula (I) described herein or a pharmaceutically acceptable salt, tautomer, isomer, a mixture of isomers, or prodrug thereof.

Also provided is a method of inhibiting a growth or a proliferation of cancer cells comprising contacting the cancer cells with an effective amount of a compound of formula (I) or a pharmaceutically acceptable salt, tautomer, isomer, a mixture of isomers, or prodrug thereof. In some embodiments, the cancer cells are of hematopoietic origin. In certain embodiment, the cancer is lymphoma, leukemia, or solid tumor.

Also provided is a kit that includes a compound of formula (I) or a pharmaceutically acceptable salt, tautomer, isomer, a mixture of isomers, or prodrug thereof. The kit may further comprise a label and/or instructions for use of the compound in the treatment of a disease or condition in a human in need thereof. In some embodiments, the disease or condition may be associated or mediated by PI3Kδ activity. In some other embodiments, the disease or condition may be associated or mediated by PI3Kδ and/or PI3Kβ activity.

Also provided are articles of manufacture that include a compound of formula (I) or a pharmaceutically acceptable salt, tautomer, isomer, a mixture of isomers, or prodrug thereof, and a container. In one embodiment, the container may be a vial, jar, ampoule, preloaded syringe, or an intravenous bag.

DETAILED DESCRIPTION

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom.

Reference to "about" a value or parameter herein includes (and describes) embodiments that are directed to that value or parameter per se. For example, description referring to "about X" includes description of "X". In some embodiments, the term "about" includes the indicated amount ±10%. In other embodiments, the term "about" includes the indicated amount ±5%.

"Alkyl" refers to a monoradical unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and iso-propyl.

"Cycloalkyl" refers to a cyclic alkyl group. As used herein, cycloalkyl has from 3 to 20 ring carbon atoms (i.e., $C_{3-20}$ cycloalkyl), or 3 to 12 ring carbon atoms (i.e., $C_{3-12}$ cycloalkyl), 3 to 8 ring carbon atoms (i.e., $C_{3-8}$ cycloalkyl), or 3 to 6 ring carbon atoms (i.e., $C_{3-6}$ cycloalyl). Examples of cycloalkyl groups include cyclopropyl, cyclobutyl, cyclopentyl, and cyclohexyl.

"Heterocycloalkyl" refers to a cyclic alkyl group, with one or more ring heteroatoms independently selected from nitrogen, oxygen and sulfur. As used herein, heterocycloalkyl has 2 to 20 ring carbon atoms (i.e., $C_{2-20}$ heterocycloalkyl), 2 to 12 ring carbon atoms (i.e., $C_{2-12}$ heterocycloalkyl), or 2 to 8 ring carbon atoms (i.e., $C_{2-8}$ heterocycloalkyl); and 1 to 5 ring heteroatoms, 1 to 4 ring heteroatoms, 1 to 3 ring heteroatoms, 1 or 2 ring heteroatoms, or 1 ring heteroatom independently selected from nitrogen, sulfur or oxygen. Examples of heterocycloalkyl groups may include pyrrolidinyl, piperidinyl, piperazinyl, oxetanyl, dioxolanyl, azetidinyl, and morpholinyl.

"Alkoxy" refers to the group "alkyl-O-". Examples of alkoxy groups may include methoxy, ethoxy, n-propoxy, isopropoxy, n-butoxy, tert-butoxy, sec-butoxy, n-pentoxy, n-hexoxy, and 1,2-dimethylbutoxy.

"Aryl" refers to an aromatic carbocyclic group having a single ring (e.g., phenyl), multiple rings (e.g., biphenyl), or multiple fused rings (e.g., naphthyl, fluorenyl, and anthryl). Examples of aryl groups may include 6 to 20 ring carbon atoms (i.e., $C_{6-20}$ aryl), or 6 to 12 carbon ring atoms (i.e., $C_{6-12}$ aryl). Aryl, however, does not encompass or overlap in any way with heteroaryl, separately defined below. If one or more aryl groups are fused with a heteroaryl ring, the resulting ring system is heteroaryl.

"Heteroaryl" refers to an aromatic group having a single ring, multiple rings, or multiple fused rings, with one or more ring heteroatoms independently selected from nitrogen, oxygen, and sulfur. Heteroaryl may be an aromatic, monocyclic or bicyclic ring containing one or more heteroatoms independently selected from nitrogen, oxygen and sulfur with the remaining ring atoms being carbon. As used herein, heteroaryl include 1 to 20 ring carbon atoms (i.e., $C_{1-20}$ heteroaryl), 1 to 12 ring carbon atoms (i.e., $C_{1-12}$ heteroaryl), or 1 to 8 carbon ring atoms (i.e., $C_{1-8}$ heteroaryl) and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. Examples of heteroaryl groups include pyridyl, pyridazinyl, pyrimidinyl, benzothiazolyl, and pyrazolyl. Heteroaryl does not encompass or overlap with aryl as defined above.

As used herein, the term "substituted" means that any one or more hydrogen atoms on the designated atom or group is replaced with a moiety other than hydrogen, provided that the designated atom's normal valence is not exceeded.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

"Substituted alkyl" refers to an alkyl group having one or more substituents including, for example, hydroxyl, haloalkyl, alkoxy, cycloalkyl, heterocycloalkyl, aryl, heteroaryl, cyano, halo, carboxyl, and $NR_2$, where each R is independently hydrogen, alkyl, haloalkyl, alkylC(O)—, alkylOC(O)—, or $H_2NC(O)$—. In some embodiments, a substituted alkyl may have 1 to 5 substituents, 1 to 3 substituents, 1 to 2 substituents, or 1 substituent. In other embodiment, a substituted alkyl may have 1 to 4 substituents. For example, a substituted alkyl is haloalkyl, cycloalkylalkyl, or heterocycloalkylalkyl. In some embodiments, a substituted alkyl is $C_{1-6}$ haloalkyl, $C_{1-6}$ cycloalkyl, $C_{1-6}$ heterocycloalkyl, $C_{1-4}$ haloalkyl, $C_{1-4}$ cycloalkyl, or $C_{1-4}$ heterocycloalkyl. In some other embodiments, a substituted alkyl is $C_{1-6}$ haloalkyl, $C_{1-6}$ cycloalkylalkyl, $C_{1-6}$ heterocycloalkylalkyl, $C_{1-4}$ haloalkyl, $C_{1-4}$ cycloalkylalkyl, or $C_{1-4}$ heterocycloalkylalkyl. Examples of the substituted alkyl group may include —$CH_2F$, —$CHF_2$, $CF_3$, —$CH_2FCH_3$, —$CHF_2CH3$, —$CH_2CH_2F$, —$CH_2CF_3$, cyclopropylmethyl, cyclopropylethyl, cyclopropylpropyl, cyclobutylmethyl, cyclobutylethyl, or cyclobutylpropyl.

"Substituted cycloalkyl" refers to a cycloalkyl group having one or more substituents including, for example, alkyl, haloalkyl, heterocycloalkyl, aryl, heteroaryl, alkoxy, cyano, halo, carboxyl, hydroxyl, and —$NR_2$, where each R is independently hydrogen, alkyl, haloalkyl, alkylC(O)—, alkylOC(O)—, or $H_2NC(O)$—. In some embodiments, a substituted cycloalkyl may have 1 to 5 substituents, 1 to 3 substituents, 1 to 2 substituents, or 1 substituent. In other embodiment, a substituted cycloalkyl may have 1 to 4 substituents. For example, a substituted alkyl is haloalkyl, cycloalkylalkyl, or heterocycloalkylalkyl. In some embodiments, a substituted alkyl is $C_{1-6}$ haloalkyl, $C_{3-6}$ cycloalkyl, $C_{1-6}$ heterocycloalkyl, $C_{1-4}$ haloalkyl, $C_{3-4}$ cycloalkyl, or $C_{1-4}$ heterocycloalkyl. In other example, a substituted cycloalkyl is halocycloalkyl, or alkylcycloalkyl. In some embodiments, a substituted cycloalkyl is $C_{3-10}$ halocycloalkyl, $C_{3-10}$cycloalkyl, $C_{2-10}$ heterocycloalkyl, $C_{3-6}$ halocycloalkyl, $C_{3-6}$ cycloalkyl, or $C_{2-5}$ heterocycloalkyl.

"Substituted heterocycloalkyl" refers to a heterocycloalkyl group having one or more substituents including, for example, alkyl, haloalkyl, cycloalkyl, aryl, heteroaryl, alkoxy, cyano, halo, carboxyl, hydroxyl, and —NR$_2$, where each R is independently hydrogen, alkyl, haloalkyl, alkylC(O)—, alkylOC(O)—, or H$_2$NC(O)—. In some embodiments, a substituted heterocycloalkyl may have 1 to 5 substituents, 1 to 3 substituents, 1 to 2 substituents, or 1 substituent. In other embodiment, a substituted heterocycloalkyl may have 1 to 4 substituents. In certain embodiments, a substituted heterocycloalkyl may contain 1, 2 or 3 heteroatoms independently selected from nitrogen, oxygen, and sulfur.

"Substituted aryl" refers to an aryl group having one or more substituents including, for example, halo, —OR, —NR$_2$, —C(O)NR'$_2$, —SO$_2$NR'$_2$, alkyl, haloalkyl, heterocycloalkyl, heteroaryl, alkoxy, amino, cyano, and carboxyl, where each R is independently hydrogen, alkyl, haloalkyl, alkylC(O)—, alkylOC(O)—, or H$_2$NC(O)— and each R' is independently hydrogen, alkyl, haloalkyl. In some embodiments, a substituted aryl may have 1 to 5 substituents, 1 to 3 substituents, 1 to 2 substituents, or 1 substituent.

"Substituted heteroaryl" refers to a heteroaryl group having one or more substituents including, for example, alkyl, haloalkyl, halo, —NR$_2$, —OR, —C(O)OR, heterocycloalkyl, aryl, and cyano, where each R is independently hydrogen, alkyl, haloalkyl, alkylC(O)—, alkylOC(O)—, or H$_2$NC(O)—. In some embodiments, a substituted heteroaryl may have 1 to 5 substituents, 1 to 3 substituents, 1 to 2 substituents, or 1 substituent. In other embodiment, a substituted heteroaryl may have 1 to 4 substituents. In certain embodiments, a substituted heteroaryl may contain 1, 2 or 3 heteroatoms independently selected from nitrogen, oxygen, and sulfur.

"Substituted sulfonyl" refers to the group "SO$_2$R" where R refers to a substituent including, for example, alkyl, haloalkyl, cycloalkyl heterocycloalkyl, heteroaryl, and aryl and R is further substituted with alkyl, haloalkyl, cycloalkyl, heterocycloalkyl, heteroaryl, or aryl. "Sulfonyl" refers to the group "—SO$_2$R" where R refers to a substituent including, for example, alkyl, haloalkyl, cycloalkyl, heterocycloalkyl, heteroaryl, and aryl. In some embodiments, the sulfonyl group is alkylsulfonyl, in which R is alkyl. Examples of the sulfonyl groups may include SO$_2$CH$_3$, SO$_2$CH$_2$CH$_3$, or SO$_2$Ph.

The term "halogen" or "halo" includes fluoro, chloro, bromo, and iodo, and the term "halogen" includes fluorine, chlorine, bromine, and iodine. "Haloalkyl" refers to an unbranched or branched chain alkyl group as defined above, wherein one or more hydrogen atoms are replaced by a halogen. For example, where a residue is substituted with more than one halogen, it may be referred to by using a prefix corresponding to the number of halogen moieties attached. For example, dihaloaryl, dihaloalkyl, and trihaloaryl refer to aryl and alkyl substituted with two ("di") or three ("tri") halo groups, which may be, but are not necessarily, the same halogen; thus, for example, 3,5-difluorophenyl, 3-chloro-5-fluorophenyl, 4-chloro-3-fluorophenyl, and 3,5-difluoro-4-chlorophenyl is within the scope of dihaloaryl. Other examples of a haloalkyl group include difluoromethyl (—CHF$_2$) and trifluoromethyl (—CF$_3$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless defined otherwise, where combinations of groups are referred to herein as one moiety, e.g. arylalkyl, the last mentioned group contains the atom by which the moiety is attached to the rest of the molecule.

PI3K Inhibitor Compounds

The present application provides the compounds that function as inhibitors of PI3K isoforms, such as PI3Kδ. In one aspect, the PI3K inhibitors are the compound having formula (II):

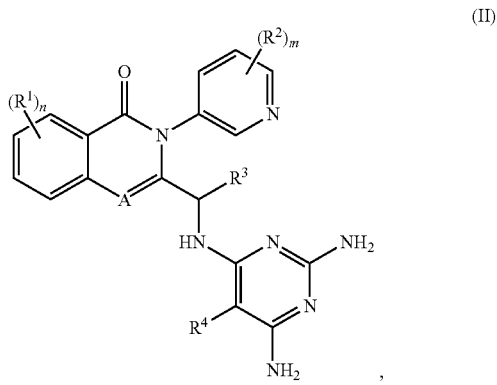

(II)

or a pharmaceutically acceptable salt, prodrug, or solvate thereof, wherein:

A is N or CH;

n is 0, 1, 2, 3, or 4;

each $R^1$ is independently selected from hydrogen, optionally substituted alkyl, optionally substituted haloalkyl, optionally substituted aryl, optionally substituted heteroaryl, halo, cyano, NHC(=O)alkylene-N($R^{1x}$)$_2$, NO$_2$, OR$^{1x}$, OCF$_3$, N($R^{1x}$)$_2$, OC(=O)R$^{1x}$, C(=O)R$^{1x}$, C(=O)OR$^{1x}$, aryl-OR$^{1y}$, Het, NR$^{1x}$C(=O)alkylene-C(=O)OR$^{1x}$, aryl-O-alkylene-N($R^{1x}$)$_2$, aryl-O—C(=O)R$^{1x}$, alkylene-C(=O)OR$^{1x}$, O-alkylene-C(=O)OR$^{1x}$, alkylene-O-alkylene-C(=O)OR$^{1x}$, C(=O)NR$^{1x}$SO$_2$R$^{1x}$, alkylene-N($R^{1x}$)$_2$, alkenylene-N($R^{1x}$)$_2$, C(=O)NR-alkylene-OR$^{1x}$, C(=O)NR$^{1x}$alkylene-Het, O-alkylene-N($R^{1x}$)$_2$, O-alkylene-CH(OR$^{1y}$)CH$_2$N($R^{1x}$)$_2$, O-alkylene-Het, O-alkylene-OR$^{1x}$, O-alkylene-NR$^{1x}$C(=O)OR$^{1x}$, NR$^{1x}$-alkylene-N(Rx)$_2$, NR$^{1x}$C(=O)R$^{1x}$, NR$^{1x}$C(=O)N($R^{1x}$)$_2$, N(SO$_2$-alkyl)$_2$, NR(SO$_2$-alkyl), SO$_2$R$^{1x}$, SO$_2$N($R^{1x}$)$_2$, OSO$_2$CF$_3$, alkylene-aryl, alkylene-Het, alkylene-OR$^{1y}$, alkylene-N($R^{1x}$)$_2$, C(=O)N($R^{1x}$)$_2$, NHC(=O)alkylene-aryl, optionally substituted cycloalkyl, optionally substituted heterocycloalkyl, aryl-O-alkylene-N($R^{1x}$)$_2$, aryl-OC(=O)R$^{1y}$, NHC(=O)alkylene-heterocycloalkyl, NHC(=O)alkylene-Het, O-alkylene-O-alkylene-C(=O)OR$^{1y}$, C(=O)alkylene-Het, or NHC(=O)halo-alkyl, wherein Het is a 5- or 6-membered heterocyclic ring containing at least one heteroatom selected from the group consisting of oxygen, nitrogen and sulfur, wherein the 5- or 6-membered heterocyclic ring is saturated, partially unsaturated or fully unsaturated, and wherein Het is optionally substituted with alkyl or C(=O)OR$^{1x}$, wherein $R^{1x}$ is independently hydrogen, optionally substituted alkyl, optionally substituted cycloalkyl, optionally substituted heterocycloalkyl, alkylene-N($R^{1x}$)$_2$, optionally substituted aryl, arylalkyl, alkylenearyl, optionally substituted heteroaryl, optionally substituted heteroarylalkyl, or alkyleneheteroaryl, or two $R^{1x}$ groups are taken together to form a 5- or 6-membered ring, optionally containing at least one heteroatom, wherein $R^{1y}$ is hydrogen, optionally substituted alkyl, optionally substituted aryl, optionally substituted heteroaryl, arylalkyl, heteroarylalkyl, alkylenearyl, and alkyleneheteroaryl;

m is 0, 1, 2, 3, or 4;

each $R^2$ is independently selected from hydrogen, halo, cyano, optionally substituted alkyl, optionally substituted haloalkyl, optionally substituted alkoxy, optionally substituted cycloalkyl, or $NR^{2x}R^{2y}$, wherein each $R^{2x}$ and $R^{2y}$ is independently hydrogen, $C(O)R^{2s}$ or $C(O)OR^{2s}$, wherein $R^{2s}$ is optionally substituted alkyl;

$R^3$ is hydrogen, optionally substituted cycloalkyl, or optionally substituted alkyl; and $R^4$ is hydrogen, cyano, $CON(R^{4a})_2$, $SO_2$-alkyl, halo, or haloalkyl, where each $R^{4a}$ is independently hydrogen or optionally substituted alkyl.

In one embodiment, the application provides the compounds having the structure of formula (I) that function as inhibitors of PI3K isoforms, such as PI3Kδ. The structure of formula (I) is shown below:

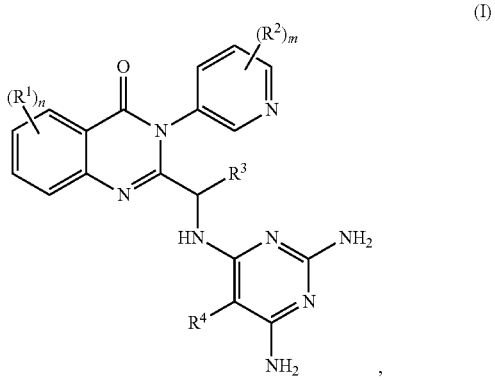

(I)

or a pharmaceutically acceptable salt, isomer, a mixture of isomers, prodrug, or solvate thereof, wherein each of n, $R^1$, m, $R^2$, $R^3$ and $R^4$ are as defined for formula (II).

In other embodiments, the compound having the structure of formula (I) wherein:

n is 0, 1, 2, 3, or 4;

each $R^1$ is independently halo, cyano, optionally substituted alkylsulfonyl, optionally substituted alkyl, optionally substituted cycloalkyl, optionally substituted heterocycloalkyl, or optionally substituted alkoxy;

m is 0, 1, 2, 3, or 4;

each $R^2$ is independently halo, optionally substituted alkoxy, optionally substituted alkyl, optionally substituted cycloalkyl, or optionally substituted heterocycloalkyl;

$R^3$ is hydrogen, optionally substituted alkyl, optionally substituted cycloalkyl, optionally substituted alkoxy, or optionally substituted heterocycloalkyl; and $R^4$ is cyano.

In other embodiments, the compounds having the structure of formula (I), wherein:

n is 1, 2, or 3;

each $R^1$ is independently halo, cyano, $C_{1-6}$ alkylsulfonyl, or $C_{1-6}$ alkyl, wherein the alkyl moiety is optionally substituted with halogen or cycloalkyl;

m is 0, 1, 2, or 3;

each $R^2$ is independently halo, $C_{1-6}$ alkoxy, $C_{1-6}$ alkyl, or $C_{3-6}$ cycloalkyl, wherein the alkoxy, alkyl, or cycloalkyl moieties are optionally substituted with halogen, alkyl, or cycloalkyl;

$R^3$ is hydrogen, $C_{1-6}$ alkyl, or $C_{3-6}$ cycloalkyl, wherein the alkyl or cycloalkyl moieties are optionally substituted with halogen, alkyl, or cycloalkyl; and $R^4$ is cyano.

In yet other embodiments, the compounds having the structure of formula (I), wherein:

n is 1 or 2;

each $R^1$ is independently selected from halogen, cyano, $C_{1-4}$ alkyl, $C_{1-4}$ haloalkyl, $C_{1-4}$ alkylsulfonyl, or $C_{3-6}$ cycloalkyl$C_{1-4}$alkyl;

m is 0, 1, or 2;

each $R^2$ is independently selected from halogen, $C_{1-4}$ alkoxy, $C_{1-4}$ alkyl, $C_{1-4}$ haloalkyl, $C_{3-6}$ cycloalkyl, or $C_{3-6}$ cycloalkyl$C_{1-4}$alkyl;

$R^3$ is selected from hydrogen, $C_{1-4}$ alkyl, $C_{3-6}$ cycloalkyl, or $C_{3-6}$ cycloalkyl$C_{1-4}$alkyl; and $R^4$ is cyano.

In another embodiment, the compounds having the structure of formula (I), wherein:

n is 1 or 2;

each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl;

m is 0, 1, or 2;

each $R^2$ is independently selected from fluoro, chloro, iodo, bromo, methoxy, ethoxy, propoxy, butoxy, pentoxy, hexoxy, methyl, ethyl, propyl, butyl, fluoromethyl, fluoroethyl, difluoromethyl, difluoroethyl, trifluoromethyl, cyclopropyl, cyclobutyl, cyclopentyl, or cyclohexyl;

$R^3$ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl; and $R^4$ is cyano.

In other embodiments, the compound having the structure of formula (I) wherein:

n is 0, 1, 2, 3, or 4;

each $R^1$ is independently halo, cyano, optionally substituted alkylsulfonyl, optionally substituted alkyl, optionally substituted cycloalkyl, optionally substituted heterocycloalkyl, or optionally substituted alkoxy;

m is 0, 1, 2, 3, or 4;

each $R^2$ is independently halo, —$NH_2$, optionally substituted alkoxyalkyl, optionally substituted alkyl, optionally substituted cycloalkyl, or optionally substituted heterocycloalkyl;

$R^3$ is hydrogen, optionally substituted alkyl, optionally substituted cycloalkyl, optionally substituted alkoxyalkyl, or optionally substituted heterocycloalkyl; and $R^4$ is cyano, halo or —$CONH_2$.

In other embodiments, the compounds having the structure of formula (I), wherein:

n is 1, 2, or 3;

each $R^1$ is independently halo, cyano, $C_{1-6}$ alkylsulfonyl, or $C_{1-6}$ alkyl, wherein the alkyl moiety is optionally substituted with halogen or cycloalkyl;

m is 0, 1, 2, or 3;

each $R^2$ is independently halo, —$NH_2$, $C_{1-6}$ alkoxy, $C_{1-6}$ alkyl, or $C_{3-6}$ cycloalkyl, wherein the alkoxy, alkyl, or cycloalkyl moieties are optionally substituted with halogen, alkyl, or cycloalkyl;

$R^3$ is hydrogen, $C_{1-6}$ alkyl, or $C_{3-6}$ cycloalkyl, wherein the alkyl or cycloalkyl moieties are optionally substituted with halogen, alkyl, or cycloalkyl; and $R^4$ is cyano, halo or —$CONH_2$.

In yet other embodiments, the compounds having the structure of formula (I), wherein:

n is 1 or 2;

each $R^1$ is independently selected from halo, cyano, $C_{1-4}$ alkyl, $C_{1-4}$ haloalkyl, $C_{1-4}$alkylsulfonyl, or $C_{3-6}$ cycloalkyl $C_{1-4}$alkyl;

m is 0, 1, or 2;

each $R^2$ is independently selected from halo, —$NH_2$, $C_{1-4}$ alkoxy, $C_{1-4}$ alkyl, $C_{1-4}$ haloalkyl, $C_{3-6}$ cycloalkyl, or $C_{3-6}$ cycloalkyl$C_{1-4}$alkyl;

$R^3$ is selected from hydrogen, $C_{1-4}$ alkyl, $C_{3-6}$ cycloalkyl, or $C_{3-6}$ cycloalkyl$C_{1-4}$alkyl; and $R^4$ is cyano, halo or —$CONH_2$.

In another embodiment, the compounds having the structure of formula (I), wherein:

n is 1 or 2;

each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl;

m is 0, 1, or 2;

each $R^2$ is independently selected from fluoro, chloro, iodo, bromo, —$NH_2$, methyl, ethyl, propyl, butyl, fluoromethyl, fluoroethyl, difluoromethyl, difluoroethyl, trifluoromethyl, cyclopropyl, cyclobutyl, cyclopentyl, or cyclohexyl;

$R^3$ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl; and $R^4$ is cyano, halo or —$CONH_2$.

In another embodiment, the compounds having the structure of formula (I), wherein:

n is 1 or 2;

each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl;

m is 0, 1, or 2;

each $R^2$ is independently selected from fluoro, chloro, iodo, bromo, —$NH_2$, methyl, ethyl, propyl, butyl, fluoromethyl, fluoroethyl, difluoromethyl, difluoroethyl, trifluoromethyl, cyclopropyl, cyclobutyl, cyclopentyl, or cyclohexyl;

$R^3$ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl; and $R^4$ is cyano.

In another embodiment, the compounds having the structure of formula (I), wherein:

n is 1 or 2;

each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl;

m is 0, 1, or 2;

each $R^2$ is independently selected from fluoro, chloro, iodo, bromo, —$NH_2$, methyl, ethyl, propyl, butyl, fluoromethyl, fluoroethyl, difluoromethyl, difluoroethyl, trifluoromethyl, cyclopropyl, cyclobutyl, cyclopentyl, or cyclohexyl;

$R^3$ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl; and $R^4$ is fluoro, chloro, or bromo.

In another embodiment, the compounds having the structure of formula (I), wherein:

n is 1 or 2;

each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl;

m is 0, 1, or 2;

each $R^2$ is independently selected from fluoro, chloro, iodo, bromo, —$NH_2$, methyl, ethyl, propyl, butyl, fluoromethyl, fluoroethyl, difluoromethyl, difluoroethyl, trifluoromethyl, cyclopropyl, cyclobutyl, cyclopentyl, or cyclohexyl;

$R^3$ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl; and $R^4$ is —$CONH_2$.

In one embodiment of formula (I), n is 0. In some embodiments, n is 1, 2, 3, or 4. In other embodiments, n is 1, 2 or 3. In certain embodiments, n is 1 or 2. In one embodiment, n is 1. In the embodiment where n is 1, the $R^1$ moiety may be located on any position of the quinazolinone ring, as depicted below.

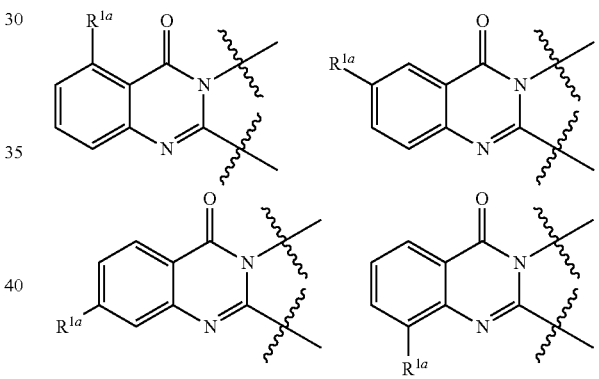

In another embodiment, n is 2. In embodiments where n is 2, both $R^1$ may be the same or different. Two $R^1$ moieties may be located on any two positions of the quinazolinone ring as depicted below. For example, two $R^1$ moieties may be in para-, meta- or ortho-positions to each other.

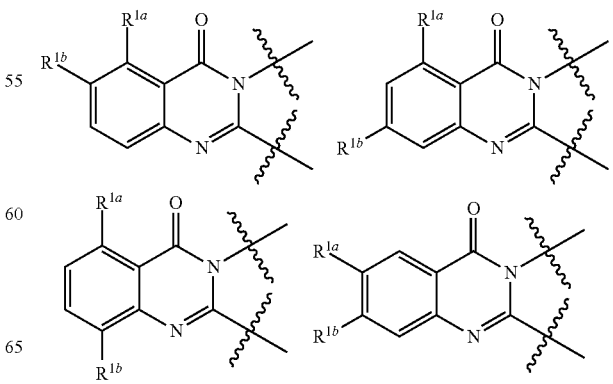

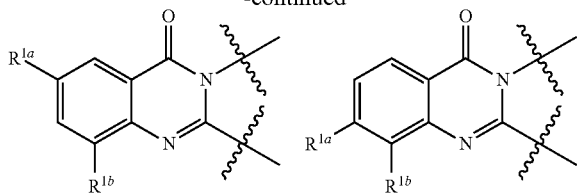

In yet another embodiment, n is 3. In embodiments where n is 3, all $R^1$ may be the same or different, or two $R^1$ may be the same and different from the third $R^1$. Three $R^1$ moieties may be located on any three positions of the quinazolinone ring as depicted below. For example, the first $R^1$ may be ortho to the second $R^1$, and the first $R^1$ may be para to the third $R^1$.

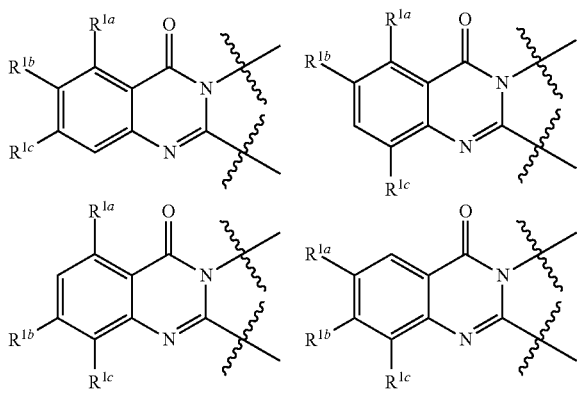

In yet another embodiment, n is 4. In embodiments where n is 4, all $R^1$ may be the same or different, three $R^1$ may be the same and different from the fourth $R^1$, two $R^1$ may be the same and different from the third and the fourth $R^1$.

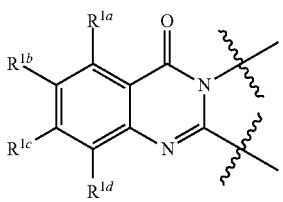

In some embodiments of formula (I), each $R^1$ is independently halo, cyano, optionally substituted alkyl, optionally substituted haloalkyl, optionally substituted alkoxy, optionally substituted cycloalkyl, or optionally substituted alkylsulfonyl. In certain embodiments, each $R^1$ is independently halo, cyano, optionally substituted alkyl, or optionally substituted alkylsulfonyl.

In some other embodiments of formula (I), each $R^1$ is independently halo, cyano, optionally substituted $C_{1-4}$ alkyl, optionally substituted $C_{1-4}$ haloalkyl, optionally substituted $C_{1-4}$ alkoxy, hydroxy, optionally substituted $C_{3-6}$ cycloalkyl, or optionally substituted $C_{1-6}$ alkylsulfonyl. In certain embodiments, each $R^1$ is independently halo, cyano, optionally substituted $C_{1-4}$ alkyl, optionally substituted $C_{3-6}$ alkoxy, optionally substituted $C_{3-6}$ cycloalkyl, or optionally substituted $C_{1-4}$ alkylsulfonyl. In other embodiments, each $R^1$ is independently halo, cyano, $C_{1-4}$ haloalkyl, $C_{1-4}$ alkyl, or $C_{1-4}$ alkylsulfonyl.

In certain embodiments of formula (I), each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl. In some embodiments, each $R^1$ is independently fluoro, chloro, iodo, cyano, methyl, difluoromethyl (—$CHF_2$), trifluoromethyl (—$CF_3$), ethyl, methoxy, methylsulfonyl (—$SO_2CH_3$), cyclopropylmethyl, or cyclopropyl. In one embodiment, each $R^1$ is independently fluoro, chloro, cyano, methylsulfonyl, methyl, or trifluoromethyl.

In some embodiments of formula (I) where n is 1, $R^1$ is halo, cyano, optionally substituted alkyl, optionally substituted haloalkyl, optionally substituted alkoxy, hydroxy, optionally substituted alkylsulfonyl, or optionally substituted cycloalkyl. In other embodiments of formula (I) wherein n is 1, $R^1$ is independently halo, cyano, $C_{1-4}$ haloalkyl, $C_{1-4}$ alkyl, or $C_{1-4}$ alkylsulfonyl. In certain embodiments where n is 1, $R^1$ is fluoro, chloro, iodo, bromo, cyano, methyl, ethyl, propyl, butyl, —$CHF_2$, —$CF_3$, fluoroethyl, fluoropropyl, methylsulfonyl, or ethylsulfonyl. In another embodiment where n is 1, $R^1$ is fluoro, chloro, cyano, methyl, trifluoromethyl (—$CF_3$), or methylsulfonyl (—$SO_2CH_3$). In another embodiment where n is 1, $R^1$ is fluoro, chloro, bromo, cyano, methyl, trifluoromethyl (—$CF_3$), or methylsulfonyl (—$SO_2CH_3$). The $R^1$ moiety may be located on any position of the quinazolinone ring.

In other embodiments of formula (I) where n is 2, both $R^1$ are independently halo, which may be the same (e.g., both $R^1$ are fluoro, chloro, or iodo) or different (e.g., one $R^1$ is fluoro and the other $R^1$ is chloro). In other embodiments where n is 2, one $R^1$ is halo and the other $R^1$ is optionally substituted alkyl. In other embodiments where n is 2, one $R^1$ is halo and the other $R^1$ is optionally substituted cycloalkyl. In other embodiments where n is 2, one $R^1$ is halo and the other $R^1$ is cyano. In additional embodiments, each $R^1$ is independently selected from fluoro, chloro, bromo, cyano, methyl, trifluoromethyl (—$CF_3$), or methylsulfonyl (—$SO_2CH_3$). In other embodiments of formula (I) where n is 2, one $R^1$ is bromo and the other $R^1$ is fluoro.

In certain embodiments where n is 2, both $R^1$ are chloro, or both $R^1$ are fluoro. In other embodiments where n is 2, one $R^1$ is chloro and the other $R^1$ is fluoro; one $R^1$ is chloro and the other $R^1$ is methyl; one $R^1$ is fluoro and the other $R^1$ is methyl; one $R^1$ is fluoro and the other $R^1$ is cyano; one $R^1$ is chloro and the other $R^1$ is cyano. In certain other embodiments where n is 2; one $R^1$ is bromo and the other $R^1$ is fluoro. The two $R^1$ moieties may be located at any two positions of the quinazolinone ring as depicted below.

In some embodiments, the moiety

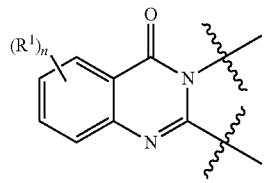

of formula (I) is:

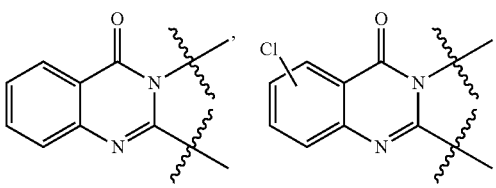

-continued
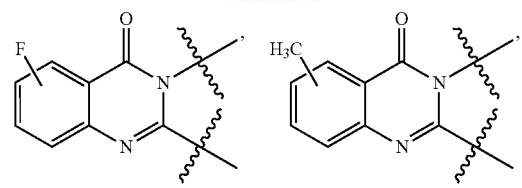
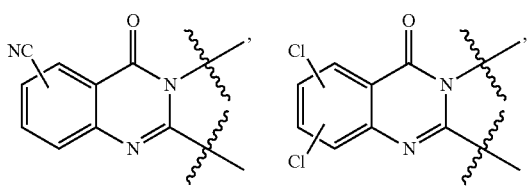
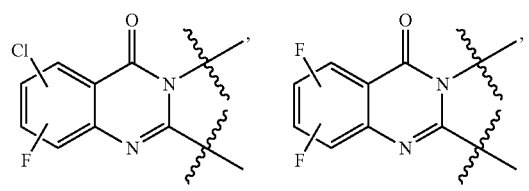
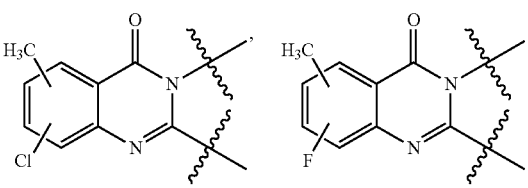
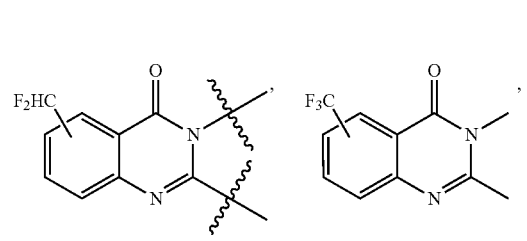
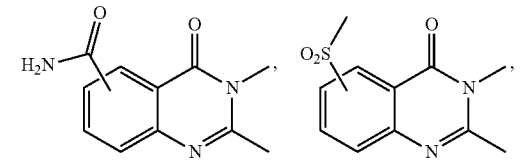
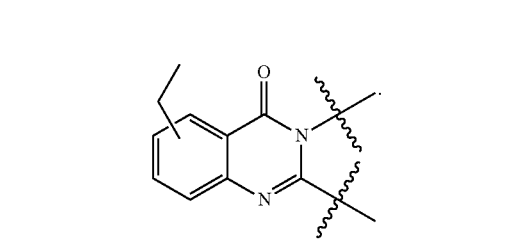
In certain embodiments, the moiety
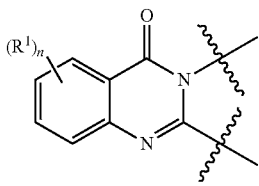
of formula (I) is:
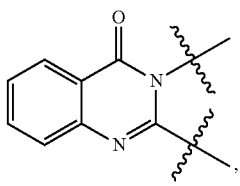
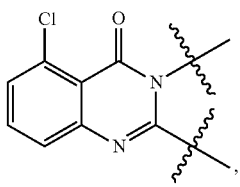
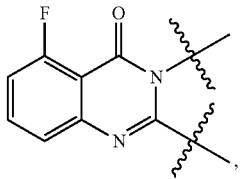
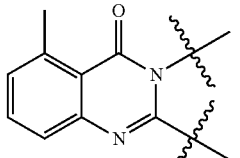
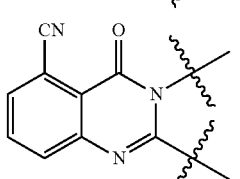
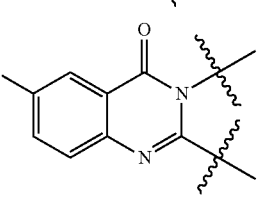
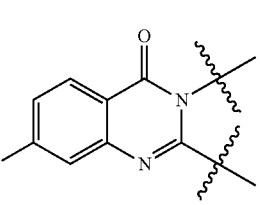

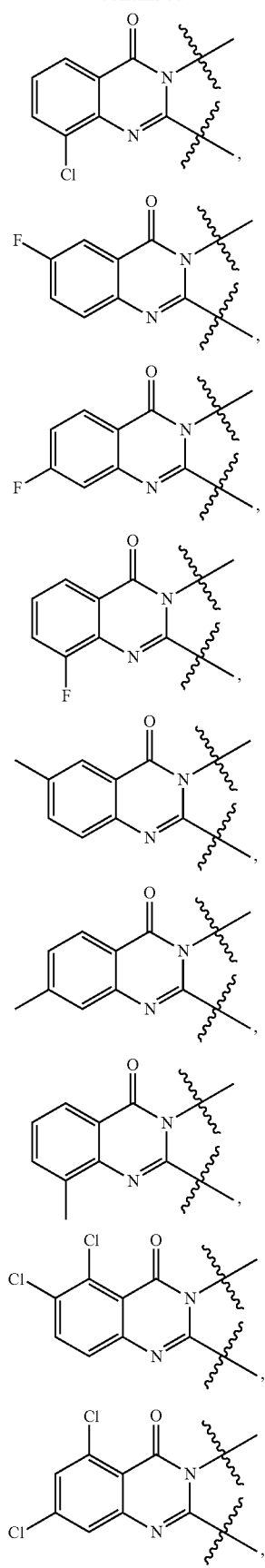
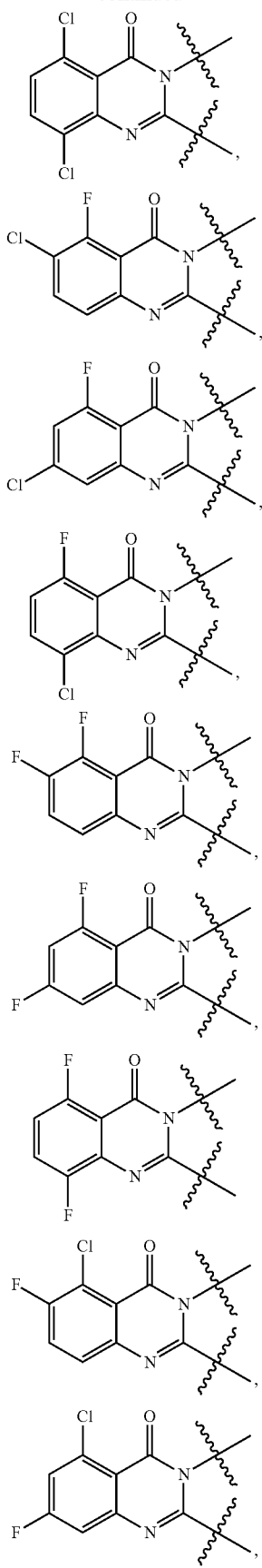

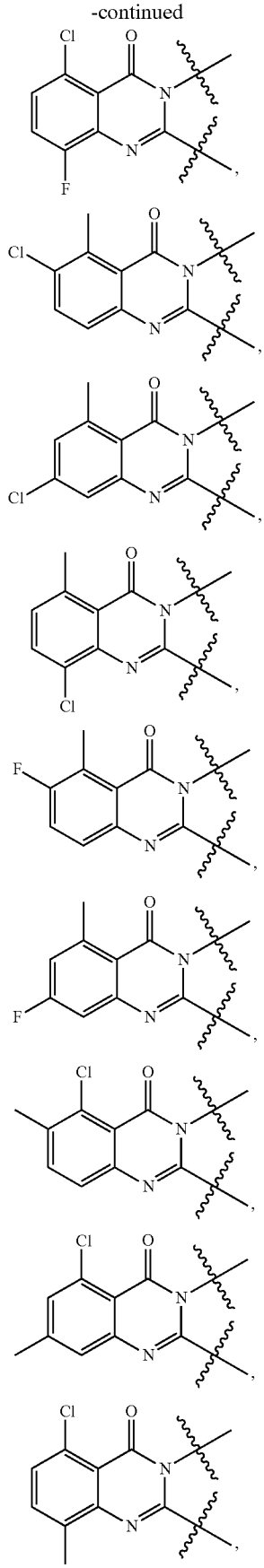
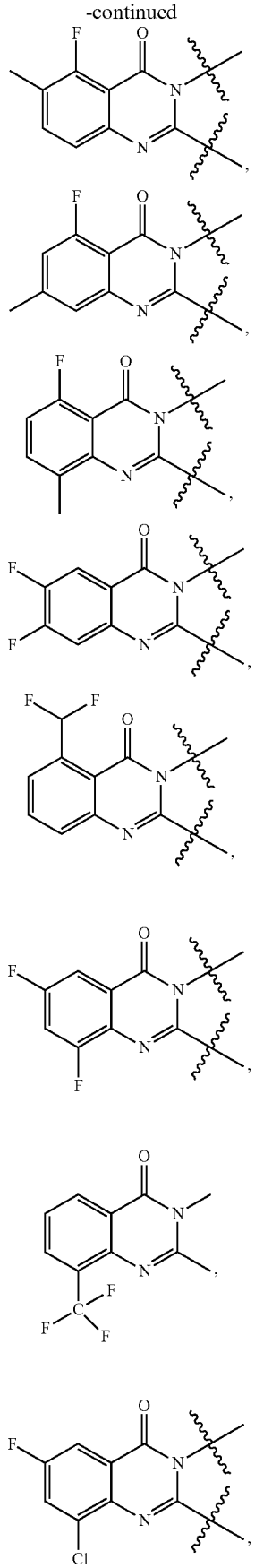

-continued

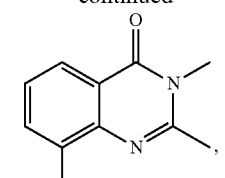,

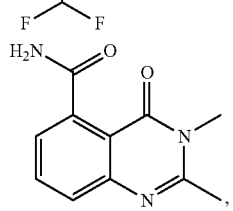,

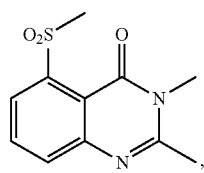,

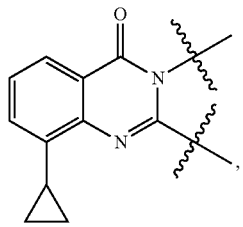,

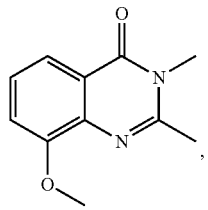,

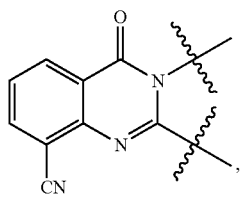,

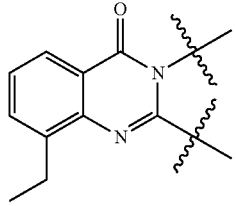,

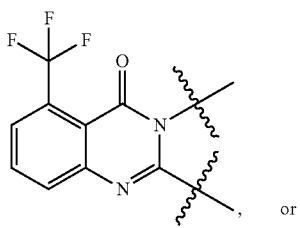, or

-continued

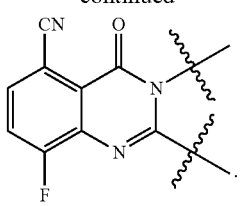.

In other embodiments, the moiety

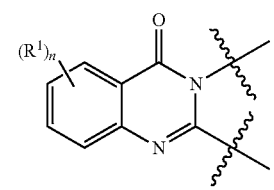

of formula (I) is

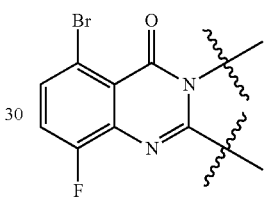 or 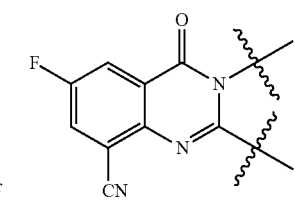.

Each and every variation of n and $R^1$ may be combined with each and every variation of m, $R^2$ and $R^3$ as described for formula (I), as if each and every combination is individually described.

In some embodiments of formula (I), m is 0. In certain embodiments, m is 1, 2, 3, or 4. In other embodiments, m is 1, 2 or 3. In yet other embodiments, m is 1 or 2. In one embodiment, m is 1. The $R^2$ moiety may be located on any position of the pyridinyl ring, as depicted below.

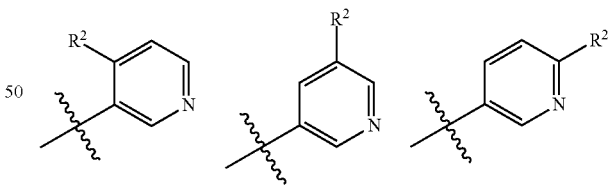

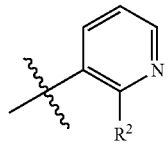

In another embodiment, m is 2. In embodiments where m is 2, both $R^2$ may be the same or different. The two $R^2$ moieties may be located on any two positions of the pyridinyl ring, as depicted below.

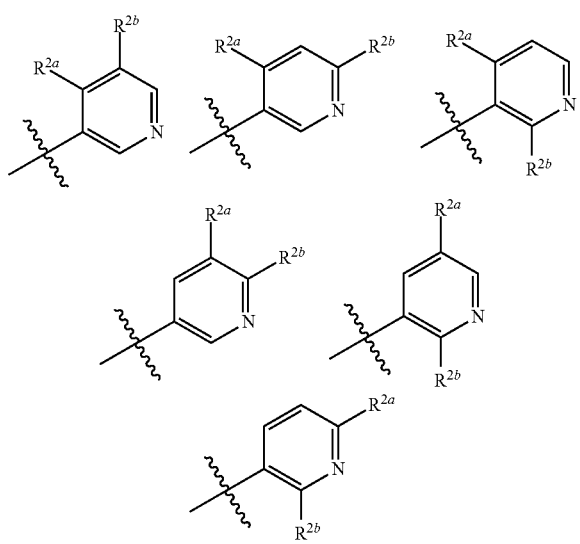

In yet another embodiment, m is 3. In embodiments where m is 3, all $R^2$ may be the same or different, or two $R^2$ may be the same and different from the third $R^2$. The three $R^2$ moieties may be located on any three positions of the pyridinyl ring, as depicted below.

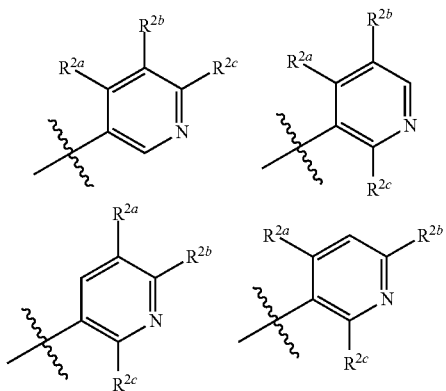

In certain embodiment, m is 4. In embodiments where m is 4, all $R^2$ may be the same or different, three $R^2$ may be the same and different from the fourth $R^2$, Of two $R^2$ may be the same and different from the third and the fourth $R^2$.

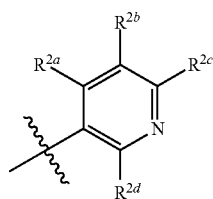

In some embodiments of formula (I), each $R^2$ is independently halo, cyano, optionally substituted alkyl, optionally substituted heteroalkyl, optionally substituted haloalkyl, optionally substituted alkoxy, optionally substituted heterocycloalkyl, or optionally substituted cycloalkyl. In other embodiments of formula (I), each $R^2$ is independently halo, cyano, optionally substituted alkyl, optionally substituted alkoxy, optionally substituted haloalkyl, or optionally substituted cycloalkyl. In certain embodiments of formula (I), each $R^2$ is independently halo, cyano, optionally substituted $C_{1-6}$ alkyl, optionally substituted $C_{1-6}$ haloalkyl, optionally substituted $C_{1-6}$ alkoxy, or optionally substituted $C_{3-8}$ cycloalkyl. In some embodiments of formula (I), each $R^2$ is independently halo, —$NH_2$, cyano, optionally substituted alkyl, optionally substituted heteroalkyl, optionally substituted haloalkyl, optionally substituted alkoxy, optionally substituted heterocycloalkyl, or optionally substituted cycloalkyl. In certain embodiments of formula (I), each $R^2$ is independently halo, —$NH_2$, cyano, optionally substituted $C_{1-6}$ alkyl, optionally substituted $C_{1-6}$ haloalkyl, optionally substituted $C_{1-6}$ alkoxy, or optionally substituted $C_{3-8}$ cycloalkyl. In certain embodiments of formula (I), each $R^2$ is independently halo, —$NH_2$, cyano, optionally substituted $C_{1-4}$ alkyl, optionally substituted $C_{1-4}$ haloalkyl, optionally substituted $C_{1-4}$ alkoxy, or optionally substituted $C_{3-6}$ cycloalkyl. In some embodiments, each $R^2$ is independently fluoro, chloro, iodo, bromo, —$NH_2$, methoxy, ethoxy, propoxy, butoxy, pentoxy, hexoxy, —$CHF_2$, —$CF_3$, fluoroethyl, difluoroethyl, methyl, ethyl, propyl, butyl, cyclopropyl, cyclobutyl, cyclopentyl, or cyclohexyl. In one embodiment, each $R^2$ is independently fluoro, chloro, methoxy, methyl, —$NH_2$, —$CHF_2$, —$CF_3$, or cyclopropyl.

In certain embodiments of formula (I), each $R^2$ is independently halo, cyano, optionally substituted $C_{1-4}$ alkyl, optionally substituted $C_{1-4}$ haloalkyl, optionally substituted $C_{1-4}$ alkoxy, or optionally substituted $C_{3-6}$ cycloalkyl. In some embodiments, each $R^2$ is independently fluoro, chloro, iodo, methoxy, ethoxy, propoxy, butoxy, pentoxy, hexoxy, —$CHF_2$, —$CF_3$, fluoroethyl, difluoroethyl, methyl, ethyl, propyl, butyl, cyclopropyl, cyclobutyl, cyclopentyl, or cyclohexyl. In one embodiment, each $R^2$ is independently fluoro, chloro, methoxy, methyl, —$CHF_2$, —$CF_3$, or cyclopropyl.

In some embodiments of formula (I) where m is 1, $R^2$ is halo, cyano, optionally substituted haloalkyl, optionally substituted alkyl, optionally substituted cycloalkyl, or optionally substituted alkoxy. In certain embodiments where m is 1, $R^2$ is fluoro, chloro, iodo, cyano, $C_{1-4}$ alkyl, $C_{1-4}$ haloalkyl, $C_{1-4}$ alkoxy, or $C_{3-6}$ cycloalkyl. In other embodiments where m is 1, $R^2$ is fluoro, chloro, methoxy, methyl, ethoxy, propoxy, butoxy, pentoxy, hexoxy, —$CHF_2$, —$CF_3$, fluoroethyl, difluoroethyl, ethyl, propyl, cyclopropyl, cyclobutyl, cyclopentyl, or cyclohexyl. In one embodiment where m is 1, $R^2$ is fluoro, chloro, methoxy, methyl, difluoromethyl (—$CHF_2$), trifluoromethyl (—$CF_3$), or cyclopropyl. The $R^2$ moiety may be located on any position of the pyridinyl ring. In certain embodiments where m is 1, $R^2$ is fluoro, chloro, iodo, bromo, —$NH_2$, cyano, $C_{1-4}$ alkyl, $C_{1-4}$ haloalkyl, $C_{1-4}$ alkoxy, or $C_{3-6}$ cycloalkyl. In other embodiments where m is 1, $R^2$ is fluoro, chloro, methoxy, methyl, ethoxy, propoxy, butoxy, pentoxy, hexoxy, —$NH_2$, —$CHF_2$, —$CF_3$, fluoroethyl, difluoroethyl, ethyl, propyl, cyclopropyl, cyclobutyl, cyclopentyl, or cyclohexyl. In one embodiment where m is 1, $R^2$ is fluoro, chloro, —$NH_2$, methoxy, methyl, difluoromethyl (—$CHF_2$), trifluoromethyl (—$CF_3$), or cyclopropyl. The $R^2$ moiety may be located on any position of the pyridinyl ring.

In some embodiments of formula (I) where m is 2, both $R^2$ are independently halo, which may be the same (e.g., both $R^2$ are fluoro or chloro) or different (e.g., one $R^2$ is fluoro and the other $R^2$ is chloro). In other embodiments where m is 2, both $R^2$ are independently optionally substituted alkyl, which may be the same (e.g., both $R^2$ are methyl) or which may be different (e.g., one $R^2$ is methyl and the other $R^2$ is ethyl). In other embodiments where m is 2, both $R^2$ are independently optionally substituted haloalkyl, which may the same (e.g., both $R^2$ are —$CF_3$) or which may be different (e.g., one $R^2$ is —$CF_3$ and the other $R^2$ is —$CHF_2$). In yet other embodiments where m is 2, both $R^2$ are independently optionally substituted alkoxy, which may be the same (e.g., both $R^2$ are methoxy) or which may be different (e.g., one $R^2$ is methoxy and the other $R^2$ is ethoxy). In some embodiments where m is 2, both $R^2$ are independently optionally substituted cycloalkyl, which may the same (e.g., both $R^2$ are cyclopropyl) or which may be different (e.g., one $R^2$ is methylcyclopropyl and the other $R^1$ is cyclopropyl). In other embodiments where m is 2, one $R^2$ is halo and the other $R^2$ is cyano, one $R^2$ is halo and the other $R^2$ is optionally substituted haloalkyl, one $R^2$ is halo and the other $R^2$ is optionally substituted alkyl, one $R^2$ is halo and the other $R^2$ is optionally substituted alkoxy, one $R^2$ is halo and the other $R^2$ is optionally substituted cycloalkyl, one $R^2$ is optionally substituted alkyl and the other $R^2$ is optionally substituted cycloalkyl, or one $R^2$ is optionally substituted alkyl and the other $R^2$ is optionally substituted alkoxy. In further embodiments, each $R^2$ is independently selected from fluoro, chloro, —$NH_2$, methoxy, methyl, difluoromethyl (—$CHF_2$), trifluoromethyl (—$CF_3$), or cyclopropyl. In yet other embodiments where m is 2, one $R^2$ is —$NH_2$ and the other $R^2$ is optionally substituted alkyl.

In certain embodiments of formula (I) where m is 2, both $R^2$ are fluoro, both $R^2$ are chloro, both $R^2$ are methoxy, both $R^2$ is methyl, or both $R^2$ is cyclopropyl. In yet other embodiments where m is 2, one $R^2$ is fluoro and the other $R^2$ is chloro, one $R^2$ is fluoro and the other $R^2$ is cyano, one $R^2$ is chloro and the other $R^2$ is cyano, one $R^2$ is fluoro and the other $R^2$ is —$CF_3$, one $R^2$ is fluoro and the other $R^2$ is —$CHF_2$, one $R^2$ is chloro and the other $R^2$ is —$CF_3$, one $R^2$ is chloro and the other $R^2$ is —$CHF_2$, one $R^2$ is cyano and the other $R^2$ is —$CF_3$, one $R^2$ is cyano and the other $R^2$ is —$CHF_2$, one $R^2$ is fluoro and the other $R^2$ is methyl, one $R^2$ is chloro and the other $R^2$ is methyl, one $R^2$ is fluoro and the other $R^2$ is cyclopropyl, or one $R^2$ is chloro and the other $R^2$ is cyclopropyl. In additional embodiments, one $R^2$ is —$NH_2$ and the other $R^2$ is methyl. The two $R^2$ moieties may be located on any two positions of the pyridinyl ring.

In yet other embodiments of formula (I) where m is 3, one or two of $R^2$ are independently halo, which may be the same (e.g., two $R^2$ are fluoro) or which may be different (e.g., one $R^2$ is fluoro and another $R^2$ is chloro), the third $R^2$ is optionally substituted alkoxy (e.g., third $R^2$ is methoxy). In another embodiment where m is 3, one $R^2$ is optionally substituted alkyl, another $R^2$ is optionally substituted alkoxy, and the third $R^2$ is halo. The three $R^2$ moieties may be located on any three positions of the pyridinyl ring.

In some embodiments, the moiety

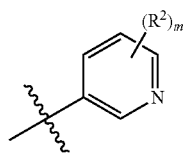

of formula (I) is:

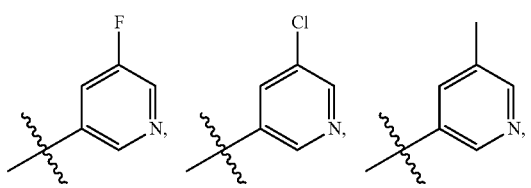

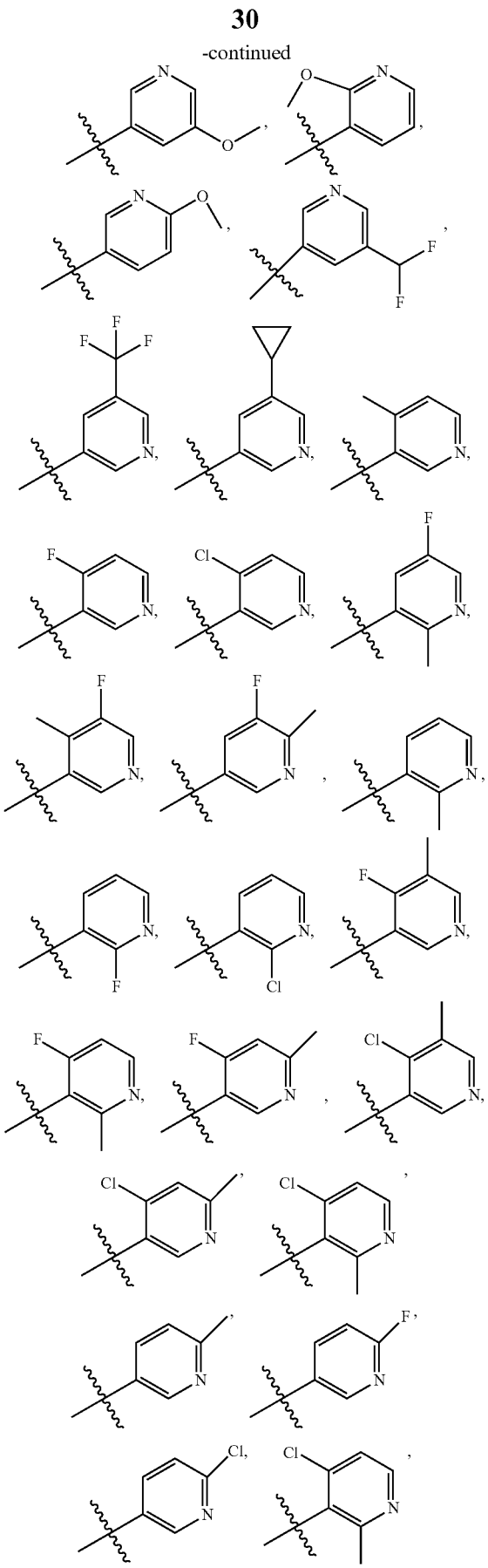

-continued

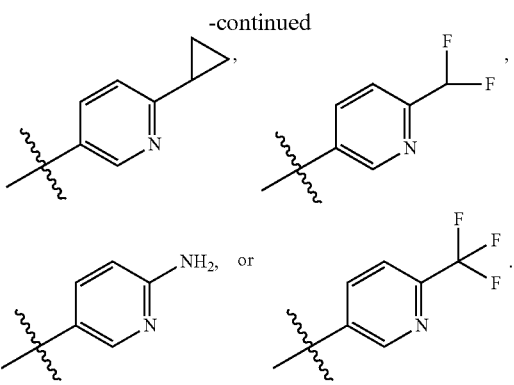

In some other embodiments, the moiety

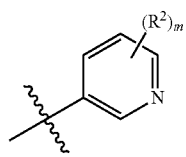

of formula (I) is

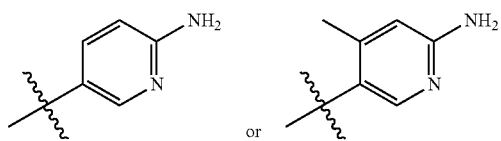

Each and every variation of m and $R^2$ may be combined with each and every variation of n, $R^1$ and $R^3$ as described for formula (I), as if each and every combination is individually described.

In some embodiments of formula (I), $R^3$ is hydrogen, optionally substituted alkyl, optionally substituted heteroalkyl, optionally substituted heterocycloalkyl, or optionally substituted cycloalkyl. In other embodiments of formula (I), $R^3$ is hydrogen, optionally substituted $C_{1-6}$ alkyl, optionally substituted $C_{3-8}$ cycloalkyl$C_{1-6}$ alkyl or optionally substituted $C_{3-8}$ cycloalkyl. In one embodiment, $R^3$ is hydrogen, $C_{1-4}$ alkyl, $C_{3-6}$ cycloalkyl, or $C_{3-8}$ cycloalkyl$C_{1-4}$ alkyl. In some embodiments, $R^3$ is hydrogen, methyl, ethyl, propyl, butyl, cyclopropylmethyl, cyclopropylbutyl, cyclobutylmethyl, or cyclopropylethyl, cyclopropyl, cyclobutyl, cyclopentyl, or cyclohexyl. In other embodiments, $R^3$ is methyl, ethyl, cyclopropylmethyl, or cyclopropyl. In other embodiments, $R^3$ is methyl, ethyl, propyl, butyl, cyclopropylmethyl, or cyclopropyl.

Each and every variation of $R^3$ may be combined with each and every variation of n, $R^1$, m and $R^2$ as described for formula (I), as if each and every combination is individually described.

In additional embodiments, $R^4$ is hydrogen, cyano, —C(O)N($R^4$)$_2$, or halo, wherein each $R^{4a}$ is independently hydrogen or optionally substituted $C_{1-6}$ alkyl. In some additional embodiments, $R^4$ is cyano, halo, —C(O)N($R^{4a}$)$_2$ wherein each $R^{4a}$ is independently hydrogen or $C_{1-4}$ alkyl. In certain additional embodiments, $R^4$ is cyano, fluoro, bromo, chloro, or —C(O)NH$_2$. In certain embodiments, $R^4$ is cyano, chloro, or —C(O)NH$_2$. It is understood by those skilled in the art that "—C(=O)NH$_2$", "—C(O)NH$_2$", and "—CONH$_2$" are equivalent and used interchangeably. Each and every variation of $R^4$ may be combined with each and every variation of n, $R^1$, m, $R^2$, and $R^3$ as described herein, as if each and every combination is individually described.

In some embodiments of formula (I),
n is 1 or 2;
each $R^1$ is independently halo, cyano, $C_{3-6}$ alkylsulfonyl, $C_{1-4}$ haloalkyl, or $C_{1-4}$ alkyl;
m is 0, 1 or 2;
each $R^2$ is independently halo, $C_{1-4}$ alkoxy, $C_{1-4}$ alkyl, $C_{1-4}$ haloalkyl, or $C_{3-6}$ cycloalkyl;
$R^3$ is hydrogen, $C_{1-4}$ alkyl, $C_{3-6}$ cycloalkyl, or $C_{3-6}$ cycloalkyl$C_{1-4}$ alkyl; and
$R^4$ is cyano.

In one embodiment of formula (I),
n is 1 or 2;
each $R^1$ is independently selected from fluoro, chloro, methylsulfonyl, cyano, methyl, trifluoromethyl;
m is 0, 1 or 2;
each $R^2$ is independently selected from fluoro, chloro, methoxy, methyl, difluoromethyl, trifluoromethyl, or cyclopropyl;
$R^3$ is methyl, ethyl, cyclopropyl, or cyclopropylmethyl; and
$R^4$ is cyano.

In some other embodiments of formula (I),
n is 1 or 2;
each $R^1$ is independently halo, cyano, $C_{3-6}$ alkylsulfonyl, $C_{1-4}$ haloalkyl, or $C_{1-4}$ alkyl;
m is 0, 1 or 2;
each $R^2$ is independently halo, —NH$_2$, $C_{1-4}$ alkoxy, $C_{1-4}$ alkyl, $C_{1-4}$ haloalkyl, or $C_{3-6}$ cycloalkyl;
$R^3$ is hydrogen, $C_{1-4}$ alkyl, $C_{3-6}$ cycloalkyl, or $C_{3-6}$ cycloalkyl$C_{1-4}$ alkyl; and
$R^4$ is cyano, halo or —CONH$_2$ In one other embodiment of formula (I),
n is 1 or 2;
each $R^1$ is independently selected from fluoro, chloro, methylsulfonyl, cyano, methyl, trifluoromethyl;
m is 0, 1 or 2;
each $R^2$ is independently selected from fluoro, chloro, —NH$_2$, methoxy, methyl, difluoromethyl, trifluoromethyl, or cyclopropyl;
$R^3$ is methyl, ethyl, cyclopropyl, or cyclopropylmethyl; and
$R^4$ is cyano, halo or —CONH$_2$.

In some other embodiments of formula (I),
n is 1 or 2;
each $R^1$ is independently halo, cyano, $C_{3-6}$ alkylsulfonyl, $C_{1-4}$ haloalkyl, or $C_{1-4}$ alkyl;
m is 0, 1 or 2;
each $R^2$ is independently halo, —NH$_2$, $C_{1-4}$ alkoxy, $C_{1-4}$ alkyl, $C_{1-4}$ haloalkyl, or $C_{3-6}$ cycloalkyl;
$R^3$ is hydrogen, $C_{1-4}$ alkyl, $C_{3-6}$ cycloalkyl, or $C_{3-6}$ cycloalkyl$C_{1-4}$ alkyl; and
$R^4$ is halo or —CONH$_2$.

In yet another embodiment of formula (I),
n is 1 or 2;
each $R^1$ is independently selected from fluoro, chloro, bromo, cyano, methyl, trifluoromethyl, and methylsulfonyl;
m is 0, 1, or 2;
each $R^2$ is independently selected from fluoro, chloro, bromo, methoxy, methyl, difluoromethyl, trifluoromethyl, and cyclopropyl;

$R^3$ is selected from methyl, ethyl, propyl, butyl, cyclopropyl, and cyclopropylmethyl; and $R^4$ is chloro, fluoro, bromo, or —$CONH_2$.

In some embodiments of formula (I) where n is 2, m is 2, and $R^4$ is cyano, the compounds have the structure of formula (IA):

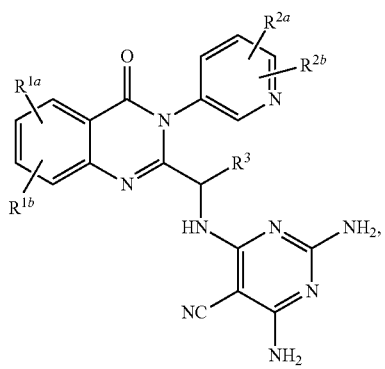

(IA)

or a pharmaceutically acceptable salt, isomer, a mixture of isomers, prodrug, or solvate thereof, wherein:

each $R^{1a}$ and $R^{1b}$ can be independently selected from the moieties defined for $R^1$ of formula (I);

each $R^{2a}$ and $R^{2b}$ can be independently selected from the moieties defined for $R^2$ of formula (I); and $R^3$ is as defined for formula (I).

In other embodiments of formula (I) where n is 1, m is 2, and $R^4$ is cyano, the compounds have the structure of formula (IB):

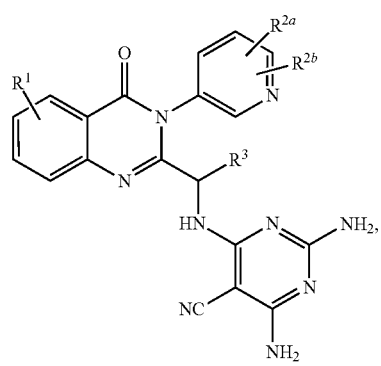

(IB)

or a pharmaceutically acceptable salt, isomer, a mixture of isomers, prodrug, or solvate thereof, wherein:

$R^1$ is as defined for formula (I);

each $R^{2a}$ and $R^{2b}$ can be independently selected from the moieties defined for $R^2$ of formula (I); and $R^3$ is as defined for formula (I).

In another embodiments where n is 2, m is 1, and $R^4$ is cyano, the compounds have the structure of formula (IC):

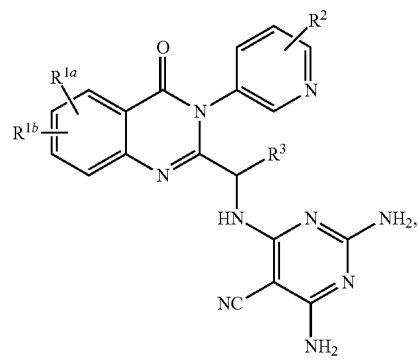

(IC)

or a pharmaceutically acceptable salt, tautomer, isomer, a mixture of isomers, prodrug, or solvate thereof, wherein:

each $R^{1a}$ and $R^{1b}$ can be independently selected from the moieties defined for $R^1$ of formula (I);

$R^2$ is as defined for formula (I); and $R^3$ is as defined for formula (I).

In another embodiments where n is 1, m is 1, and $R^4$ is cyano, the compounds have the structure of formula (ID):

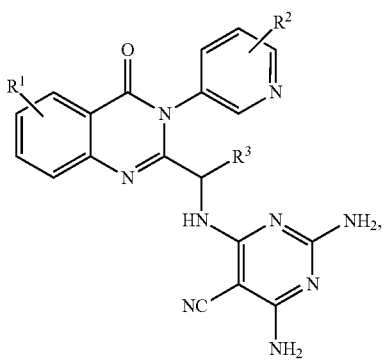

(ID)

or a pharmaceutically acceptable salt, tautomer, isomer, a mixture of isomers, or prodrug thereof, wherein:

$R^1$ is as defined for formula (I);

$R^2$ is as defined for formula (I); and $R^3$ is as defined for formula (I).

In another embodiments where n is 1, m is 0, and $R^4$ is cyano, the compounds have the structure of formula (IE):

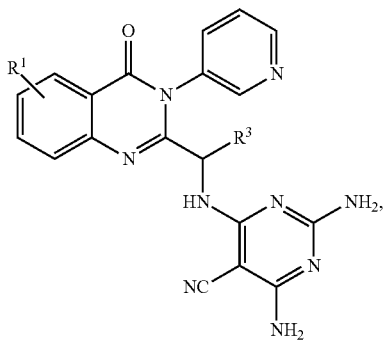

(IE)

or a pharmaceutically acceptable salt, tautomer, isomer, a mixture of isomers, or prodrug thereof, wherein:

R¹ is as defined for formula (I); and

R³ is as defined for formula (I).

In another embodiments where n is 2, m is 0, and R⁴ is cyano, the compounds have the structure of formula (IF):

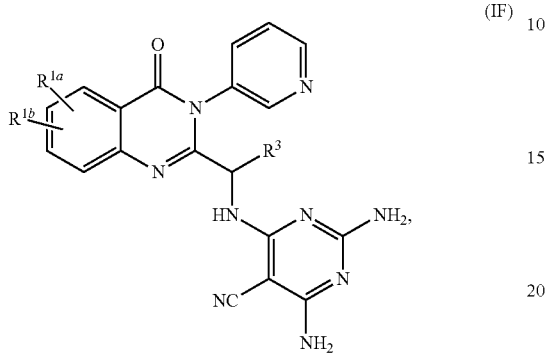

(IF)

or a pharmaceutically acceptable salt, tautomer, isomer, a mixture of isomers, or prodrug thereof, wherein:

each R¹ᵃ and R¹ᵇ can be selected from the moieties defined for R¹ of formula (I); and R³ is as defined for formula (I).

It should be understood that the embodiments and structures as described herein with respect to formula (I) are suitable for compounds of any formulae detailed herein where applicable.

For compounds of the present application bearing one or more chiral centers, each unique stereoisomer has an unique compound number. As an example, the structure below bearing one chiral center can be resolved into the (S) and (R) enantiomer.

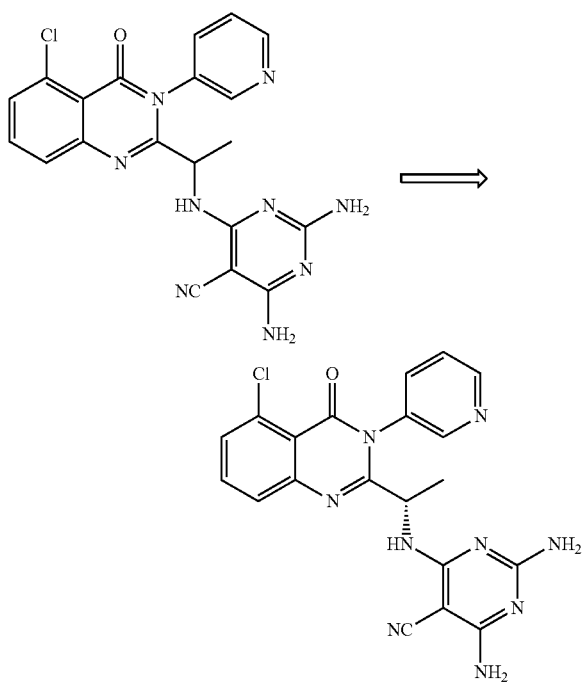

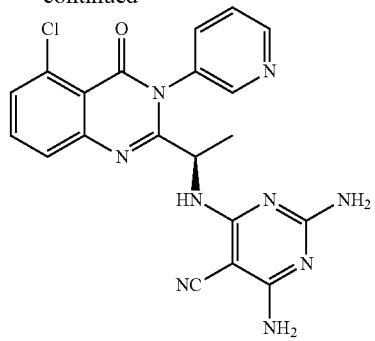

In any one of the foregoing embodiments, the compound according to any of the formulae described herein or a pharmaceutically acceptable salt thereof, is the (S)-enantiomer.

In any one of the foregoing embodiments, the compound according to any of the formulae described herein or a pharmaceutically acceptable salt thereof, is the (R)-enantiomer.

The application also provides a composition containing a mixture of enantiomers of the compound according to any of the formulae described herein or a pharmaceutically acceptable salt thereof. In some embodiments, the composition contains the (S)-enantiomer of the compound and is substantially free of its corresponding (R)-enantiomer. In certain embodiments, a composition substantially free of the (R)-enantiomer has less than or about 40%, 35%, 30%, 25%, 20%, 15%, 10%, 5%, 1%, 0.05%, or 0.01% of the (R)-enantiomer. In other embodiments, the composition containing the (S)-enantiomer of a compound according to any of formulae described herein or a pharmaceutically acceptable salt thereof, predominates over its corresponding (R)-enantiomer by a molar ratio of at least or about 9:1, at least or about 19:1, at least or about 40:1, at least or about 80:1, at least or about 160:1, or at least or about 320:1.

The composition containing a compound according to any of the formulae described herein or a pharmaceutically acceptable salt thereof, may also contain the compound in enantiomeric excess (e.e.). For instance, a compound with 95% (S)-isomer and 5% (R)-isomer will have an e.e. of 90%. In some embodiments, the compound has an e.e. of at least or about 60%, 75%, 80%, 85%, 90%, 95%, 98% or 99%. In some of the foregoing embodiments, the compound is enantiomerically-enriched in the (S)-isomer of compound according to any of the formula described herein.

Provided is also a composition comprising a mixture of the (S)-enantiomer and the (R)-enantiomer of a compound according to any of the formulae described herein or a pharmaceutically acceptable salt thereof. In one embodiment, the mixture is a racemic mixture. In other embodiments, the composition comprises the (S)-enantiomer of a compound according to any of formulae described herein or a pharmaceutically acceptable salt thereof, wherein the (S)-enantiomer of the compound is present in excess of over the corresponding the (R)-enantiomer of the compound, or a pharmaceutically acceptable salt thereof.

In any one of the foregoing embodiments, the compound according to any of the formulae described herein or a pharmaceutically acceptable salt thereof, is an atropisomer. A composition containing a mixture of atropisomers of the compound of any of the formulae described herein or a pharmaceutically acceptable salt thereof, is also provided herein. "Atropisomers" refers to conformational stereoisomers which occur when rotation about a single bond in the molecule is prevented, or greatly hindered, as a result of steric interactions with other parts of the molecule and the substituents at both ends of the single bond are asymmetrical, i.e., they do not require a stereocenter. Where the rotational barrier about the single bond is high enough, and interconversion between conformations is slow enough, separation and isolation of the isomeric species may be permitted. Atropisomers are enantiomers without a single asymmetric atom. In some embodiments, the compounds described herein may contain a mixture of diastereomers.

In any one of the foregoing embodiments, the compound according to any of the formulae described herein or a pharmaceutically acceptable salt thereof, is the atropisomer. As an example, atropisomers are exemplified by the below structures.

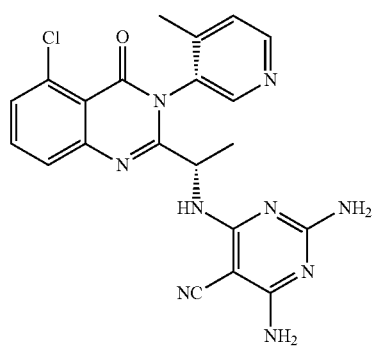

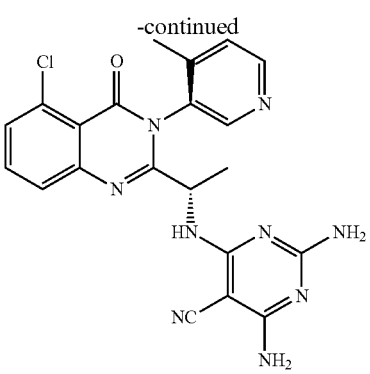

Representative compounds of the present application are listed in Table 1 below. The compounds in Table 1 are named using ChemBioDraw Ultra 12.0 and it should be understood that other names may be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). Table 1 shows the naming and numbering of the compounds that represent the formulae described herein. The compounds provided in Table 1 may be a single enantiomer (e.g., (S)-enantiomer, (R)-enantiomer), or the compounds may be present in a composition having an enantiomeric mixture. Additional representative compounds are listed in Table 1a below. As those in Table 1, the compounds in Table 1a are named using ChemBioDraw Ultra 12.0. The compounds provided in Table 1a may be a single enantiomer (e.g., (S)-enantiomer, (R)-enantiomer), or the compounds may be present in a composition having an enantiomeric mixture. In some embodiments, the compounds provided in Tables 1 and 1a are atropisomers.

TABLE 1

| | Representative Compounds | |
|---|---|---|
| No. | STRUCTURE | Name |
| 1 | (structure) | (S)-2,4-diamino-6-(1-(5-chloro-4-oxo-3-(pyridin-3-yl)-3,4-dihydroquinazolin-2-yl)ethylamino)pyrimidine-5-carbonitrile |

TABLE 1-continued

Representative Compounds

| No. | STRUCTURE | Name |
|---|---|---|
| 2 | 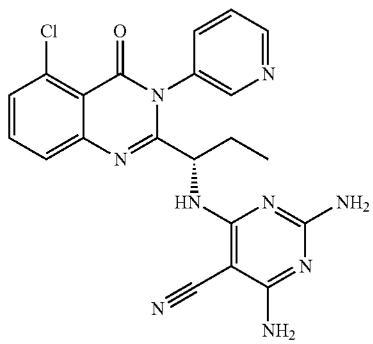 | (S)-2,4-diamino-6-(1-(5-chloro-4-oxo-3-(pyridin-3-yl)-3,4-dihydroquinazolin-2-yl)propylamino)pyrimidine-5-carbonitrile |
| 3 | 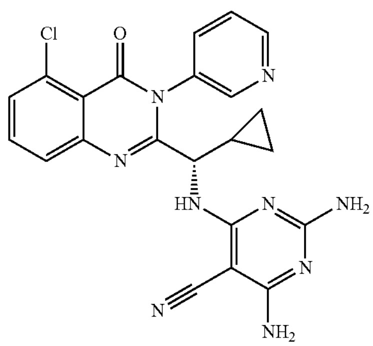 [SMILES: N#Cc1c(N)nc(N)nc1N[C@H](c1nc2cccc(Cl)c2c(=O)n1-c1cccnc1)C1CC1] | (S)-2,4-diamino-6-((5-chloro-4-oxo-3-(pyridin-3-yl)-3,4-dihydroquinazolin-2-yl)(cyclopropyl)methylamino)pyrimidine-5-carbonitrile |
| 4 | 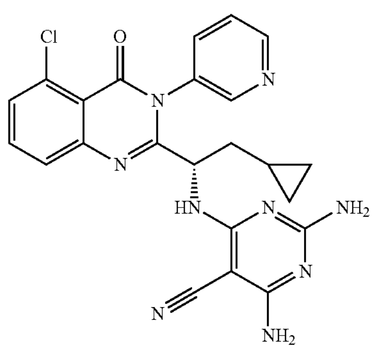 | (S)-2,4-diamino-6-(1-(5-chloro-4-oxo-3-(pyridin-3-yl)-3,4-dihydroquinazolin-2-yl)-2-cyclopropylethylamino)pyrimidine-5-carbonitrile |
| 5 | 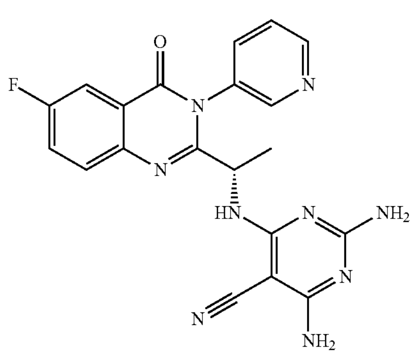 [SMILES: C[C@H](Nc1nc(N)nc(N)c1C#N)c1nc2ccc(F)cc2c(=O)n1-c1cccnc1] | (S)-2,4-diamino-6-(1-(6-fluoro-4-oxo-3-(pyridin-3-yl)-3,4-dihydroquinazolin-2-yl)ethylamino)pyrimidine-5-carbonitrile |

TABLE 1-continued

Representative Compounds

| No. | STRUCTURE | Name |
|---|---|---|
| 7 | 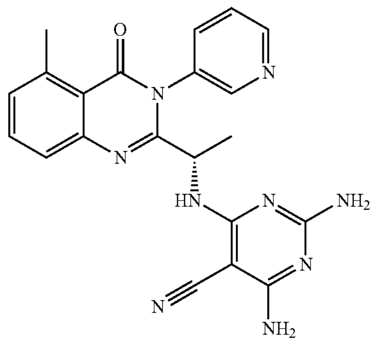 | (S)-2,4-diamino-6-(1-(5-methyl-4-oxo-3-(pyridin-3-yl)-3,4-dihydroquinazolin-2-yl)ethylamino)pyrimidine-5-carbonitrile |
| 8 | 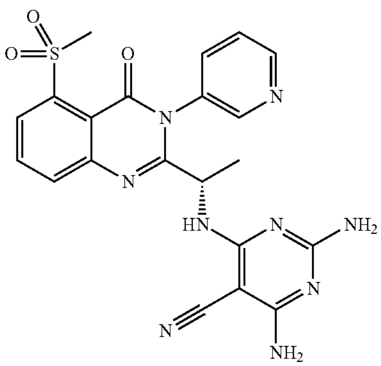 [SMILES: C[C@H](Nc1nc(N)nc(N)c1C#N)c1nc2cccc(S(C)(=O)=O)c2c(=O)n1-c1cccnc1] | (S)-2,4-diamino-6-(1-(5-(methylsulfonyl)-4-oxo-3-(pyridin-3-yl)-3,4-dihydroquinazolin-2-yl)ethylamino)pyrimidine-5-carbonitrile |
| 9 | 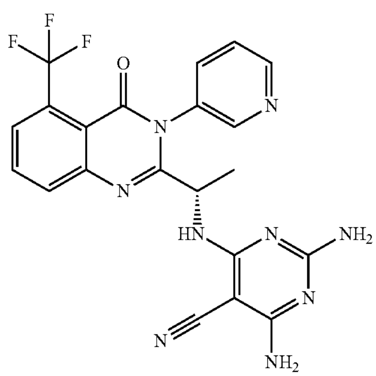 [SMILES: C[C@H](Nc1nc(N)nc(N)c1C#N)c1nc2cccc(C(F)(F)F)c2c(=O)n1-c1cccnc1] | (S)-2,4-diamino-6-(1-(4-oxo-3-(pyridin-3-yl)-5-(trifluoromethyl)-3,4-dihydroquinazolin-2-yl)ethylamino)pyrimidine-5-carbonitrile |
| 10 | 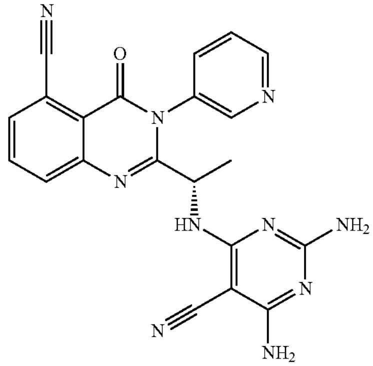 [SMILES: C[C@H](Nc1nc(N)nc(N)c1C#N)c1nc2cccc(C#N)c2c(=O)n1-c1cccnc1] | (S)-2-(1-(2,6-diamino-5-cyanopyrimidin-4-ylamino)ethyl)-4-oxo-3-(pyridin-3-yl)-3,4-dihydroquinazoline-5-carbonitrile |

TABLE 1-continued

Representative Compounds

| No. | STRUCTURE | Name |
|---|---|---|
| 11 | 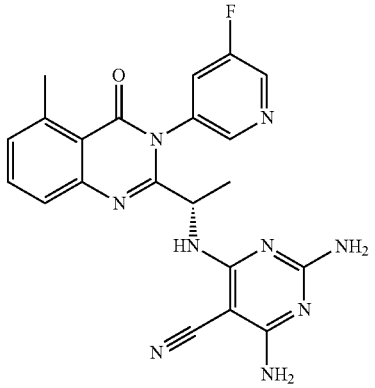 [SMILES: Cc1cccc2nc([C@H](C)Nc3nc(N)nc(N)c3C#N)n(-c3cncc(F)c3)c(=O)c12] | (S)-2,4-diamino-6-(1-(3-(5-fluoropyridin-3-yl)-5-methyl-4-oxo-3,4-dihydroquinazolin-2-yl)ethylamino)pyrimidine-5-carbonitrile |
| 12 | 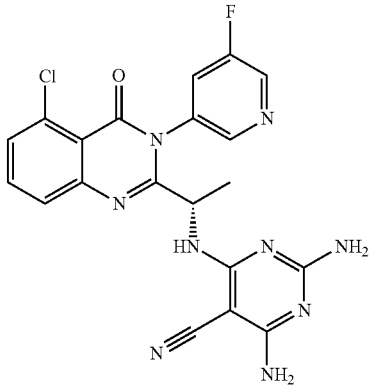 [SMILES: C[C@H](Nc1nc(N)nc(N)c1C#N)c1nc2cccc(Cl)c2c(=O)n1-c1cncc(F)c1] | (S)-2,4-diamino-6-(1-(5-chloro-3-(5-fluoropyridin-3-yl)-4-oxo-3,4-dihydroquinazolin-2-yl)ethylamino)pyrimidine-5-carbonitrile |
| 13 | 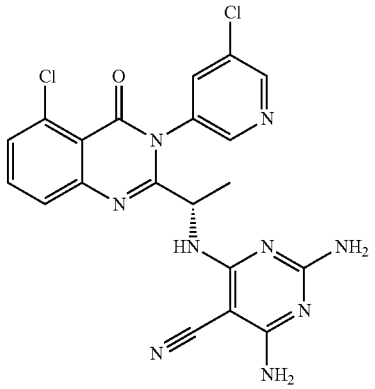 [SMILES: C[C@H](Nc1nc(N)nc(N)c1C#N)c1nc2cccc(Cl)c2c(=O)n1-c1cncc(Cl)c1] | (S)-2,4-diamino-6-(1-(5-chloro-3-(5-chloropyridin-3-yl)-4-oxo-3,4-dihydroquinazolin-2-yl)ethylamino)pyrimidine-5-carbonitrile |
| 14 | 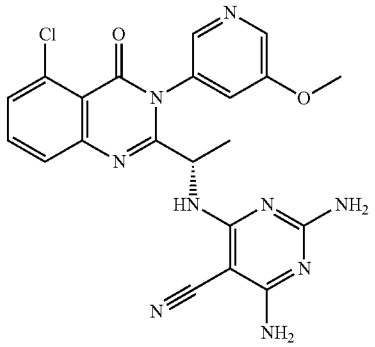 [SMILES: COc1cncc(-n2c([C@H](C)Nc3nc(N)nc(N)c3C#N)nc3cccc(Cl)c3c2=O)c1] | (S)-2,4-diamino-6-(1-(5-chloro-3-(5-methoxypyridin-3-yl)-4-oxo-3,4-dihydroquinazolin-2-yl)ethylamino)pyrimidine-5-carbonitrile |

TABLE 1-continued

Representative Compounds

| No. | STRUCTURE | Name |
|---|---|---|
| 15 | 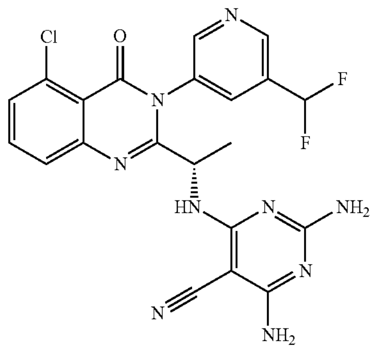 [SMILES: C[C@H](Nc1nc(N)nc(N)c1C#N)c1nc2cccc(Cl)c2c(=O)n1-c1cncc(C(F)F)c1] | (S)-2,4-diamino-6-(1-(5-chloro-3-(5-(difluoromethyl)pyridin-3-yl)-4-oxo-3,4-dihydroquinazolin-2-yl)ethylamino)pyrimidine-5-carbonitrile |
| 16 | 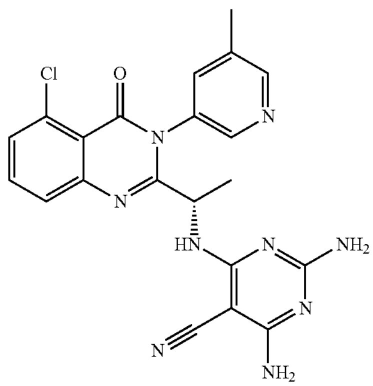 [SMILES: Cc1cncc(-n2c([C@H](C)Nc3nc(N)nc(N)c3C#N)nc3cccc(Cl)c3c2=O)c1] | (S)-2,4-diamino-6-(1-(5-chloro-3-(5-methylpyridin-3-yl)-4-oxo-3,4-dihydroquinazolin-2-yl)ethylamino)pyrimidine-5-carbonitrile |
| 17 | 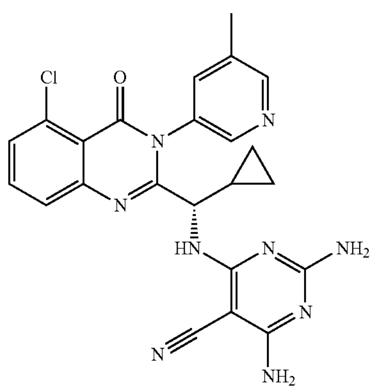 [SMILES: Cc1cncc(-n2c([C@@H](Nc3nc(N)nc(N)c3C#N)C3CC3)nc3cccc(Cl)c3c2=O)c1] | (S)-2,4-diamino-6-((5-chloro-3-(5-methylpyridin-3-yl)-4-oxo-3,4-dihydroquinazolin-2-yl)(cyclopropyl)methylamino)pyrimidine-5-carbonitrile |
| 18 | 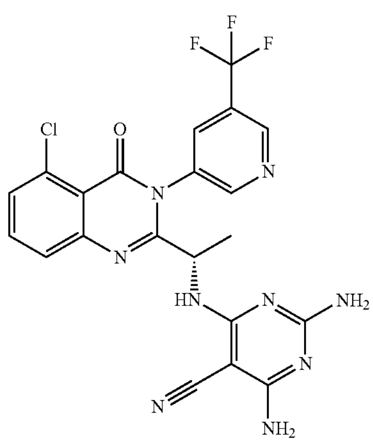 [SMILES: C[C@H](Nc1nc(N)nc(N)c1C#N)c1nc2cccc(Cl)c2c(=O)n1-c1cncc(C(F)(F)F)c1] | (S)-2,4-diamino-6-(1-(5-chloro-4-oxo-3-(5-(trifluoromethyl)pyridin-3-yl)-3,4-dihydroquinazolin-2-yl)ethylamino)pyrimidine-5-carbonitrile |

TABLE 1-continued

Representative Compounds

| No. | STRUCTURE | Name |
|---|---|---|
| 19 | 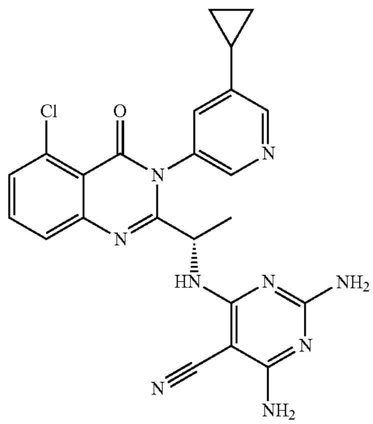 [SMILES: C[C@H](Nc1nc(N)nc(N)c1C#N)c1nc2cccc(Cl)c2c(=O)n1-c1cncc(C2CC2)c1] | (S)-2,4-diamino-6-(1-(5-chloro-3-(5-cyclopropylpyridin-3-yl)-4-oxo-3,4-dihydroquinazolin-2-yl)ethylamino)pyrimidine-5-carbonitrile |
| 20 | 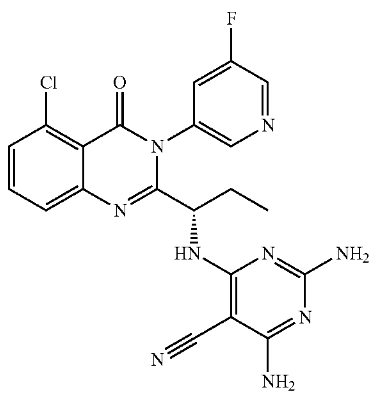 [SMILES: CC[C@H](Nc1nc(N)nc(N)c1C#N)c1nc2cccc(Cl)c2c(=O)n1-c1cncc(F)c1] | (S)-2,4-diamino-6-(1-(5-chloro-3-(5-fluoropyridin-3-yl)-4-oxo-3,4-dihydroquinazolin-2-yl)propylamino)pyrimidine-5-carbonitrile |
| 21 | 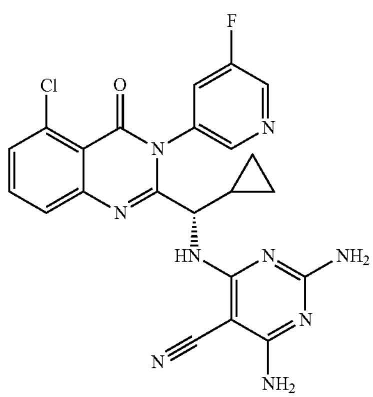 [SMILES: N#Cc1c(N)nc(N)nc1N[C@H](c1nc2cccc(Cl)c2c(=O)n1-c1cncc(F)c1)C1CC1] | (S)-2,4-diamino-6-((5-chloro-3-(5-fluoropyridin-3-yl)-4-oxo-3,4-dihydroquinazolin-2-yl)(cyclopropyl)methylamino)pyrimidine-5-carbonitrile |
| 22 | 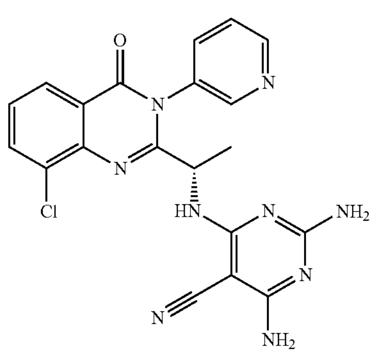 | (S)-2,4-diamino-6-(1-(8-chloro-4-oxo-3-(pyridin-3-yl)-3,4-dihydroquinazolin-2-yl)ethylamino)pyrimidine-5-carbonitrile |

TABLE 1-continued

Representative Compounds

| No. | STRUCTURE | Name |
|---|---|---|
| 23 | 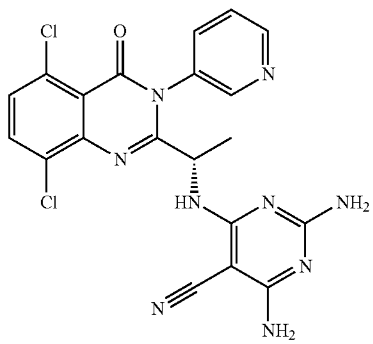 | (S)-2,4-diamino-6-(1-(5,8-dichloro-4-oxo-3-(pyridin-3-yl)-3,4-dihydroquinazolin-2-yl)ethylamino)pyrimidine-5-carbonitrile |
| 24 | 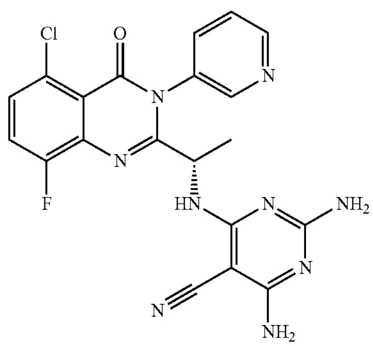 | (S)-2,4-diamino-6-(1-(5-chloro-8-fluoro-4-oxo-3-(pyridin-3-yl)-3,4-dihydroquinazolin-2-yl)ethylamino)pyrimidine-5-carbonitrile |
| 25 | 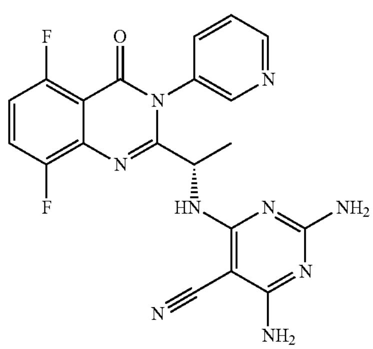 | (S)-2,4-diamino-6-(1-(5,8-difluoro-4-oxo-3-(pyridin-3-yl)-3,4-dihydroquinazolin-2-yl)ethylamino)pyrimidine-5-carbonitrile |
| 26 | 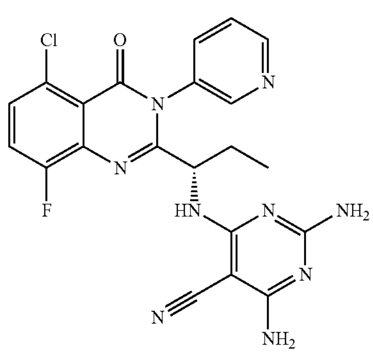 | (S)-2,4-diamino-6-(1-(5-chloro-8-fluoro-4-oxo-3-(pyridin-3-yl)-3,4-dihydroquinazolin-2-yl)propylamino)pyrimidine-5-carbonitrile |

TABLE 1-continued

Representative Compounds

| No. | STRUCTURE | Name |
|---|---|---|
| 27 | 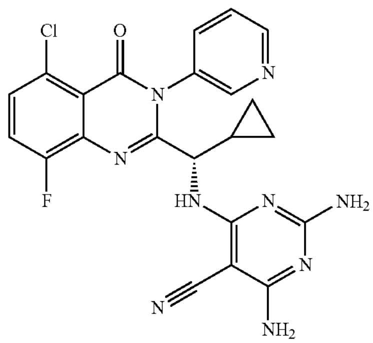 | (S)-2,4-diamino-6-((5-chloro-8-fluoro-4-oxo-3-(pyridin-3-yl)-3,4-dihydroquinazolin-2-yl)(cyclopropyl)methylamino)pyrimidine-5-carbonitrile |
| 28 | 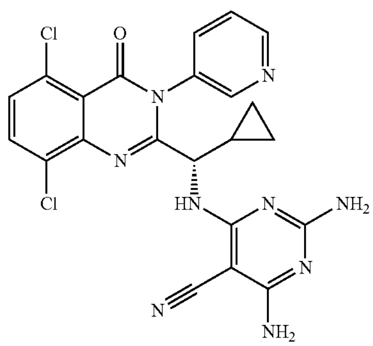 | (S)-2,4-diamino-6-(cyclopropyl(5,8-dichloro-4-oxo-3-(pyridin-3-yl)-3,4-dihydroquinazolin-2-yl)methylamino)pyrimidine-5-carbonitrile |
| 29 | 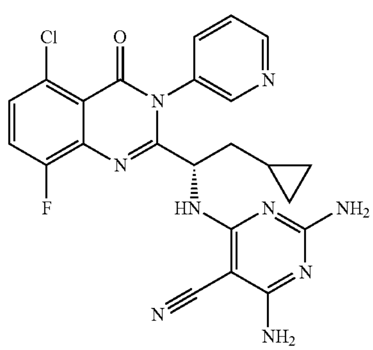 [SMILES: N#Cc1c(N)nc(N)nc1N[C@@H](CC1CC1)c1nc2c(F)ccc(Cl)c2c(=O)n1-c1cccnc1] | (S)-2,4-diamino-6-(1-(5-chloro-8-fluoro-4-oxo-3-(pyridin-3-yl)-3,4-dihydroquinazolin-2-yl)-2-cyclopropylethylamino)pyrimidine-5-carbonitrile |
| 30 | 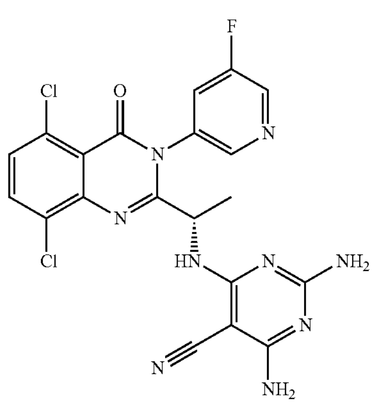 | (S)-2,4-diamino-6-(1-(5,8-dichloro-3-(5-fluoropyridin-3-yl)-4-oxo-3,4-dihydroquinazolin-2-yl)ethylamino)pyrimidine-5-carbonitrile |

TABLE 1-continued

Representative Compounds

| No. | STRUCTURE | Name |
|---|---|---|
| 31 | 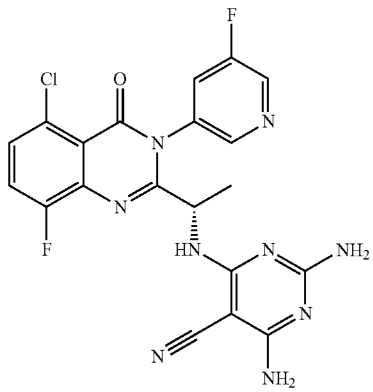 | (S)-2,4-diamino-6-(1-(5-chloro-8-fluoro-3-(5-fluoropyridin-3-yl)-4-oxo-3,4-dihydroquinazolin-2-yl)ethylamino)pyrimidine-5-carbonitrile |
| 32 | 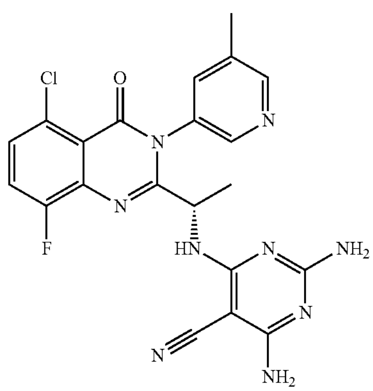 | (S)-2,4-diamino-6-(1-(5-chloro-8-fluoro-3-(5-methylpyridin-3-yl)-4-oxo-3,4-dihydroquinazolin-2-yl)ethylamino)pyrimidine-5-carbonitrile |
| 33 | 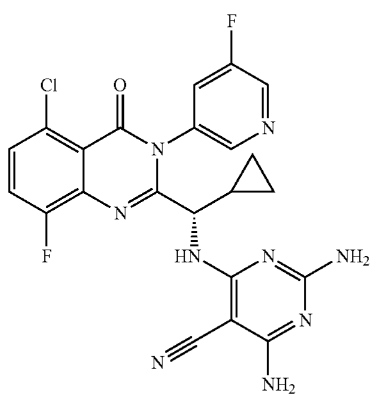 [SMILES: N#Cc1c(N)nc(N)nc1N[C@H](c1nc2c(F)ccc(Cl)c2c(=O)n1-c1cncc(F)c1)C1CC1] | (S)-2,4-diamino-6-((5-chloro-8-fluoro-3-(5-fluoropyridin-3-yl)-4-oxo-3,4-dihydroquinazolin-2-yl)(cyclopropyl)methylamino)pyrimidine-5-carbonitrile |
| 34 | 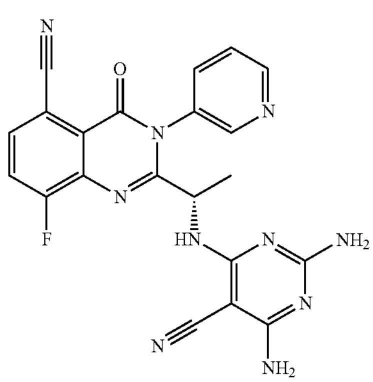 [SMILES: C[C@H](Nc1nc(N)nc(N)c1C#N)c1nc2c(F)ccc(C#N)c2c(=O)n1-c1cccnc1] | (S)-2-(1-(2,6-diamino-5-cyanopyrimidin-4-ylamino)ethyl)-8-fluoro-4-oxo-3-(pyridin-3-yl)-3,4-dihydroquinazoline-5-carbonitrile |

TABLE 1-continued

Representative Compounds

| No. | STRUCTURE | Name |
|-----|-----------|------|
| 35 | 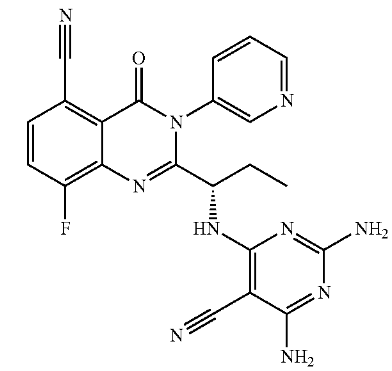 [SMILES: CC[C@H](Nc1nc(N)nc(N)c1C#N)c1nc2c(F)ccc(C#N)c2c(=O)n1-c1cccnc1] | (S)-2-(1-(2,6-diamino-5-cyanopyrimidin-4-ylamino)propyl)-8-fluoro-4-oxo-3-(pyridin-3-yl)-3,4-dihydroquinazoline-5-carbonitrile |
| 36 | 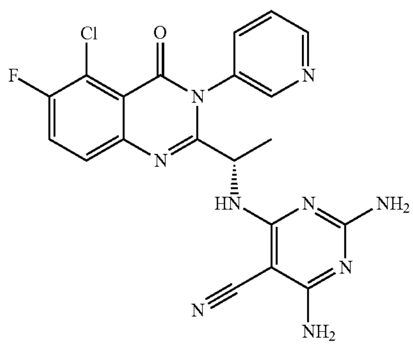 | (S)-2,4-diamino-6-(1-(5-chloro-6-fluoro-4-oxo-3-(pyridin-3-yl)-3,4-dihydroquinazolin-2-yl)ethylamino)pyrimidine-5-carbonitrile |
| 37 | 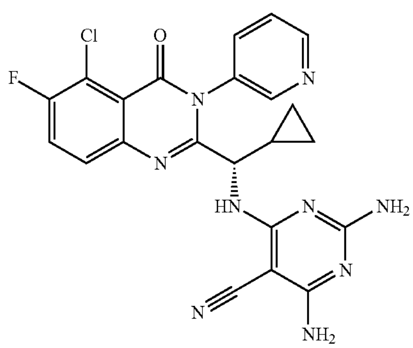 [SMILES: N#Cc1c(N)nc(N)nc1N[C@H](c1nc2ccc(F)c(Cl)c2c(=O)n1-c1cccnc1)C1CC1] | (S)-2,4-diamino-6-((5-chloro-6-fluoro-4-oxo-3-(pyridin-3-yl)-3,4-dihydroquinazolin-2-yl)(cyclopropyl)methylamino)pyrimidine-5-carbonitrile |
| 38 | 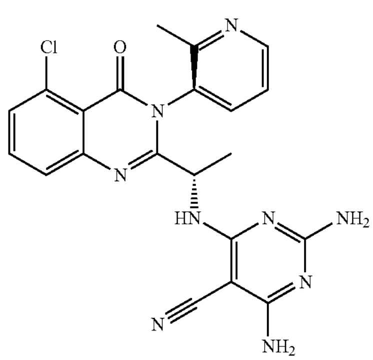 | (S)-2,4-diamino-6-(1-(5-chloro-3-(2-methylpyridin-3-yl)-4-oxo-3,4-dihydroquinazolin-2-yl)ethylamino)pyrimidine-5-carbonitrile |

TABLE 1-continued

Representative Compounds

| No. | STRUCTURE | Name |
|---|---|---|
| 39 | 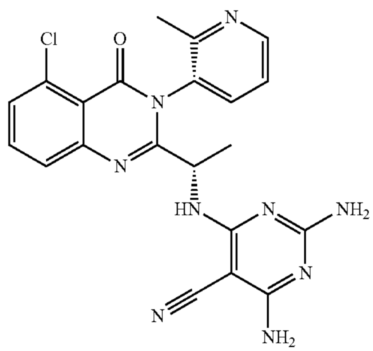 | (S)-2,4-diamino-6-(1-(5-chloro-3-(2-methylpyridin-3-yl)-4-oxo-3,4-dihydroquinazolin-2-yl)ethylamino)pyrimidine-5-carbonitrile |
| 40 | 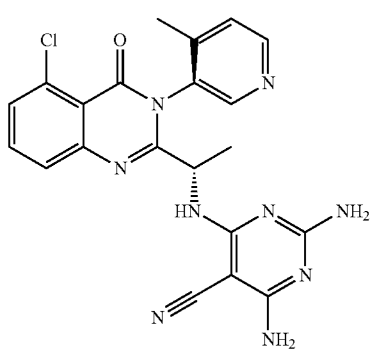 | (S)-2,4-diamino-6-(1-(5-chloro-3-(4-methylpyridin-3-yl)-4-oxo-3,4-dihydroquinazolin-2-yl)ethylamino)pyrimidine-5-carbonitrile |
| 41 | 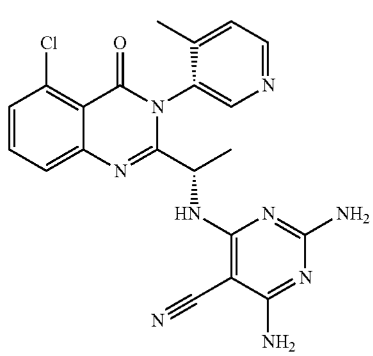 | (S)-2,4-diamino-6-(1-(5-chloro-3-(4-methylpyridin-3-yl)-4-oxo-3,4-dihydroquinazolin-2-yl)ethylamino)pyrimidine-5-carbonitrile |
| 42 | 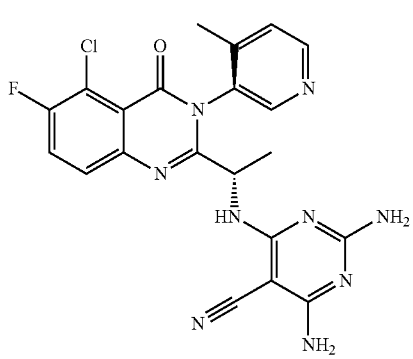 | (S)-2,4-diamino-6-(1-(5-chloro-6-fluoro-3-(4-methylpyridin-3-yl)-4-oxo-3,4-dihydroquinazolin-2-yl)ethylamino)pyrimidine-5-carbonitrile |

TABLE 1-continued

Representative Compounds

| No. | STRUCTURE | Name |
|---|---|---|
| 43 | 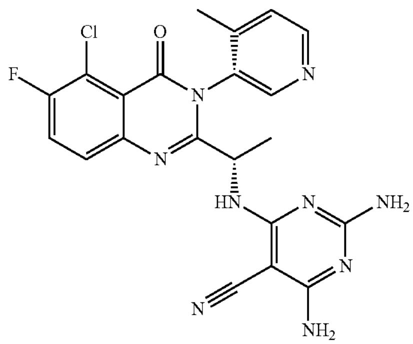 | (S)-2,4-diamino-6-(1-(5-chloro-6-fluoro-3-(4-methylpyridin-3-yl)-4-oxo-3,4-dihydroquinazolin-2-yl)ethylamino)pyrimidine-5-carbonitrile |
| 44 | 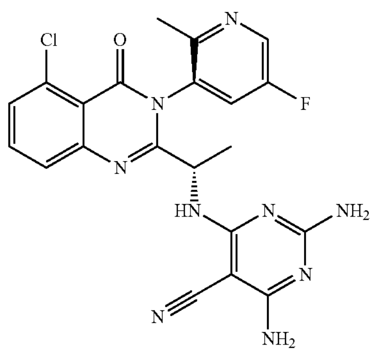 | (S)-2,4-diamino-6-(1-(5-chloro-3-(5-fluoro-2-methylpyridin-3-yl)-4-oxo-3,4-dihydroquinazolin-2-yl)ethylamino)pyrimidine-5-carbonitrile |
| 45 | 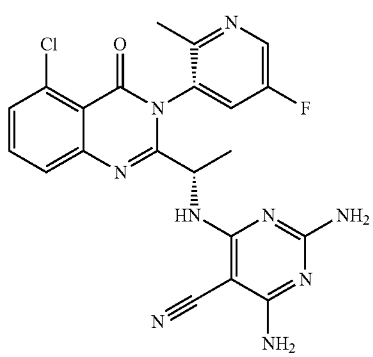 | (S)-2,4-diamino-6-(1-(5-chloro-3-(5-fluoro-2-methylpyridin-3-yl)-4-oxo-3,4-dihydroquinazolin-2-yl)ethylamino)pyrimidine-5-carbonitrile |
| 46 | 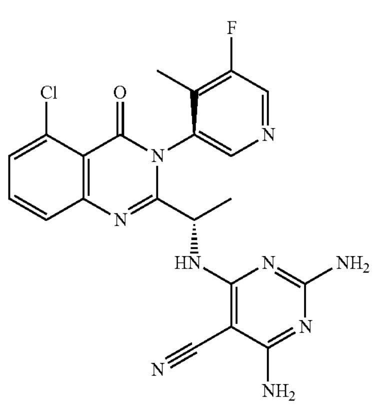 | (S)-2,4-diamino-6-(1-(5-chloro-3-(5-fluoro-4-methylpyridin-3-yl)-4-oxo-3,4-dihydroquinazolin-2-yl)ethylamino)pyrimidine-5-carbonitrile |

TABLE 1-continued

Representative Compounds

| No. | STRUCTURE | Name |
|---|---|---|
| 47 | 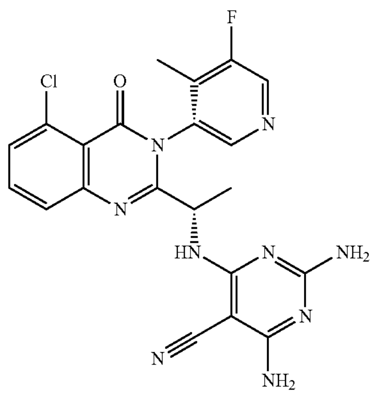 | (S)-2,4-diamino-6-(1-(5-chloro-3-(5-fluoro-4-methylpyridin-3-yl)-4-oxo-3,4-dihydroquinazolin-2-yl)ethylamino)pyrimidine-5-carbonitrile |

TABLE 1a

Representative Compounds

| No. | Structure | Name |
|---|---|---|
| 48 | 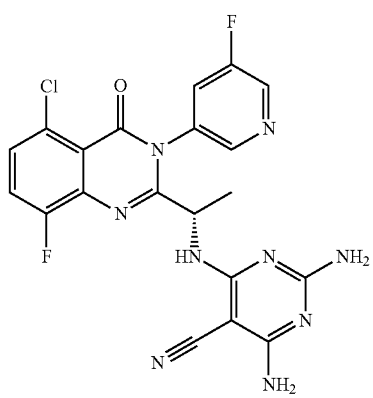 | (S)-2,4-Diamino-6-((1-(5-chloro-8-fluoro-3-(5-fluoropyridin-3-yl)-4-oxo-3,4-dihydroquinazolin-2-yl)propyl)amino)pyrimidine-5-carbonitrile |
| 49 | 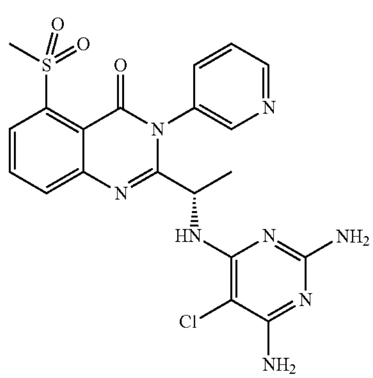 [SMILES: C[C@H](Nc1nc(N)nc(N)c1Cl)c1nc2cccc(S(C)(=O)=O)c2c(=O)n1-c1cccnc1] | (S)-2-(1-((2,6-diamino-5-chloropyrimidin-4-yl)amino)ethyl)-5-(methylsulfonyl)-3-(pyridin-3-yl)quinazolin-4(3H)-one |

TABLE 1a-continued

Representative Compounds

| No. | Structure | Name |
|---|---|---|
| 50 | 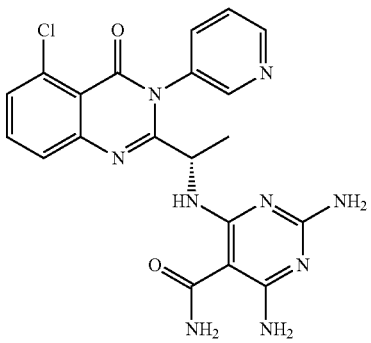 [SMILES: C[C@H](Nc1nc(N)nc(N)c1C(N)=O)c1nc2cccc(Cl)c2c(=O)n1-c1cccnc1] | (S)-2,4-Diamino-6-((1-(5-chloro-4-oxo-3-(pyridin-3-yl)-3,4-dihydroquinazolin-2-yl)ethyl)amino)pyrimidine-5-carboxamide |
| 51 | 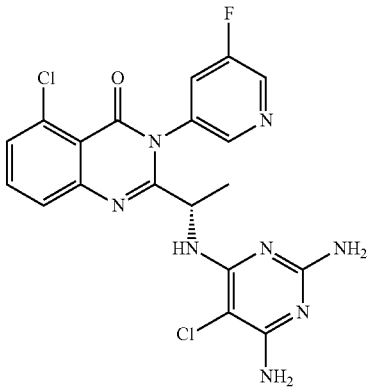 [SMILES: C[C@H](Nc1nc(N)nc(N)c1Cl)c1nc2cccc(Cl)c2c(=O)n1-c1cncc(F)c1] | (S)-5-Chloro-2-(1-((2,6-diamino-5-chloropyrimidin-4-yl)amino)ethyl)-3-(5-fluoropyridin-3-yl)quinazolin-4(3h)-one |
| 52 | 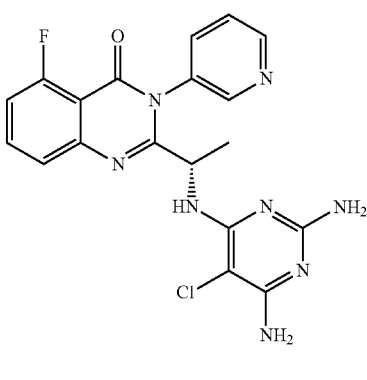 | (S)-2-(1-((2,6-Diamino-5-chloropyrimidin-4-yl)amino)ethyl)-5-fluoro-3-(pyridin-3-yl)quinazolin-4(3H)-one |
| 53 | 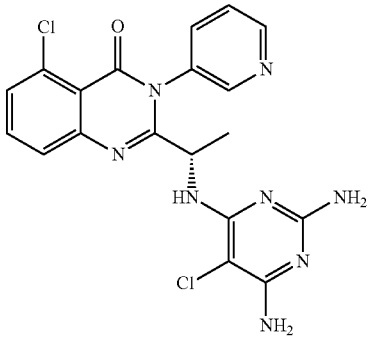 [SMILES: C[C@H](Nc1nc(N)nc(N)c1Cl)c1nc2cccc(Cl)c2c(=O)n1-c1cccnc1] | (S)-5-Chloro-2-(1-((2,6-diamino-5-chloropyrimidin-4-yl)amino)ethyl)-3-(pyridin-3-yl)quinazolin-4(3H)-one |

TABLE 1a-continued

Representative Compounds

| No. | Structure | Name |
|---|---|---|
| 54 | 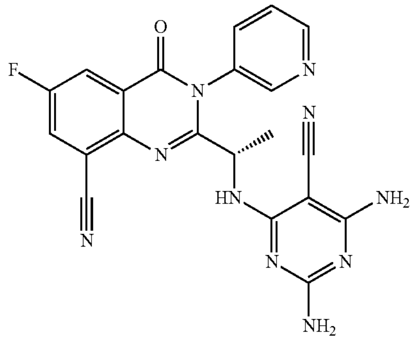 [SMILES: C[C@H](Nc1nc(N)nc(N)c1C#N)c1nc2c(C#N)cc(F)cc2c(=O)n1-c1cccnc1] | (S)-2-(1-((2,6-Diamino-5-cyanopyrimidin-4-yl)amino)ethyl)-6-fluoro-4-oxo-3-(pyridin-3-yl)-3,4-dihydroquinazoline-8-carbonitrile |
| 55 | 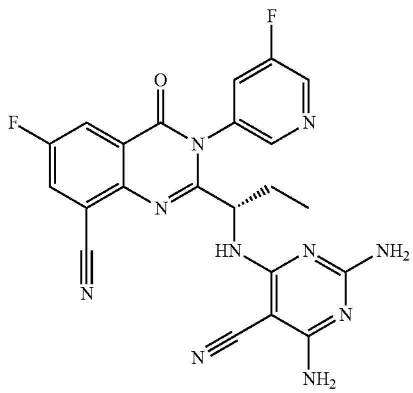 [SMILES: CC[C@H](Nc1nc(N)nc(N)c1C#N)c1nc2c(C#N)cc(F)cc2c(=O)n1-c1cncc(F)c1] | (S)-2-(1-((2,6-Diamino-5-cyanopyrimidin-4-yl)amino)propyl)-6-fluoro-3-(5-fluoropyridin-3-yl)-4-oxo-3,4-dihydroquinazoline-8-carbonitrile |
| 56 | 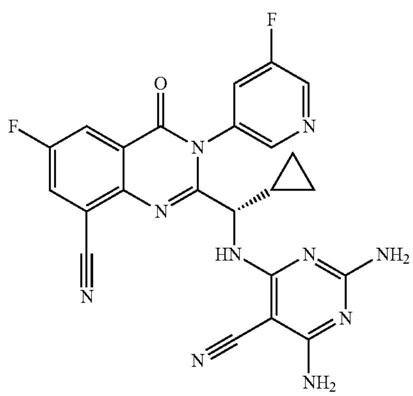 [SMILES: N#Cc1c(N)nc(N)nc1N[C@H](c1nc2c(C#N)cc(F)cc2c(=O)n1-c1cncc(F)c1)C1CC1] | (S)-2-(Cyclopropyl((2,6-diamino-5-cyanopyrimidin-4-yl)amino)methyl)-6-fluoro-3-(5-fluoropyridin-3-yl)-4-oxo-3,4-dihydroquinazoline-8-carbonitrile |
| 57 | 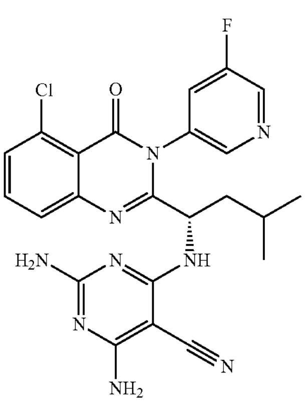 [SMILES: CC(C)C[C@H](Nc1nc(N)nc(N)c1C#N)c1nc2cccc(Cl)c2c(=O)n1-c1cncc(F)c1] | (S)-2,4-Diamino-6-((1-(5-chloro-3-(5-fluoropyridin-3-yl)-4-oxo-3,4-dihydroquinazolin-2-yl)-3-methylbutyl)amino)pyrimidine-5-carbonitrile |

TABLE 1a-continued

| No. | Structure | Name |
|---|---|---|
| 58 | 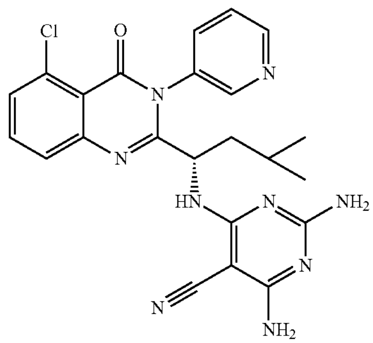 [SMILES: CC(C)C[C@H](Nc1nc(N)nc(N)c1C#N)c1nc2cccc(Cl)c2c(=O)n1-c1cccnc1] | (S)-2,4-Diamino-6-((1-(5-chloro-4-oxo-3-(pyridin-3-yl)-3,4-dihydroquinazolin-2-yl)-3-methylbutyl)amino)pyrimidine-5-carbonitrile |
| 59 | 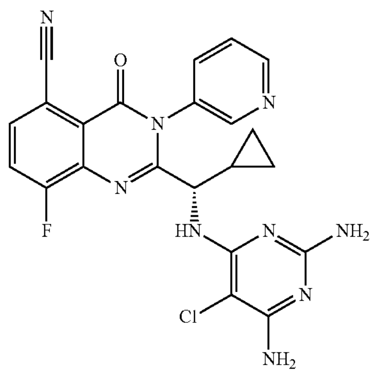 [SMILES: N#Cc1ccc(F)c2nc([C@@H](Nc3nc(N)nc(N)c3Cl)C3CC3)n(-c3cccnc3)c(=O)c12] | (S)-2-(cyclopropyl((2,6-diamino-5-chloropyrimidin-4-yl)amino)methyl)-8-fluoro-4-oxo-3-(pyridin-3-yl)-3,4-dihydroquinazoline-5-carbonitrile |
| 60 | 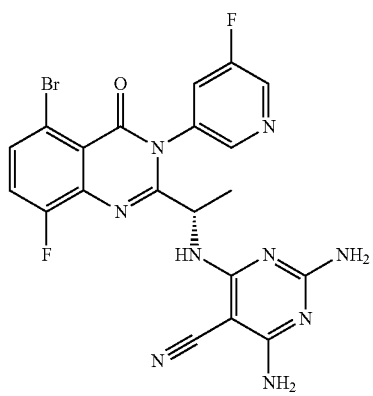 [SMILES: C[C@H](Nc1nc(N)nc(N)c1C#N)c1nc2c(F)ccc(Br)c2c(=O)n1-c1cncc(F)c1] | (S)-2,4-diamino-6-((1-(5-bromo-8-fluoro-3-(5-fluoropyridin-3-yl)-4-oxo-3,4-dihydroquinazolin-2-yl)ethyl)amino)pyrimidine-5-carbonitrile |
| 61 | 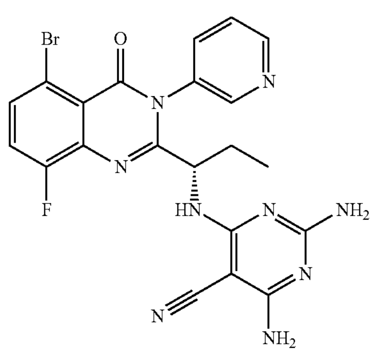 [SMILES: CC[C@H](Nc1nc(N)nc(N)c1C#N)c1nc2c(F)ccc(Br)c2c(=O)n1-c1cccnc1] | (S)-2,4-diamino-6-((1-(5-bromo-8-fluoro-4-oxo-3-(pyridin-3-yl)-3,4-dihydroquinazolin-2-yl)propyl)amino)pyrimidine-5-carbonitrile |

TABLE 1a-continued

Representative Compounds

| No. | Structure | Name |
|---|---|---|
| 62 | 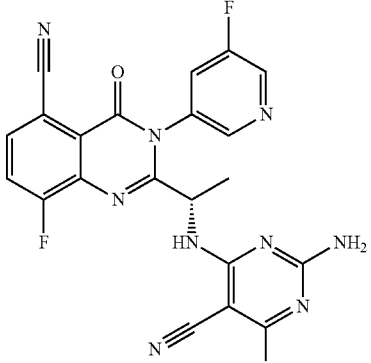 | (S)-2-(1-((2,6-diamino-5-cyanopyrimidin-4-yl)amino)ethyl)-8-fluoro-3-(5-fluoropyridin-3-yl)-4-oxo-3,4-dihydroquinazoline-5-carbonitrile |
| 63 | 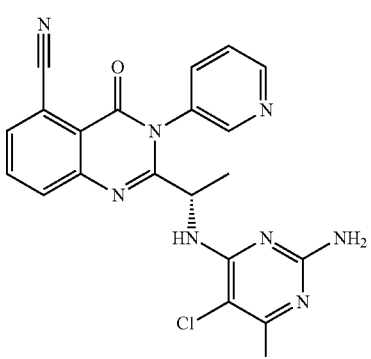 | (S)-2-(1-((2,6-diamino-5-chloropyrimidin-4-yl)amino)ethyl)-4-oxo-3-(pyridin-3-yl)-3,4-dihydroquinazoline-5-carbonitrile |
| 64 | 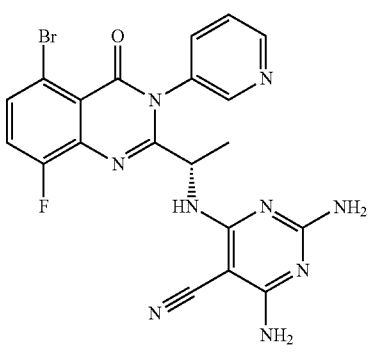 [SMILES: C[C@H](Nc1nc(N)nc(N)c1C#N)c1nc2c(F)ccc(Br)c2c(=O)n1-c1cccnc1] | (S)-2,4-diamino-6-((1-(5-bromo-8-fluoro-4-oxo-3-(pyridin-3-yl)-3,4-dihydroquinazolin-2-yl)ethyl)amino)pyrimidine-5-carbonitrile |
| 65 | 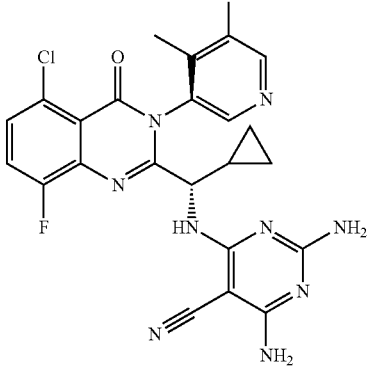 | (S)-2,4-Diamino-6-(((5-chloro-8-fluoro-3-(5-fluoro-4-methylpyridin-3-yl)-4-oxo-3,4-dihydroquinazolin-2-yl)(cyclopropyl)methyl)amino)pyrimidine-5-carbonitrile |

TABLE 1a-continued

Representative Compounds

| No. | Structure | Name |
|---|---|---|
| 66 | 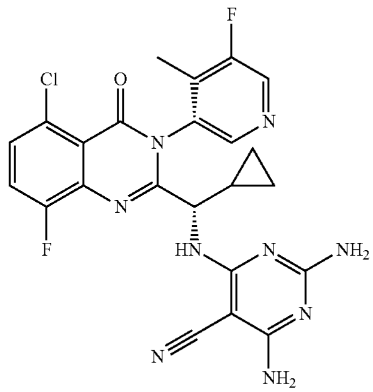 | (S)-2,4-Diamino-6-(((5-chloro-8-fluoro-3-(5-fluoro-4-methylpyridin-3-yl)-4-oxo-3,4-dihydroquinazolin-2-yl)(cyclopropyl)methyl)amino)pyrimidine-5-carbonitrile |
| 67 | 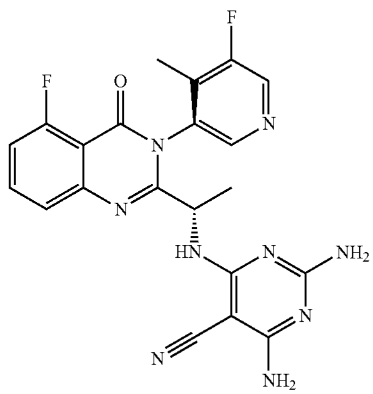 | (S)-2,4-diamino-6-((1-(5-fluoro-3-(5-fluoro-4-methylpyridin-3-yl)-4-oxo-3,4-dihydroquinazolin-2-yl)ethyl)amino)pyrimidine-5-carbonilrile |
| 68 | 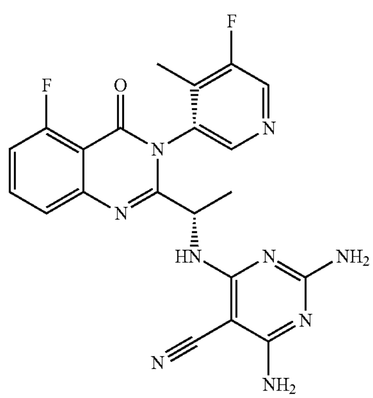 | (S)-2,4-diamino-6-((1-(5-fluoro-3-(5-fluoro-4-methylpyridin-3-yl)-4-oxo-3,4-dihydroquinazolin-2-yl)ethyl)amino)pyrimidine-5-carbonitrile |
| 69 | 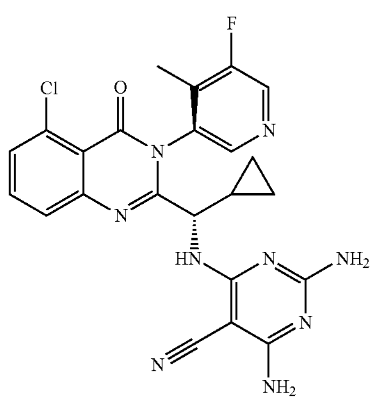 | (S)-2,4-diamino-6-(((5-chloro-3-(5-fluoro-4-methylpyridin-3-yl)-4-oxo-3,4-dihydroquinazolin-2-yl)(cyclopropyl)methyl)amino)pyrimidine-5-carbonitrile |

TABLE 1a-continued

Representative Compounds

| No. | Structure | Name |
|---|---|---|
| 70 | 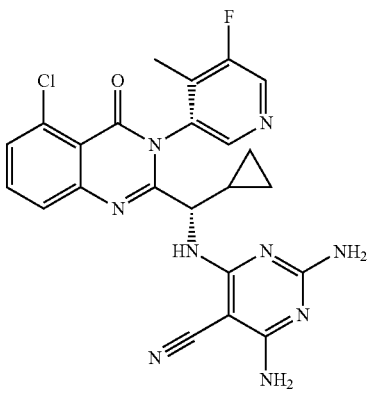 | (S)-2,4-diamino-6-(((5-chloro-3-(5-fluoro-4-methylpyridin-3-yl)-4-oxo-3,4-dihydroquinazolin-2-yl)(cyclopropyl)methyl)amino)pyrimidine-5-carbonitrile |
| 71 | 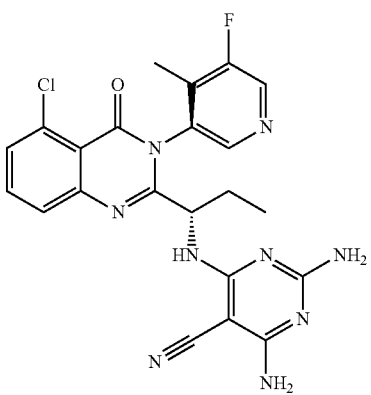 | (S)-2,4-diamino-6-((1-(5-chloro-3-(5-fluoro-4-methylpyridin-3-yl)-4-oxo-3,4-dihydroquinazolin-2-yl)propyl)amino)pyrimidine-5-carbonitrile |
| 72 | 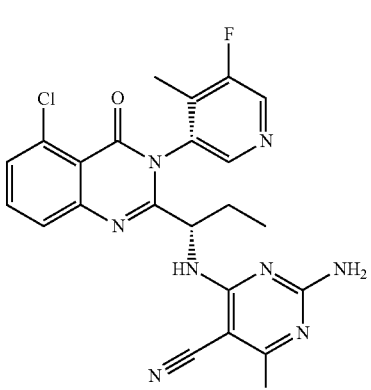 | (S)-2,4-diamino-6-((1-(5-chloro-3-(5-fluoro-4-methylpyridin-3-yl)-4-oxo-3,4-dihydroquinazolin-2-yl)propyl)amino)pyrimidine-5-carbonitrile |

TABLE 1a-continued

Representative Compounds

| No. | Structure | Name |
|-----|-----------|------|
| 73 | 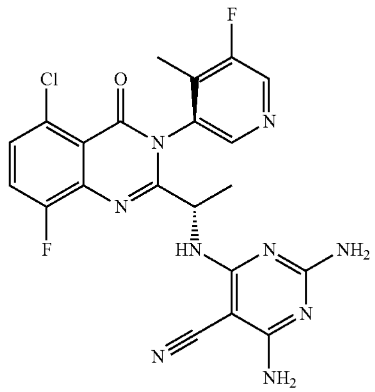 | (S)-2,4-diamino-6-((1-(5-chloro-8-fluoro-3-(5-fluoro-4-methylpyridin-3-yl)-4-oxo-3,4-dihydroquinazolin-2-yl)ethyl)amino)pyrimidine-5-carbonitrile |
| 74 | 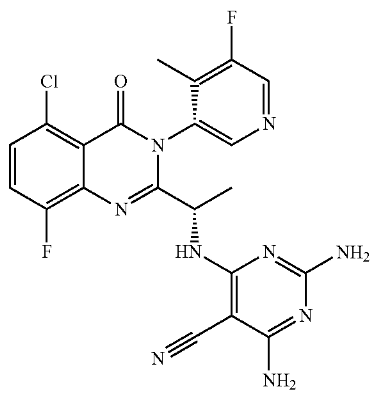 | (S)-2,4-diamino-6-((1-(5-chloro-8-fluoro-3-(5-fluoro-4-methylpyridin-3-yl)-4-oxo-3,4-dihydroquinazolin-2-yl)ethyl)amino)pyrimidine-5-carbonitrile |
| 75 | 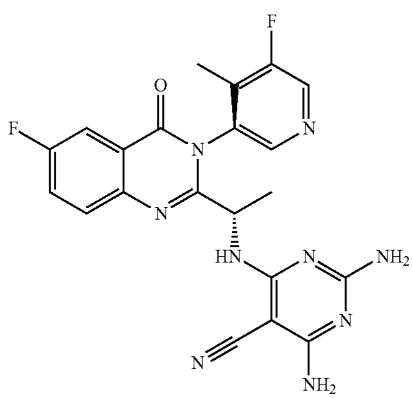 | (S)-2,4-diamino-6-((1-(6-fluoro-3-(5-fluoro-4-methylpyridin-3-yl)-4-oxo-3,4-dihydroquinazolin-2-yl)ethyl)amino)pyrimidine-5-carbonitrile |
| 76 | 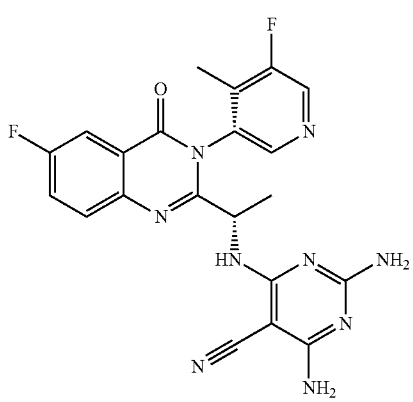 | (S)-2,4-diamino-6-((1-(6-fluoro-3-(5-fluoro-4-methylpyridin-3-yl)-4-oxo-3,4-dihydroquinazolin-2-yl)ethyl)amino)pyrimidine-5-carbonitrile |

TABLE 1a-continued

Representative Compounds

| No. | Structure | Name |
|---|---|---|
| 77 | 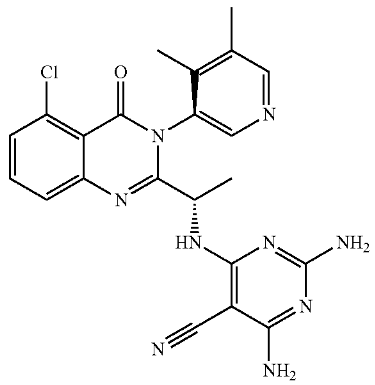 | (S)-2,4-diamino-6-((1-(5-chloro-3-(4,5-dimethylpyridin-3-yl)-4-oxo-3,4-dihydroquinazolin-2-yl)ethyl)amino)pyrimidine-5-carbonitrile |
| 78 | 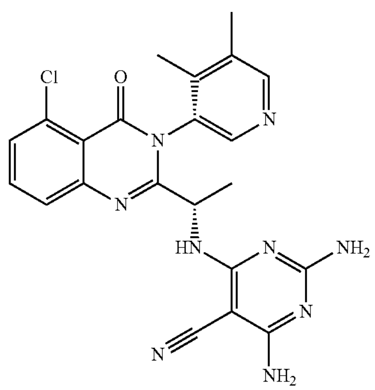 | (S)-2,4-diamino-6-((1-(5-chloro-3-(4,5-dimethylpyridin-3-yl)-4-oxo-3,4-dihydroquinazolin-2-yl)ethyl)amino)pyrimidine-5-carbonitrile |
| 79 | 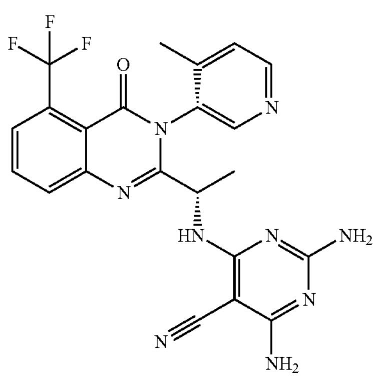 | (S)-2,4-Diamino-6-((1-(3-(4-methylpyridin-3-yl)-4-oxo-5-(trifluoromethyl)-3,4-dihydroquinazolin-2-yl)ethyl)amino)pyrimidine-5-carbonitrile |
| 80 | 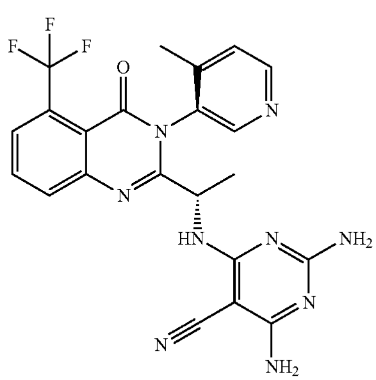 | (S)-2,4-Diamino-6-((1-3-(4-methylpyridin-3-yl)-4-oxo-5-(trifluoromethyl)-3,4-dihydroquinazolin-2-yl)ethyl)amino)pyrimidine-5-carbonitrile |

TABLE 1a-continued

Representative Compounds

| No. | Structure | Name |
|---|---|---|
| 81 | 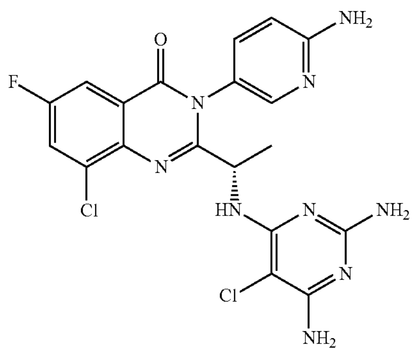 [SMILES: C[C@H](Nc1nc(N)nc(N)c1Cl)c1nc2c(Cl)cc(F)cc2c(=O)n1-c1ccc(N)nc1] | (S)-3-(6-aminopyridin-3-yl)-8-chloro-2-(1-((2,6-diamino-5-chloropyrimidin-4-yl)amino)ethyl)-6-fluoroquinazolin-4(3H)-one |
| 82 | 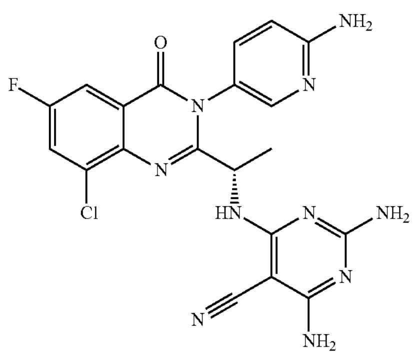 [SMILES: C[C@H](Nc1nc(N)nc(N)c1C#N)c1nc2c(Cl)cc(F)cc2c(=O)n1-c1ccc(N)nc1] | (S)-2,4-diamino-6-((1-(3-(6-aminopyridin-3-yl)-8-chloro-6-fluoro-4-oxo-3,4-dihydroquinazolin-2-yl)ethyl)amino)pyrimidine-5-carbonitrile |
| 83 | 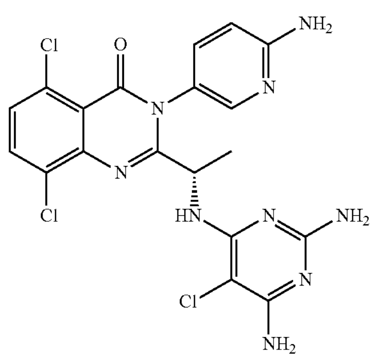 [SMILES: C[C@H](Nc1nc(N)nc(N)c1Cl)c1nc2c(Cl)ccc(Cl)c2c(=O)n1-c1ccc(N)nc1] | (S)-3-(6-aminopyridin-3-yl)-5,8-dichloro-2-(1-((2,6-diamino-5-chloropyrimidin-4-yl)amino)ethyl)quinazolin-4(3H)-one |
| 84 | 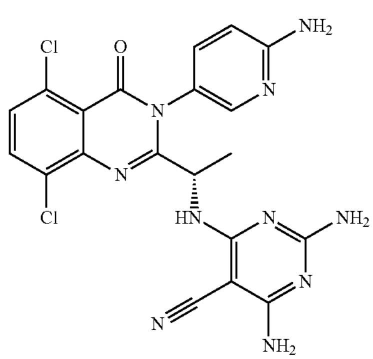 [SMILES: C[C@H](Nc1nc(N)nc(N)c1C#N)c1nc2c(Cl)ccc(Cl)c2c(=O)n1-c1ccc(N)nc1] | (S)-2,4-diamino-6-((1-(3-(6-aminopyridin-3-yl)-5,8-dichloro-4-oxo-3,4-dihydroquinazolin-2-yl)ethyl)amino)pyrimidine-5-carbonitrile |

TABLE 1a-continued

Representative Compounds

| No. | Structure | Name |
|---|---|---|
| 85 | 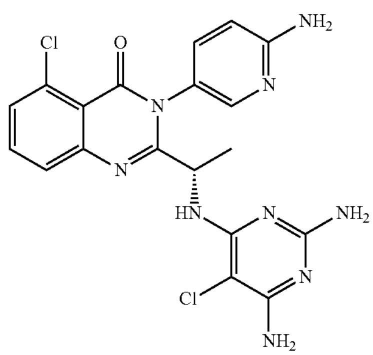 [SMILES: C[C@H](Nc1nc(N)nc(N)c1Cl)c1nc2cccc(Cl)c2c(=O)n1-c1ccc(N)nc1] | (S)-3-(6-aminopyridin-3-yl)-5-chloro-2-(1-((2,6-diamino-5-chloropyrimidin-4-yl)amino)ethyl)quinazolin-4(3H)-one |
| 86 | 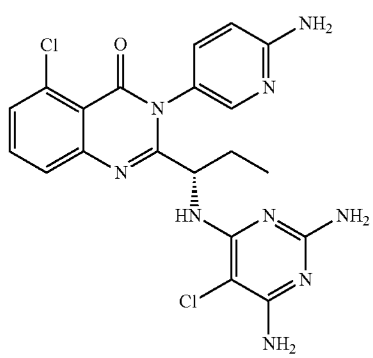 [SMILES: CC[C@H](Nc1nc(N)nc(N)c1Cl)c1nc2cccc(Cl)c2c(=O)n1-c1ccc(N)nc1] | (S)-3-(6-aminopyridin-3-yl)-5-chloro-2-(1-((2,6-diamino-5-chloropyrimidin-4-yl)amino)propyl)quinazolin-4(3H)-one |
| 87 | 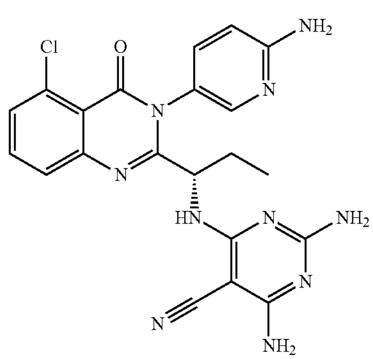 [SMILES: CC[C@H](Nc1nc(N)nc(N)c1C#N)c1nc2cccc(Cl)c2c(=O)n1-c1ccc(N)nc1] | (S)-2,4-diamino-6-((1-(3-(6-aminopyridin-3-yl)-5-chloro-4-oxo-3,4-dihydroquinazolin-2-yl)propyl)amino)pyrimidine-5-carbonitrile |
| 88 | 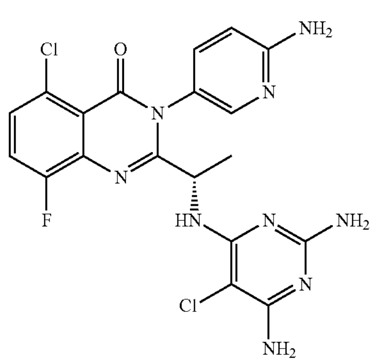 [SMILES: C[C@H](Nc1nc(N)nc(N)c1Cl)c1nc2c(F)ccc(Cl)c2c(=O)n1-c1ccc(N)nc1] | (S)-3-(6-aminopyridin-3-yl)-5-chloro-2-(1-((2,6-diamino-5-chloropyrimidin-4-yl)amino)ethyl)-8-fluoroquinazolin-4(3H)-one |

TABLE 1a-continued

Representative Compounds

| No. | Structure | Name |
| --- | --- | --- |
| 89 | 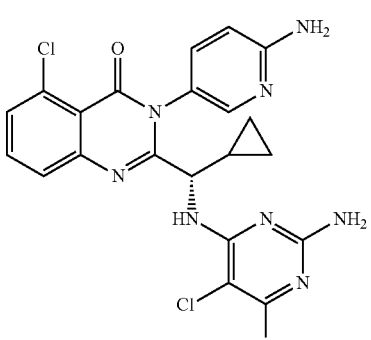 | (S)-3-(6-aminopyridin-3-yl)-5-chloro-2-(cyclopropyl((2,6-diamino-5-chloropyrimidin-4-yl)amino)methyl)quinazolin-4(3H)-one |
| 90 | 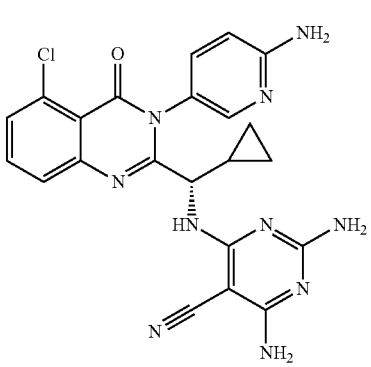 [SMILES: N#Cc1c(N)nc(N)nc1N[C@H](c1nc2cccc(Cl)c2c(=O)n1-c1ccc(N)nc1)C1CC1] | (S)-2,4-diamino-6-(((3-(6-aminopyridin-3-yl)-5-chloro-4-oxo-3,4-dihydroquinazolin-2-yl)(cyclopropyl)methyl)amino)pyrimidine-5-carbonitrile |
| 91 | 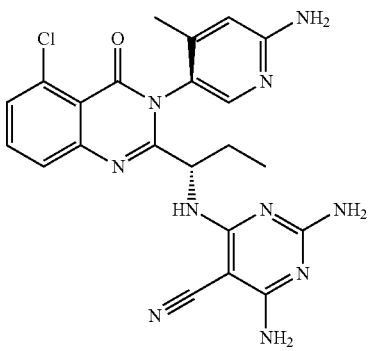 | (S)-2,4-diamino-6-((1-(3-(6-amino-4-methylpyridin-3-yl)-5-chloro-4-oxo-3,4-dihydroquinazolin-2-yl)propyl)amino)pyrimidine-5-carbonitrile |
| 92 | 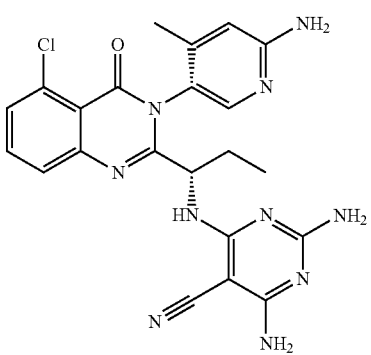 | (S)-2,4-diamino-6-((1-(3-(6-amino-4-methylpyridin-3-yl)-5-chloro-4-oxo-3,4-dihydroquinazolin-2-yl)propyl)amino)pyrimidine-5-carbonitrile |

TABLE 1a-continued

Representative Compounds

| No. | Structure | Name |
|---|---|---|
| 93 | 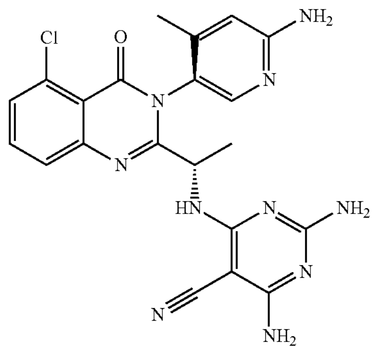 | (S)-2,4-diamino-6-((1-(3-(6-amino-4-methylpyridin-3-yl)-5-chloro-4-oxo-3,4-dihydroquinazolin-2-yl)ethyl)amino)pyrimidine-5-carbonitrile |
| 94 | 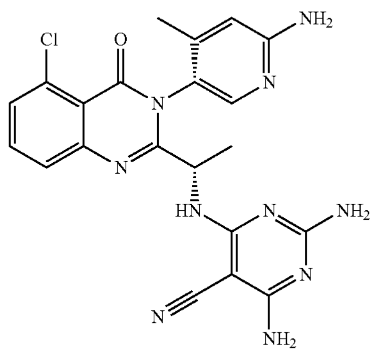 | (S)-2,4-diamino-6-((1-(3-(6-amino-4-methylpyridin-3-yl)-5-chloro-4-oxo-3,4-dihydroquinazolin-2-yl)ethyl)amino)pyrimidine-5-carbonitrile |
| 95 | 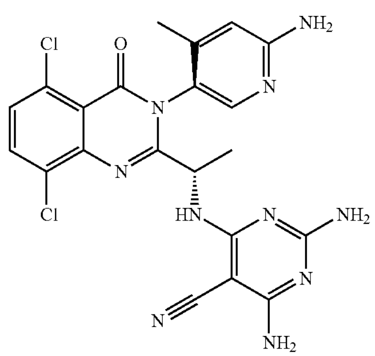 | (S)-2,4-diamino-6-((1-(3-(6-amino-4-methylpyridin-3-yl)-5,8-dichloro-4-oxo-3,4-dihydroquinazolin-2-yl)ethyl)amino)pyrimidine-5-carbonitrile |
| 96 | 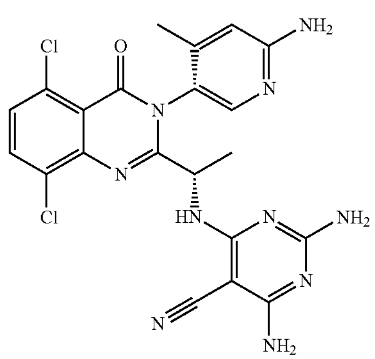 | (S)-2,4-diamino-6-((1-(3-(6-amino-4-methylpyridin-3-yl)-5,8-dichloro-4-oxo-3,4-dihydroquinazolin-2-yl)ethyl)amino)pyrimidine-5-carbonitrile |

TABLE 1a-continued

Representative Compounds

| No. | Structure | Name |
|---|---|---|
| 97 | 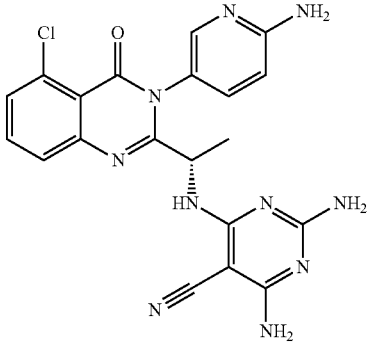 [SMILES: C[C@H](Nc1nc(N)nc(N)c1C#N)c1nc2cccc(Cl)c2c(=O)n1-c1ccc(N)nc1] | (S)-2,4-diamino-6-((1-(3-(6-aminopyridin-3-yl)-5-chloro-4-oxo-3,4-dihydroquinazolin-2-yl)ethyl)amino)pyrimidine-5-carbonitrile |
| 98 | 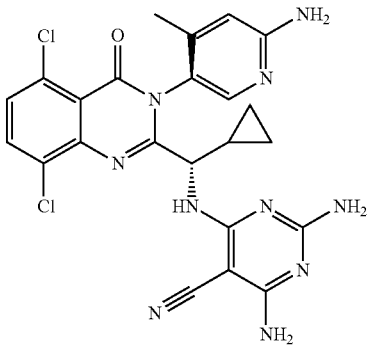 | (S)-2,4-diamino-6-(((3-(6-amino-4-methylpyridin-3-yl)-5,8-dichloro-4-oxo-3,4-dihydroquinazolin-2-yl)(cyclopropyl)methyl)amino)pyrimidine-5-carbonitrilc |
| 99 | 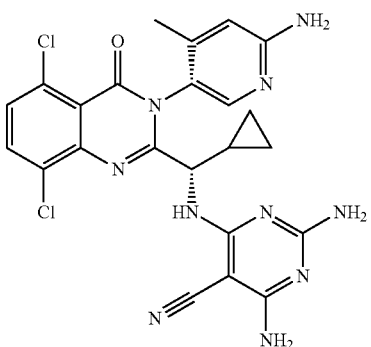 | (S)-2,4-diamino-6-(((3-(6-amino-4-methylpyridin-3-yl)-5,8-dichloro-4-oxo-3,4-dihydroquinazolin-2-yl)(cyclopropyl)methyl)amino)pyrimidine-5-carbonitrile |
| 100 | 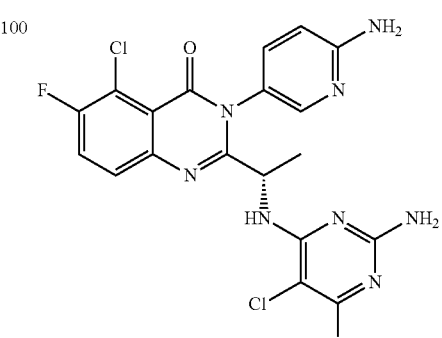 | (S)-3-(6-aminopyridin-3-yl)-5-chloro-2-(1-((2,6-diamino-5-chloropyrimidin-4-yl)amino)ethyl)-6-fluoroquinazolin-4(3H)-one |

TABLE 1a-continued

Representative Compounds

| No. | Structure | Name |
|---|---|---|
| 101 | 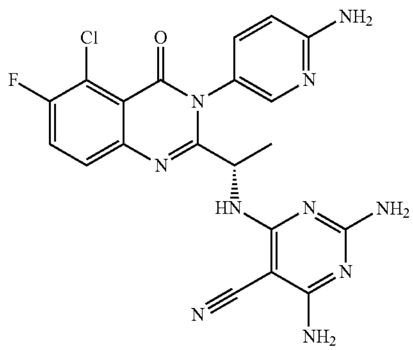 [SMILES: C[C@H](Nc1nc(N)nc(N)c1C#N)c1nc2ccc(F)c(Cl)c2c(=O)n1-c1ccc(N)nc1] | (S)-2,4-diamino-6-((1-(3-(6-aminopyridin-3-yl)-5-chloro-6-fluoro-4-oxo-3,4-dihydroquinazolin-2-yl)ethyl)amino)pyrimidine-5-carbonitrile |
| 102 | 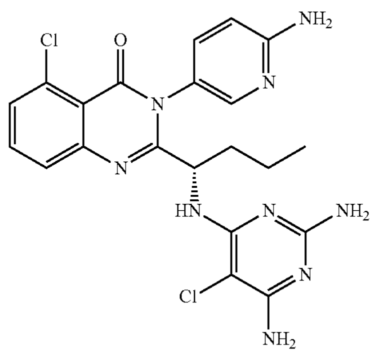 [SMILES: CCC[C@H](Nc1nc(N)nc(N)c1Cl)c1nc2cccc(Cl)c2c(=O)n1-c1ccc(N)nc1] | (S)-3-(6-aminopyridin-3-yl)-5-chloro-2-(1-((2,6-diamino-5-chloropyrimidin-4-yl)amino)butyl)quinazolin-4(3H)-one |
| 103 | 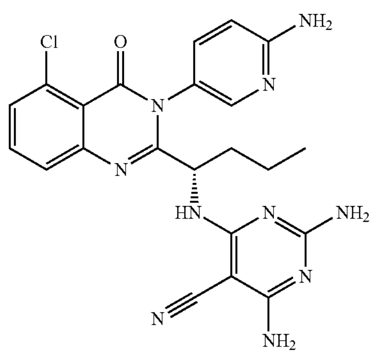 [SMILES: CCC[C@H](Nc1nc(N)nc(N)c1C#N)c1nc2cccc(Cl)c2c(=O)n1-c1ccc(N)nc1] | (S)-2,4-diamino-6-((1-(3-(6-aminopyridin-3-yl)-5-chloro-4-oxo-3,4-dihydroquinazolin-2-yl)butyl)amino)pyrimidine-5-carbonitrile |
| 104 | 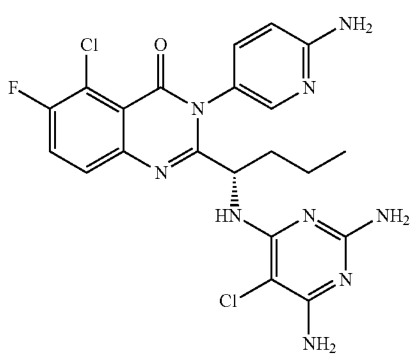 [SMILES: CCC[C@H](Nc1nc(N)nc(N)c1Cl)c1nc2ccc(F)c(Cl)c2c(=O)n1-c1ccc(N)nc1] | (S)-3-(6-aminopyridin-3-yl)-5-chloro-2-(1-((2,6-diamino-5-chloropyrimidin-4-yl)amino)butyl)-6-fluoroquinazolin-4(3H)-one |

TABLE 1a-continued

| No. | Structure | Name |
|---|---|---|
| 105 | 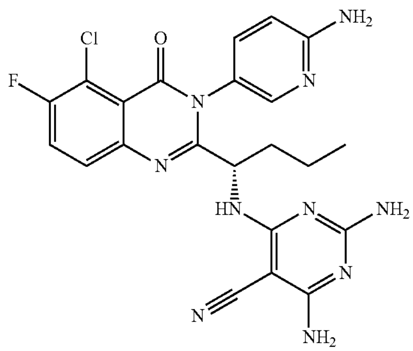 [SMILES: CCC[C@H](Nc1nc(N)nc(N)c1C#N)c1nc2ccc(F)c(Cl)c2c(=O)n1-c1ccc(N)nc1] | (S)-2,4-diamino-6-((1-(3-(6-aminopyridin-3-yl)-5-chloro-6-fluoro-4-oxo-3,4-dihydroquinazolin-2-yl)butyl)amino)pyrimidine-5-carbonitrile |
| 106 | 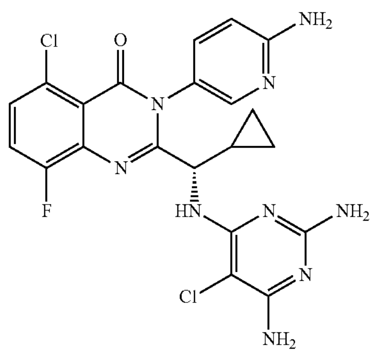 [SMILES: Nc1ccc(-n2c([C@@H](Nc3nc(N)nc(N)c3Cl)C3CC3)nc3c(F)ccc(Cl)c3c2=O)cn1] | (S)-3-(6-aminopyridin-3-yl)-5-chloro-2-(cyclopropyl((2,6-diamino-5-chloropyrimidin-4-yl)amino)methyl)-8-fluoroquinazolin-4(3H)-one |
| 107 | 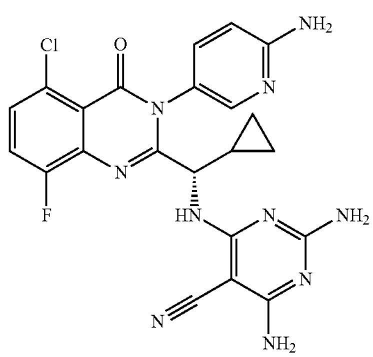 [SMILES: N#Cc1c(N)nc(N)nc1N[C@H](c1nc2c(F)ccc(Cl)c2c(=O)n1-c1ccc(N)nc1)C1CC1] | (S)-2,4-diamino-6-(((3-(6-aminopyridin-3-yl)-5-chloro-8-fluoro-4-oxo-3,4-dihydroquinazolin-2-yl)(cyclopropyl)methyl)amino)pyrimidine-5-carbonitrile |
| 108 | 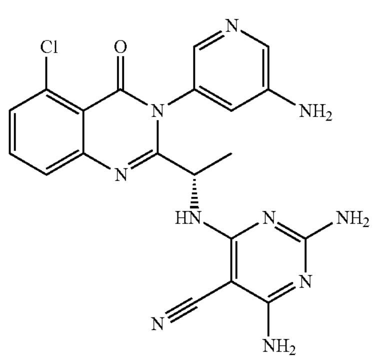 [SMILES: C[C@H](Nc1nc(N)nc(N)c1C#N)c1nc2cccc(Cl)c2c(=O)n1-c1cncc(N)c1] | (S)-2,4-diamino-6-((1-(3-(5-aminopyridin-3-yl)-5-chloro-4-oxo-3,4-dihydroquinazolin-2-yl)ethyl)amino)pyrimidine-5-carbonitrile |

TABLE 1a-continued

Representative Compounds

| No. | Structure | Name |
|---|---|---|
| 109 | 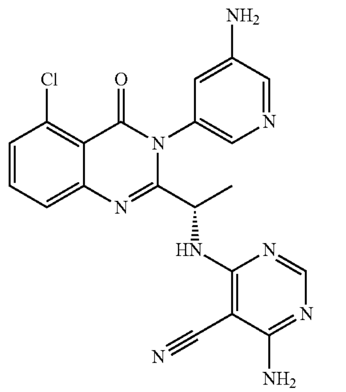 [SMILES: C[C@H](Nc1ncnc(N)c1C#N)c1nc2cccc(Cl)c2c(=O)n1-c1cncc(N)c1] | (S)-4-amino-6-((1-(3-(5-aminopyridin-3-yl)-5-chloro-4-oxo-3,4-dihydroquinazolin-2-yl)ethyl)amino)pyrimidine-5-carbonitrile |
| 110 | 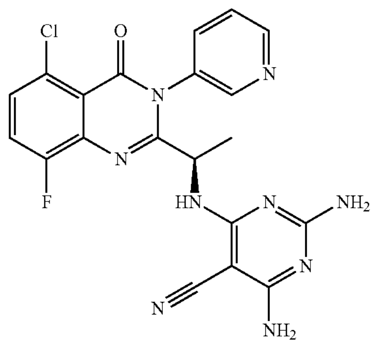 [SMILES: C[C@@H](Nc1nc(N)nc(N)c1C#N)c1nc2c(F)ccc(Cl)c2c(=O)n1-c1cccnc1] | (R)-2,4-Diamino-6-((1-(5-chloro-8-fluoro-4-oxo-3-(pyridin-3-yl)-3,4-dihydroquinazolin-2-yl)ethyl)amino)pyrimidine-5-carbonitrile |
| 111 | 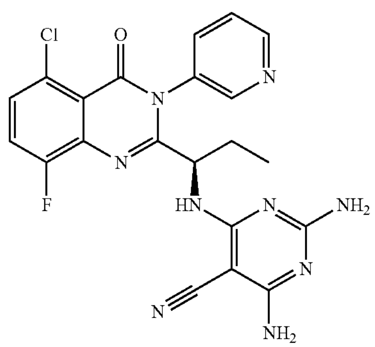 [SMILES: CC[C@@H](Nc1nc(N)nc(N)c1C#N)c1nc2c(F)ccc(Cl)c2c(=O)n1-c1cccnc1] | (R)-2,4-Diamino-6-((1-(5-chloro-8-fluoro-4-oxo-3-(pyridin-3-yl)-3,4-dihydroquinazolin-2-yl)propyl)amino)pyrimidine-5-carbonitrile |
| 112 | 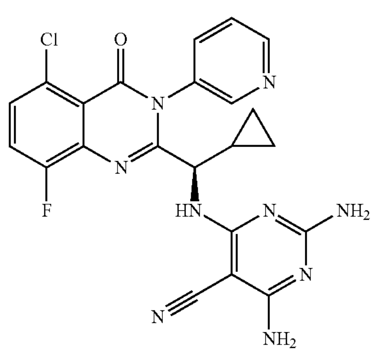 [SMILES: N#Cc1c(N)nc(N)nc1N[C@@H](c1nc2c(F)ccc(Cl)c2c(=O)n1-c1cccnc1)C1CC1] | (R)-2,4-Diamino-6-(((5-chloro-8-fluoro-4-oxo-3-(pyridin-3-yl)-3,4-dihydroquinazolin-2-yl)(cyclopropyl)methyl)amino)pyrimidine-5-carbonitrile |

TABLE 1a-continued

Representative Compounds

| No. | Structure | Name |
|---|---|---|
| 113 | 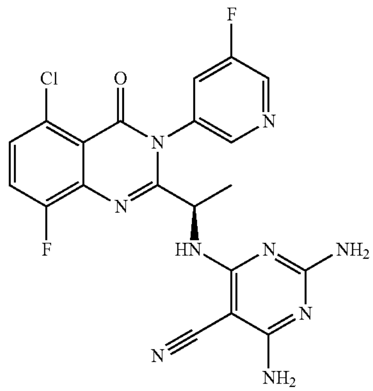 [SMILES: C[C@@H](Nc1nc(N)nc(N)c1C#N)c1nc2c(F)ccc(Cl)c2c(=O)n1-c1cncc(F)c1] | (R)-2,4-Diamino-6-((1-(5-chloro-8-fluoro-3-(5-fluoropyridin-3-yl)-4-oxo-3,4-dihydroquinazolin-2-yl)ethyl)amino)pyrimidine-5-carbonitrile |
| 114 | 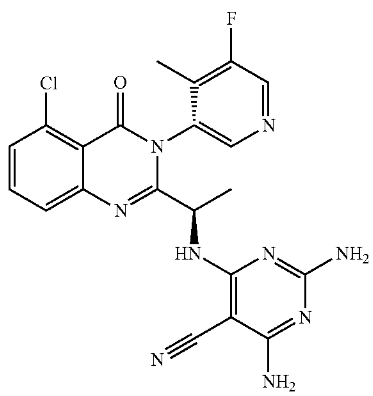 | (R)-2,4-diamino-6-((1-(5-chloro-3-(5-fluoro-4-methylpyridin-3-yl)-4-oxo-3,4-dihydroquinazolin-2-yl)ethyl)amino)pyrimidine-5-carbonitrile |
| 115 | 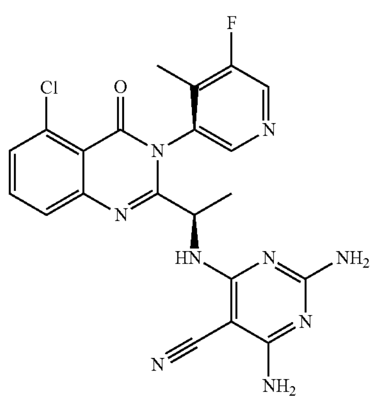 | (R)-2,4-diamino-6-((1-(5-chloro-3-(5-fluoro-4-methylpyridin-3-yl)-4-oxo-3,4-dihydroquinazolin-2-yl)ethyl)amino)pyrimidine-5-carbonitrile |

In addition, the present application provides the compounds according to any of the formulae described herein or pharmaceutically acceptable salts, tautomers, isomers, prodrugs, or solvates thereof, in which from 1 to n hydrogen atoms attached to a carbon atom may be replaced by a deuterium atom or D, in which n is the number of hydrogen atoms in the molecule. It is known that the deuterium atom is a non-radioactive isotope of the hydrogen atom. Such compounds may increase resistance to metabolism, and thus may be useful for increasing the half-life of the compounds of any of the formulae described herein or pharmaceutically acceptable salts, isomers, prodrugs, or solvates thereof, when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

The present application also provides pharmaceutically acceptable salts, hydrates, solvates, tautomeric forms, polymorphs, and prodrugs of the compounds of any of the formulae described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" refer to salts of pharmaceutical compounds that retain the biological effectiveness and properties of the underlying compound, and which are not biologically or otherwise undesirable. There are acid addition salts and base addition salts. Pharmaceutically acceptable acid addition salts may be prepared from inorganic and organic acids. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources.

"Pharmaceutically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Examples of pharmaceutically acceptable salts include, but are not limited to salts with inorganic acids, such as hydrochlorate, phosphate, diphosphate, hydrobromate, sulfate, sulfinate, nitrate; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4. Similarly, pharmaceutically acceptable cations include, but are not limited to sodium, potassium, calcium, aluminum, lithium, and ammonium. In addition, if the compounds described herein are obtained as an acid addition salt, the free base can be obtained by basifying a solution of the acid salt. Those skilled in the art will recognize various synthetic methodologies that may be used to prepare nontoxic pharmaceutically acceptable addition salts.

A "solvate" is formed by the interaction of a solvent and a compound. Solvates of salts of the compounds of any of the formulae described herein are also provided. Hydrates of the compounds of any of the formulae are also provided.

A "prodrug" includes any compound that becomes a compound of the formulae described herein when administered to a subject, e.g., upon metabolic processing of the prodrug.

In certain embodiments, provided are optical isomers, racemates, or other mixtures thereof, of the compounds of any of the formulae described herein or pharmaceutically acceptable salts, prodrugs, or solvates thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the compounds of the formulae described herein or pharmaceutically acceptable salts, prodrugs, or solvates thereof with carbon-carbon double bonds. Provided are also all tautomeric forms of the compounds of any of the formulae or pharmaceutically acceptable salts, isomers, prodrugs, or solvates thereof.

In some embodiments, provided herein are the free base forms of the compounds of the formulae described herein or pharmaceutically acceptable salts, isomers, or mixture of isomers, prodrugs or solvates thereof. In certain embodiments, provided herein are the (S)-enantiomers of the compounds of the formulae described herein or pharmaceutically acceptable salts, isomers, or mixture of isomers, prodrugs or solvates thereof. In some other embodiments, provided herein are the (R)-enantiomers of the compounds of the formulae described herein or pharmaceutically acceptable salts, isomers, or mixture of isomers, prodrugs or solvates thereof. In other embodiments, provided herein are the atropisomers of the compounds of the formulae described herein or pharmaceutically acceptable salts, isomers, or mixture of isomers, prodrugs or solvates thereof.

Compositions provided herein that include a compound of the formulae described herein or a pharmaceutically acceptable salt, prodrug, or solvate thereof, may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In certain embodiments, provided herein are also crystalline and amorphous forms of the compounds of the formulae described herein or pharmaceutically acceptable salts, isomer, a mixture of isomers, prodrugs, or solvates thereof.

In certain embodiments, provided are also chelates, non-covalent complexes, and mixtures thereof, of the compounds of the formula described herein or pharmaceutically acceptable salts, prodrugs, or solvates thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The compounds of the formulae described herein or a pharmaceutically acceptable salt, isomers, prodrug, or solvate thereof may be used for the treatment of diseases and/or conditions mediated by PI3K isomers, such as PI3Kδ. Thus, provided herein are methods for inhibiting one or more PI3K isomers, such as PI3K α, β, δ, and γ. In one embodiment, provided are methods for inhibiting PI3Kδ activity using a compound of the formulae described herein or a pharmaceutically acceptable salt, isomers, prodrug, or solvate thereof. The PI3K isomers may be selectively or specifically inhibited. Additionally, the compounds may be used to inhibit PI3K activity therapeutically or prophylactically. Also, the compounds according to the present application may be used in combination with other therapeutic agents. The therapeutic agents may be in the forms of compounds, antibodies, polypeptides, or polynucleotides. As used herein, the terms "PI3K isomers" and "PI3K isoforms" are equivalent and used interchangeably. In one embodiment, the application provides a product comprising a compound described herein and an additional therapeutic agent as a combined preparation for simultaneous, separate or sequential use in therapy, e.g. a method of treating a disease, disorder, or condition that is mediated by PI3K isoforms.

Also, the therapeutic agents may be those that inhibit or modulate the activities of Bruton's tyrosine kinase, spleen tyrosine kinase, apoptosis signal-regulating kinase, Janus kinase, lysyl oxidase, lysyl oxidase-like proteins, or matrix metallopeptidase. In further embodiments, the therapeutic agents may be those that inhibit or modulate the activites of bromodomain-containing protein, adenosine A2B receptor, isocitrate dehydrogenase, serine/threonine kinase TPL2, discoidin domain receptor, serine/threonine-protein kinase, IKK, MEK, EGFR, histone deacetylase, protein kinase C, or any combination thereof.

In some embodiments, the methods include administering a compound of the formula described herein or a pharmaceutically acceptable salt, isomers, prodrug, or solvate thereof, in a therapeutically effective amount to a human in need thereof. The method can be employed to treat a patient who has or is believed to have a disease or condition whose symptoms or pathology is mediated by PI3Kδ expression or activity. Additionally, the method can be employed to treat a patient who has or is believed to have a disease or condition whose symptoms or pathology is mediated by PI3Kβ expression or activity. The patient may be a mammal or a human.

In addition to the therapeutic uses, certain compounds of any of the formulae described herein or a pharmaceutically acceptable salt, isomers, prodrug, or solvate thereof, have one or more properties selected from: (i) selectivity to any PI3K isoforms, such as PI3Kβ; (ii) hepatocyte stability; and (iii) potency in a cellular assay. In one embodiment, certain compounds of the formulae or a pharmaceutically acceptable salt, prodrug, isomers, or solvate thereof, have selectivity to any PI3K isoforms, such as PI3Kδ. In other embodiments, certain compounds of the formulae described herein or a pharmaceutically acceptable salt, prodrug, or solvate thereof, have selectivity to at least PI3Kδ. In some other embodiments, certain compounds of the formulae or a pharmaceutically acceptable salt, prodrug, isomers, or solvate thereof, have selectivity to PI3Kδ and/or PI3Kβ. In yet other embodiments, certain compounds of the formulae or a pharmaceutically acceptable salt, prodrug, or solvate thereof, have one of the properties selected from: (i) selectivity to PI3Kδ; (ii) hepatocyte stability; and (iii) potency in a cellular assay. In yet other embodiments, certain compounds of the formulas according to the present application or a pharmaceutically acceptable salt, prodrug, or solvate thereof, have: selectivity to PI3Kδ and hepatocyte stability; or selectivity to PI3Kδ and potency in a cellular assay; or hepatocyte stability and potency in a cellular assay. In some embodiments, certain compounds of the formulae or a pharmaceutically acceptable salt, prodrug, or solvate thereof, have selectivity to PI3Kδ, hepatocyte stability, and potency in a cellular assay.

In another embodiment, certain compounds of the formulae described herein or a pharmaceutically acceptable salt, isomers, prodrug, or solvate thereof have hepatocyte stability. Hepatocyte stability of a compound can be determined using any methods currently known in the art, including the methods described in the Examples below. For example, hepatocyte stability may be characterized based on half-life. In some embodiments, the half-life is greater than or about 3 hours, 4 hours, 5 hours, 6 hours, 7 hours, 8 hours, 9 hours, 10 hours, 11 hours, 12 hours, or 15 hours when incubated in human hepatocytes.

In yet another embodiment, certain compounds of the formulae described herein or a pharmaceutically acceptable salt, prodrug, or solvate thereof have potency in a cellular assay. Potency in a cellular assay can be determined using any methods currently known in the art, including the methods described in the Examples below. In some embodiments, the activity in the cellular assay is less than 10 nM, 9 nM, 8 nM, 7 nM, 6 nM, 5 nM, 4 nM, 3 nM, 2 nM, 1nM, 0.1 nM, or 0.01 nM.

For example, certain compounds inhibit at least one PI3K isomer, including PI3Kδ. For example, the compounds have an $EC_{50}$ in the described cellular assay less than 10 nM, and have a half life in hepatocytes of greater than 3 hours.

"Treatment" or "treating" is an approach for obtaining beneficial or desired results including clinical results. Beneficial or desired clinical results may include one or more of the following:
 a) inhibiting the disease or condition (e.g., decreasing one or more symptoms resulting from the disease or condition, and/or diminishing the extent of the disease or condition);
 b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or
 c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

The terms "Subject" or "patient" refer to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human. "Human in need thereof" refers to a human who may have or is suspect to have diseases or conditions that would benefit from certain treatment; for example, being treated with the PI3K inhibitor of the compounds according to the present application.

The term "therapeutically effective amount" of a compound of the present application or a pharmaceutically acceptable salt, isomers, prodrug, or solvate thereof, means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of PI3Kδ activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. The term "inhibition of activity of PI3K isomers" or variants thereof refer to a decrease in activity in any PI3K isomer (e.g., alpha, beta, gamma, or delta) as a direct or indirect response to the presence of a compound of any of the formula (I), (IA), (IB), (IC), (ID), (IE), (IF), or (II) or a pharmaceutically acceptable salt, isomer, a mixture of isomers, prodrug, or solvent thereof, relative to the activity of PI3K isomer in the absence of such compound or a pharmaceutically acceptable salt, isomer, a mixture of isomers, prodrug, or solvent thereof. "Inhibition of PI3Kδ activity" or variants thereof refer to a decrease in PI3Kδ activity as a direct or indirect response to the presence of a compound of formula (I), (IA), (IB), (IC), (ID), (IE), (IF) or (II) or a pharmaceutically acceptable salt, isomer, a mixture of isomers, prodrug, or solvate thereof, relative to the activity of PI3Kδ in the absence of such compound. In some embodiments, the inhibition of PI3Kδ activity may be compared in the same subject prior to treatment, or other subjects not receiving the treatment. In some other embodiments, the compounds inhibit PI3Kδ activity also inhibit PI3K β activity.

Without wishing to be bound to any theory, the decrease in PI3Kδ activity may be due to the direct interaction of the compound with PI3Kδ, or due to the interaction of the compounds described herein with one or more other factors that in turn affect PI3Kδ activity. For example, the presence of the compounds of the formulae described herein or a pharmaceutically acceptable salt, prodrug, or solvate thereof, may decrease PI3Kδ activity by directly binding to the PI3Kδ, by causing (directly or indirectly) another factor to decrease PI3Kδ activity, or by (directly or indirectly) decreasing the amount of PI3Kδ present in the cell or organism.

The terms "a compound of the present application," "a compound of any of the formulae described herein," or variant thereof refers to a compound having the structure of any of the formula (I), (IA), (IB), (IC), (ID), (IE), (IF), or (II). In some embodiment, the PI3K inhibitors are the compounds having the structure of the formula (I). In one embodiment, the PI3K inhibitors are the compounds having the structure of the formula (IA). In some embodiment, the PI3K inhibitors are the compounds having the structure of the formula (IB). In certain embodiment, the PI3K inhibitors are the compounds having the structure of the formula (IC). In another embodiment, the PI3K inhibitors are the compound having the structure of formula (ID). In yet another embodiment, the PI3K inhibitors are the compounds having the structure of formula (IE). In other embodiment, the PI3K inhibitors are the compound having the structure of formula (IF).

The term "PI3K inhibitor" or variant thereof refers to a compound that inhibits the activity of PI3K. The term "PI3K isoform selective inhibitor" or variant thereof refers to a compound that inhibits the activity of one or more PI3K isoforms more effectively than the other remaining PI3K isoforms. By way of example, the term "PI3Kδ selective inhibitor" generally refers to a compound that inhibits the activity of the PI3Kδ isoform more effectively than other isoforms of the PI3K family (e.g., PI3K α, β, or γ). The term "PI3Kα selective inhibitor" generally refers to a compound that inhibits the activity of the PI3Kα isoform more effectively than other isoforms of the PI3K family (e.g., PI3K α, δ, or γ). The term "PI3Kβ selective inhibitor" generally refers to a compound that inhibits the activity of the PI3Kβ isoform more effectively than other isoforms of the PI3K family (e.g., PI3K α, δ, or γ). The term "dual PI3Kα/β selective inhibitor generally refers to a compound that inhibits the activity of the PI3Kα and PI3Kβ isoforms more effectively than other isoforms of the PI3K family (e.g., PI3K δ or γ).

The relative efficacies of compounds as inhibitors of an enzyme activity (or other biological activity) can be established by determining the concentrations at which each compound inhibits the activity to a predefined extent and then comparing the results. In one embodiment, the efficacy of a compound as an inhibitor of one or more PI3K isoforms can be measured by the concentration that inhibits 50% of the activity in a biochemical assay, i.e., the 50% inhibitory concentration or "$IC_{50}$". $IC_{50}$ determinations can be accomplished using conventional techniques known in the art, including the techniques describes in the Examples below. In general, an $IC_{50}$ can be determined by measuring the activity of a given enzyme in the presence of a range of concentrations of the compound under study. The experimentally obtained values of enzyme activity may then be plotted against the compound concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it may be desirable to establish a 90% inhibitory concentration, i.e., $IC_{90}$.

In one embodiment, a PI3Kδ selective inhibitor is a compound that exhibits a 50% inhibitory concentration ($IC_{50}$) with respect to PI3Kδ that is at least 10-fold, in another aspect at least 20-fold, and in another aspect at least 30-fold, lower than the $IC_{50}$ value with respect to any or all of the other Class I PI3K family members. In another embodiment, a PI3Kδ selective inhibitor is a compound that exhibits an $IC_{50}$ with respect to PI3Kδ that is at least 50-fold, in another aspect at least 100-fold, in an additional aspect at least 200-fold, and in yet another aspect at least 500-fold, lower than the $IC_{50}$ with respect to any or all of the other PI3K Class I family members. A PI3Kδ selective inhibitor is typically administered in an amount such that it selectively inhibits PI3Kδ activity, as described above.

In one embodiment, a PI3Kα selective inhibitor is a compound that exhibits a 50% inhibitory concentration ($IC_{50}$) with respect to PI3Kα that is at least 10-fold, in another aspect at least 20-fold, and in another aspect at least 30-fold, lower than the $IC_{50}$ value with respect to any or all of the other Class I PI3K family members. In another embodiment, a PI3Kα selective inhibitor is a compound that exhibits an $IC_{50}$ with respect to PI3Kα that is at least 50-fold, in another aspect at least 100-fold, in an additional aspect at least 200-fold, and in yet another aspect at least 500-fold, lower than the $IC_{50}$ with respect to any or all of the other PI3K Class I family members. A PI3Kα selective inhibitor is typically administered in an amount such that it selectively inhibits PI3Kα activity, as described above In one embodiment, a PI3Kβ selective inhibitor is a compound that exhibits a 50% inhibitory concentration ($IC_{50}$) with respect to PI3Kβ that is at least 10-fold, in another aspect at least 20-fold, and in another aspect at least 30-fold, lower than the $IC_{50}$ value with respect to any or all of the other Class I PI3K family members. In another embodiment, a PI3Kβ selective inhibitor is a compound that exhibits an $IC_{50}$ with respect to PI3Kβ that is at least 50-fold, in another aspect at least 100-fold, in an additional aspect at least 200-fold, and in yet another aspect at least 500-fold, lower than the $IC_{50}$ with respect to any or all of the other PI3K Class I family members. A PI3Kβ selective inhibitor is typically administered in an amount such that it selectively inhibits PI3Kβ activity, as described above.

In one embodiment, a dual PI3Kα/β selective inhibitor is a compound that exhibits a 50% inhibitory concentration ($IC_{50}$) with respect to PI3Kα and PI3Kβ that is at least 10-fold, in another aspect at least 20-fold, and in another aspect at least 30-fold, lower than the $IC_{50}$ value with respect to any or all of the other Class I PI3K family members. In another embodiment, a dual PI3Kα/β selective inhibitor is a compound that exhibits an $IC_{50}$ with respect to PI3Kα and PI3Kβ that is at least 50-fold, in another aspect at least 100-fold, in an additional aspect at least 200-fold, and in yet another aspect at least 500-fold, lower than the $IC_{50}$ with respect to any or all of the other PI3K Class I family members. In another embodiment, a PI3Kα/β selective inhibitor is a compound that exhibits an $IC_{50}$ with respect to PI3Kβ and PI3Kδ that is at least 10-fold, at least 20-fold, at least 50-fold, at least 100-fold, at least 200-fold, at least 300-fold, at least 400-fold, and at least 500-fold, lower than the $IC_{50}$ with respect to either PI3Kα or PI3Kγ or to both PI3Kα and PI3Kγ. A dual PI3Kα/β selective inhibitor is typically administered in an amount such that it selectively inhibits PI3Kα and PI3Kβ activity, as described above.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo to determine the optimal schedule and/or dosing of administration of a PI3Kδ selective inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The selected compounds of the formula described herein or a pharmaceutically acceptable salt, prodrug, or solvate thereof, may be further characterized to examine the safety or tolerance dosage in human or non-human subjects. Such properties may be examined using commonly known methods to those skilled in the art.

Compared to other PI3K isoforms, PI3Kδ is generally expressed in hematopoietic cells. Consequently, the direct effects of selective inhibitors of PI3Kδ can be observed in hematopoietic cells. Hematopoietic cells typically differentiate into either lymphoid progenitor cells or myeloid progenitor cells, both of which ultimately differentiate into various mature cell types including leukocytes. Aberrant proliferation of hematopoietic cells of one type often interferes with the production or survival of other hematopoietic cell types, which can result in compromised immunity, anemia, and/or thrombocytopenia. The methods described herein may treat aberrant proliferation of hematopoietic cells by inhibiting aberrant proliferation of hematopoietic cells. As a result, these methods may also ameliorate the symptoms and secondary conditions that result from a primary effect such as excessive system or localized levels of leukocytes or lymphocytes.

In some embodiments, the compounds described herein may be used to treat subjects having various disease states, disorders, and conditions (also collectively referred to as "indications") involving aberrant proliferation of hematopoietic cells (including excessive production of lymphoid progenitor cell-derived cells and/or myeloid progenitor cell-derived cells). Such indications may include, for example, leukemias, lymphomas, myeloproliferative disorders, myelodysplastic syndromes, and plasma cell neoplasms. In certain embodiments, the compounds described herein may be used to treat hematologic malignancies, inflammation, autoimmune disorders, allergic conditions, cardiovascular disease, and autoimmune diseases. In certain embodiments, allergic conditions may include all forms of hypersensitivity.

In other embodiments, the compounds described herein may be used to treat cancers that are mediated by, dependent on or associated with PI3K activity, such as PI3Kδ activity. In certain embodiments, the disease is a hematologic malignancy. In particular embodiments, the hematologic malignancy is leukemia or lymphoma. In specific embodiments, the disease is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the disease is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL).

In other embodiments, the disease is a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), Sjoegren's syndrome, or autoimmune hemolytic anemia. In other embodiments, the disease is inflammation. In yet other embodiments, the disease is excessive or destructive immune reactions, such as asthma, rheumatoid arthritis, multiple sclerosis, and lupus. In yet other embodiments, the disease is excessive or destructive immune reactions, such as psoriasis or chronic obstructive pulmonary disease (COPD).

The present application also provides a method for treating a subject, who has or is suspected of having a disease or condition responsive or believed to be responsive to the inhibition of PI3Kδ activity by administering to the subject a compound of the formulae described herein or a pharmaceutically acceptable salt, prodrug, or solvate thereof.

Additionally, the application provides a method of inhibiting kinase activity of a phosphatidylinositol 3-kinase delta polypeptide by contacting the polypeptide with a compound of the formulae described herein or a pharmaceutically acceptable salt, prodrug, or solvate thereof.

Provided is also a method of disrupting leukocyte function comprising contacting the leukocytes with an effective amount of a compound of any of the formulae described herein or a pharmaceutically acceptable salt, prodrug, or solvate thereof, in a subject in need thereof (e.g., a human).

Provided is also a method of inhibiting a growth or a proliferation of cancer cells of hematopoietic origin comprising contacting the cancer cells with an effective amount of a compound of the formulae described herein or a pharmaceutically acceptable salt, prodrug, or solvate thereof.

Kits

Provided herein are also kits that include a compound of the formulae of the present application or a pharmaceutically acceptable salt, prodrug, or solvate thereof, and suitable packaging. In one embodiment, a kit further includes instructions for use. In one aspect, a kit includes a compound of the formulae described herein or a pharmaceutically acceptable salt, prodrug, or solvate thereof, and a label and/or instructions for use of the compounds in the treatment of the indications, including the diseases or conditions, described herein.

Provided herein are also articles of manufacture that include a compound of any of the formulae described herein or a pharmaceutically acceptable salt, prodrug, or solvate thereof, in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provides herein are also pharmaceutical compositions that contain one or more of the compounds of any of the formulae, including (I), (IA), (IB), (IC), (ID), (IE), (IF), or (II), or a pharmaceutically acceptable salt, isomers, prodrug, or solvate thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound of any of the formulae described herein or a pharmaceutically acceptable salt, prodrug, or solvate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of any of the formulae described herein or a pharmaceutically acceptable salt, prodrug, or solvate thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound of any of the above formulae or a pharmaceutically acceptable salt, prodrug, or solvate thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the formulae described herein for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound of the formula per kilogram of the subject's body weight (mg/kg). Dosages of between about 0.01 and 150 mg/kg may be appropriate. Dosages of between about 0.001 and 10 mg/kg, between about 0.005 and 5 mg/kg, and between about 0.01 and 50 mg/kg may be appropriate. In some embodiments, about 0.01 and 100 mg/kg may be appropriate. In other embodiments a dosage of between 0.05 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound of the formulae administered per dose or per day. Daily dosage of a compound may be between about 1 mg and 2,000 mg, between about 1,000 to 2,000 mg/day, between about 1 to 1,000 mg/day, between about 1 to 500 mg/day, between about 5 to 400 mg/day, between about 10 to 300 mg/day, between about 25 to 250 mg/day, between about 50 to 225 mg/day, between about 75 to 200 mg/day, between about 100 to 150 mg/day, between about 1 to 100 mg/day between about between about 1 to 75 mg/day, between about 1 to 50 mg/day, between about 1 to 25 mg/day, between about 1 to 20 mg/day, between about 1 to 15 mg/day, between about 1 to 10 mg/day, between about 1 to 5 mg/day, between about 5 to 100 mg/day, between about between about 5 to 75 mg/day, between about 5 to 50 mg/day, between about 5 to 25 mg/day, between about 5 to 15 mg/day, between about 5 to 10 mg/day, between about 25 to 400 mg/day between about between about 25 to 300 mg/day, between about 25 to 200 mg/day, between about 25 to 150 mg/day, between about 25 to 125 mg/day, between about 25 to 100 mg/day, between about 25 to 75 mg/day, between about 25 to 50 mg/day, between about 25 to 40 mg/day, between about 50 to 500 mg/day, between about 50 to 400 mg/day, between about 50 to 300 mg/day, between about 50 to 250 mg/day, between 50 to 225 mg/day, between about 50 to 200 mg/day, between about 50 to 175 mg/day, between about 50 to 150 mg/day, between about 50 to 125 mg/day, between about 50 to 100 mg/day, between about 75 to 200 mg/day, between 75 to 150 mg/day, between 75 to 125 mg/day, between about 75 to 100 mg/day, between about 100 to 125 mg/day, between about 100 to 150 mg/day, between about 100 to 175 mg/day, between about 10 to 150 mg/day, between about 10 to 125 mg/day, between about 10 to 100 mg/day, or between about 10 to 50 mg/day. In other embodiments, daily dosage of a compound may be between about 0.01 mg and 1,000 mg, between about 0.05 mg and 500 mg, between about 0.075 mg and 250 mg, between about 0.1 mg and 100 mg, between about 0.5 mg and 50 mg, between about 0.75 mg and 25 mg, between about 1 mg and 10 mg, When administered orally, the total daily dosage for a human subject may be between 1 mg and 1,000 mg, between about 1 to 100 mg/day, between about 1 to 50 mg/day, between about 5 to 50 mg/day, between 5 to 25 mg/day, between about 5 to 75 mg/day, between about 10-500 mg/day, between about 10 to 150 mg/day, between about 10 to 200 mg/day, between about 50-300 mg/day, between about 75-200 mg/day, between about 75 to 150 mg/day, or between about 100-150 mg/day. In additional embodiments, daily dosage for a human may be administered between about 0.01 mg and 1,000 mg, between about 0.05 mg and 500 mg, between about 0.075 mg and 250 mg, between about 0.1 mg and 100 mg, between about 0.5 mg and 50 mg, between about 0.75 mg and 25 mg, between about 1 mg and 10 mg, The compounds of the present application or the compositions thereof may be administered once, twice, three, or four times daily, using any suitable mode described above. Also, administration or treatment with the compounds according to any of the formulae described herein may be continued for a number of days; for example, commonly treatment would continue for at least 7 days, 14 days, or 28 days, for one cycle of treatment. In some embodiments, the compounds or the composition thereof may be administered continuously, i.e. every day. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound of the above formula and increasing the dose by increments until clinical efficacy is achieved. Increments of about 5, 10, 25, 50, or 100 mg can be used to increase the dose. In other embodiments, the methods comprising administering to the subject an initial daily dose of about 0.01 to 100 mg of the compound described herein and increasing the dose by increments of about 0.01, 0.05, 0.1, 0.5, 1, 2, 2.5, 5, 10, 25, 50, or 100 mg. The dosage can be increased daily, every other day, twice per week, or once per week.

Synthesis of the Compounds of Formula (I)

The compounds of formula (I), (IA), (IB), (IC), (ID), (IE), (IF), or (II) may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds of Formula I

The compounds of formula (I) may be prepared using the method shown in Reaction Scheme I.

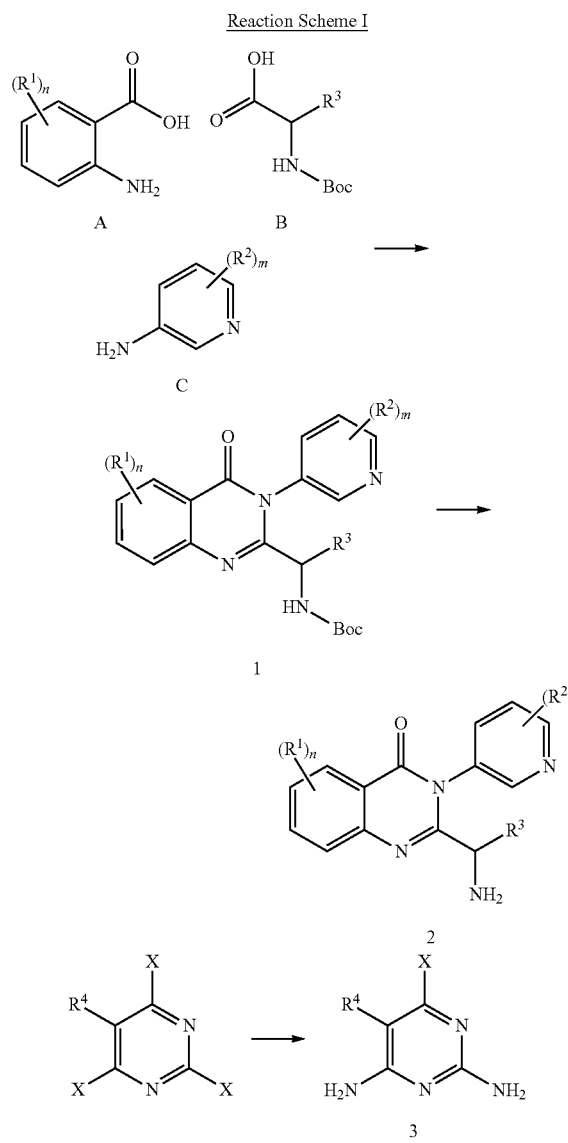

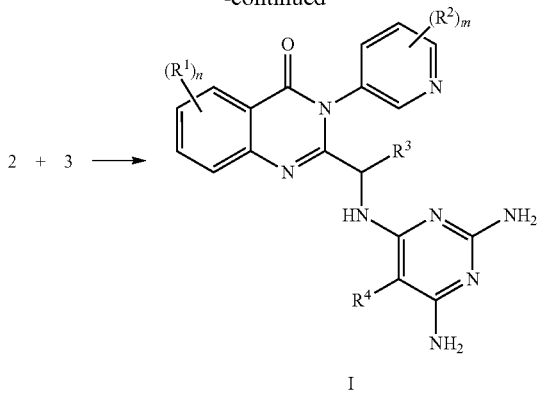

Step 1—Preparation of a Compound of Formula (1)

The compound of formula (1) can be made by combining compounds (A), (B) and (C) in the presence of a dehydrating agent. Compounds (A), (B) and (C) are commercially available or can be made by the methods that are commonly known or used by one skilled in the art. $R^1$, $R^2$, and $R^3$ are defined as in the formula (I). Compound (A) is mixed with Compound (B) in the presence of a coupling agent such as diphenyl phosphite in a solvent such as pyridine. After stirring at a temperature between ambient and 100° C. for 1 to 5 hours, compound (C) is added. The mixture is further stirred at a temperature between ambient and 100° C. for 5 to 24 hours and cooled to room temperature. To extract the compound of formula (1), an organic solvent such as ethyl acetate (EtOAc) is added. Then the reaction is washed with mild acid, water, and brine. The organic phase is concentrated to obtain the compound of formula (1). The compound of formula (1) is purified by any suitable methods known in the art, such as chromatography on silica gel. Alternatively, the compound of formula (1) is used in the next step without purification. In some instance, the compound of formula (1) is purified directly without an aqueous work-up. In cases where an $R^1$ is a cyano, the corresponding bromide can be converted to a nitrile by methods known in the art. For example, treatment of a bromide with zinc cyanide in the presence of a palladium catalyst, such as tetrakis(triphenylphosphine)palladium, at a temperature between ambient and 100° C. for 5 to 24 hours can give the compound of formula (1).

Step 2—Preparation of a Compound of Formula (2)

The compound of formula (2) can be made by removing the protecting group(s) from the compound of formula (1). The compound of formula (1) is dissolved in a suitable solvent and treated with a suitable acid. By way of example, suitable solvents include dichloromethane or dioxane, and suitable acids include trifluoroacetic acid, hydrochloric acid, or boron tribromide ($BBr_3$). The reaction is carried out at temperatures between −78° C. to ambient temperature. After the reaction is complete, solvent is removed to obtain the compound of formula (2).

Step 3—Preparation of a Compound of Formula (3)

The compound of formula (3) can be made by treating 5-substituted-2,4,6-trihalopyrimidine with ammonium hydroxide in a suitable solvent such as dioxane, where the halo is either chloro or fluoro. The reaction is carried out at an elevated temperature between 30 and 80° C. between 2 and 8 hours or when the reaction was complete. Then, water is added to the cooled solution, and the precipitate is collected by filtration. If necessary, separation of regiosiomers is accomplished by standard methods, such as chromatography. The nitrile can be converted to the carboxamide under standard conditions.

Step 4—Preparation of a Compound of Formula (I)

The compound of formula (I) can generally be prepared by coupling compound of formula (2) and compound of formula (3) in the presence of a suitable base in a suitable solvent. An example of a suitable base is diisopropylethylamine. An example of a suitable solvent is N-methylpyrrolidone (NMP), DMF, DMSO, or isopropanol. Also, an additive such as potassium fluoride may be used. The reaction is typically performed at a temperature between 50° C. to 150° C. for about 30 minutes to 24 hours. Alternatively the reaction can be performed in a microwave at a temperature between 100° C. to 150° C. for about 30 minutes to 24 hours. Water can be added to quench the reaction upon completion, and the precipitate may be filtered then dissolved in an organic solvent such as dichloromethane (DCM). The product can be isolated by methods known in the art, for example by removal of solvent under reduced pressure. The product can be purified using any suitable methods known in the art, for example, chromatography of the residue on a silica column. In certain instance, the product can be purified using recrystallization or precipitation.

It should be understood that the compounds of formula (I) can be prepared according to the methods provided in Reaction Scheme 1, starting from materials known to one of skill in the art.

EXAMPLE 1

Preparation of a Compound of Formula (1)

A. Preparation of a Compound of Formula (1) wherein n is 1, $R^1$ is chloro, m is 0, and $R^3$ is methyl

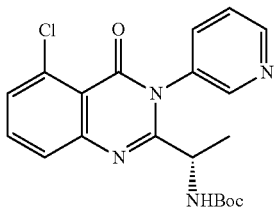 [SMILES: C[C@H](NC(=O)OC(C)(C)C)c1nc2cccc(Cl)c2c(=O)n1-c1cccnc1]

Diphenyl phosphite (1.9 mL, 10 mmol) was added to a solution of 2-amino-6-chlorobenzoic acid (495 mg, 2.9 mmol) and (S)-2-(tert-butoxycarbonylamino)propanoic acid (710 mg, 3.77 mmol) in pyridine (3 mL). The reaction mixture was stirred at 40° C. for 2 hours. 3-Aminopyridine (274 mg, 3.48 mmol) was then added to the reaction mixture, which was then stirred at 55° C. for 12 hours. The reaction mixture was cooled to room temperature and loaded onto a hexane primed $SiO_2$ column. The title compound was then purified by eluting with EtOAc in hexanes (0-50%) to afford (S)-tert-butyl 1-(5-chloro-4-oxo-3-(pyridin-3-yl)-3,4-dihydroquinazolin-2-yl)ethylcarbamate as a solid. ES/MS m/z=401.1 $(M+H^+)$.

B. Preparation of a Compound of Formula (1), Varying $R^1$, $R^2$, and $R^3$

Following the procedure described in Example 1A and Reaction Scheme I with varying $R^1$, $R^2$ and $R^3$ substituents, other compounds of formula (1) were prepared including:

(S)-tert-butyl 1-(5-chloro-4-oxo-3-(pyridin-3-yl)-3,4-dihydroquinazolin-2-yl)propylcarbamate, (S)-tert-butyl (5-chloro-4-oxo-3-(pyridin-3-yl)-3,4-dihydroquinazolin-2-yl)(cyclopropyl)methylcarbamate, (S)-tert-butyl 1-(5-chloro-4-oxo-3-(pyridin-3-yl)-3,4-dihydroquinazolin-2-yl)-2-cyclopropylethylcarbamate, (S)-tert-butyl 1-(6-fluoro-4-oxo-3-(pyridin-3-yl)-3,4-dihydroquinazolin-2-yl)ethylcarbamate, (S)-tert-butyl 1-(5-methyl-4-oxo-3-(pyridin-3-yl)-3,4-dihydroquinazolin-2-yl)ethylcarbamate, (S)-tert-butyl 1-(5-(methylsulfonyl)-4-oxo-3-(pyridin-3-yl)-3,4-dihydroquinazolin-2-yl)ethylcarbamate;

(S)-tert-butyl 1-(4-oxo-3-(pyridin-3-yl)-5-(trifluoromethyl)-3,4-dihydroquinazolin-2-yl)ethylcarbamate;

(S)-tert-butyl 1-(5-bromo-4-oxo-3-(pyridin-3-yl)-3,4-dihydroquinazolin-2-yl)ethylcarbamate;

(S)-tert-butyl 1-(3-(5-fluoropyridin-3-yl)-5-methyl-4-oxo-3,4-dihydroquinazolin-2-yl)ethylcarbamate;

(S)-tert-butyl 1-(5-chloro-3-(5-fluoropyridin-3-yl)-4-oxo-3,4-dihydroquinazolin-2-yl)ethylcarbamate;

(S)-tert-butyl 1-(5-chloro-3-(5-choropyridin-3-yl)-4-oxo-3,4-dihydroquinazolin-2-yl)ethylcarbamate;

(S)-tert-butyl 1-(5-chloro-3-(5-methoxypyridin-3-yl)-4-oxo-3,4-dihydroquinazolin-2-yl)ethylcarbamate;

(S)-tert-butyl 1-(5-chloro-3-(5-(difluoromethyl)pyridin-3-yl)-4-oxo-3,4-dihydroquinazolin-2-yl)ethylcarbamate;

(S)-tert-butyl 1-(5-chloro-3-(5-methylpyridin-3-yl)-4-oxo-3,4-dihydroquinazolin-2-yl)ethylcarbamate;

(S)-tert-butyl (5-chloro-3-(5-methylpyridin-3-yl)-4-oxo-3,4-dihydroquinazolin-2-yl)(cyclopropyl)methylcarbamate;

(S)-tert-butyl 1-(5-chloro-4-oxo-3-(5-(trifluoromethyl)pyridin-3-yl)-3,4-dihydroquinazolin-2-yl)ethylcarbamate;

(S)-tert-butyl 1-(5-chloro-3-(5-cyclopropylpyridin-3-yl)-4-oxo-3,4-dihydroquinazolin-2-yl)ethylcarbamate;

(S)-tert-butyl 1-(5-chloro-3-(5-fluoropyridin-3-yl)-4-oxo-3,4-dihydroquinazolin-2-yl)propylcarbamate;

(S)-tert-butyl (5-chloro-3-(5-fluoropyridin-3-yl)-4-oxo-3,4-dihydroquinazolin-2-yl)(cyclopropyl)methylcarbamate;

(S)-tert-butyl 1-(8-chloro-4-oxo-3-(pyridin-3-yl)-3,4-dihydroquinazolin-2-yl)ethylcarbamate;

(S)-tert-butyl 1-(5,8-dichloro-4-oxo-3-(pyridin-3-yl)-3,4-dihydroquinazolin-2-yl)ethylcarbamate;

(S)-tert-butyl 1-(5-chloro-8-fluoro-4-oxo-3-(pyridin-3-yl)-3,4-dihydroquinazolin-2-yl)ethylcarbamate;

(S)-tert-butyl 1-(5,8-difluoro-4-oxo-3-(pyridin-3-yl)-3,4-dihydroquinazolin-2-yl)ethylcarbamate;

(S)-tert-butyl 1-(5-chloro-8-fluoro-4-oxo-3-(pyridin-3-yl)-3,4-dihydroquinazolin-2-yl)propylcarbamate;

(S)-tert-butyl (5-chloro-8-fluoro-4-oxo-3-(pyridin-3-yl)-3,4-dihydroquinazolin-2-yl)(cyclopropyl)methylcarbamate;

(S)-tert-butyl cyclopropyl(5,8-dichloro-4-oxo-3-(pyridin-3-yl)-3,4-dihydroquinazolin-2-yl)methylcarbamate;

(S)-tert-butyl 1-(5-chloro-8-fluoro-4-oxo-3-(pyridin-3-yl)-3,4-dihydroquinazolin-2-yl)-2-cyclopropylethylcarbamate;

(S)-tert-butyl 1-(5,8-dichloro-3-(5-fluoropyridin-3-yl)-4-oxo-3,4-dihydroquinazolin-2-yl)ethylcarbamate;

(S)-tert-butyl 1-(5-chloro-8-fluoro-3-(5-fluoropyridin-3-yl)-4-oxo-3,4-dihydroquinazolin-2-yl)ethylcarbamate;

(S)-tert-butyl 1-(5-chloro-8-fluoro-3-(5-methylpyridin-3-yl)-4-oxo-3,4-dihydroquinazolin-2-yl)ethylcarbamate;

(S)-tert-butyl (5-chloro-8-fluoro-3-(5-fluoropyridin-3-yl)-4-oxo-3,4-dihydroquinazolin-2-yl)(cyclopropyl)methylcarbamate;

(S)-tert-butyl 1-(5-bromo-8-fluoro-4-oxo-3-(pyridin-3-yl)-3,4-dihydroquinazolin-2-yl)ethylcarbamate;

(S)-tert-butyl 1-(5-bromo-8-fluoro-4-oxo-3-(pyridin-3-yl)-3,4-dihydroquinazolin-2-yl)propylcarbamate;

(S)-tert-butyl 1-(5-chloro-6-fluoro-4-oxo-3-(pyridin-3-yl)-3,4-dihydroquinazolin-2-yl)ethylcarbamate;

(S)-tert-butyl (5-chloro-6-fluoro-4-oxo-3-(pyridin-3-yl)-3,4-dihydroquinazolin-2-yl)(cyclopropyl)methylcarbamate;
(S)-tert-butyl 1-(5-chloro-3-(2-methylpyridin-3-yl)-4-oxo-3,4-dihydroquinazolin-2-yl)ethylcarbamate;
(S)-tert-butyl 1-(5-chloro-3-(2-methylpyridin-3-yl)-4-oxo-3,4-dihydroquinazolin-2-yl)ethylcarbamate;
(S)-tert-butyl 1-(5-chloro-3-(4-methylpyridin-3-yl)-4-oxo-3,4-dihydroquinazolin-2-yl)ethylcarbamate;
(S)-tert-butyl 1-(5-chloro-3-(4-methylpyridin-3-yl)-4-oxo-3,4-dihydroquinazolin-2-yl)ethylcarbamate;
(S)-tert-butyl 1-(5-chloro-6-fluoro-3-(4-methylpyridin-3-yl)-4-oxo-3,4-dihydroquinazolin-2-yl)ethylcarbamate;
(S)-tert-butyl 1-(5-chloro-6-fluoro-3-(4-methylpyridin-3-yl)-4-oxo-3,4-dihydroquinazolin-2-yl)ethylcarbamate;
(S)-tert-butyl 1-(5-chloro-3-(5-fluoro-2-methylpyridin-3-yl)-4-oxo-3,4-dihydroquinazolin-2-yl)ethylcarbamate;
(S)-tert-butyl 1-(5-chloro-3-(5-fluoro-2-methylpyridin-3-yl)-4-oxo-3,4-dihydroquinazolin-2-yl)ethylcarbamate;
(S)-tert-butyl 1-(5-chloro-3-(5-fluoro-4-methylpyridin-3-yl)-4-oxo-3,4-dihydroquinazolin-2-yl)ethylcarbamate;
(S)-tert-butyl 1-(5-chloro-3-(5-fluoro-4-methylpyridin-3-yl)-4-oxo-3,4-dihydroquinazolin-2-yl)ethylcarbamate;
(S)-tert-butyl (1-(5-chloro-8-fluoro-3-(5-fluoropyridin-3-yl)-4-oxo-3,4-dihydroquinazolin-2-yl)propyl)carbamate;
(S)-tert-butyl (1-(3-(4-methylpyridin-3-yl)-4-oxo-5-(trifluoromethyl)-3,4-dihydroquinazolin-2-yl)ethyl)carbamate;
(S)-tert-butyl (1-(8-cyano-6-fluoro-4-oxo-3-(pyridin-3-yl)-3,4-dihydroquinazolin-2-yl)ethyl)carbamate;
(S)-tert-butyl (1-(8-cyano-6-fluoro-3-(5-fluoropyridin-3-yl)-4-oxo-3,4-dihydroquinazolin-2-yl)propyl)carbamate;
(S)-tert-butyl ((8-cyano-6-fluoro-3-(5-fluoropyridin-3-yl)-4-oxo-3,4-dihydroquinazolin-2-yl)(cyclopropyl)methyl)carbamate;
(S)-tert-butyl (1-(5-chloro-3-(5-fluoropyridin-3-yl)-4-oxo-3,4-dihydroquinazolin-2-yl)-3-methylbutyl)carbamate;
(R)-tert-butyl (1-(5-chloro-8-fluoro-4-oxo-3-(pyridin-3-yl)-3,4-dihydroquinazolin-2-yl)ethyl)carbamate;
(S)-tert-butyl (1-(5-chloro-4-oxo-3-(pyridin-3-yl)-3,4-dihydroquinazolin-2-yl)-3-methylbutyl)carbamate;
(R)-tert-butyl (1-(5-chloro-8-fluoro-3-(5-fluoropyridin-3-yl)-4-oxo-3,4-dihydroquinazolin-2-yl)ethyl)carbamate;
(R)-tert-butyl (1-(5-chloro-8-fluoro-4-oxo-3-(pyridin-3-yl)-3,4-dihydroquinazolin-2-yl)propyl)carbamate;
(R)-tert-butyl ((5-chloro-8-fluoro-4-oxo-3-(pyridin-3-yl)-3,4-dihydroquinazolin-2-yl)(cyclopropyl)methyl)carbamate;
(S)-tert-butyl (1-(5-bromo-8-fluoro-3-(5-fluoropyridin-3-yl)-4-oxo-3,4-dihydroquinazolin-2-yl)ethyl)carbamate;
(S)-tert-butyl (1-(5-bromo-8-fluoro-4-oxo-3-(pyridin-3-yl)-3,4-dihydroquinazolin-2-yl)propyl)carbamate;
(S)-tert-butyl (1-(5-bromo-8-fluoro-4-oxo-3-(pyridin-3-yl)-3,4-dihydroquinazolin-2-yl)ethyl)carbamate;
(S)-tert-butyl ((5-chloro-8-fluoro-3-(5-fluoro-4-methylpyridin-3-yl)-4-oxo-3,4-dihydroquinazolin-2-yl)(cyclopropyl)methyl)carbamate;
(S)-tert-butyl (1-(5-fluoro-3-(5-fluoro-4-methylpyridin-3-yl)-4-oxo-3,4-dihydroquinazolin-2-yl)ethyl)carbamate;
(S)-tert-butyl ((5-chloro-3-(5-fluoro-4-methylpyridin-3-yl)-4-oxo-3,4-dihydroquinazolin-2-yl)(cyclopropyl)methyl)carbamate;
(S)-tert-butyl (1-(5-chloro-3-(5-fluoro-4-methylpyridin-3-yl)-4-oxo-3,4-dihydroquinazolin-2-yl)propyl)carbamate;
(S)-tert-butyl (1-(5-chloro-8-fluoro-3-(5-fluoro-4-methylpyridin-3-yl)-4-oxo-3,4-dihydroquinazolin-2-yl)ethyl)carbamate;
(S)-tert-butyl (1-(6-fluoro-3-(5-fluoro-4-methylpyridin-3-yl)-4-oxo-3,4-dihydroquinazolin-2-yl)ethyl)carbamate;
(S)-tert-butyl (1-(5-chloro-3-(4,5-dimethylpyridin-3-yl)-4-oxo-3,4-dihydroquinazolin-2-yl)ethyl)carbamate;
(S)-tert-butyl (1-(3-(6-aminopyridin-3-yl)-8-chloro-6-fluoro-4-oxo-3,4-dihydroquinazolin-2-yl)ethyl)carbamate;
(S)-tert-butyl (1-(3-(6-aminopyridin-3-yl)-5,8-dichloro-4-oxo-3,4-dihydroquinazolin-2-yl)ethyl)carbamate;
(S)-tert-butyl (1-(3-(6-aminopyridin-3-yl)-5-chloro-4-oxo-3,4-dihydroquinazolin-2-yl)ethyl)carbamate;
(S)-tert-butyl (1-(3-(6-aminopyridin-3-yl)-5-chloro-4-oxo-3,4-dihydroquinazolin-2-yl)propyl)carbamate;
(S)-tert-butyl (1-(3-(6-aminopyridin-3-yl)-5-chloro-8-fluoro-4-oxo-3,4-dihydroquinazolin-2-yl)ethyl)carbamate;
(S)-tert-butyl ((3-(6-aminopyridin-3-yl)-5-chloro-4-oxo-3,4-dihydroquinazolin-2-yl)(cyclopropyl)methyl)carbamate;
(S)-tert-butyl (1-(3-(6-amino-4-methylpyridin-3-yl)-5-chloro-4-oxo-3,4-dihydroquinazolin-2-yl)propyl)carbamate;
(S)-tert-butyl (1-(3-(6-amino-4-methylpyridin-3-yl)-5-chloro-4-oxo-3,4-dihydroquinazolin-2-yl)ethyl)carbamate;
(S)-tert-butyl (1-(3-(6-amino-4-methylpyridin-3-yl)-5,8-dichloro-4-oxo-3,4-dihydroquinazolin-2-yl)propyl)carbamate;
(S)-tert-butyl ((3-(6-amino-4-methylpyridin-3-yl)-5,8-dichloro-4-oxo-3,4-dihydroquinazolin-2-yl)(cyclopropyl)methyl)carbamate;
(S)-tert-butyl (1-(3-(6-aminopyridin-3-yl)-5-chloro-6-fluoro-4-oxo-3,4-dihydroquinazolin-2-yl)ethyl)carbamate;
(S)-tert-butyl (1-(3-(6-aminopyridin-3-yl)-5-chloro-4-oxo-3,4-dihydroquinazolin-2-yl)butyl)carbamate;
(S)-tert-butyl (1-(3-(6-aminopyridin-3-yl)-5-chloro-6-fluoro-4-oxo-3,4-dihydroquinazolin-2-yl)butyl)carbamate;
(S)-tert-butyl ((3-(6-aminopyridin-3-yl)-5-chloro-8-fluoro-4-oxo-3,4-dihydroquinazolin-2-yl)(cyclopropyl)methyl)carbamate; and
(S)-tert-butyl (1-(3-(5-aminopyridin-3-yl)-5-chloro-4-oxo-3,4-dihydroquinazolin-2-yl)ethyl)carbamate.

C. Preparation of a Compound of Formula (1) wherein n is 1, $R^1$ is cyano, m is 0, and $R^3$ is methyl

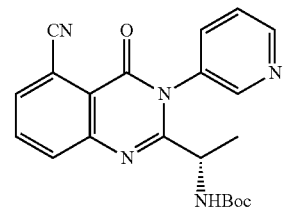 [SMILES: C[C@H](NC(=O)OC(C)(C)C)c1nc2cccc(C#N)c2c(=O)n1-c1cccnc1]

To a solution of (S)-tert-butyl 1-(5-bromo-4-oxo-3-(pyridin-3-yl)-3,4-dihydroquinazolin-2-yl)ethylcarbamate (255 mg, 0.58 mmol) in NMP (2 mL) was added zinc cyanide (74 mg, 0.63 mmol) and $(PPh_3)_4Pd$ (66 mg, 0.06 mmol). The resulting suspension was degassed under Argon and heated to 80° C. for 5 hours. The reaction was poured into EtOAc, washed twice with aq. $NaHCO_3$ and once with brine. Purification by flash chromatography (0-75% EtOAc/hexanes) provided (S)-tert-butyl 1-(5-cyano-4-oxo-3-(pyridin-3-yl)-3,4-dihydroquinazolin-2-yl)ethylcarbamate 196 mg (87%). ES/MS 392.1 (M+H$^+$).

D. Preparation of a Compound of Formula (1) where one $R^1$=cyano and Varying Other $R^1$, $R^2$, and $R^3$ (S)-tert-butyl 1-(5-cyano-8-fluoro-4-oxo-3-(pyridin-3-yl)-3,4-dihydroquinazolin-2-yl)ethylcarbamate;

(S)-tert-butyl 1-(5-cyano-8-fluoro-4-oxo-3-(pyridin-3-yl)-3,4-dihydroquinazolin-2-yl)propylcarbamate;

EXAMPLE 2

Preparation of a Compound of Formula (2)

A. Preparation of a Compound of Formula (2) wherein n is 1, $R^1$ is chloro, m is 0, and $R^3$ is methyl

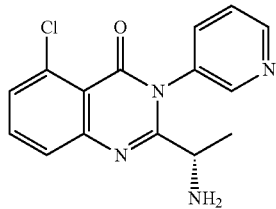 [SMILES: C[C@H](N)c1nc2cccc(Cl)c2c(=O)n1-c1cccnc1]

Trifluoroacetic acid (3 mL) was added to a solution of (S)-tert-butyl 1-(5-chloro-4-oxo-3-phenyl-3,4-dihydroquinazolin-2-yl)ethylcarbamate (1 g, 2.5 mmol) in dichloromethane (3 mL). The mixture was stirred at room temperature for 3 hours. The solvents was removed in vacuuo to obtain the title compound (S)-2-(1-aminoethyl)-5-chloro-3-(pyridin-3-yl)quinazolin-4(3H)-one. ES/MS m/z=301.7 (M+H$^+$).

B. Preparation of a Compound of Formula (2), Varying $R^1$, $R^2$, and $R^3$

Following the procedure described in Example 2A and Reaction Scheme I with varying $R^1$, $R^2$, and $R^3$ substituents, other compounds of formula (2) were prepared including:

(S)-2-(1-aminopropyl)-5-chloro-3-(pyridin-3-yl)quinazolin-4(3H)-one;
(S)-2-(amino(cyclopropyl)methyl)-5-chloro-3-(pyridin-3-yl)quinazolin-4(3H)-one;
(S)-2-(1-amino-2-cyclopropylethyl)-5-chloro-3-(pyridin-3-yl)quinazolin-4(3H)-one;
(S)-2-(1-aminoethyl)-6-fluoro-3-(pyridin-3-yl)quinazolin-4(3H)-one;
(S)-2-(1-aminoethyl)-5-methyl-3-(pyridin-3-yl)quinazolin-4(3H)-one;
(S)-2-(1-aminoethyl)-5-(methylsulfonyl)-3-(pyridin-3-yl)quinazolin-4(3H)-one;
(S)-2-(1-aminoethyl)-3-(pyridin-3-yl)-5-(trifluoromethyl)quinazolin-4(3H)-one;
(S)-2-(1-aminoethyl)-4-oxo-3-(pyridin-3-yl)-3,4-dihydroquinazoline-5-carbonitrile;
(S)-2-(1-aminoethyl)-3-(5-fluoropyridin-3-yl)-5-methylquinazolin-4(3H)-one;
(S)-2-(1-aminoethyl)-5-chloro-3-(5-fluoropyridin-3-yl)quinazolin-4(3H)-one;
(S)-2-(1-aminoethyl)-5-chloro-3-(5-chloropyridin-3-yl)quinazolin-4(3H)-one;
(S)-2-(1-aminoethyl)-5-chloro-3-(5-methoxypyridin-3-yl)quinazolin-4(3H)-one;
(S)-2-(1-aminoethyl)-5-chloro-3-(5-(difluoromethyl)pyridin-3-yl)quinazolin-4(3H)-one;
(S)-2-(1-aminoethyl)-5-chloro-3-(5-methylpyridin-3-yl)quinazolin-4(3H)-one;
(S)-2-(amino(cyclopropyl)methyl)-5-chloro-3-(5-methylpyridin-3-yl)quinazolin-4(3H)-one;
(S)-2-(1-aminoethyl)-5-chloro-3-(5-(trifluoromethyl)pyridin-3-yl)quinazolin-4(3H)-one;
(S)-2-(1-aminoethyl)-5-chloro-3-(5-cyclopropylpyridin-3-yl)quinazolin-4(3H)-one;
(S)-2-(1-aminopropyl)-5-chloro-3-(5-fluoropyridin-3-yl)quinazolin-4(3H)-one;
(S)-2-(amino(cyclopropyl)methyl)-5-chloro-3-(5-fluoropyridin-3-yl)quinazolin-4(3H)-one;
(S)-2-(1-aminoethyl)-8-chloro-3-(pyridin-3-yl)quinazolin-4(3H)-one;
(S)-2-(1-aminoethyl)-5,8-dichloro-3-(pyridin-3-yl)quinazolin-4(3H)-one;
(S)-2-(1-aminoethyl)-5-chloro-8-fluoro-3-(pyridin-3-yl)quinazolin-4(3H)-one;
(S)-2-(1-aminoethyl)-5,8-difluoro-3-(pyridin-3-yl)quinazolin-4(3H)-one;
(S)-2-(1-aminopropyl)-5-chloro-8-fluoro-3-(pyridin-3-yl)quinazolin-4(3H)-one;
(S)-2-(amino(cyclopropyl)methyl)-5-chloro-8-fluoro-3-(pyridin-3-yl)quinazolin-4(3H)-one;
(S)-2-(amino(cyclopropyl)methyl)-5,8-dichloro-3-(pyridin-3-yl)quinazolin-4(3H)-one;
(S)-2-(1-amino-2-cyclopropylethyl)-5-chloro-8-fluoro-3-(pyridin-3-yl)quinazolin-4(3H)-one;
(S)-2-(1-aminoethyl)-5,8-dichloro-3-(5-fluoropyridin-3-yl)quinazolin-4(3H)-one;
(S)-2-(1-aminoethyl)-5-chloro-8-fluoro-3-(5-fluoropyridin-3-yl)quinazolin-4(3H)-one;
(S)-2-(1-aminoethyl)-5-chloro-8-fluoro-3-(5-methylpyridin-3-yl)quinazolin-4(3H)-one;
(S)-2-(amino(cyclopropyl)methyl)-5-chloro-8-fluoro-3-(5-fluoropyridin-3-yl)quinazolin-4(3H)-one;
(S)-2-(1-aminoethyl)-8-fluoro-4-oxo-3-(pyridin-3-yl)-3,4-dihydroquinazoline-5-carbonitrile;
(S)-2-(1-aminopropyl)-8-fluoro-4-oxo-3-(pyridin-3-yl)-3,4-dihydroquinazoline-5-carbonitrile;
(S)-2-(1-aminoethyl)-5-chloro-6-fluoro-3-(pyridin-3-yl)quinazolin-4(3H)-one;
(S)-2-(amino(cyclopropyl)methyl)-5-chloro-6-fluoro-3-(pyridin-3-yl)quinazolin-4(3H)-one;
(S)-2-(1-aminoethyl)-5-chloro-3-(2-methylpyridin-3-yl)quinazolin-4(3H)-one;
(S)-2-(1-aminoethyl)-5-chloro-3-(2-methylpyridin-3-yl)quinazolin-4(3H)-one;
(S)-2-(1-aminoethyl)-5-chloro-3-(4-methylpyridin-3-yl)quinazolin-4(3H)-one;
(S)-2-(1-aminoethyl)-5-chloro-3-(4-methylpyridin-3-yl)quinazolin-4(3H)-one;
(S)-2-(1-aminoethyl)-5-chloro-6-fluoro-3-(4-methylpyridin-3-yl)quinazolin-4(3H)-one;
(S)-2-(1-aminoethyl)-5-chloro-6-fluoro-3-(4-methylpyridin-3-yl)quinazolin-4(3H)-one;
(S)-2-(1-aminoethyl)-5-chloro-3-(5-fluoro-2-methylpyridin-3-yl)quinazolin-4(3H)-one;
(S)-2-(1-aminoethyl)-5-chloro-3-(5-fluoro-2-methylpyridin-3-yl)quinazolin-4(3H)-one;
(S)-2-(1-aminoethyl)-5-chloro-3-(5-fluoro-4-methylpyridin-3-yl)quinazolin-4(3H)-one;
(S)-2-(1-aminoethyl)-5-chloro-3-(5-fluoro-4-methylpyridin-3-yl)quinazolin-4(3H)-one;
(S)-2-(1-aminopropyl)-5-chloro-8-fluoro-3-(5-fluoropyridin-3-yl)quinazolin-4(3H)-one;
(S)-2-(1-aminoethyl)-3-(4-methylpyridin-3-yl)-5-(trifluoromethyl)quinazolin-4(3H)-one;

(S)-2-(1-aminoethyl)-6-fluoro-4-oxo-3-(pyridin-3-yl)-3,4-dihydroquinazoline-8-carbonitrile;
(S)-2-(1-aminopropyl)-6-fluoro-3-(5-fluoropyridin-3-yl)-4-oxo-3,4-dihydroquinazoline-8-carbonitrile;
(S)-2-(amino(cyclopropyl)methyl)-6-fluoro-3-(5-fluoropyridin-3-yl)-4-oxo-3,4-dihydroquinazoline-8-carbonitrile;
(S)-2-(1-amino-3-methylbutyl)-5-chloro-3-(5-fluoropyridin-3-yl)quinazolin-4(3H)-one;
(R)-2-(1-aminoethyl)-5-chloro-8-fluoro-3-(pyridin-3-yl)quinazolin-4(3H)-one;
(S)-2-(1-amino-3-methylbutyl)-5-chloro-3-(pyridin-3-yl)quinazolin-4(3H)-one;
(R)-2-(1-aminoethyl)-5-chloro-8-fluoro-3-(5-fluoropyridin-3-yl)quinazolin-4(3H)-one;
(R)-2-(1-aminopropyl)-5-chloro-8-fluoro-3-(pyridin-3-yl)quinazolin-4(3H)-one;
(R)-2-(amino(cyclopropyl)methyl)-5-chloro-8-fluoro-3-(pyridin-3-yl)quinazolin-4(3H)-one;
(S)-2-(1-aminoethyl)-5-bromo-8-fluoro-3-(5-fluoropyridin-3-yl)quinazolin-4(3H)-one;
(S)-2-(1-aminopropyl)-5-bromo-8-fluoro-3-(pyridin-3-yl)quinazolin-4(3H)-one;
(S)-2-(1-aminoethyl)-5-bromo-8-fluoro-3-(pyridin-3-yl)quinazolin-4(3H)-one;
(S)-2-(1-aminoethyl)-4-oxo-3-(pyridin-3-yl)-3,4-dihydroquinazoline-5-carbonitrile;
(S)-2-(1-aminoethyl)-8-fluoro-4-oxo-3-(pyridin-3-yl)-3,4-dihydroquinazoline-5-carbonitrile;
(S)-2-(amino(cyclopropyl)methyl)-5-chloro-8-fluoro-3-(5-fluoro-4-methylpyridin-3-yl)quinazolin-4(3H)-one;
(S)-2-(1-aminoethyl)-5-fluoro-3-(5-fluoro-4-methylpyridin-3-yl)quinazolin-4(3H)-one;
(S)-2-(amino(cyclopropyl)methyl)-5-chloro-3-(5-fluoro-4-methylpyridin-3-yl)quinazolin-4(3H)-one;
(S)-2-(1-aminopropyl)-5-chloro-3-(5-fluoro-4-methylpyridin-3-yl)quinazolin-4(3H)-one;
(S)-2-(1-aminoethyl)-5-chloro-8-fluoro-3-(5-fluoro-4-methylpyridin-3-yl)quinazolin-4(3H)-one;
(S)-2-(1-aminoethyl)-6-fluoro-3-(5-fluoro-4-methylpyridin-3-yl)quinazolin-4(3H) one;
(S)-2-(1-aminoethyl)-5-chloro-3-(4,5-dimethylpyridin-3-yl)quinazolin-4(3H)-one;
(S)-2-(1-aminoethyl)-3-(6-aminopyridin-3-yl)-8-chloro-6-fluoroquinazolin-4(3H)-one;
(S)-2-(1-aminoethyl)-3-(6-aminopyridin-3-yl)-5,8-dichloroquinazolin-4(3H)-one;
(S)-2-(1-aminoethyl)-3-(6-aminopyridin-3-yl)-5-chloroquinazolin-4(3H)-one;
(S)-2-(1-aminopropyl)-3-(6-aminopyridin-3-yl)-5-chloroquinazolin-4(3H)-one;
(S)-2-(1-aminoethyl)-3-(6-aminopyridin-3-yl)-5-chloro-8-fluoroquinazolin-4(3H)-one;
(S)-2-(amino(cyclopropyl)methyl)-3-(6-aminopyridin-3-yl)-5-chloroquinazolin-4(3H)-one;
(S)-3-(6-amino-4-methylpyridin-3-yl)-2-(1-aminopropyl)-5-chloroquinazolin-4(3H)-one;
(S)-3-(6-amino-4-methylpyridin-3-yl)-2-(1-aminoethyl)-5-chloroquinazolin-4(3H)-one;
(S)-3-(6-amino-4-methylpyridin-3-yl)-2-(1-aminopropyl)-5,8-dichloroquinazolin-4(3H)-one;
(S)-2-(amino(cyclopropyl)methyl)-3-(6-amino-4-methylpyridin-3-yl)-5,8-dichloroquinazolin-4(3H)-one;
(S)-2-(1-aminoethyl)-3-(6-aminopyridin-3-yl)-5-chloro-6-fluoroquinazolin-4(3H)-one;
(S)-2-(1-aminobutyl)-3-(6-aminopyridin-3-yl)-5-chloroquinazolin-4(3H)-one;
(S)-2-(1-aminobutyl)-3-(6-aminopyridin-3-yl)-5-chloro-6-fluoroquinazolin-4(3H)-one;
(S)-2-(amino(cyclopropyl)methyl)-3-(6-aminopyridin-3-yl)-5-chloro-8-fluoroquinazolin-4(3H)-one; and
(S)-2-(1-aminoethyl)-3-(5-aminopyridin-3-yl)-5-chloroquinazolin-4(3H)-one.

EXAMPLE 3

Preparation of a Compound of Formula (3)

A. Preparation of a Compound of Formula (3) wherein $R^4$ is CN and X is Cl (2,4-diamino-6-chloropyrimidine-5-carbonitrile)

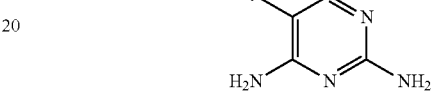

Ammonium hydroxide (20 mL) was added to a solution of 2,4,6-trichloropyrimidine-5-carbonitrile (5.0 g, 24 mmol) in dioxane (20 mL) at room temperature. The solution was warmed to 50° C. and stirred for 3 hrs. The reaction mixture was cooled to 10° C. and water (50 mL) was added. The resulting solid was filtered, washed with water, and dried under high vacuum to obtain the title compound as a white solid (4.5 g) $^{13}$H NMR (100 MHz, DMSO) 164.8, 162.6, 161.9, 115.8, 77.6. ES/MS m/z=169.9 (M+H)$^+$.

A. Preparation of a Compound of Formula (3), Varying $R^3$
2,4-diamino-6-chloropyrimidine-5-carboxamide; and
5-chloro-6-fluoropyrimidine-2,4-diamine;

EXAMPLE 4

Preparation of a Compound of Formula (I)

A. Preparation of a Compound of Formula (I) wherein n is 1, $R^1$ is chloro, m is 0, $R^3$ is methyl, and $R^4$ is cyano (Compound 1)

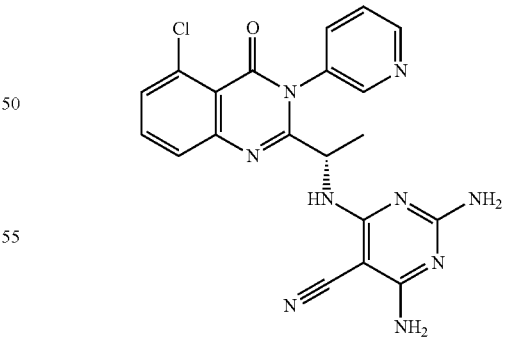

Potassium fluoride (138 mg, 2.38 mmol) was added to a solution of (S)-2-(1-aminoethyl)-5-chloro-3-(pyridin-3-yl)quinazolin-4(3H)-one (400 mg, 1.33 mmol) and 2,4-diamino-6-chloropyrimidine-5-carbonitrile (237 mg, 1.4 mmol) in diisopropylethylamine (1.0 mL, 6.0 mmol) and DMSO (3 mL). The resultant mixture was heated to 90° C. for 14 hours. Then it was cooled to room temperature, filtered, and purified by HPLC eluting with 5%-95% water/acetonitrile (0.1% v/v trifluoroacetic acid). The appropriate fractions were pooled and lyophilized to obtain the title compound of (S)-2,4-diamino-6-((1-(5-chloro-4-oxo-3-(pyridin-3-yl)-3,4-dihydroquinazolin-2-yl)ethyl)amino)pyrimidine-5-carbonitrile as a solid (479 mg). $^1$H NMR (400 MHz, DMSO) δ 8.74 (d, J=2.4 Hz, 0.5H), 8.58 (dd, J=4.8, 1.5 Hz, 0.5H), 8.51 (dd, J=4.9, 1.7 Hz, 1.5H), 8.06 (dm, J=8.5 Hz, 0.5H), 7.85 (dm, J=8.0 Hz, 0.5H), 7.8 (td, J=8.1, 1.4 Hz, 1H), 7.68 (ddd, J=8.2, 3.9, 1.2 Hz, 1H), 7.60 (dt, J=7.9, 1.3 Hz, 1H), 7.55 (ddd, J=8.1, 4.8, 0.7 Hz, 0.5H), 7.48 (ddt, J=8.1, 4.8, 0.7 Hz, 0.5H), 4.85 (m, 1H), 1.35 (d, J=6.8 Hz, 3H). ES/MS 434.1 (M+H$^+$).

B. Preparation of a Compound of Formula (I), Varying R$^1$, R$^2$ and R$^3$

Other compounds of formula (I) were prepared including:

(S)-2,4-diamino-6-(1-(5-chloro-4-oxo-3-(pyridin-3-yl)-3,4-dihydroquinazolin-2-yl)propylamino)pyrimidine-5-carbonitrile (Compound 2). 1H NMR (400 MHz, DMSO-d6) δ 8.83-8.35 (m, 2H), 8.00 (t, J=9.9 Hz, 1H), 7.75 (t, J=8.0 Hz, 1H), 7.70-7.38 (m, 3H), 6.75 (dd, J=19.0, 7.5 Hz, 1H), 6.57 (s, 2H), 6.39-5.86 (m, 2H), 4.49 (td, J=7.5, 3.9 Hz, 1H), 1.98-1.43 (m, 2H), 0.66 (q, J=6.9 Hz, 3H). ES/MS 448.1 (M+H$^+$);

(S)-2,4-diamino-6-((5-chloro-4-oxo-3-(pyridin-3-yl)-3,4-dihydroquinazolin-2-yl)(cyclopropyl)methylamino)pyrimidine-5-carbonitrile (Compound 3). 1H NMR (400 MHz, DMSO-d6) δ 8.65 (d, J=2.5 Hz, 1H), 8.58-8.42 (m, 1H), 7.95 (ddt, J=8.2, 2.7, 1.3 Hz, 1H), 7.87-7.72 (m, 1H), 7.66 (ddt, J=8.2, 4.2, 1.1 Hz, 1H), 7.63-7.44 (m, 1H), 7.38 (dd, J=8.1, 4.8 Hz, 1H), 6.72-6.43 (m, 3H), 6.18 (s, 2H), 5.72 (d, J=1.0 Hz, 1H), 4.53-4.27 (m, 1H), 1.46-0.95 (m, 2H), 0.07 (dd, J=5.7, 2.8 Hz, 2H). ES/MS 460.5 (M+H$^+$);

(S)-2,4-diamino-6-(1-(5-chloro-4-oxo-3-(pyridin-3-yl)-3,4-dihydroquinazolin-2-yl)-2-cyclopropylethylamino)pyrimidine-5-carbonitrile (Compound 4). 1H NMR (400 MHz, DMSO-d6) δ 8.89-8.58 (m, 2H), 8.05 (dddd, J=50.5, 8.1, 2.5, 1.5 Hz, 1H), 7.82-7.64 (m, 1H), 7.68-7.45 (m, 3H), 6.84 (dd, J=7.5, 3.8 Hz, 1H), 6.70-6.37 (m, 2H), 6.39-6.02 (m, 2H), 4.70-4.42 (m, 1H), 1.91-1.76 (m, 1H), 1.48-1.22 (m, 1H), 0.60 (dtt, J=16.3, 7.9, 4.3 Hz, 1H), 0.26 (tt, J=8.5, 4.4 Hz, 1H), 0.20--0.17 (m, 2H), −0.48--0.92 (m, 1H). ES/MS 474.1 (M+H$^+$);

(S)-2,4-diamino-6-(1-(6-fluoro-4-oxo-3-(pyridin-3-yl)-3,4-dihydroquinazolin-2-yl)ethylamino)pyrimidine-5-carbonitrile (Compound 5). 1H NMR (400 MHz, DMSO-d6) δ 8.80-8.46 (m, 2H), 7.97 (dddd, J=25.8, 8.1, 2.5, 1.5 Hz, 1H), 7.82-7.68 (m, 3H), 7.50 (dddd, J=27.4, 8.1, 4.9, 0.8 Hz, 1H), 6.88 (dd, J=15.9, 7.1 Hz, 1H), 6.50 (d, J=6.5 Hz, 2H), 6.22 (s, 2H), 4.73 (dt, J=9.6, 6.9 Hz, 1H), 1.30 (dd, J=6.7, 1.7 Hz, 3H). ES/MS 418.1 (M+H$^+$);

(S)-2,4-diamino-6-(1-(5-methyl-4-oxo-3-(pyridin-3-yl)-3,4-dihydroquinazolin-2-yl)ethylamino)pyrimidine-5-carbonitrile (Compound 7). 1H NMR (400 MHz, DMSO-d6) δ 8.87-8.32 (m, 2H), 7.96 (dddd, J=13.4, 8.1, 2.6, 1.4 Hz, 1H), 7.68 (t, J=7.8 Hz, 1H), 7.51 (dtd, J=11.7, 8.1, 4.9 Hz, 1H), 7.29 (dd, J=7.6, 1.5 Hz, 1H), 7.05-6.74 (m, 2H), 6.68-6.34 (m, 2H), 6.25 (s, 1H), 4.88-4.48 (m, 1H), 2.69 (s, 3H), 1.28 (d, J=6.7 Hz, 3H). ES/MS 414.5 (M+H$^+$);

(S)-2,4-diamino-6-(1-(5-(methylsulfonyl)-4-oxo-3-(pyridin-3-yl)-3,4-dihydroquinazolin-2-yl)ethylamino)pyrimidine-5-carbonitrile (Compound 8). 1H NMR (400 MHz, DMSO-d6) δ 8.76 (dd, J=2.5, 0.7 Hz, 0.5H), 8.69 (dd, J=2.5, 0.7 Hz, 0.5H), 8.64 (dd, J=4.8, 1.5 Hz, 0.5H), 8.59 (dd, J=4.8, 1.5 Hz, 0.5H), 8.35-8.30 (m, 1H), 8.12-8.04 (m, 2H), 8.00 (dd, J=2.5, 1.6 Hz, 0.5H), 7.98 (dd, J=2.5, 1.5 Hz, 0.5H), 7.59 (ddd, J=8.1, 4.8, 0.8 Hz, 0.5H), 7.52 (ddd, J=8.1, 4.8, 0.8 Hz, 0.5H), 6.97 (d, J=7.2 Hz, 0.5H), 6.94 (d, J=7.2 Hz, 0.5H), 6.55 (br s, 2H), 6.26 (br s, 2H), 4.80 (dt, J=8.5, 6.9 Hz, 1H), 3.49 (s, 3H), 1.36 (dd, J=6.6, 1.3 Hz, 3H). ES/MS 478.1 (M+H$^+$);

(S)-2,4-diamino-6-(1-(4-oxo-3-(pyridin-3-yl)-5-(trifluoromethyl)-3,4-dihydroquinazolin-2-yl)ethylamino)pyrimidine-5-carbonitrile (Compound 9). 1H NMR (400 MHz, DMSO-d6) δ 8.75 (d, J=2.5 Hz, 1H), 8.67-8.36 (m, 2H), 8.27-7.92 (m, 5H), 7.94-7.67 (m, 2H), 7.51 (dddd, J=31.6, 8.2, 4.8, 0.8 Hz, 2H), 4.89 (td, J=7.0, 4.3 Hz, 1H), 1.37 (d, J=6.6 Hz, 3H). ES/MS 468.1 (M+H$^+$);

(S)-2-(1-((2,6-diamino-5-cyanopyrimidin-4-yl)amino)ethyl)-4-oxo-3-(pyridin-3-yl)-3,4-dihydroquinazoline-5-carbonitrile (Compound 10). $^1$H NMR (400 MHz, DMSO-d$_6$) δ 8.71 (ddd, J=17.0, 2.5, 0.7 Hz, 1H), 8.59 (ddd, J=15.9, 4.8, 1.5 Hz, 1H), 8.11-8.03 (m, 1H), 8.03-7.91 (m, 3H), 7.63-7.40 (m, 1H), 6.88 (dd, J=13.2, 6.9 Hz, 1H), 6.52 (br. s, 2H), 6.24 (br. s, 2H), 4.70 (td, J=6.8, 4.6 Hz, 1H), 1.31 (d, J=6.7 Hz, 3H). ES/MS 425.1 (M+H$^+$);

(S)-2,4-diamino-6-(1-(3-(5-fluoropyridin-3-yl)-5-methyl-4-oxo-3,4-dihydroquinazolin-2-yl)ethylamino)pyrimidine-5-carbonitrile (Compound 11). 1H NMR (400 MHz, DMSO-d6) 8.67-8.39 (m, 2H), 8.25-7.95 (m, 1H), 7.97-7.79 (m, 1H), 7.69 (td, J=7.8, 1.6 Hz, 1H), 7.58-7.38 (m, 1H), 7.40-7.18 (m, 1H), 6.91 (ddd, J=23.3, 7.2, 1.7 Hz, 1H), 6.53 (d, J=8.3 Hz, 2H), 6.21 (s, 2H), 4.96-4.37 (m, 1H), 2.70 (d, J=1.7 Hz, 3H), 1.32 (dt, J=6.6, 1.6 Hz, 3H). ES/MS 432.3 (M+H$^+$);

(S)-2,4-diamino-6-(1-(5-chloro-3-(5-fluoropyridin-3-yl)-4-oxo-3,4-dihydroquinazolin-2-yl)ethylamino)pyrimidine-5-carbonitrile (Compound 12). 1H NMR (400 MHz, DMSO) δ 8.66 (m, 0.5H), 8.62 (d, J=2.8 Hz, 0.5H), 8.55 (d, J=2.6 Hz, 0.5H), 8.40 (m, 0.5H), 8.16 (dd, J=2.65, 2.0 Hz, 0.5H), 8.13 (dd, J=2.6, 2.0 Hz, 0.5H), 7.82 (ddd, J=8.0, 8.0, 2.2 Hz, 1H), 7.78 (m, 0.5H), 7.69 (ddd, 8.18, 3.7, 1.2 Hz, 1H), 7.61 (ddd, J=7.8, 2.15, 1.2 Hz, 1H), 4.86 (m, 1H), 1.37 (d, J=6.7 Hz, 1.5H), 1.36 (d, J=6.5 Hz, 1.5H). ES/MS 452.8 (M+H$^+$);

(S)-2,4-diamino-6-(1-(5-chloro-3-(5-chloropyridin-3-yl)-4-oxo-3,4-dihydroquinazolin-2-yl)ethylamino)pyrimidine-5-carbonitrile (Compound 13). 1H NMR (400 MHz, DMSO) δ 8.52 (d, J=5.6 Hz, 1H), 7.82 (t, J=8.0 Hz, 1H), 7.70 (dd, J=8.2, 1.0 Hz, 1H), 7.62 (dd, J=8.0, 1.1 Hz, 1H), 7.55 (dm, J=5.6 Hz, 1H), 5.03 (m, 1H), 1.38 (d, J=6.6 Hz, 3H). ES/MS 469.3 (M+H$^+$);

(S)-2,4-diamino-6-(1-(5-chloro-3-(5-methoxypyridin-3-yl)-4-oxo-3,4-dihydroquinazolin-2-yl)ethylamino)pyrimidine-5-carbonitrile (Compound 14). 1H NMR (400 MHz, DMSO) δ 8.35 (d, J=1.9 Hz, 0.5H), 8.31 (d, J=2.8 Hz, 0.5H), 8.24 (d, J=2.7 Hz, 0.5H), 8.13 (d, J=1.9 Hz, 0.5H), 7.84 (t, J=8.3 Hz, 1H), 7.78 (dd, J=2.7, 1.9 Hz, 0.5H), 7.72 (ddd, J=8.2, 1.8, 1.2 Hz, 1H), 7.64 (ddd, J=7.8, 1.3, 0.6 Hz, 1H), 7.41 (dd, J=2.8, 2.0 Hz, 1H), 4.98 (m, 1H), 3.85 (s, 1.5H), 3.79 (s, 1.5H), 1.40 (d, 3H). ES/MS 464.8 (M+H$^+$);

(S)-2,4-diamino-6-(1-(5-chloro-3-(5-(difluoromethyl)pyridin-3-yl)-4-oxo-3,4-dihydroquinazolin-2-yl)ethylamino)pyrimidine-5-carbonitrile (Compound 15). 1H NMR (400 MHz, DMSO) δ 8.9 (s, 0.5H), 8.75 (s, 0.5H), 8.69 (s, 0.5H), 8.67 (s, 0.5H), 8.33 (s, 0.5H), 7.96 (s, 0.5H), 7.81 (ddd, J=8.0, 8.0, 4.0 Hz, 0.5H), 7.70 (ddd, J=9.3, 8.2, 1.15 Hz, 0.5H), 7.61 (ddd, 7.8, 3.2, 1.2 Hz, 0.5H), 7.3 (m, 0.5H), 7.15 (m, 1H), 4.86 (m, 1H), 1.37 (d, J=6.7 Hz, 1.5H), 1.34 (d, J=6.8 Hz, 1.5H). ES/MS 484.8 (M+H$^+$);

(S)-2,4-diamino-6-(1-(5-chloro-3-(5-methylpyridin-3-yl)-4-oxo-3,4-dihydroquinazolin-2-yl)ethylamino)pyrimidine-5-carbonitrile (Compound 16). 1H NMR (400 MHz, DMSO-d6) δ 8.55-8.23 (m, 2H), 7.91-7.70 (m, 1H), 7.73-7.44 (m, 3H), 6.92 (dd, J=22.9, 7.2 Hz, 1H), 6.51 (d, J=5.1 Hz, 2H), 6.20 (d, J=17.4 Hz, 2H), 4.78 (h, J=6.6 Hz, 1H), 2.40-2.11 (m, 3H), 1.39-1.19 (m, 3H). ES/MS 448.1 (M+H$^+$);

(S)-2,4-diamino-6-((5-chloro-3-(5-methylpyridin-3-yl)-4-oxo-3,4-dihydroquinazolin-2-yl)(cyclopropyl)methylamino)pyrimidine-5-carbonitrile (Compound 17). 1H NMR (400 MHz, DMSO-d6) δ 8.54-8.17 (m, 2H), 7.88-7.47 (m, 3H), 6.71 (dd, J=57.5, 7.7 Hz, 1H), 6.51 (s, 2H), 6.10 (s, 2H), 4.48 (dt, J=26.1, 7.8 Hz, 1H), 2.42-2.02 (m, 3H), 1.61-1.28 (m, 1H), 0.64-0.30 (m, 3H), 0.25--0.11 (m, 1H). ES/MS 474.1 (M+H$^+$);

(S)-2,4-diamino-6-(1-(5-chloro-4-oxo-3-(5-(trifluoromethyl)pyridin-3-yl)-3,4-dihydroquinazolin-2-yl)ethylamino)pyrimidine-5-carbonitrile (Compound 18). 1H NMR (400 MHz, DMSO-d6) δ 9.24-8.72 (m, 2H), 8.58 (td, J=2.2, 0.7 Hz, 1H), 7.90-7.47 (m, 3H), 6.92 (dd, J=40.0, 7.3 Hz, 1H), 6.47 (d, J=21.5 Hz, 2H), 6.14 (s, 2H), 4.76 (dp, J=26.9, 6.6 Hz, 1H), 1.32 (dd, J=12.3, 6.5 Hz, 3H). ES/MS 502.1 (M+H$^+$);

(S)-2,4-diamino-6-(1-(5-chloro-3-(5-cyclopropylpyridin-3-yl)-4-oxo-3,4-dihydroquinazolin-2-yl)ethylamino)pyrimidine-5-carbonitrile (Compound 19). 1H NMR (400 MHz, DMSO-d6) δ 8.54-8.15 (m, 2H), 7.84-7.70 (m, 1H), 7.70-7.44 (m, 3H), 6.88 (dd, J=6.9, 4.8 Hz, 1H), 6.51 (s, 2H), 6.19 (s, 2H), 4.64 (dt, J=12.6, 6.7 Hz, 1H), 2.05-1.77 (m, 1H), 1.28 (dd, J=9.0, 6.7 Hz, 3H), 1.05-0.88 (m, 2H), 0.80-0.56 (m, 2H). ES/MS 474.1 (M+H$^+$);

(S)-2,4-diamino-6-(1-(5-chloro-3-(5-fluoropyridin-3-yl)-4-oxo-3,4-dihydroquinazolin-2-yl)propylamino)pyrimidine-5-carbonitrile (Compound 20). 1H NMR (400 MHz, DMSO-d6) δ 8.74-8.45 (m, 2H), 8.02 (ddt, J=103.9, 9.0, 2.1 Hz, 2H), 7.78 (td, J=8.0, 0.8 Hz, 1H), 7.61 (ddt, J=25.7, 8.0, 1.1 Hz, 1H), 6.77 (d, J=31.6 Hz, 1H), 6.55 (s, 2H), 6.19 (s, 2H), 4.77-4.39 (m, 1H), 2.05-1.57 (m, 2H), 0.82-0.44 (m, 3H). ES/MS 468.1 (M+H$^+$);

(S)-2,4-diamino-6-((5-chloro-3-(5-fluoropyridin-3-yl)-4-oxo-3,4-dihydroquinazolin-2-yl)(cyclopropyl)methylamino)pyrimidine-5-carbonitrile (Compound 21). 1H NMR (400 MHz, DMSO-d6) δ 8.65-8.17 (m, 2H), 8.19-7.25 (m, 4H), 6.85-6.24 (m, 3H), 6.13 (s, 2H), 4.45 (dt, J=20.2, 8.0 Hz, 1H), 1.42 (h, J=7.3 Hz, 1H), 0.58-0.25 (m, 3H), 0.08 (dq, J=10.0, 5.5, 5.1 Hz, 1H). ES/MS 478.1 (M+H$^+$);

(S)-2,4-diamino-6-(1-(8-chloro-4-oxo-3-(pyridin-3-yl)-3,4-dihydroquinazolin-2-yl)ethylamino)pyrimidine-5-carbonitrile (Compound 22). 1H NMR (400 MHz, DMSO-d6) δ 8.75 (d, J=2.5 Hz, 1H), 8.65-8.42 (m, 2H), 8.16-7.94 (m, 3H), 7.92-7.58 (m, 1H), 7.65-7.47 (m, 2H), 7.51-7.38 (m, 1H), 7.31 (s, 2H), 4.94 (h, J=6.7 Hz, 1H), 1.39 (dd, J=6.6, 2.6 Hz, 3H). ES/MS 434.9 (M+H$^+$);

(S)-2,4-diamino-6-(1-(5,8-dichloro-4-oxo-3-(pyridin-3-yl)-3,4-dihydroquinazolin-2-yl)ethylamino)pyrimidine-5-carbonitrile (Compound 23). 1H NMR (400 MHz, DMSO-d6) δ 8.87-8.38 (m, 4H), 8.02 (tdd, J=7.4, 6.6, 5.6, 2.9 Hz, 2H), 7.89-7.65 (m, 2H), 7.65-7.32 (m, 3H), 5.03-4.68 (m, 1H), 1.57-1.15 (m, 3H). ES/MS 469.2 (M+H$^+$);

(S)-2,4-diamino-6-(1-(5-chloro-8-fluoro-4-oxo-3-(pyridin-3-yl)-3,4-dihydroquinazolin-2-yl)ethylamino)pyrimidine-5-carbonitrile (Compound 24). 1H NMR (400 MHz, DMSO-d6) δ 8.80-8.42 (m, 2H), 8.12-7.81 (m, 1H), 7.80-7.68 (m, 1H), 7.62-7.51 (m, 1H), 7.46 (dt, J=10.6, 5.3 Hz, 1H), 6.87 (dd, J=16.8, 7.0 Hz, 1H), 6.51 (d, J=5.7 Hz, 2H), 6.21 (d, J=21.8 Hz, 2H), 4.76-4.60 (m, 1H), 1.30 (dd, J=6.6, 1.5 Hz, 3H). ES/MS 452.1 (M+H$^+$);

(S)-2,4-diamino-6-(1-(5,8-difluoro-4-oxo-3-(pyridin-3-yl)-3,4-dihydroquinazolin-2-yl)ethylamino)pyrimidine-5-carbonitrile (Compound 25). 1H NMR (400 MHz, DMSO-d6) δ 8.73 (d, J=2.5 Hz, 1H), 8.65-8.36 (m, 2H), 8.02 (dt, J=8.2, 2.0 Hz, 1H), 8.02-7.70 (m, 6H), 7.55 (dd, J=8.1, 4.8 Hz, 1H), 7.47 (dd, J=8.1, 4.8 Hz, 1H), 7.47-7.25 (m, 1H), 4.83 (q, J=6.7 Hz, 1H), 1.48-1.26 (m, 3H). ES/MS 436.4 (M+H$^+$);

(S)-2,4-diamino-6-(1-(5-chloro-8-fluoro-4-oxo-3-(pyridin-3-yl)-3,4-dihydroquinazolin-2-yl)propylamino)pyrimidine-5-carbonitrile (Compound 26). 1H NMR (400 MHz, DMSO-d6) δ 8.81-8.46 (m, 2H), 8.10-7.80 (m, 1H), 7.71 (dd, J=9.7, 8.7 Hz, 1H), 7.64-7.38 (m, 2H), 6.76 (dd, J=20.9, 7.5 Hz, 1H), 6.58 (s, 2H), 6.19 (d, J=38.7 Hz, 2H), 4.54 (tt, J=7.8, 5.3 Hz, 1H), 1.91-1.59 (m, 2H), 0.69 (td, J=7.2, 4.4 Hz, 3H). ES/MS 466.1 (M+H$^+$);

(S)-2,4-diamino-6-((5-chloro-8-fluoro-4-oxo-3-(pyridin-3-yl)-3,4-dihydroquinazolin-2-yl)(cyclopropyl)methylamino)pyrimidine-5-carbonitrile (Compound 27). 1H NMR (400 MHz, DMSO-d6) δ 8.76-8.39 (m, 2H), 8.00-7.64 (m, 2H), 7.68-7.22 (m, 2H), 6.74-6.41 (m, 3H), 6.15 (d, J=24.2 Hz, 2H), 4.48 (td, J=7.8, 1.5 Hz, 1H), 1.54-1.24 (m, 1H), 0.53-0.21 (m, 3H), 0.07--0.13 (m, 1H). ES/MS 478.1 (M+H$^+$);

(S)-2,4-diamino-6-(cyclopropyl(5,8-dichloro-4-oxo-3-(pyridin-3-yl)-3,4-dihydroquinazolin-2-yl)methylamino)pyrimidine-5-carbonitrile (Compound 28). 1H NMR (400 MHz, DMSO-d6) δ 8.78-8.39 (m, 2H), 8.10-7.70 (m, 2H), 7.66-7.13 (m, 2H), 6.74-6.33 (m, 3H), 6.19 (s, 2H), 4.60 (t, J=7.6 Hz, 1H), 1.48-1.21 (m, 1H), 0.49-0.23 (m, 2H), 0.14--0.04 (m, 2H). ES/MS 494.1 (M+H+);

(S)-2,4-diamino-6-(1-(5-chloro-8-fluoro-4-oxo-3-(pyridin-3-yl)-3,4-dihydroquinazolin-2-yl)-2-cyclopropylethylamino)pyrimidine-5-carbonitrile (Compound 29). 1H NMR (400 MHz, DMSO-d6) δ 9.00-8.41 (m, 2H), 8.25-7.82 (m, 1H), 7.80-7.38 (m, 3H), 6.86 (t, J=6.9 Hz, 1H), 6.58 (s, 2H), 6.25 (d, J=26.1 Hz, 2H), 4.59 (qd, J=7.7, 3.9 Hz, 1H), 2.02-1.68 (m, 1H), 1.38 (dddd, J=34.1, 13.0, 7.9, 4.1 Hz, 1H), 0.61 (h, J=6.3 Hz, 1H), 0.42--0.23 (m, 2H), –0.65 (ddq, J=72.7, 9.9, 4.8 Hz, 2H). ES/MS 492.1 (M+H$^+$);

(S)-2,4-diamino-6-(1-(5,8-dichloro-3-(5-fluoropyridin-3-yl)-4-oxo-3,4-dihydroquinazolin-2-yl)ethylamino)pyrimidine-5-carbonitrile (Compound 30). 1H NMR (400 MHz, DMSO-d6) δ 8.78-8.30 (m, 2H), 8.25-7.64 (m, 2H), 7.59 (dt, J=8.5, 1.2 Hz, 1H), 6.87 (dd, J=24.3, 7.4 Hz, 1H), 6.51 (d, J=11.3 Hz, 2H), 6.23 (s, 2H), 4.87 (ddd, J=13.5, 9.8, 6.7 Hz, 1H), 1.43-1.32 (m, 3H). ES/MS 486.0 (M+H$^+$);

(S)-2,4-diamino-6-(1-(5-chloro-8-fluoro-3-(5-fluoropyridin-3-yl)-4-oxo-3,4-dihydroquinazolin-2-yl)ethylamino)pyrimidine-5-carbonitrile (Compound 31). 1H NMR (400 MHz, DMSO-d6) δ 8.83-8.25 (m, 2H), 8.23-7.66 (m, 2H), 7.59 (dd, J=8.8, 4.5 Hz, 1H), 6.90 (dd, J=23.2, 7.2 Hz, 1H), 6.52 (d, J=9.2 Hz, 2H), 6.24 (s, 2H), 4.97-4.46 (m, 1H), 1.33 (dd, J=6.6, 1.6 Hz, 3H). ES/MS 470.1 (M+H$^+$);

(S)-2,4-diamino-6-(1-(5-chloro-8-fluoro-3-(5-methylpyridin-3-yl)-4-oxo-3,4-dihydroquinazolin-2-yl)ethylamino)pyrimidine-5-carbonitrile (Compound 32). 1H NMR (400 MHz, DMSO-d6) δ 8.60-8.15 (m, 2H), 7.93-7.66 (m, 1H), 7.64-7.31 (m, 2H), 7.03-6.67 (m, 1H), 6.51 (d, J=8.2 Hz, 2H), 6.18 (s, 2H), 4.81 (td, J=6.8, 4.8 Hz, 1H), 2.27 (ddd, J=63.2, 1.3, 0.7 Hz, 3H), 1.32 (dd, J=11.5, 6.6 Hz, 3H). ES/MS 466.1 (M+H$^+$);

(S)-2,4-diamino-6-((5-chloro-8-fluoro-3-(5-fluoropyridin-3-yl)-4-oxo-3,4-dihydroquinazolin-2-yl)(cyclopropyl)methylamino)pyrimidine-5-carbonitrile (Compound 33). 1H NMR (400 MHz, DMSO-d6) δ 8.67-8.25 (m, 2H), 8.07 (ddd, J=9.3, 2.7, 1.8 Hz, 1H), 7.93-7.47 (m, 2H), 6.83-6.41 (m, 3H), 6.14 (s, 2H), 4.48 (dt, J=20.2, 7.9 Hz, 1H), 1.67-1.32 (m, 1H), 0.65-0.29 (m, 3H), 0.27-0.01 (m, 1H). ES/MS 496.1 (M+H$^+$);

(S)-2-(1-((2,6-diamino-5-cyanopyrimidin-4-yl)amino)ethyl)-8-fluoro-4-oxo-3-(pyridin-3-yl)-3,4-dihydroquinazoline-5-carbonitrile (Compound 34). $^1$H NMR (400 MHz, DMSO-d$_6$) δ 8.74 (ddd, J=20.2, 2.4, 0.7 Hz, 1H), 8.64 (ddd, J=16.5, 4.8, 1.5 Hz, 1H), 8.14 (dd, J=8.4, 4.5 Hz, 1H), 8.09-7.91 (m, 2H), 7.65-7.49 (m, 1H), 6.93 (dd, J=15.4, 6.9 Hz, 1H), 6.57 (br. s, 2H), 6.37-6.14 (m, 2H), 4.82-4.69 (m, 1H), 1.35 (d, J=6.7 Hz, 3H). ES/MS 443.1 (M+H$^+$);

(S)-2-(1-((2,6-diamino-5-cyanopyrimidin-4-yl)amino)propyl)-8-fluoro-4-oxo-3-(pyridin-3-yl)-3,4-dihydroquinazoline-5-carbonitrile (Compound 35). $^1$H NMR (400 MHz, DMSO-d$_6$) δ 8.72 (ddd, J=7.6, 2.5, 0.7 Hz, 1H), 8.64 (ddd, J=10.1, 4.8, 1.5 Hz, 1H), 8.10 (dd, J=8.4, 4.5 Hz, 1H), 8.01 (dddd, J=11.2, 8.1, 2.5, 1.5 Hz, 1H), 7.92 (ddd, J=9.6, 8.5, 1.0 Hz, 1H), 7.64-7.50 (m, 1H), 6.85-6.71 (m, 1H), 6.55 (br. s, 2H), 6.23 (br. s, 2H), 4.63-4.46 (m, 1H), 1.92-1.61 (m, 2H), 0.68 (td, J=7.3, 5.4 Hz, 3H). ES/MS 457.1 (M+H$^+$);

(S)-2,4-diamino-6-(1-(5-chloro-6-fluoro-4-oxo-3-(pyridin-3-yl)-3,4-dihydroquinazolin-2-yl)ethylamino)pyrimidine-5-carbonitrile (Compound 36). 1H NMR (400 MHz, DMSO-d6) δ 8.74-8.43 (m, 2H), 8.08-7.82 (m, 2H), 7.71 (ddd, J=9.1, 5.0, 3.2 Hz, 1H), 7.51 (dddd, J=28.0, 8.1, 4.8, 0.8 Hz, 1H), 6.85 (dd, J=14.4, 7.0 Hz, 1H), 6.52 (s, 2H), 6.20 (d, J=25.5 Hz, 2H), 4.67 (h, J=6.7 Hz, 1H), 1.29 (d, J=6.7 Hz, 3H). ES/MS 452.1 (M+H$^+$);

(S)-2,4-diamino-6-((5-chloro-6-fluoro-4-oxo-3-(pyridin-3-yl)-3,4-dihydroquinazolin-2-yl)(cyclopropyl)methylamino)pyrimidine-5-carbonitrile (Compound 37). 1H NMR (400 MHz, DMSO-d6) δ 8.74-8.32 (m, 2H), 8.04-7.86 (m, 1H), 7.82-7.58 (m, 1H), 7.44 (dddd, J=60.7, 8.1, 4.8, 0.8 Hz, 1H), 6.72-6.46 (m, 4H), 6.16 (s, 2H), 4.44 (td, J=7.9, 1.7 Hz, 1H), 1.52-1.19 (m, 1H), 0.39 (dddd, J=16.8, 9.7, 7.4, 4.2 Hz, 3H), 0.12--0.19 (m, 1H). ES/MS 478.1 (M+H$^+$);

(S)-2,4-diamino-6-(1-(5-chloro-3-(2-methylpyridin-3-yl)-4-oxo-3,4-dihydroquinazolin-2-yl)ethylamino)pyrimidine-5-carbonitrile (Compound 38). 1H NMR (400 MHz, DMSO) δ 8.31 (dd, J=5.2, 1.5 Hz, 1H), 7.94 (dd, J=7.8, 1.3 Hz, 1H), 7.82 (t, 8.11 Hz, 1H), 7.72 (dd, J=8.11, 1.16 Hz, 1H), 7.61 (dd, J=7.94, 1.04 Hz, 1H), 7.34 (dd, J=7.85, 4.85 Hz, 1H), 5.18 (m, 1H), 2.23 (s, 3H), 1.38 (d, J=6.7 Hz, 3H). ES/MS 448.8 (M+H$^+$);

(S)-2,4-diamino-6-(1-(5-chloro-3-(2-methylpyridin-3-yl)-4-oxo-3,4-dihydroquinazolin-2-yl)ethylamino)pyrimidine-5-carbonitrile (Compound 39). 1H NMR (400 MHz, DMSO) δ 8.4 (dd, J=4.7, 1.6 Hz, 1H), 7.81 (dd, J=8.0, 1.6 Hz, 1H), 7.80 (t, 8.03 Hz, 1H), 7.66 (dd, J=8.21, 1.17 Hz, 1H), 7.59 (dd, J=7.8, 1.17 Hz, 1H), 7.27 (dd, J=7.9, 4.8 Hz, 1H), 4.68 (m, 1H), 2.25 (s, 3H), 1.26 (d, J=6.67 Hz, 3H). ES/MS 448.8 (M+H$^+$);

(S)-2,4-diamino-6-(1-(5-chloro-3-(4-methylpyridin-3-yl)-4-oxo-3,4-dihydroquinazolin-2-yl)ethylamino)pyrimidine-5-carbonitrile (Compound 40). 1H NMR (400 MHz, DMSO) δ 8.68 (s, 1H), 8.37 (d, J=4.9 Hz, 1H), 8.31 (bs, 1H), 7.90 (bs, 1H), 7.83 (t, 8.09 Hz, 1H), 7.74 (dd, J=8.09, 1.22 Hz, 1H), 7.62 (dd, J=7.75, 1.22 Hz, 1H), 7.30 (dd, J=5.25 Hz, 1H), 5.25 (m, 1H), 2.13 (s, 3H), 1.40 (d, J=6.4 Hz, 3H). ES/MS 448.8 (M+H$^+$);

(S)-2,4-diamino-6-(1-(5-chloro-3-(4-methylpyridin-3-yl)-4-oxo-3,4-dihydroquinazolin-2-yl)ethylamino)pyrimidine-5-carbonitrile (Compound 41). 1H NMR (400 MHz, DMSO) δ 8.4 (s, 1H), 8.38 (d, J=5.0 Hz, 1H), 8.11 (bs, 1H), 7.90 (bs, 1H), 7.83 (t, 7.86 Hz, 1H), 7.71 (dd, J=7.9, 1.25 Hz, 1H), 7.63 (dd, J=7.9, 1.25 Hz, 1H), 7.44 (d, J=5.0 Hz, 1H), 4.75 (m, 1H), 2.12 (s, 3H), 1.34 (d, J=6.6 Hz, 3H). ES/MS 448.8 (M+H$^+$);

(S)-2,4-diamino-6-(1-(5-chloro-6-fluoro-3-(4-methylpyridin-3-yl)-4-oxo-3,4-dihydroquinazolin-2-yl)ethylamino)pyrimidine-5-carbonitrile (Compound 42). 1H NMR (400 MHz, DMSO-d6) δ 8.54 (s, 1H), 8.41-8.26 (m, 1H), 7.93 (t, J=9.0 Hz, 1H), 7.84-7.66 (m, 1H), 7.19 (dt, J=5.0, 0.7 Hz, 1H), 6.93 (d, J=8.6 Hz, 1H), 6.47 (s, 2H), 5.73 (s, 2H), 5.25-4.90 (m, 1H), 2.09 (s, 3H), 1.46-1.22 (m, 3H). ES/MS 466.1 (M+H$^+$);

(S)-2,4-diamino-6-(1-(5-chloro-6-fluoro-3-(4-methylpyridin-3-yl)-4-oxo-3,4-dihydroquinazolin-2-yl)ethylamino)pyrimidine-5-carbonitrile (Compound 43). 1H NMR (400 MHz, DMSO-d6) δ 8.58-8.30 (m, 2H), 7.93 (td, J=9.0, 1.3 Hz, 1H), 7.75 (ddd, J=9.0, 5.0, 1.4 Hz, 1H), 7.41 (d, J=5.0 Hz, 1H), 6.94 (d, J=7.4 Hz, 1H), 6.53 (s, 2H), 6.23 (s, 2H), 4.69 (qd, J=7.3, 5.8 Hz, 1H), 2.11 (d, J=1.5 Hz, 3H), 1.26 (dd, J=6.6, 1.5 Hz, 3H). ES/MS 466.1 (M+H$^+$);

(S)-2,4-diamino-6-(1-(5-chloro-3-(5-fluoro-2-methylpyridin-3-yl)-4-oxo-3,4-dihydroquinazolin-2-yl)ethylamino)pyrimidine-5-carbonitrile (Compound 44). 1H NMR (400 MHz, DMSO) δ 8.3 (d, J=2.5 Hz, 2H), 8.16 (bs, 1H), 8.04 (dd, 8.8, 2.6 Hz, 1H), 7.83 (t, J=8.24 Hz, 1H), 7.74 (d, J=8.2 Hz, 1H), 7.66 (d, J=7.7 Hz, 1H), 5.25 (m, 1H), 2.20 (s, 3H), 1.40 (d, J=6.5 Hz, 3H). ES/MS 466.1 (M+H$^+$);

(S)-2,4-diamino-6-(1-(5-chloro-3-(5-fluoro-2-methylpyridin-3-yl)-4-oxo-3,4-dihydroquinazolin-2-yl)ethylamino)pyrimidine-5-carbonitrile (Compound 45). 1H NMR (400 MHz, DMSO) δ 8.5 (d, J=2.8 Hz, 2H), 7.83 (t, J=8.15 Hz, 1H), 7.7 (dd, J=8.15, 1.3 Hz, 1H), 7.66 (dd, J=8.8, 2.7 Hz, 1H), 7.63 (dd, J=7.8, 1.4 Hz, 1H), 7.38 (m, 1H), 7.2 (ddt, J=8.1, 6.7, 1.13 Hz, 1H), 7.16 (ddd, J=6.4, 2.0, 1.2 Hz, 1H), 6.90 (bs, 1H), 4.77 (m, 1H), 2.25 (s, 3H), 1.36 (d, J=6.5 Hz, 3H). ES/MS 466.1 (M+H$^+$);

(S)-2,4-diamino-6-(1-(5-chloro-3-(5-fluoro-4-methylpyridin-3-yl)-4-oxo-3,4-dihydroquinazolin-2-yl)ethylamino)pyrimidine-5-carbonitrile (Compound 46). 1H NMR (400 MHz, DMSO) δ 8.60 (s, 1H), 8.45 (s, 1H), 8.33 (bs, 1H), 7.87 (t, J=8.0 Hz, 1H), 7.78 (dd, J=8.2, 1.2 Hz, 1H), 7.67 (dd, J=7.8, 1.2 Hz, 1H), 7.31 (bs, 1H), 5.30 (m, 1H), 2.08 (s, 3H), 1.44 (d, J=6.5 Hz, 3H). ES/MS 466.8 (M+H$^+$);

(S)-2,4-diamino-6-(1-(5-chloro-3-(5-fluoro-4-methylpyridin-3-yl)-4-oxo-3,4-dihydroquinazolin-2-yl)ethylamino)pyrimidine-5-carbonitrile (Compound 47). 1H NMR (400 MHz, DMSO) δ 8.49 (s, 1H), 8.32 (s, 1H), 7.87 (t, J=8.0 Hz, 2H), 7.76 (dd, J=8.2, 1.2 Hz, 1H), 7.67 (dd, J=7.9, 1.25 Hz, 1H), 4.86 (m, 1H), 2.14 (s, 3H), 1.39 (d, J=6.67 Hz, 3H). ES/MS 466.8 (M+H$^+$);

(S)-2,4-Diamino-6-((1-(5-chloro-8-fluoro-3-(5-fluoropyridin-3-yl)-4-oxo-3,4-dihydroquinazolin-2-yl)propyl)amino)pyrimidine-5-carbonitrile (Compound 48). $^1$H NMR (400 MHz, DMSO-d6) 8.80-8.36 (m, 2H), 7.94-7.38 (m, 3H), 6.94-6.63 (m, 1H), 6.53 (d, J=8.1 Hz, 2H), 6.16 (s, 2H), 4.62 (t, J=7.8 Hz, 1H), 2.10-1.42 (m, 2H), 1.04-0.64 (m, 3H). ES/MS 484.1 (M+H$^+$);

(S)-2-(1-((2,6-diamino-5-chloropyrimidin-4-yl)amino)ethyl)-5-(methylsulfonyl)-3-(pyridin-3-yl)quinazolin-4(3H)-one (Compound 49): $^1$H NMR (400 MHz, DMSO) δ 8.79-8.73 (m, 1H), 8.69-8.63 (m, 1H), 8.35-8.26 (m, 1H), 8.13-7.99 (m, 3H), 7.66-7.53 (m, 1H), 6.34-6.28 (m, 1H), 5.99 (br s, 2H), 5.54 (br s, 1H), 5.48 (br s, 1H), 4.71-4.60 (m, 1H), 3.48 (s, 3H), 1.36-1.32 (m, 3H). ES/MS 487.1 (M+H$^+$);

(S)-2,4-Diamino-6-((1-(5-chloro-4-oxo-3-(pyridin-3-yl)-3,4-dihydroquinazolin-2-yl)ethyl)amino)pyrimidine-5-carboxamide (Compound 50). $^1$H NMR (400 MHz, DMSO-d$_6$) δ 8.71 (dd, J=27.8, 8.2 Hz, 1H), 8.20-7.86 (m, 1H), 7.76-7.42 (m, 2H), 7.02 (d, J=23.4 Hz, 1H), 6.27 (d, J=7.8 Hz, 1H), 5.96-5.52 (m, 1H), 4.57 (dd, J=7.5, 6.7 Hz, 1H), 4.08 (d, J=5.2 Hz, 1H), 3.13 (d, J=4.4 Hz, 2H), 1.34-1.03 (m, 3H). ES/MS 482.1 (M+H$^+$);

(S)-5-Chloro-2-(1-((2,6-diamino-5-chloropyrimidin-4-yl)amino)ethyl)-3-(5-fluoropyridin-3-yl)quinazolin-4(3h)-one (Compound 51). $^1$H NMR (400 MHz, DMSO-d$_6$) δ 8.81-8.44 (m, 2H), 7.78-7.47 (m, 3H), 6.27 (dd, J=7.5, 5.0 Hz, 1H), 5.98-5.84 (m, 1H), 5.47 (s, 1H), 4.87-4.36 (m, 1H), 1.56-1.17 (m, 3H). ES/MS 462.2 (M+H$^+$);

(S)-2-(1-((2,6-Diamino-5-chloropyrimidin-4-yl)amino)ethyl)-5-fluoro-3-(pyridin-3-yl)quinazolin-4(3H)-one (Compound 52). $^1$H NMR (400 MHz, DMSO-$d_6$) δ 8.90-8.34 (m, 2H), 8.10-7.62 (m, 2H), 7.66-7.42 (m, 1H), 7.29 (dd, J=11.0, 8.2 Hz, 1H), 6.18 (d, J=110.3 Hz, 2H), 5.59 (s, 1H), 4.72-4.21 (m, 1H), 1.39-1.12 (m, 3H). ES/MS 426.9 (M+H$^+$);

(S)-5-Chloro-2-(1-((2,6-diamino-5-chloropyrimidin-4-yl)amino)ethyl)-3-(pyridin-3-yl)quinazolin-4(3H)-on (Compound 53). $^1$H NMR (400 MHz, DMSO-$d_6$) δ 8.83-8.51 (m, 2H), 8.25-7.88 (m, 1H), 7.86-7.37 (m, 3H), 6.25 (t, J=8.2 Hz, 1H), 5.97 (s, 2H), 5.50 (d, J=18.3 Hz, 2H), 4.65-4.45 (m, 1H), 1.27 (dd, J=6.7, 1.8 Hz, 3H). ES/MS 444.1 (M+H$^+$);

(S)-2-(1-((2,6-Diamino-5-cyanopyrimidin-4-yl)amino)ethyl)-6-fluoro-4-oxo-3-(pyridin-3-yl)-3,4-dihydroquinazoline-8-carbonitrile (Compound 54): $^1$H NMR (400 MHz, DMSO) δ 8.78 (d, J=2.4 Hz, 0.5H), 8.59 (m, 1H), 8.57 (t, J=2.8 Hz, 0.5H), 8.51 (dd, J=4.8, 1.6 Hz, 0.5H), 8.48 (d, J=2.4 Hz, 0.5H), 8.22 (m, 1H), 8.06 (m, 0.5H), 7.88 (bm, 4H), 7.79 (m, 0.5H), 7.58 (dd, J=8.0, 4.8 Hz, 0.5H), 7.47 (dd, J=8.0, 4.8 Hz, 0.5H), 5.02 (m, 1H), 1.46 (d, J=6.4 Hz, 3H). ES/MS 443.1 (M+H$^+$);

(S)-2-(1-((2,6-Diamino-5-cyanopyrimidin-4-yl)amino)propyl)-6-fluoro-3-(5-fluoropyridin-3-yl)-4-oxo-3,4-dihydroquinazoline-8-carbonitrile (Compound 55): $^1$H NMR (400 MHz, DMSO) δ 8.71 (s, 1H), 8.64 (d, J=2.8 Hz, 1H), 8.58 (m, 3H), 8.34 (s, 1H), 8.23 (m, 2H), 8.18 (m, 1H), 7.84 (bs, 1H), 7.71 (m, 1H), 4.92 (m, 1H), 2.08 (m, 1H), 1.88 (m, 1H), 0.90 (m, 3H). ES/MS 475.1 (M+H$^+$);

(S)-2-(Cyclopropyl((2,6-diamino-5-cyanopyrimidin-4-yl)amino)methyl)-6-fluoro-3-(5-fluoropyridin-3-yl)-4-oxo-3,4-dihydroquinazoline-8-carbonitrile (Compound 56): $^1$H NMR (400 MHz, DMSO) δ 8.69 (s, 0.5H), 8.60 (m, 1.5H), 8.49 (d, J=2.4 Hz, 0.5H), 8.23 (m, 1.5H), 8.17 (m, 0.5H), 7.95 (bs, 1H), 7.78 (bs, 1H), 7.71 (bs, 1H), 7.59 (m, 0.5H), 4.60 (m, 1H), 1.64 (ml, 1H), 0.60 (m, 1H), 0.50 (m, 2H), 0.29 (m, 1H). ES/MS 487.1 (M+H$^+$);

(S)-2,4-Diamino-6-((1-(5-chloro-3-(5-fluoropyridin-3-yl)-4-oxo-3,4-dihydroquinazolin-2-yl)-3-methylbutyl)amino)pyrimidine-5-carbonitrile (Compound 57). $^1$H NMR (400 MHz, DMSO) δ 8.83-8.58 (m, 2H), 8.24 (dd, J=9.3, 2.2 Hz, 1H), 8.09 (m, 1H), 7.83-7.70 (m, 1H), 7.70-7.49 (m, 2H), 4.70 (m, 1H), 4.01-3.29 (br m, 5H) 1.81 (m, 1H), 1.50 (m, 2H), 0.78 (m, 3H), 0.48-0.33 (m, 3H). ES/MS 494.2 (M+H$^+$);

(R)-2,4-Diamino-6-((1-(5-chloro-8-fluoro-4-oxo-3-(pyridin-3-yl)-3,4-dihydroquinazolin-2-yl)ethyl)amino)pyrimidine-5-carbonitrile (Compound 110). $^1$H NMR (400 MHz, DMSO) δ 8.75-8.51 (m, 2H), 8.05-7.89 (m, 1H), 7.84-7.75 (m, 1H), 7.67-7.45 (m, 2H), 4.83 (m, 1H) 4.42-3.27 (br m, 5H) 1.36 (d, J=6.6 Hz, 3H). ES/MS 452.1 (M+H$^+$);

(S)-2,4-Diamino-6-((1-(5-chloro-4-oxo-3-(pyridin-3-yl)-3,4-dihydroquinazolin-2-yl)-3-methylbutyl)amino)pyrimidine-5-carbonitrile (Compound 58). $^1$H NMR (400 MHz, DMSO) δ 8.82-8.75 (m, 1H), 8.67 (ddd, J=13.2, 4.8, 1.5 Hz, 1H), 8.09 (ddd, J=8.3, 5.3, 3.3 Hz, 1H), 7.78 (td, J=8.1, 2.0 Hz, 1H), 7.69-7.55 (m, 3H), 7.51-6.88 (br m, 5H) 4.70 (m, 1H), 1.83 (d, J=9.8 Hz, 1H), 1.50-1.37 (m, 2H), 0.76 (dd, J=9.3, 5.9 Hz, 3H), 0.37-0.25 (m, 3H). ES/MS 476.1 (M+H$^+$);

(R)-2,4-Diamino-6-((1-(5-chloro-8-fluoro-3-(5-fluoropyridin-3-yl)-4-oxo-3,4-dihydroquinazolin-2-yl)ethyl)amino)pyrimidine-5-carbonitrile (Compound 113). $^1$H NMR (400 MHz, DMSO) δ 8.68 (m, 1H), 8.58-8.42 (m, 1H), 8.15-7.81 (m, 2H), 7.66 (d, J=8.5 Hz, 1H), 7.56-7.37 (br m, 2H), 7.26-7.00 (br m, 2H), 6.83-6.67 (m, 1H) 4.92 (m, 1H), 1.39 (m, 3H). ES/MS 470.1 (M+H$^+$);

(S)-5-Chloro-2-(1-((2,6-diamino-5-chloropyrimidin-4-yl)amino)ethyl)-8-fluoro-3-(pyridin-3-yl)quinazolin-4(3h)-one;

(R)-2,4-Diamino-6-((1-(5-chloro-8-fluoro-4-oxo-3-(pyridin-3-yl)-3,4-dihydroquinazolin-2-yl)propyl)amino)pyrimidine-5-carbonitrile (compound 111). $^1$H NMR (400 MHz, DMSO) δ 8.82-8.50 (m, 2H), 8.15-7.93 (m, 1H), 7.91-7.74 (m, 2H), 7.71-7.48 (m, 3H), 7.41 (ddd, J=8.6, 7.4, 1.4 Hz, 1H), 7.28-7.12 (m, 2H), 6.79-6.69 (m, 1H), 4.71 (m, 1H), 2.05-1.90 (m, 1H), 1.90-1.74 (m, 1H), 0.82-0.68 (m, 3H). ES/MS 466.1 (M+H$^+$);

(R)-2,4-Diamino-6-(((5-chloro-8-fluoro-4-oxo-3-(pyridin-3-yl)-3,4-dihydroquinazolin-2-yl)(cyclopropyl)methyl)amino)pyrimidine-5-carbonitrile (Compound 112). $^1$H NMR (400 MHz, DMSO) δ 8.78-8.32 (m, 2H), 8.12-7.88 (m, 5H), 7.82 (m, 1H), 7.74-7.62 (m, 2H), 7.39 (m, 1H), 6.77-6.70 (m, 1H), 4.54-4.42 (m, 1H), 1.63-1.47 (m, 1H), 0.62-0.08 (m, 4H). ES/MS 478.1 (M+H$^+$);

(S)-2,4-diamino-6-((1-(5-bromo-8-fluoro-3-(5-fluoropyridin-3-yl)-4-oxo-3,4-dihydroquinazolin-2-yl)ethyl)amino)pyrimidine-5-carbonitrile (Compound 60). $^1$H NMR (400 MHz, DMSO-$d_6$) δ 8.65-8.43 (m, 2H), 8.15-8.06 (m, 1H), 7.84-7.76 (m, 1H), 7.68 (t, J=9.2 Hz, 1H), 6.95-6.81 (m, 1H), 6.51 (d, J=10.8 Hz, 2H), 6.22 (s, 2H), 4.88-4.71 (m, 1H), 1.39-1.27 (m, 3H). ES/MS 514.0 (M+H$^+$);

(S)-2,4-Diamino-6-((1-(5-bromo-8-fluoro-4-oxo-3-(pyridin-3-yl)-3,4-dihydroquinazolin-2-yl)propyl)amino)pyrimidine-5-carbonitrile (Compound 61). $^1$H NMR (400 MHz, DMSO-$d_6$) δ 8.81-8.61 (m, 1H), 8.60-8.48 (m, 1H), 8.11-7.64 (m, 3H), 7.64-7.48 (m, 2H), 7.33 (br. s, 4H), 4.76-4.58 (m, 1H), 2.05-1.69 (m, 2H), 0.84-0.66 (m, 3H). ES/MS 510.1 (M+H$^+$);

(S)-2-(1-((2,6-diamino-5-cyanopyrimidin-4-yl)amino)ethyl)-8-fluoro-3-(5-fluoropyridin-3-yl)-4-oxo-3,4-dihydroquinazoline-5-carbonitrile (Compound 62). $^1$H NMR (400 MHz, DMSO-$d_6$) δ 8.73-8.45 (m, 2H), 8.24-7.83 (m, 3H), 7.83-7.01 (br. m, 5H), 5.03-4.87 (m, 1H), 1.42 (d, J=6.6 Hz, 3H). ES/MS 461.1 (M+H$^+$);

(S)-2-(1-((2,6-diamino-5-chloropyrimidin-4-yl)amino)ethyl)-4-oxo-3-(pyridin-3-yl)-3,4-dihydroquinazoline-5-carbonitrile (Compound 63). $^1$H NMR (400 MHz, DMSO-$d_6$) δ 8.82-8.75 (m, 1H), 8.72-8.62 (m, 1H), 8.15-7.92 (m, 4H), 7.67-7.52 (m, 1H), 6.32-6.24 (m, 1H), 6.00 (s, 2H), 5.53 (d, J=17.8 Hz, 2H), 4.67-4.51 (m, 1H), 1.40-1.25 (m, 3H). ES/MS 434.1 (M+H$^+$);

(S)-2,4-Diamino-6-((1-(5-bromo-8-fluoro-4-oxo-3-(pyridin-3-yl)-3,4-dihydroquinazolin-2-yl)ethyl)amino)pyrimidine-5-carbonitrile (Compound 64). $^1$H NMR (400 MHz, DMSO-$d_6$) δ 8.77-8.64 (m, 1H), 8.64-8.51 (m, 1H), 8.08-7.89 (m, 1H), 7.85-7.76 (m, 1H), 7.69 (t, J=9.2 Hz, 1H), 7.61-7.45 (m, 1H), 6.97-6.82 (m, 1H), 6.55 (d, J=5.4 Hz, 2H), 6.25 (br. d, J=16.7 Hz, 2H), 4.80-4.65 (m, 1H), 1.33 (d, J=6.6 Hz, 3H). ES/MS 496.1 (M+H$^+$);

(S)-2,4-Diamino-6-(((5-chloro-8-fluoro-3-(5-fluoro-4-methylpyridin-3-yl)-4-oxo-3,4-dihydroquinazolin-2-yl)(cyclopropyl)methyl)amino)pyrimidine-5-carbonitrile (Compound 65): $^1$H NMR (400 MHz, DMSO-$d_6$) δ 8.55 (m, 1H), 8.38 (m, 1H), 7.82 (dd, J=9.6, 8.8 Hz, 1H), 7.65 (dd, J=8.8, 4.5 Hz, 1H), 4.63 (t, J=8.7 Hz, 1H), 2.01 (s, 3H), 1.63 (m, 1H), 0.61 (m, 1H), 0.41 (m, 2H), 0.30 (m, 1H). ES/MS 510.1 (M+H$^+$);

(S)-2,4-Diamino-6-(((5-chloro-8-fluoro-3-(5-fluoro-4-methylpyridin-3-yl)-4-oxo-3,4-dihydroquinazolin-2-yl)(cyclopropyl)methyl)amino)pyrimidine-5-carbonitrile (Compound 66). $^1$H NMR (400 MHz, DMSO-$d_6$) δ 8.38 (s, 1H), 8.15 (s, 1H), 7.80 (dd, J=9.6, 8.8 Hz, 1H), 7.65 (dd, J=8.8, 4.5 Hz, 1H), 4.24 (t, J=8.34 Hz, 1H), 2.09 (s, 3H), 1.59 (m, 1H), 0.55 (m, 1H), 0.44 (m, 2H), 0.07 (m, 1H). ES/MS 510.1 (M+H$^+$);

(S)-2,4-diamino-6-((1-(5-fluoro-3-(5-fluoro-4-methylpyridin-3-yl)-4-oxo-3,4-dihydroquinazolin-2-yl)ethyl)amino)pyrimidine-5-carbonitrile (Compound 67): $^1$H NMR (400 MHz, DMSO-d$_6$) δ 8.55 (s, 1H), 8.39 (s, 1H), 7.90 (td, J=8.2, 8.2, 5.5 Hz, 1H), 7.62 (dd, J=8.3, 1.0 Hz, 1H) 7.37 (ddd, J=10.9, 8.2, 1.0 Hz, 1H), 5.28 (dd, J=8.6, 6.5 Hz, 1H), 2.05 (s, 3H), 1.40 (d, J=6.5 Hz, 3H). ES/MS 450.1 (M+H$^+$);

(S)-2,4-diamino-6-((1-(5-fluoro-3-(5-fluoro-4-methylpyridin-3-yl)-4-oxo-3,4-dihydroquinazolin-2-yl)ethyl)amino)pyrimidine-5-carbonitrile (Compound 68): $^1$H NMR (400 MHz, DMSO-d$_6$) 8.44 (s, 1H), 8.31 (s, 1H), 7.90 (td, J=8.2, 8.2, 5.5 Hz, 1H), 7.59 (dd, J=8.2, 1.0 Hz, 1H) 7.37 (ddd, J=11.0, 8.3, 1.1 Hz, 1H), 4.82 (p, J=6.8, 6.7 Hz, 1H), 2.08 (s, 3H), 1.36 (d, J=6.6 Hz, 3H). S/MS 450.1 (M+H$^+$);

(S)-2,4-diamino-6-(((5-chloro-3-(5-fluoro-4-methylpyridin-3-yl)-4-oxo-3,4-dihydroquinazolin-2-yl)(cyclopropyl)methyl)amino)pyrimidine-5-carbonitrile (Compound 69): $^1$H NMR (400 MHz, DMSO-d$_6$) δ 8.54 (s, 1H), 8.38 (s, 1H), 7.84 (t, J=8.0 Hz, 1H), 7.75 (d, J=8.0 Hz, 1H), 7.64 (d, J=7.8 Hz, 1H), 4.60 (t, J=8.8 Hz, 1H), 2.00 (s, 3H), 1.62 (m, 1H), 0.61 (m, 1H), 0.41 (m, 2H), 0.30 (m, 1H). ES/MS 492.1 (M+H$^+$);

(S)-2,4-diamino-6-(((5-chloro-3-(5-fluoro-4-methylpyridin-3-yl)-4-oxo-3,4-dihydroquinazolin-2-yl)(cyclopropyl)methyl)amino)pyrimidine-5-carbonitrile (Compound 70): $^1$H NMR (400 MHz, DMSO-d$_6$) δ 8.39 (s, 1H), 8.16 (s, 1H), 7.84 (t, J=8.0 Hz, 1H), 7.75 (dd, J=8.0, 1.2 Hz, 1H), 7.65 (dd, J=7.8, 1.2 Hz, 1H), 4.21 (t, J=8.4 Hz, 1H), 2.07 (s, 3H), 1.59 (m, 1H), 0.57 (m, 1H), 0.43 (m, 2H), 0.02 (m, 1H). ES/MS 492.1 (M+H$^+$);

(S)-2,4-diamino-6-((1-(5-chloro-3-(5-fluoro-4-methylpyridin-3-yl)-4-oxo-3,4-dihydroquinazolin-2-yl)propyl)amino)pyrimidine-5-carbonitrile (Compound 71): $^1$H NMR (400 MHz, DMSO-d$_6$) δ 8.56 (s, 1H), 8.42 (s, 1H), 7.83 (t, J=8.0 Hz, 1H), 7.73 (dd, J=8.1, 1.3 Hz, 1H), 7.63 (dd, J=7.8, 1.3 Hz, 1H), 5.09 (q, J=7.8 Hz, 1H), 2.13 (dt, J=13.9, 7.0 Hz, 1H), 2.00 (s, 3H), 1.79 (dt, J=14.5, 7.5 Hz, 1H), 0.82 (t, J=7.4 Hz, 1H). ES/MS 480.1 (M+H$^+$);

(S)-2,4-diamino-6-((1-(5-chloro-3-(5-fluoro-4-methylpyridin-3-yl)-4-oxo-3,4-dihydroquinazolin-2-yl)propyl)amino)pyrimidine-5-carbonitrile (Compound 72): $^1$H NMR (400 MHz, DMSO-d$_6$) 8.44 (s, 1H), 8.23 (s, 1H), 7.83 (t, J=8.0 Hz, 1H), 7.73 (dd, J=8.0 Hz, 1H), 7.63 (d, J=8.0 Hz, 1H), 4.63 (q, J=7.1 Hz, 1H), 2.1 (s, 3H), 2.04 (dq, J=13.9, 7.0 Hz, 1H), 1.67 (dp, J=14.3, 7.4, 7.2 Hz, 1H), 0.80 (t, J=7.3 Hz, 1H). ES/MS 480.1 (M+H$^+$);

(S)-2,4-diamino-6-((1-(5-chloro-8-fluoro-3-(5-fluoro-4-methylpyridin-3-yl)-4-oxo-3,4-dihydroquinazolin-2-yl)ethyl)amino)pyrimidine-5-carbonitrile (Compound 73): $^1$H NMR (400 MHz, DMSO-d$_6$) 88.57 (s, 1H), 8.42 (s, 1H), 7.82 (dd, J=9.6, 8.8 Hz, 1H), 7.65 (dd, J=8.8, 4.5 Hz, 1H), 5.28 (m, 1H), 2.05 (s, 3H), 1.42 (d, J=6.5 Hz, 3H). ES/MS 484.1 (M+H$^+$);

(S)-2,4-diamino-6-((1-(5-chloro-8-fluoro-3-(5-fluoro-4-methylpyridin-3-yl)-4-oxo-3,4-dihydroquinazolin-2-yl)ethyl)amino)pyrimidine-5-carbonitrile (Compound 74): $^1$H NMR (400 MHz, DMSO-d$_6$) δ 8.45 (s, 1H), 8.28 (s, 1H), 7.81 (dd, J=9.6, 8.8 Hz, 1H), 7.65 (dd, J=8.8, 4.5 Hz, 1H), 4.83 (m, 1H), 2.12 (s, 3H), 1.36 (d, J=6.6 Hz, 3H). ES/MS 484.1 (M+H$^+$);

(S)-2,4-diamino-6-((1-(6-fluoro-3-(5-fluoro-4-methylpyridin-3-yl)-4-oxo-3,4-dihydroquinazolin-2-yl)amino)pyrimidine-5-carbonitrile (Compound 75): $^1$H NMR (400 MHz, DMSO-d$_6$) δ 8.57 (s, 1H), 8.41 (s, 1H), 7.9-7.8 (m, 3H), 5.32 (m, 1H), 2.03 (s, 3H), 1.42 (d, J=6.5 Hz, 3H). ES/MS 450.1 (M+H$^+$);

(S)-2,4-diamino-6-((1-(6-fluoro-3-(5-fluoro-4-methylpyridin-3-yl)-4-oxo-3,4-dihydroquinazolin-2-yl)ethyl)amino)pyrimidine-5-carbonitrile (Compound 76): $^1$H NMR (400 MHz, DMSO-d$_6$) δ 8.45 (s, 1H), 8.29 (s, 1H), 7.9-7.8 (m, 3H), 4.86 (m, 1H), 2.08 (s, 3H), 1.37 (d, J=6.6 Hz, 3H). ES/MS 450.1 (M+H$^+$);

(S)-2,4-diamino-6-((1-(5-chloro-3-(4,5-dimethylpyridin-3-yl)-4-oxo-3,4-dihydroquinazolin-2-yl)ethyl)amino)pyrimidine-5-carbonitrile (Compound 77): $^1$H NMR (400 MHz, DMSO-d$_6$) δ 8.57 (s, 1H), 8.29 (s, 1H), 7.83 (t, J=8.2 Hz, 1H), 7.74 (dd, J=8.2, 1.3 Hz, 1H) 7.62 (dd, J=7.8, 1.3 Hz, 1H), 5.28 (m, 1H), 2.12 (s, 3H), 2.03 (s, 3H), 1.40 (d, J=6.5 Hz, 3H). ES/MS 462.1 (M+H$^+$);

(S)-2,4-diamino-6-((1-(5-chloro-3-(4,5-dimethylpyridin-3-yl)-4-oxo-3,4-dihydroquinazolin-2-yl)ethyl)amino)pyrimidine-5-carbonitrile (Compound 78): $^1$H NMR (400 MHz, DMSO-d$_6$) δ 8.24 (s, 1H), 8.21 (s, 1H), 7.82 (t, J=8.2 Hz, 1H), 7.71 (dd, J=8.2, 1.2 Hz, 1H) 7.62 (dd, J=7.8, 1.2 Hz, 1H), 4.83 (m, 1H), 2.30 (s, 3H), 2.05 (s, 3H), 1.33 (d, J=6.6 Hz, 3H). ES/MS 462.1 (M+H$^+$);

(S)-2,4-Diamino-6-((1-(3-(4-methylpyridin-3-yl)-4-oxo-5-(trifluoromethyl)-3,4-dihydroquinazolin-2-yl)ethyl)amino)pyrimidine-5-carbonitrile (Compound 79). $^1$H NMR (400 MHz, DMSO-d6) δ 8.57 (d, J=0.9 Hz, 1H), 8.33 (dd, J=4.9, 1.0 Hz, 1H), 8.17-7.90 (m, 3H), 7.36-7.07 (m, 1H), 6.97 (d, J=8.7 Hz, 1H), 6.46 (s, 2H), 5.31-4.94 (m, 1H), 2.07 (s, 3H), 1.37 (d, J=6.4 Hz, 3H). ES/MS 482.2 (M+H$^+$);

(S)-2,4-Diamino-6-((1-(3-(4-methylpyridin-3-yl)-4-oxo-5-(trifluoromethyl)-3,4-dihydroquinazolin-2-yl)ethyl)amino)pyrimidine-5-carbonitrile (Compound 80). $^1$H NMR (400 MHz, DMSO-d6) δ 8.52 (s, 1H), 8.41 (d, J=5.0 Hz, 1H), 7.42 (dt, J=5.1, 0.7 Hz, 1H), 6.98 (d, J=7.1 Hz, 1H), 6.52 (s, 2H), 4.74 (p, J=6.7 Hz, 1H), 2.08 (s, 3H), 1.27 (d, J=6.7 Hz, 3H). ES/MS 482.2 (M+H$^+$);

(S)-3-(6-aminopyridin-3-yl)-8-chloro-2-(1-((2,6-diamino-5-chloropyrimidin-4-yl)amino)ethyl)-6-fluoroquinazolin-4(3H)-one (Compound 81). $^1$H NMR (400 MHz, DMSO-d$_6$) δ 8.11 (dt, J=9.6, 3.2 Hz, 1H), 8.06-7.96 (m, 1H), 7.80 (dd, J=8.0, 2.9 Hz, 1H), 7.53 (ddd, J=8.6, 5.3, 2.8 Hz, 1H), 6.59 (dd, J=8.7, 6.1 Hz, 1H), 6.39 (d, J=9.0 Hz, 2H), 6.03 (d, J=7.2 Hz, 2H), 5.62 (d, J=12.1 Hz, 2H), 4.79 (dt, J=30.2, 7.2 Hz, 1H), 1.36-1.21 (m, 3H). ES/MS 476.1 (M+H$^+$);

(S)-2,4-diamino-6-((1-(3-(6-aminopyridin-3-yl)-8-chloro-6-fluoro-4-oxo-3,4-dihydroquinazolin-2-yl)ethyl)amino)pyrimidine-5-carbonitrile (Compound 82). $^1$H NMR (400 MHz, DMSO-d$_6$) δ 8.12 (dt, J=8.7, 2.3 Hz, 1H), 8.01 (dd, J=21.8, 2.6 Hz, 1H), 7.81 (dd, J=8.3, 3.0 Hz, 1H), 7.51 (ddd, J=9.0, 6.3, 2.7 Hz, 1H), 6.89 (dd, J=42.5, 6.9 Hz, 2H), 6.62-6.52 (m, 2H), 6.37 (d, J=6.6 Hz, 3H), 4.86 (dt, J=23.9, 6.6 Hz, 1H), 1.38-1.21 (m, 3H). ES/MS 467.1 (M+H$^+$);

(S)-3-(6-aminopyridin-3-yl)-5,8-dichloro-2-(1-((2,6-diamino-5-chloropyrimidin-4-yl)amino)ethyl)quinazolin-4(3H)-one (Compound 83). $^1$H NMR (400 MHz, DMSO-d$_6$) δ 8.05-7.92 (m, 1H), 7.54 (ddt, J=11.5, 8.0, 3.4 Hz, 1H), 6.69-6.47 (m, 1H), 6.39 (dd, J=8.4, 4.1 Hz, 1H), 6.02 (d, J=6.5 Hz, 1H), 5.62 (d, J=10.2 Hz, 1H), 4.74 (dt, J=33.1, 7.0 Hz, 1H), 2.54 (s, 2H), 1.35-1.21 (m, 3H). ES/MS 492.1 (M+H$^+$);

(S)-2,4-diamino-6-((1-(3-(6-aminopyridin-3-yl)-5,8-dichloro-4-oxo-3,4-dihydroquinazolin-2-yl)ethyl)amino)pyrimidine-5-carbonitrile (Compound 84). $^1$H NMR (400 MHz, DMSO-d$_6$) δ 8.06-7.90 (m, 2H), 7.60-7.47 (m, 2H), 6.88 (dd, J=44.9, 6.9 Hz, 2H), 6.63-6.52 (m, 2H), 6.37 (d, J=8.0 Hz, 3H), 4.83 (dq, J=26.5, 6.7 Hz, 1H), 1.38-1.21 (m, 3H). ES/MS 483.1 (M+H$^+$);

(S)-3-(6-aminopyridin-3-yl)-5-chloro-2-(1-((2,6-diamino-5-chloropyrimidin-4-yl)amino)ethyl)quinazolin-4(3H)-one (Compound 85). $^1$H NMR (400 MHz, DMSO-d$_6$) δ

8.01 (dt, J=39.3, 2.5 Hz, 2H), 7.79-7.67 (m, 1H), 7.64-7.47 (m, 4H), 6.58 (ddd, J=11.5, 8.8, 2.0 Hz, 1H), 6.38-6.21 (m, 3H), 6.02 (d, J=8.8 Hz, 1H), 5.56 (d, J=13.9 Hz, 1H), 4.81-4.49 (m, 1H), 1.31 (ddd, J=12.4, 7.1, 2.2 Hz, 3H). ES/MS 458.1 (M+H$^+$);

(S)-3-(6-aminopyridin-3-yl)-5-chloro-2-(1-((2,6-diamino-5-chloropyrimidin-4-yl)amino)propyl)quinazolin-4(3H)-one (Compound 86). $^1$H NMR (400 MHz, DMSO-d$_6$) δ 8.16-7.89 (m, 1H), 7.73 (td, J=8.0, 2.7 Hz, 1H), 7.62-7.47 (m, 4H), 6.61 (ddd, J=19.4, 8.8, 0.8 Hz, 1H), 6.35 (d, J=11.5 Hz, 1H), 6.18-6.01 (m, 3H), 5.56 (d, J=15.9 Hz, 1H), 4.59 (dtd, J=35.7, 8.3, 3.6 Hz, 1H), 1.86-1.58 (m, 2H), 0.76-0.68 (m, 3H). ES/MS 472.1 (M+H$^+$);

(S)-2,4-diamino-6-((1-(3-(6-aminopyridin-3-yl)-5-chloro-4-oxo-3,4-dihydroquinazolin-2-yl)propyl)amino)pyrimidine-5-carbonitrile (Compound 87). $^1$H NMR (400 MHz, DMSO-d$_6$) δ 8.19-7.89 (m, 1H), 7.76 (td, J=8.0, 2.4 Hz, 1H), 7.65-7.45 (m, 2H), 6.91-6.50 (m, 3H), 6.37 (s, 3H), 4.66 (dtd, J=30.1, 7.7, 3.9 Hz, 1H), 1.93-1.59 (m, 2H), 0.71 (td, J=7.3, 4.8 Hz, 3H). ES/MS 463.1 (M+H$^+$);

(S)-3-(6-aminopyridin-3-yl)-5-chloro-2-(1-((2,6-diamino-5-chloropyrimidin-4-yl)amino)ethyl)-8-fluoroquinazolin-4(3H)-one (Compound 88). $^1$H NMR (400 MHz, DMSO-d$_6$) δ 8.01 (d, J=37.3 Hz, 1H), 7.70 (t, J=9.3 Hz, 1H), 7.68-7.35 (m, 1H), 6.58 (t, J=8.4 Hz, 2H), 6.49-6.20 (m, 1H), 6.01 (s, 1H), 5.57 (d, J=12.7 Hz, 2H), 4.73 (s, 1H), 1.42-1.11 (m, 3H). ES/MS 476.1 (M+H$^+$);

(S)-3-(6-aminopyridin-3-yl)-5-chloro-2-(cyclopropyl((2,6-diamino-5-chloropyrimidin-4-yl)amino)methyl)quinazolin-4(3H)-one (Compound 89). $^1$H NMR (400 MHz, DMSO-d$_6$) δ 8.08-7.88 (m, 1H), 7.83-7.68 (m, 1H), 7.69-7.40 (m, 2H), 6.59 (dd, J=8.6, 3.1 Hz, 1H), 6.46-6.27 (m, 1H), 6.16-5.86 (m, 2H), 5.57 (d, J=6.6 Hz, 1H), 4.67 (q, J=8.1 Hz, 1H), 1.21 (d, J=22.0 Hz, 2H), 0.54-0.34 (m, 2H), 0.34-0.19 (m, 1H). ES/MS 484.1 (M+H+);

(S)-2,4-diamino-6-(((3-(6-aminopyridin-3-yl)-5-chloro-4-oxo-3,4-dihydroquinazolin-2-yl)(cyclopropyl)methyl)amino)pyrimidine-5-carbonitrile (Compound 90). $^1$H NMR (400 MHz, DMSO-d$_6$) δ 8.01-7.91 (m, 1H), 7.78 (td, J=8.0, 2.0 Hz, 1H), 7.66-7.54 (m, 2H), 7.48 (dd, J=8.9, 3.0 Hz, 1H), 6.66 (d, J=9.5 Hz, 2H), 6.56 (dd, J=12.7, 8.7 Hz, 2H), 6.35 (s, 2H), 4.70 (dt, J=10.0, 7.3 Hz, 1H), 1.22 (d, J=11.5 Hz, 1H), 0.45-0.37 (m, 2H), 0.18-0.02 (m, 2H). ES/MS 475.1 (M+H$^+$);

(S)-2,4-diamino-6-((1-(3-(6-amino-4-methylpyridin-3-yl)-5-chloro-4-oxo-3,4-dihydroquinazolin-2-yl)propyl)amino)pyrimidine-5-carbonitrile (Compound 91). $^1$H NMR (400 MHz, DMSO-d$_6$) δ 7.87 (s, 1H), 7.80 (t, J=8.0 Hz, 1H), 7.61 (ddd, J=17.6, 7.9, 1.3 Hz, 1H), 6.67 (s, 1H), 6.49-6.41 (m, 2H), 6.21 (s, 1H), 4.82 (td, J=8.2, 4.2 Hz, 1H), 1.90 (s, 3H), 1.67 (dp, J=14.4, 7.2 Hz, 1H), 1.25 (dd, J=11.4, 5.0 Hz, 1H), 0.74 (t, J=7.3 Hz, 3H). ES/MS 477.1 (M+H$^+$);

(S)-2,4-diamino-6-((1-(3-(6-amino-4-methylpyridin-3-yl)-5-chloro-4-oxo-3,4-dihydroquinazolin-2-yl)propyl)amino)pyrimidine-5-carbonitrile (Compound 92). $^1$H NMR (400 MHz, DMSO-d$_6$) δ 7.94 (s, 1H), 7.80 (t, J=8.0 Hz, 1H), 7.61 (ddd, J=16.0, 8.0, 1.2 Hz, 2H), 6.86 (d, J=7.0 Hz, 1H), 6.63 (s, 2H), 6.45 (d, J=7.0 Hz, 1H), 6.35 (s, 2H), 6.27 (s, 2H), 4.78 (td, J=6.8, 4.8 Hz, 1H), 1.94 (s, 3H), 1.84-1.69 (m, 1H), 1.60 (dp, J=13.7, 7.0 Hz, 1H), 0.73 (t, J=7.3 Hz, 3H). ES/MS 477.1 (M+H$^+$);

(S)-2,4-diamino-6-((1-(3-(6-amino-4-methylpyridin-3-yl)-5-chloro-4-oxo-3,4-dihydroquinazolin-2-yl)ethyl)amino)pyrimidine-5-carbonitrile (Compound 93). $^1$H NMR (400 MHz, DMSO-d$_6$) 7.98 (s, 1H), 7.79 (t, J=8.0 Hz, 1H), 7.60 (ddd, J=13.9, 8.1, 1.2 Hz, 2H), 6.99 (d, J=6.6 Hz, 1H), 6.62 (s, 2H), 6.43 (s, 1H), 6.37 (s, 2H), 6.22 (s, 2H), 4.83 (p, J=6.6 Hz, 1H), 1.93 (s, 3H), 1.24 (d, J=6.7 Hz, 3H). ES/MS 463.1 (M+H$^+$);

(S)-2,4-diamino-6-((1-(3-(6-amino-4-methylpyridin-3-yl)-5-chloro-4-oxo-3,4-dihydroquinazolin-2-yl)ethyl)amino)pyrimidine-5-carbonitrile (Compound 94). $^1$H NMR (400 MHz, DMSO-d$_6$) δ 7.98 (s, 1H), 7.80 (dd, J=7.8 Hz, 1H), 7.66-7.55 (m, 2H), 6.98 (d, J=6.6 Hz, 1H), 6.61 (s, 2H), 6.43 (t, J=0.8 Hz, 1H), 6.37 (s, 2H), 6.22 (s, 2H), 4.83 (p, J=6.6 Hz, 1H), 1.93 (d, J=0.7 Hz, 3H), 1.24 (d, J=6.7 Hz, 3H). ES/MS 463.1 (M+H$^+$);

(S)-2,4-diamino-6-((1-(3-(6-amino-4-methylpyridin-3-yl)-5,8-dichloro-4-oxo-3,4-dihydroquinazolin-2-yl)ethyl)amino)pyrimidine-5-carbonitrile (Compound 95): $^1$H NMR (400 MHz, DMSO-d$_6$) δ 8.13 (s, 1H), 8.04 (d, J=8.5 Hz, 1H), 7.62 (d, J=8.5 Hz, 2H), 7.32 (s, 1H), 6.83 (s, 1H), 6.58 (s, 1H), 6.5 (s, 1H), 5.39 (q, J=7.1, 6.6 Hz, 1H), 2.05 (s, 3H), 1.45 (d, J=6.5 Hz, 3H). ES/MS 498.1 (M+H$^+$);

(S)-2,4-diamino-6-((1-(3-(6-amino-4-methylpyridin-3-yl)-5,8-dichloro-4-oxo-3,4-dihydroquinazolin-2-yl)ethyl)amino)pyrimidine-5-carbonitrile (Compound 96): $^1$H NMR (400 MHz, DMSO-d$_6$) δ 8.05 (d, J=8.5 Hz, 1H), 7.92 (s, 1H), 7.65 (d, J=8.5 Hz, 1H), 6.84 (s, 1H), 4.98 (p, J=6.7 Hz, 1H), 2.12 (s, 3H), 1.39 (d, J=6.6 Hz, 3H). ES/MS 498.1 (M+H$^+$);

(S)-2,4-diamino-6-((1-(3-(6-aminopyridin-3-yl)-5-chloro-4-oxo-3,4-dihydroquinazolin-2-yl)ethyl)amino)pyrimidine-5-carbonitrile (Compound 97): $^1$H NMR (400 MHz, DMSO-d$_6$) δ 8.09-8.03 (m, 0.5H), 7.98-7.92 (m, 0.5H), 7.77 (td, J=8.0, 2.3 Hz, 1H), 7.58 (ddt, J=12.1, 7.9, 1.3 Hz, 1H), 6.89 (d, J=6.8 Hz, 0.5H), 6.81 (d, J=6.9 Hz, 0.5H), 6.64-6.52 (m, 2H), 6.33 (d, J=7.1 Hz, 2H), 4.73 (dp, J=30.3, 6.7 Hz, 1H), 1.32 (dd, J=14.1, 6.7 Hz, 3H). ES/MS 449.1 (M+H$^+$);

(S)-2,4-diamino-6-(((3-(6-amino-4-methylpyridin-3-yl)-5,8-dichloro-4-oxo-3,4-dihydroquinazolin-2-yl)(cyclopropyl)methyl)amino)pyrimidine-5-carbonitrile (Compound 98): $^1$H NMR (400 MHz, DMSO-d$_6$) δ 7.99 (d, J=8.5 Hz, 1H), 7.87 (s, 1H), 7.58 (d, J=8.5 Hz, 1H), 6.66 (s, 2H), 6.43 (ddd, J=8.4, 1.9, 1.2 Hz, 1H), 6.22 (s, 2H), 4.95 (dd, J=8.6, 6.2 Hz, 1H), 1.86 (d, J=0.8 Hz, 3H), 1.36-1.21 (m, 1H), 0.47-0.32 (m, 3H), 0.18-0.06 (m, 1H). ES/MS 524.1 (M+H$^+$);

(S)-2,4-diamino-6-(((3-(6-amino-4-methylpyridin-3-yl)-5,8-dichloro-4-oxo-3,4-dihydroquinazolin-2-yl)(cyclopropyl)methyl)amino)pyrimidine-5-carbonitrile (Compound 99): $^1$H NMR (400 MHz, DMSO-d$_6$) δ 8.06 (d, J=8.5 Hz, 1H), 7.84 (s, 1H), 7.77 (s, 1H), 7.65 (d, J=8.5 Hz, 1H), 7.58 (s, 1H), 6.88 (s, 1H), 4.49 (t, J=8.1 Hz, 1H), 2.11 (s, 3H), 1.56 (tq, J=8.3, 5.2, 4.3 Hz, 1H), 0.63-0.40 (m, 3H), 0.14-0.03 (m, 1H). ES/MS 524.1 (M+H$^+$);

(S)-3-(6-aminopyridin-3-yl)-5-chloro-2-(1-((2,6-diamino-5-chloropyrimidin-4-yl)amino)ethyl)-6-fluoroquinazolin-4(3H)-one (Compound 100). $^1$H NMR (400 MHz, DMSO-d$_6$) δ 8.01 (m, 1H), 7.93-7.82 (m, 1H), 7.72-7.46 (m, 2H), 6.58 (m, 1H), 6.35 (d, J=8.4 Hz, 2H), 6.25 (dd, J=21.7, 7.5 Hz, 2H), 6.02 (d, J=7.5 Hz, 2H), 5.56 (d, J=14.0 Hz, 2H), 4.81-4.55 (m, 1H), 1.30 (m, 3H). ES/MS 536.1 (M+H$^+$);

(S)-2,4-diamino-6-((1-(3-(6-aminopyridin-3-yl)-5-chloro-6-fluoro-4-oxo-3,4-dihydroquinazolin-2-yl)ethyl)amino)pyrimidine-5-carbonitrile (Compound 101). $^1$H NMR (400 MHz, DMSO-d$_6$) δ 8.42-7.84 (m, 3H), 7.84-7.46 (m, 3H), 7.75-7.50 (m, 4H), 7.01-6.63 (m, 1H), 5.00 (m, 1H), 1.38 (dd, J=19.7, 6.6 Hz, 3H). ES/MS 467.1 (M+H$^+$);

(S)-3-(6-aminopyridin-3-yl)-5-chloro-2-(1-((2,6-diamino-5-chloropyrimidin-4-yl)amino)butyl)quinazolin-4(3H)-one (Compound 102). $^1$H NMR (400 MHz, DMSO-d$_6$) δ 8.02 (ddd, J=52.2, 2.7, 0.7 Hz, 1H), 7.87-7.41 (m, 3H), 6.61 (ddd, J=27.6, 8.7, 0.7 Hz, 1H), 6.49-5.85 (m, 4H), 5.53 (d, J=21.9 Hz, 1H), 4.69 (dtd, J=45.0, 8.8, 3.3 Hz, 1H), 2.01-1.55 (m, 2H), 1.35-0.77 (m, 2H), 0.61 (dt, J=20.1, 7.4 Hz, 3H). ES/MS 486.1 (M+H+);

(S)-2,4-diamino-6-((1-(3-(6-aminopyridin-3-yl)-5-chloro-4-oxo-3,4-dihydroquinazolin-2-yl)butyl)amino)pyrimidine-5-carbonitrile (Compound 103). $^1$H NMR (400 MHz, DMSO-$d_6$) δ 8.21-7.87 (m, 1H), 7.82-7.19 (m, 3H), 6.95-6.46 (m, 3H), 6.32 (d, J=6.8 Hz, 4H), 5.08-4.39 (m, 1H), 1.71 (dd, J=40.5, 13.9 Hz, 2H), 1.40-0.94 (m, 2H), 0.80-0.38 (m, 3H). ES/MS 477.1 (M+H+);

(S)-3-(6-aminopyridin-3-yl)-5-chloro-2-(1-((2,6-diamino-5-chloropyrimidin-4-yl)amino)butyl)-6-fluoroquinazolin-4(3H)-one (Compound 104). $^1$H NMR (400 MHz, DMSO-$d_6$) δ 8.09 (dd, J=2.7, 0.7 Hz, 1H), 7.85 (td, J=9.0, 3.2 Hz, 1H), 7.72-7.37 (m, 3H), 6.62 (ddd, J=27.1, 8.7, 0.7 Hz, 1H), 6.34 (d, J=8.8 Hz, 2H), 6.16-5.84 (m, 4H), 5.53 (d, J=21.7 Hz, 2H), 4.69 (dtd, J=44.3, 9.0, 3.2 Hz, 1H), 1.68 (m, 2H), 1.43-0.87 (m, 2H), 0.61 (dt, J=20.1, 7.4 Hz, 3H). ES/MS 504.1 (M+H+);

(S)-2,4-diamino-6-((1-(3-(6-aminopyridin-3-yl)-5-chloro-6-fluoro-4-oxo-3,4-dihydroquinazolin-2-yl)butyl)amino)pyrimidine-5-carbonitrile (Compound 105). $^1$H NMR (400 MHz, DMSO-$d_6$) δ 8.03 (dd, J=57.4, 2.5 Hz, 1H), 7.93-7.34 (m, 3H), 6.88-6.42 (m, 3H), 6.33 (d, J=23.6 Hz, 3H), 4.74 (m, 1H), 1.82-1.54 (m, 2H), 1.43-0.87 (m, 2H), 0.74-0.45 (m, 3H). ES/MS 495.1 (M+H+);

(S)-3-(6-aminopyridin-3-yl)-5-chloro-2-(cyclopropyl((2,6-diamino-5-chloropyrimidin-4-yl)amino)methyl)-8-fluoroquinazolin-4(3H)-one (Compound 106). $^1$H NMR (400 MHz, DMSO-$d_6$) δ 8.10 (s, 1H), 7.89-7.57 (m, 2H), 7.60-7.12 (m, 3H), 6.61 (s, 1H), 4.57 (s, 1H), 1.49 (d, J=22.8 Hz, 1H), 1.37-1.01 (m, 3H), 0.45 (s, 2H), 0.18 (d, J=21.1 Hz, 1H). ES/MS 502.1 (M+H+);

(S)-2,4-diamino-6-(((3-(6-aminopyridin-3-yl)-5-chloro-8-fluoro-4-oxo-3,4-dihydroquinazolin-2-yl)(cyclopropyl)methyl)amino)pyrimidine-5-carbonitrile (Compound 107). $^1$H NMR (400 MHz, DMSO-$d_6$) δ 7.96 (dd, J=20.6, 2.6 Hz, 1H), 7.80-7.64 (m, 1H), 7.67-7.36 (m, 2H), 6.65 (d, J=7.5 Hz, 2H), 6.62-6.24 (m, 6H), 4.72 (dt, J=10.3, 7.2 Hz, 1H), 1.24 (tt, J=12.5, 5.8 Hz, 1H), 0.50-0.25 (m, 3H), 0.15-0.03 (m, 1H). ES/MS 493.1 (M+H+);

(S)-2,4-diamino-6-((1-(3-(5-aminopyridin-3-yl)-5-chloro-4-oxo-3,4-dihydroquinazolin-2-yl)ethyl)amino)pyrimidine-5-carbonitrile (Compound 108). Exists as a ~11 mixture of diastereomers. 1H NMR (400 MHz, DMSO-d6) δ 7.97-7.90 (m, 1.5H), 7.85 (d, J=2.0 Hz, 0.5H), 7.78 (td, J=8.0, 2.4 Hz, 1H), 7.66-7.56 (m, 2H), 7.24 (s, 0.5H), 7.11 (s, 0.5H), 4.91 (p, J=7.3 Hz, 0.5H), 4.80 (p, J=6.8 Hz, 0.5H), 1.34 (dd, J=6.7, 1.4 Hz, 3H). ES/MS 449.1 (M+H+); and (S)-4-amino-6-((1-(3-(5-aminopyridin-3-yl)-5-chloro-4-oxo-3,4-dihydroquinazolin-2-yl)ethyl)amino)pyrimidine-5-carbonitrile (Compound 109). Exists as a ~11 mixture of diastereomers. 1H NMR (400 MHz, DMSO-d6) δ 8.09 (s, 0.5H), 8.00 (d, J=2.5 Hz, 0.5H), 7.94 (s, 0.5H), 7.89 (d, J=2.4 Hz, 0.5H), 7.87 (s, 0.5H), 7.77 (td, J=8.0, 2.5 Hz, 1H), 7.72 (d, J=6.9 Hz, 0.5H), 7.67-7.55 (m, 2.5H), 7.44 (s, 0.5H), 7.32 (d, J=14.0 Hz, 2.5H), 4.87 (p, J=7.1 Hz, 0.5H), 4.81 (p, J=6.7 Hz, 0.5H), 1.37 (dd, J=6.7, 3.1 Hz, 3H). ES/MS 434.1 (M+H+).

C. Preparation of a Compound of Formula (I) wherein n is 2, $R^1$ is cyano, R1 is fluoro, m is 0, $R^3$ is cyclopropyl, and $R^4$ is chloro

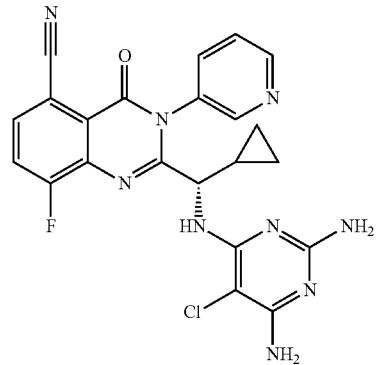 [SMILES: N#Cc1ccc(F)c2nc([C@@H](Nc3nc(N)nc(N)c3Cl)C3CC3)n(-c3cccnc3)c(=O)c12]

(S)-5-chloro-2-(1-((2,6-diamino-5-chloropyrimidin-4-yl)amino)ethyl)-8-fluoro-3-(pyridin-3-yl)quinazolin-4(3H)-one (141 mg, 0.3 mmol), Zn(CN)$_2$ (40 mg, 0.35 mmol), and Pd(PPh3)4 (34 mg, 0.03 mmol) were dissolved in NMP (3 mL). Argon was bubbled through (1 min.) and then heated to 120° C. using microwave for 1 h. The reaction mixture was purified by HPLC to give (S)-2-(cyclopropyl((2,6-diamino-5-chloropyrimidin-4-yl)amino)methyl)-8-fluoro-4-oxo-3-(pyridin-3-yl)-3,4-dihydroquinazoline-5-carbonitrile (Compound 59). 1H NMR (400 MHz, DMSO-d6) δ 8.80-8.54 (m, 1H), 8.51-8.31 (m, 1H), 8.19 (ddd, J=8.5, 4.5, 1.5 Hz, 1H), 8.09-7.89 (m, 2H), 7.83-7.50 (m, 5H), 7.46-7.26 (m, 2H), 4.48 (dt, J=14.0, 8.2 Hz, 1H), 1.66-1.48 (m, 1H), 0.63-0.38 (m, 3H), 0.16 (ddt, J=15.4, 9.2, 4.4 Hz, 1H). ES/MS 478.1 (M+H+).

EXAMPLE 5

Characterization of Compounds of Formula (I)

This Example characterizes the biological activity of the compounds of formula (I) and further compares with Compounds X, Y and Z having the following structures:

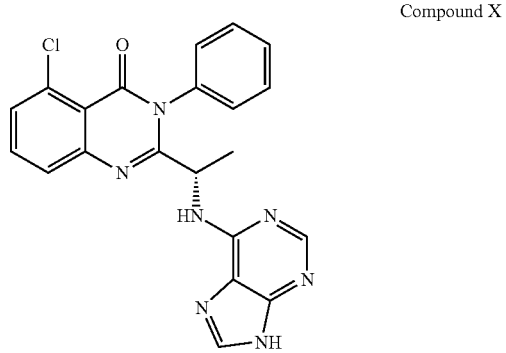

Compound X

Compound Y

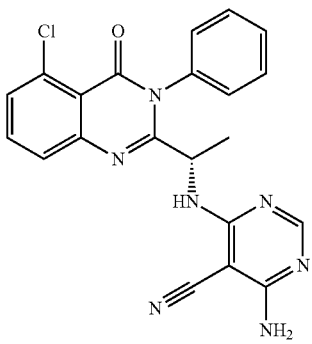

Compound Z

Enzymatic activity of PI3K isoforms was measured to determine the inhibitory activities to the PI3K isoforms selectivity of the compounds tested, including the activities against PI3Kδ. A cellular assay measuring the inhibition of basophil activation was used to assess the potency of the compounds in a cellular assay. Stability in human hepatocytes was also measured to assess the half-life of the tested compounds in human subjects.

i. Enzymatic Activity of PI3K Isoforms

Enzymatic activity of the class I PI3K isoforms in the presence of the compounds of Table 1 and Compounds X, Y and Z was measured using a time-resolved fluorescence resonance energy transfer (TR-FRET) assay. The TR-FRET assay was used to monitor formation of the product 3,4,5-inositol triphosphate molecule (PIP3) as it competed with fluorescently labeled PIP3 for binding to the GRP-1 pleckstrin homology domain protein. An increase in phosphatidylinositide 3-phosphate product results in a decrease in TR-FRET signal as the labeled fluorophore is displaced from the GRP-1 protein binding site.

Class I PI3K isoforms were expressed and purified as heterodimeric recombinant proteins. All assay reagents and buffers for the TR-FRET assay were purchased from Millipore. PI3K isoforms were assayed under initial rate conditions in the presence of 25 mM Hepes (pH 7.4), and 2× Km ATP (75-500 μM), 2 μM PIP2, 5% glycerol, 5 mM MgCl2, 50 mM NaCl, 0.05% (v/v) Chaps, 1 mM dithiothreitol, 1% (v/v) DMSO at the following concentrations for each isoforms: PI3Kα, PI3Kβ, and PI3Kδ between 25 and 50 pM, and PI3Kγ at 2 nM. After an assay reaction time of 30 minutes at 25° C., reactions were terminated with a final concentration of 10 mM EDTA, 10 nM labeled-PIP3, and 35 nM Europium labeled GRP-1 detector protein before reading TR-FRET on an Envision plate reader (Ex: 340 nm; Em: 615/665 nm; 10lps delay and 500 μs read window).

Data were normalized based on positive (1 LM wortmanin) and negative (DMSO) controls. α, β, δ, and γ $IC_{50}$ values were calculated from the fit of the dose-response curves to a four-parameter equation. All $IC_{50}$ values represent geometric mean values if more than one value was obtained. $IC_{50}$ values were reported in units of nM.

Table 2 below summarizes the $IC_{50}$ values (nM) that were collected for PI3Kδ for compounds in the Example. Table 2a summarizes the $IC_{50}$ (nM) values for PI3Kβ and half life (hours) values in cryopreserved human hepatocytes.

TABLE 2

The PI3Kδ $IC_{50}$ Values for Representative Compounds

| Compound | $IC_{50}$ (nM) |
|---|---|
| 1 | 0.6 |
| 2 | 2 |
| 3 | 0.6 |
| 4 | 5 |
| 5 | 14 |
| 7 | 0.4 |
| 8 | 9 |
| 9 | 2 |
| 10 | 9 |
| 11 | 0.8 |
| 12 | 2 |
| 13 | 8 |
| 14 | 4 |
| 15 | 4 |
| 16 | 1 |
| 17 | 4 |
| 18 | 18 |
| 19 | 5 |
| 20 | 3 |
| 21 | 2 |
| 22 | 6 |
| 23 | 0.7 |
| 24 | 0.4 |
| 25 | 8 |
| 26 | 1 |
| 27 | 1 |
| 28 | 0.6 |
| 29 | 8 |
| 30 | 1 |
| 31 | 1 |
| 32 | 2 |
| 33 | 2 |
| 34 | 21 |
| 35 | 35 |
| 36 | 4 |
| 37 | 5 |
| 38 | 13 |
| 39 | 1 |
| 40 | 9 |
| 41 | 0.4 |
| 42 | 27 |
| 43 | 4 |
| 44 | 34 |
| 45 | 6 |
| 46 | 38 |
| 47 | 0.5 |
| 48 | 4 |
| 49 | 67 |
| 50 | 2 |
| 51 | 7 |
| 52 | 63 |
| 53 | 4 |
| 54 | 10 |
| 55 | 60 |
| 56 | 30 |
| 57 | 14 |
| 58 | 14 |
| 59 | 380 |
| 60 | 1 |
| 61 | 1 |
| 62 | 42 |
| 63 | 95 |

TABLE 2-continued

The PI3Kδ IC$_{50}$ Values for Representative Compounds

| Compound | IC$_{50}$ (nM) |
|---|---|
| 64 | 0.6 |
| 65 | 42 |
| 66 | 3 |
| 67 | 120 |
| 68 | 7 |
| 69 | 60 |
| 70 | 3 |
| 71 | 49 |
| 72 | 1 |
| 73 | 59 |
| 74 | 1 |
| 75 | 510 |
| 76 | 14 |
| 77 | 75 |
| 78 | 0.8 |
| 79 | 2 |
| 80 | 27 |
| 81 | 84 |
| 82 | 5 |
| 83 | 12 |
| 84 | 0.5 |
| 85 | 3 |
| 86 | 9 |
| 87 | 0.6 |
| 88 | 6 |
| 89 | 9 |
| 90 | 0.6 |
| 91 | 4 |
| 92 | 0.8 |
| 93 | 2 |
| 94 | 0.5 |
| 95 | 4 |
| 96 | 1 |
| 97 | 0.8 |
| 98 | 21 |
| 99 | 640 |
| 100 | 48 |
| 101 | 8 |
| 102 | 15 |
| 103 | 1 |
| 104 | 94 |
| 105 | 9 |
| 106 | 31 |
| 107 | 1 |
| 108 | 0.6 |
| 109 | 2 |
| 110 | 61 |
| 111 | 9 |
| 112 | 7 |
| 113 | 620 |
| 114 | 220 |
| 115 | 4 |

TABLE 2a

The PI3Kβ IC$_{50}$ and the Half-Life Values for Representative Compounds

| Compound | IC$_{50}$ (nM) | t$_{1/2}$ (hours) |
|---|---|---|
| 81 | 180 | ND |
| 82 | 5 | >10 |
| 83 | 42 | ND |
| 84 | 1 | 10 |
| 85 | 9 | >10 |
| 86 | 35 | ND |
| 87 | 0.8 | >10 |
| 88 | 11 | >10 |
| 89 | 27 | ND |
| 90 | 2 | ND |
| 91 | 99 | ND |
| 92 | 1 | 4 |
| 93 | 30 | ND |
| 94 | 1 | 10 |
| 95 | 28 | ND |
| 96 | 3 | 4 |
| 97 | 0.7 | >10 |
| 98 | 160 | ND |
| 99 | 3600 | ND |
| 100 | 100 | ND |
| 101 | 11 | ND |
| 102 | 62 | ND |
| 103 | 3 | ND |
| 104 | 530 | ND |
| 105 | 41 | ND |
| 106 | 180 | ND |
| 107 | 3 | ND |
| 108 | 33 | ND |
| 109 | 460 | ND |

ND: not determined.

ii. Activity on Basophils

Effect on basophil activation was measured in human whole blood using the Flow2 CAST® kit (Buhlmann Laboratories AG, Baselstrasse, Switzerland) following the protocol provided by the manufacturer with minor modifications. Human whole blood was collected into K$_2$-EDTA venipuncture tubes. Whole blood samples were treated with either DMSO (0.3% final) or a serial dilution of compounds in DMSO for 60 minutes at 37° C. Basophils were then activated either with anti-FcεRI mAb or with fMLP. To activate basophils using the anti-FcεRI mAb; 50 μL of whole blood was mixed with 110 μL of stimulation buffer (B-BAT-STB) and 20 μl of anti-FcεRI (B-BAT-STCON). To activate basophils with fMLP; 50 μL of whole blood was mixed with 80 μL of stimulation buffer (B-BAT-STB) and 50 μL of fMLP (B-CCR-FMLP). Stimulation buffer was used as a negative control. 20 μL of the staining reagent (combination of anti-human CD63-FITC and anti-human CCR3-PE mAbs) was then added to each tube. The tubes were mixed gently and incubated for 25 minutes at 37° C. Subsequently, erythrocytes were lysed and fixed by the addition of 2 mL of lysing solution (B-BAT-LYR) for 10 minutes at room temperature. Cells were pelleted by centrifugation at 1200 rpm for 10 minutes at room temperature in a swing-out rotor. Supernatant was aspirated and cell pellet resuspended in 400 μL of wash buffer. Flow cytometric analysis of the basophil activation was performed on a FC500MPL flow cytometer (Beckman Coulter Inc., Fullerton, Calif.). CCR3-staining and side scatter were applied to gate at least 200 basophils that expressed a high density of CCR3. The percent CD63 positive cells within the gated basophil population were determined in different treatment groups and normalized to the vehicle control (0.3% DMSO) with anti-FcεRI mAb of fMLP stimulus as 100%. Final compound concentration was adjusted to correct for dilution effect of added reagents. The EC$_{50}$ values were calculated from the analysis of the dose-response curves to a four-parameter equation. All EC$_{50}$ values represented geometric mean values and were reported in units of nM. Table 3 below summarizes the ECso data collected in the Example.

iii. Hepatocyte Stability

This assay was used to evaluate the metabolic stability of test articles (TA) following incubation in cryopreserved hepatocytes by monitoring parent drug disappearance via LC/MC. The TA was incubated with 1 million hepatocytes/mL at 2 μM substrate in duplicate. The incubation was carried out at 37° C. with 5% CO$_2$ and saturating humidity. Samples were taken at 0, 1, 2, and 4 hours to monitor the disappearance of TA and a half-life ($t_{1/2}$) was determined. Table 3 below summarizes the human hepatocyte $t_{1/2}$ values (hours) collected in the Example.

The symbols used in Table 3 below are as follows:

| | |
|---|---|
| #### = <1 nM | * = <1 h |
| ### = >1 nM AND <10 nM | ** >1 AND <3 h |
| ## = >10 nM AND <50 nM | *** = >3 AND <6 h |
| # = >50 nM | **** = >6 AND <10 h |
| | ***** = >10 h |

TABLE 3

The $EC_{50}$ and the Half-Life Values for Representative Compounds

| Compound | $EC_{50}$ | $EC_{50}$ (nM) | $t_{1/2}$ | $t_{1/2}$ (hours) |
|---|---|---|---|---|
| 1 | #### | 0.9 | ***** | >10 |
| 2 | ### | 2 | ***** | >10 |
| 3 | ### | 2 | ***** | >10 |
| 4 | ## | 22 | ND | ND |
| 5 | ### | 2 | ***** | >10 |
| 7 | #### | 0.3 | ND | ND |
| 8 | # | 100 | ND | ND |
| 9 | ### | 3 | ***** | >10 |
| 10 | ## | 17 | ND | ND |
| 11 | #### | 0.5 | *** | 5 |
| 12 | ### | 1 | ***** | >10 |
| 13 | ### | 4 | ND | ND |
| 14 | ### | 3 | **** | 8 |
| 15 | ## | 19 | ***** | >10 |
| 16 | #### | 0.7 | ND | ND |
| 17 | ### | 5 | ND | ND |
| 18 | ## | 22 | ND | ND |
| 19 | ### | 7 | **** | 7 |
| 20 | ### | 3 | ***** | >10 |
| 21 | ### | 4 | ***** | >10 |
| 22 | ### | 5 | **** | 9 |
| 23 | #### | 0.8 | ***** | >10 |
| 24 | #### | 0.3 | ***** | >10 |
| 25 | ## | 11 | ND | ND |
| 26 | #### | 0.7 | ***** | >10 |
| 27 | #### | 0.7 | ***** | >10 |
| 28 | ### | 4 | **** | 9 |
| 29 | ## | 10 | ***** | >10 |
| 30 | #### | 0.7 | **** | 9 |
| 31 | #### | 0.5 | ***** | >10 |
| 32 | #### | 0.4 | ***** | >10 |
| 33 | ### | 5 | ***** | >10 |
| 34 | ## | 22 | ND | ND |
| 35 | # | 62 | ND | ND |
| 36 | ### | 2 | ND | ND |
| 37 | ## | 16 | ND | ND |
| 38 | ### | 9 | ND | ND |
| 39 | ### | 2 | *** | 3 |
| 40 | ### | 7 | ND | ND |
| 41 | ### | 4 | ***** | >10 |
| 42 | ### | 8 | ND | ND |
| 43 | ### | 2 | ND | ND |
| 44 | ND | ND | ND | ND |
| 45 | ### | 7 | *** | 4 |
| 46 | ND | ND | **** | 8 |
| 47 | #### | 0.4 | ***** | >10 |

ND: not determined.

The results from the above Example indicate that certain compounds of formula (I) have greater stability in human hepatocytes and longer half-life compared to compounds X, Y and Z. By way of example, Table 4 below summarizes the $t_{1/2}$ and $EC_{50}$ values of compounds 1, X, Y and Z.

TABLE 4

The Comparisons of the $EC_{50}$ And the Half-Life Values.

| | Compound 1 | Compound X | Compound Y | Compound Z |
|---|---|---|---|---|
| $t_{1/2}$ | >10 hours | <2 hours | <2 hours | <5 hours |
| $EC_{50}$ | <1 nM | >5 nM | >10 nM | <1 nM |

What is claimed is:
1. A compound having the structure of formula (I):

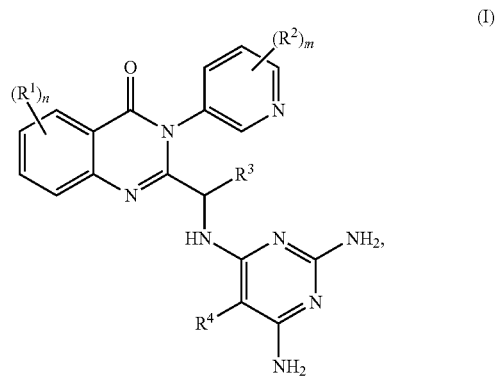

a pharmaceutically acceptable salt thereof, or an isomer thereof, wherein:
n is 0, 1, 2, 3, or 4;
each $R^1$ is independently selected from halo, cyano, alkyl, or alkylsulfonyl, wherein the alkyl moiety may be optionally substituted with 1 to 3 halogen;
m is 0, 1, 2, or 3;
each $R^2$ is independently selected from halo, —$NH_2$, alkoxy, alkyl, or cycloalkyl, wherein the alkyl moiety may be optionally substituted with 1 to 3 halogen;
$R^3$ is hydrogen, alkyl, or cycloalkyl, wherein the alkyl moiety may be optionally substituted with cycloalkyl; and
$R^4$ is cyano, halo, or $CONH_2$.
2. The compound of claim 1, wherein
n is 1 or 2;
each $R^1$ is independently selected from halo, cyano, alkyl, or alkylsulfanyl, wherein the alkyl moiety may be optionally substituted with 1 to 3 halogen;
m is 0, 1, or 2;
each $R^2$ is independently selected from halo, alkoxy, alkyl, or cycloalkyl, wherein the alkyl moiety may be optionally substituted with 1 to 3 halogen;
$R^3$ is hydrogen, alkyl, or cycloalkyl, wherein, the alkyl moiety may be optionally substituted with cycloalkyl; and
$R^4$ is cyano.
3. The compound of claim 1, wherein each $R^1$ is independently selected from halo, cyano, $C_{1-4}$alkyl, $C_{1-4}$haloalkyl, or $C_{1-4}$alkylsulfonyl.
4. The compound of claim 3, wherein each $R^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl.
5. The compound of claim 1, wherein each $R^2$ is independently selected from halo, —$NH_2$, $C_{1-4}$alkoxy, $C_{1-4}$alkyl, $C_{1-4}$haloalkyl, or $C_{3-6}$cycloalkyl.

6. The compound of claim 5, wherein each $R^2$ is independently selected from —$NH_2$, fluoro, chloro, iodo, bromo, methoxy, ethoxy, propoxy, hutoxy, pentoxy, hexoxy, methyl, ethyl, propyl, butyl, fluoromethyl, fluoroethyl, difluoromethyl, difluoroethyl, trifluoromethyl, cyclopropyl, cyclobutyl, cyclopentyl, or eyclohexyl.

7. The compound of claim 1, wherein $R^3$ is selected from hydrogen, alkyl, cycloalkyl, or cycloalkylalkyl.

8. The compound of claim 7, wherein $R^3$ is selected from hydrogen, $C_{1-4}$alkyl, $C_{3-6}$cycloalkyl, or $C_{3-6}$cycloalkyl $C_{1-4}$alkyl.

9. The compound of claim 8, wherein $R^3$ is selected from hydrogen, methyl, ethyl, propyl, butyl, cyclopropyl, cyclobutyl, cyclopentyl, cyclohexyl, cyclopropylmethyl, cyclopropylethyl, cyclobutylmethyl, or cyclopropylbutyl.

10. The compound of claim 1, wherein $R^4$ is selected from cyano, fluoro, chloro, bromo, or $CONH_2$.

11. The compound of claim 1, wherein n is 1.

12. The compound of claim 1, wherein n is 2.

13. The compound of claim 1, wherein m is 0.

14. The compound of claim 1, wherein m is 1.

15. The compound of claim 1, wherein m is 2.

16. The compound of claim 1, wherein the compound is a (S)-enantiomer.

17. The compound of claim 1, wherein the compound is a (R)-enantiomer.

18. The compound of claim 1, wherein the compound is an atropisomer.

19. The compound of claim 1, wherein the compound is selected from the group consisting of:

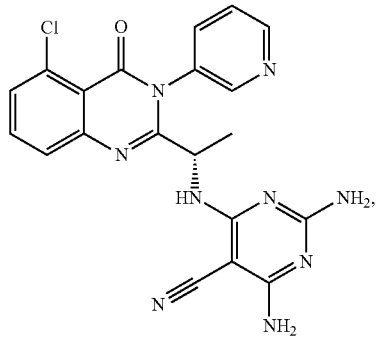

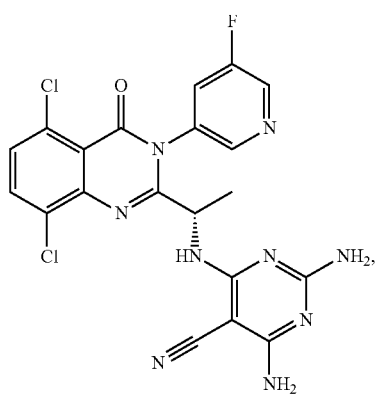

-continued

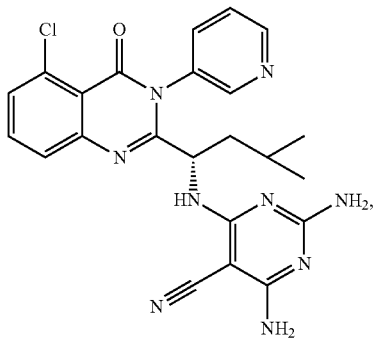

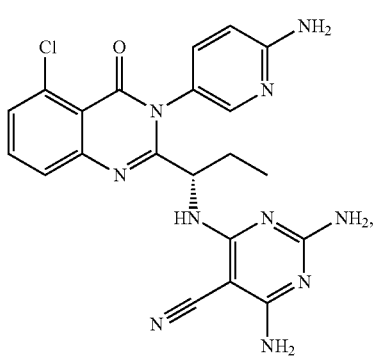

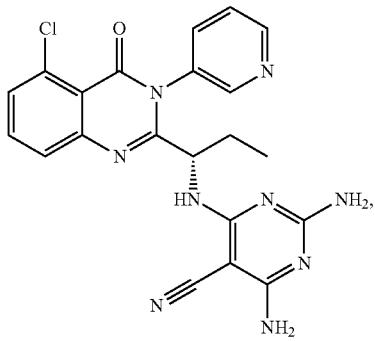

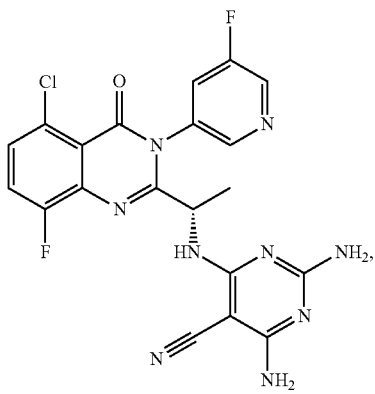

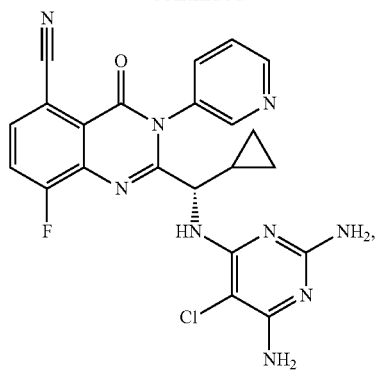
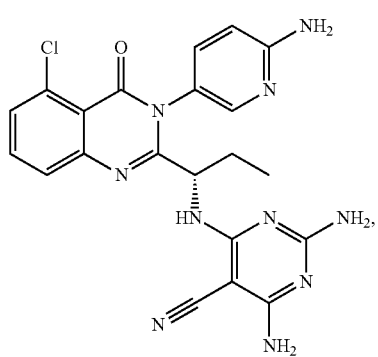
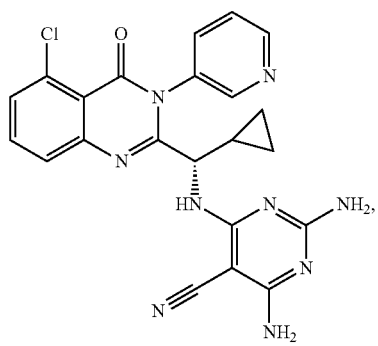
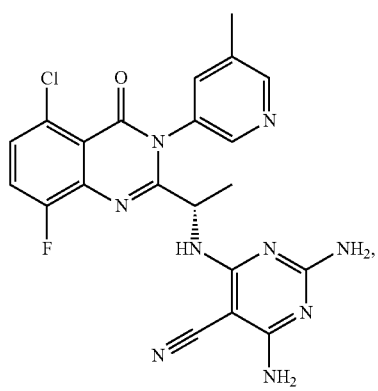
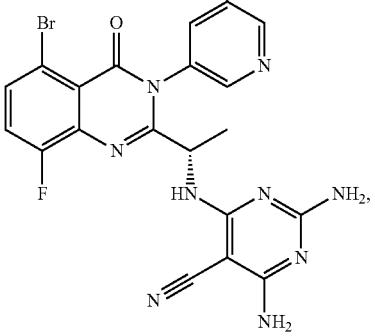
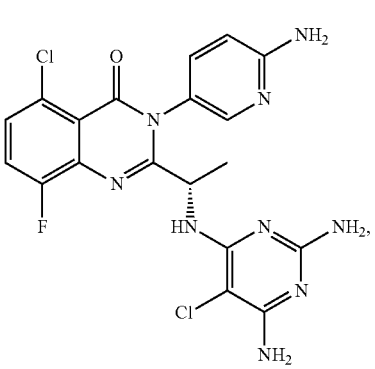
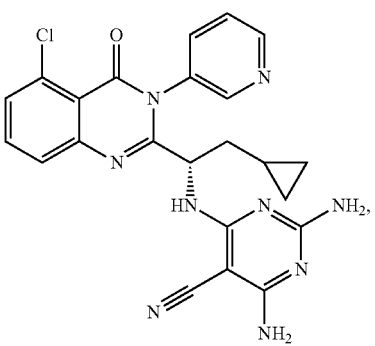
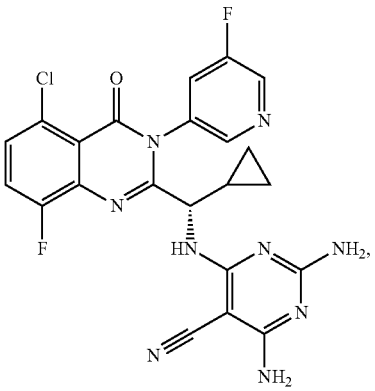

143
-continued
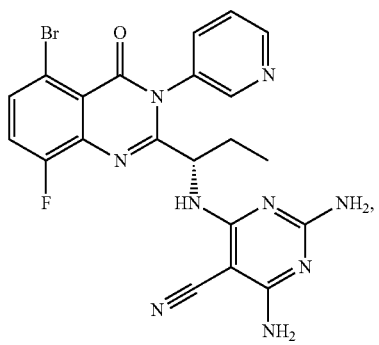
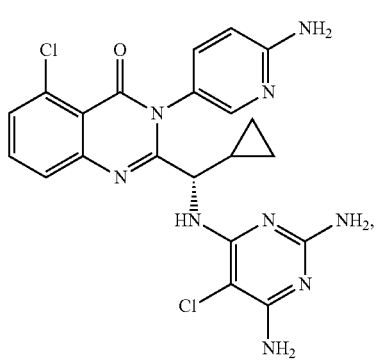
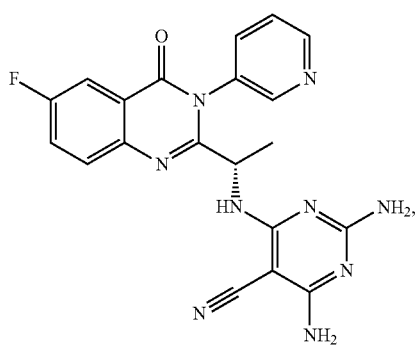
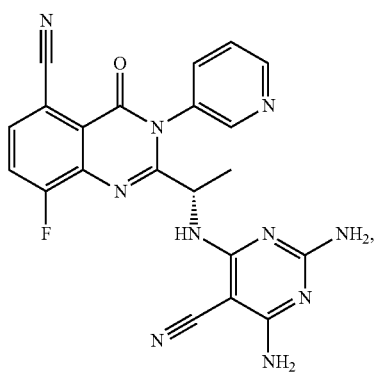
144
-continued
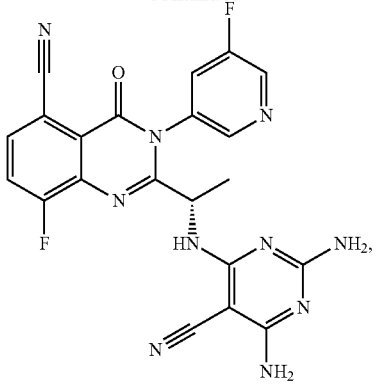
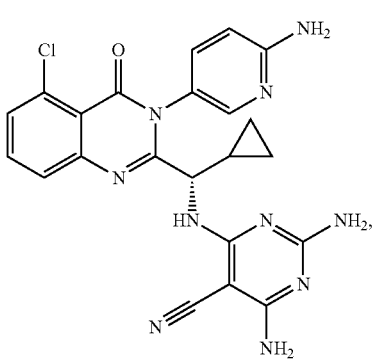
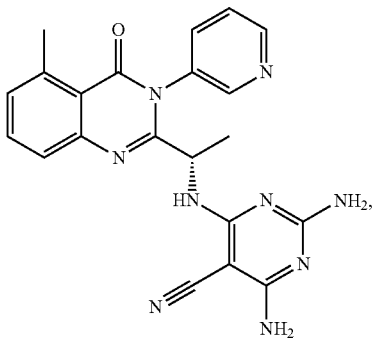
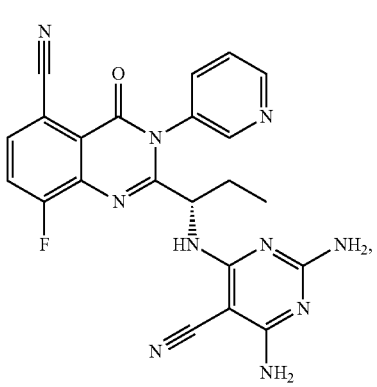

-continued

-continued
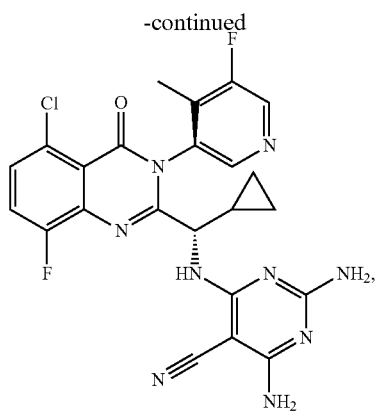
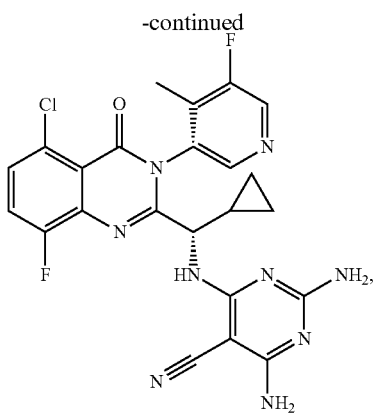
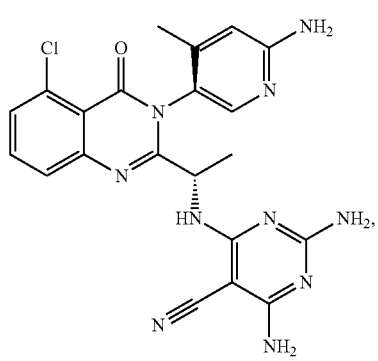
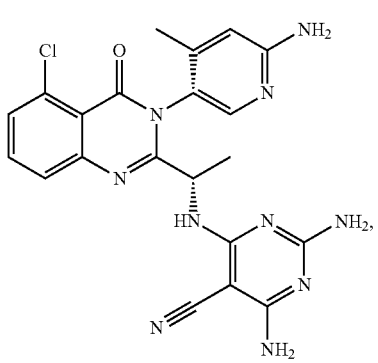
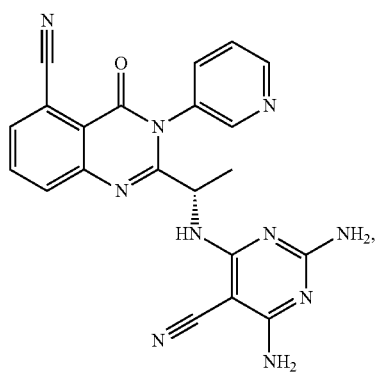
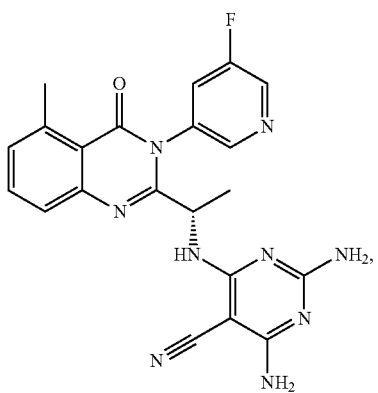
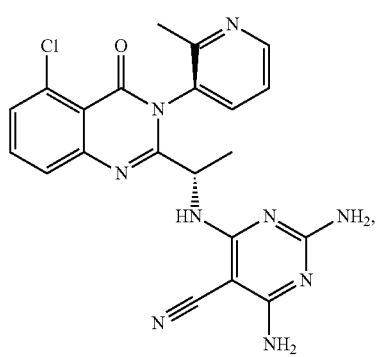
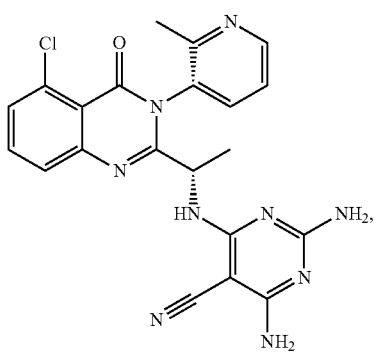

149
-continued
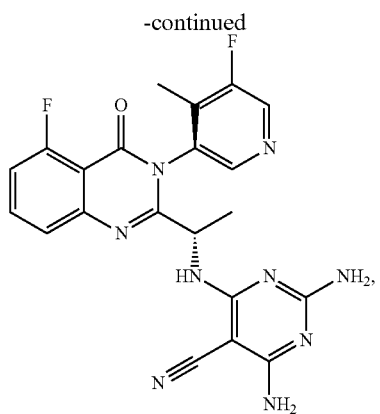
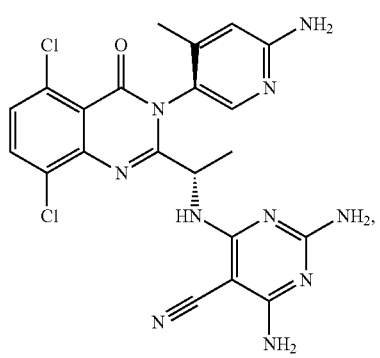
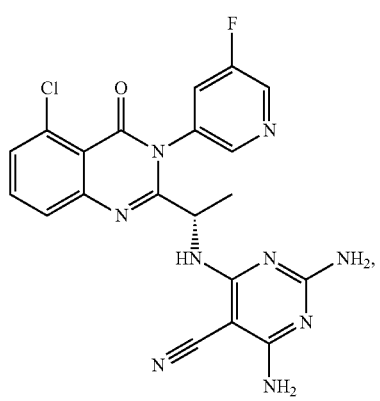
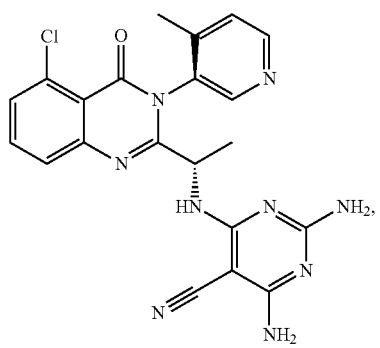
150
-continued
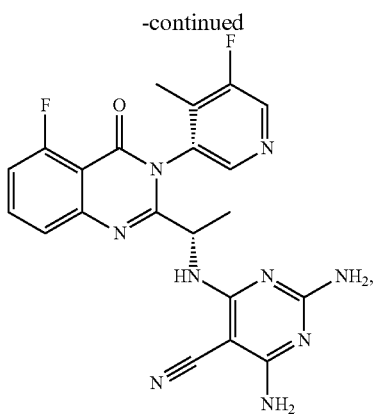
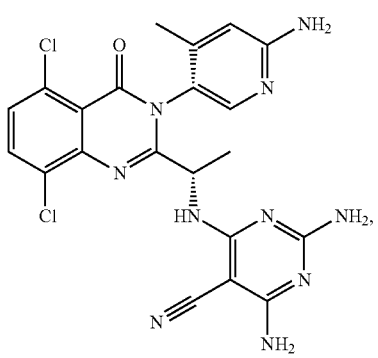
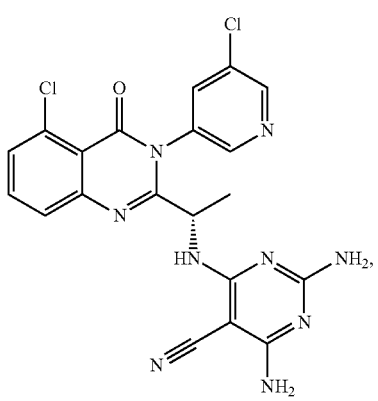
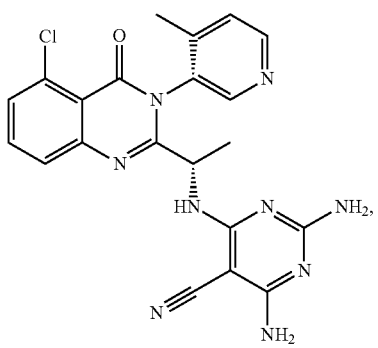

151
-continued
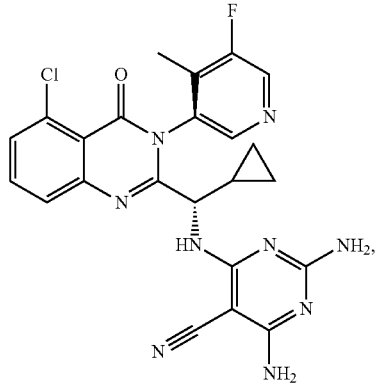
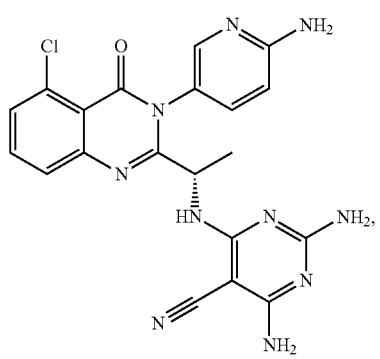
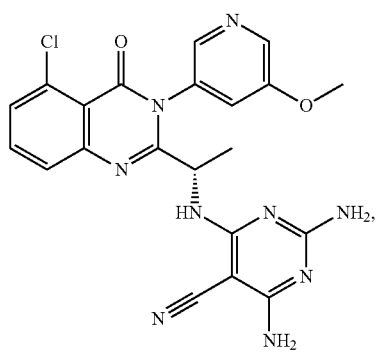
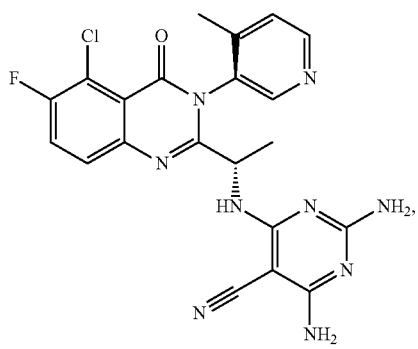
152
-continued
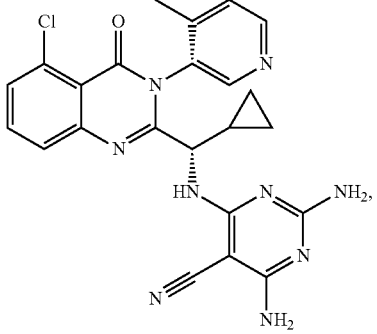
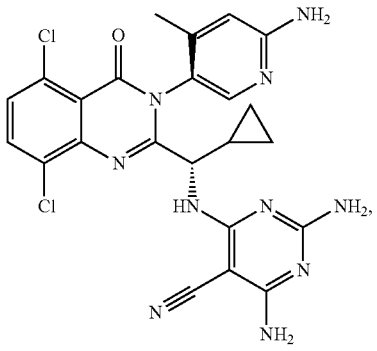
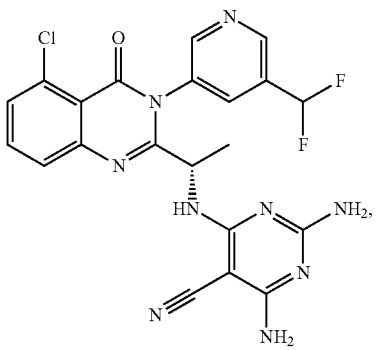
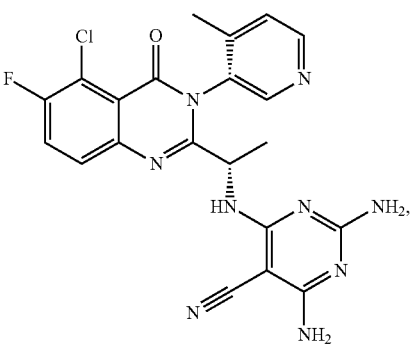

153
-continued
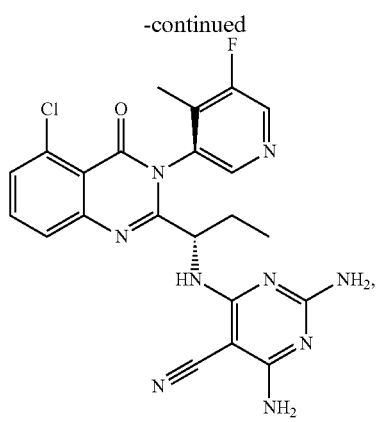
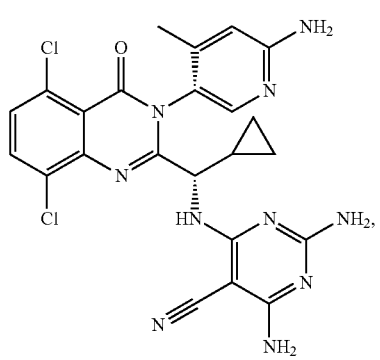
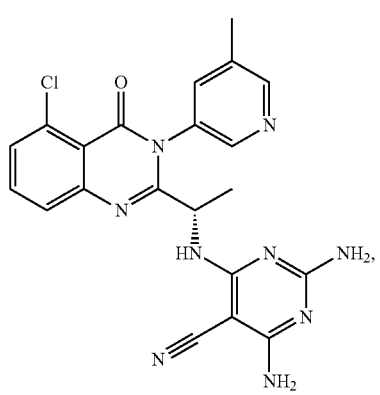
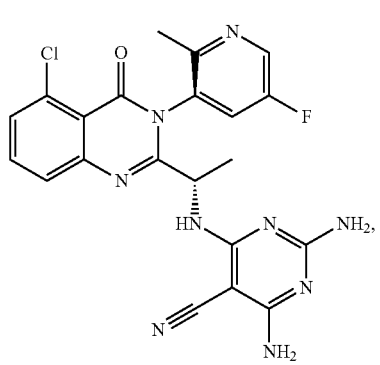
154
-continued
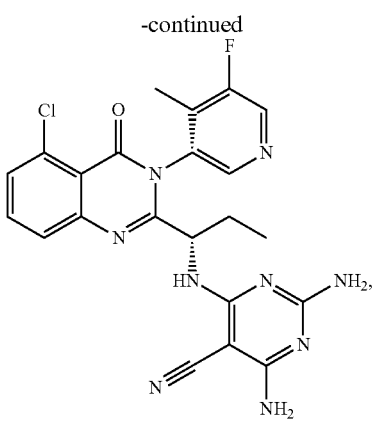
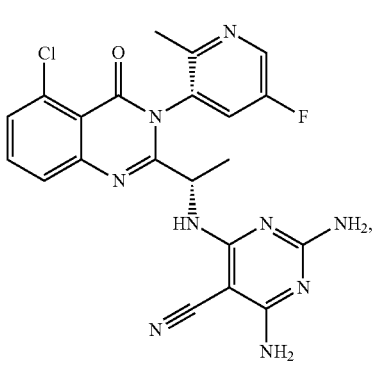

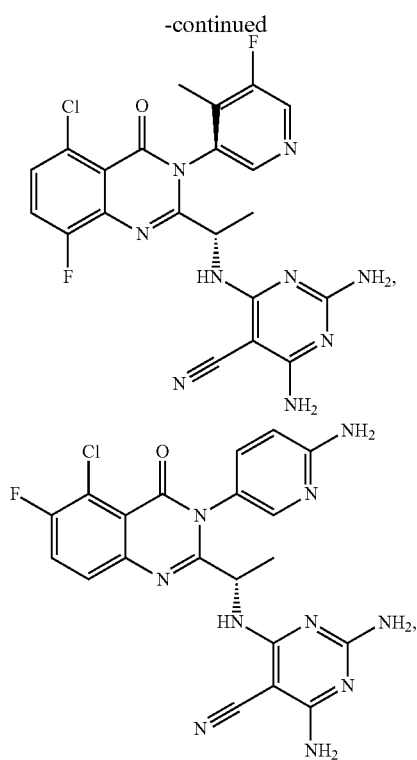
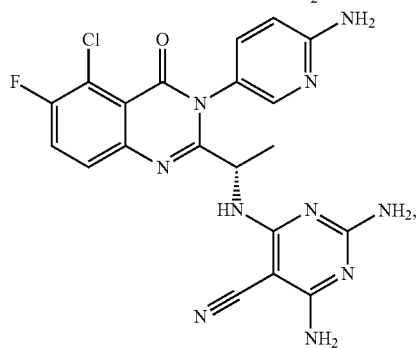
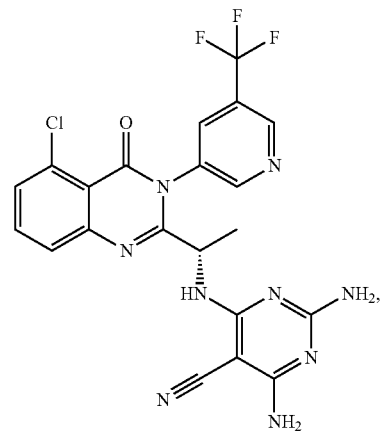
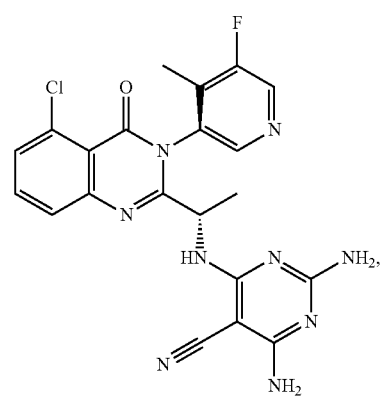
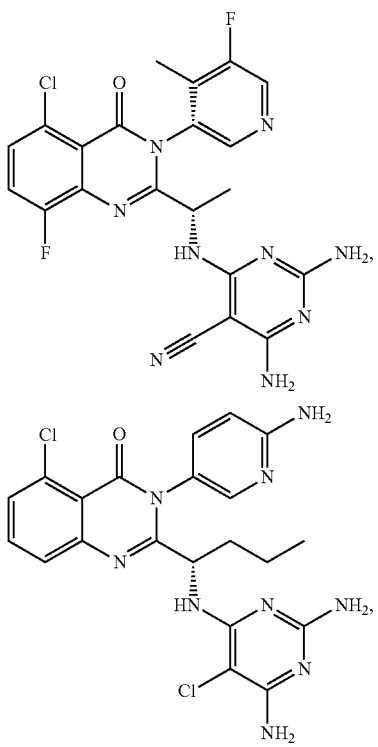
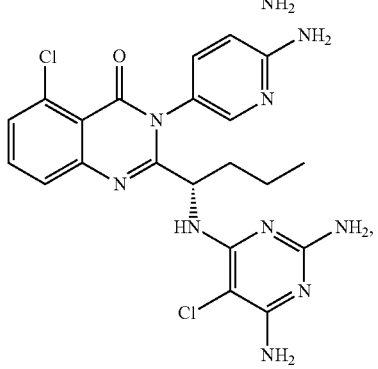
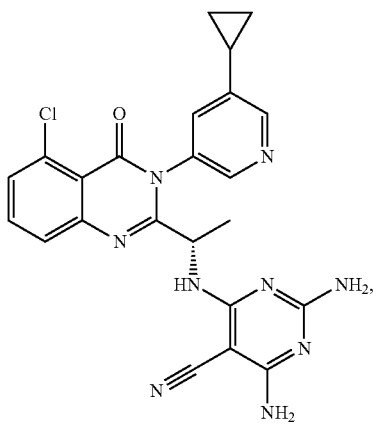
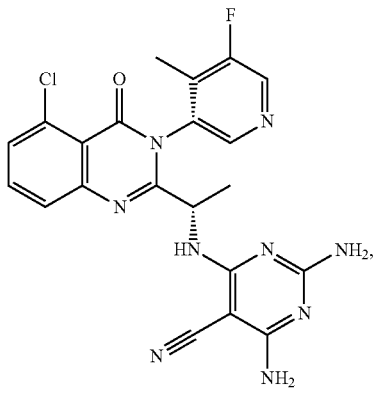

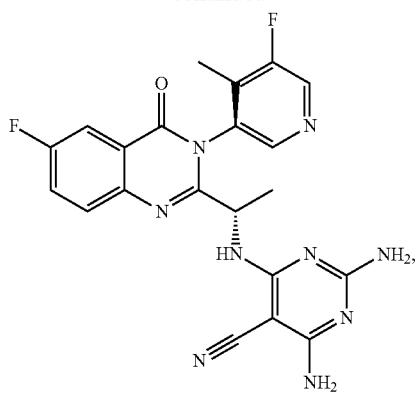
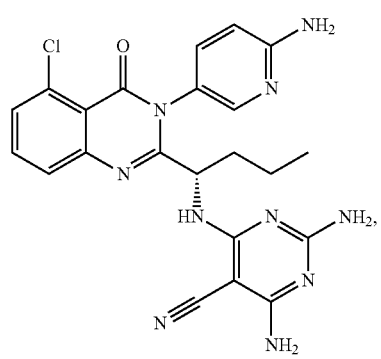
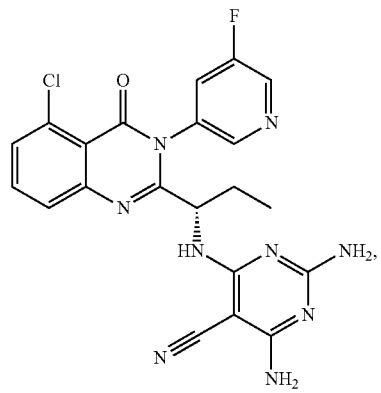
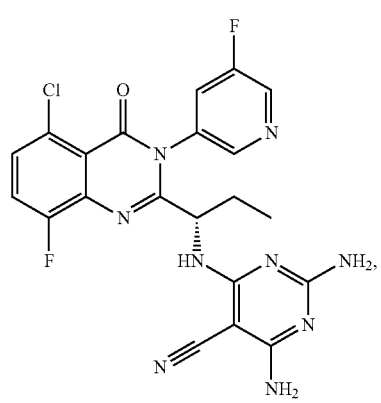
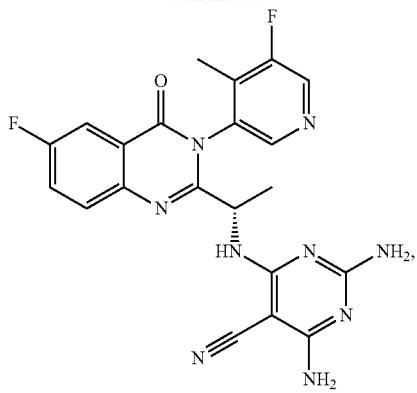
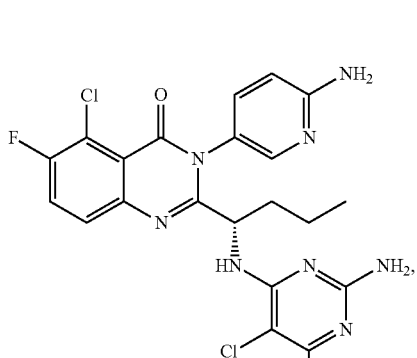
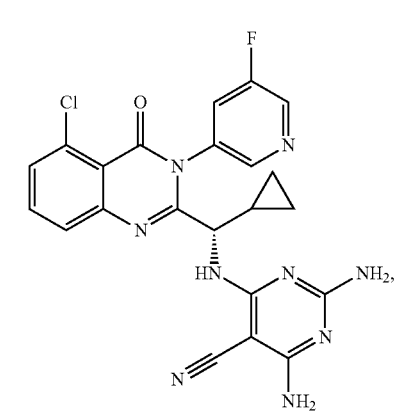
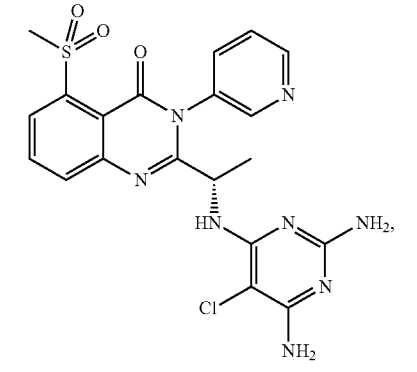

159
-continued
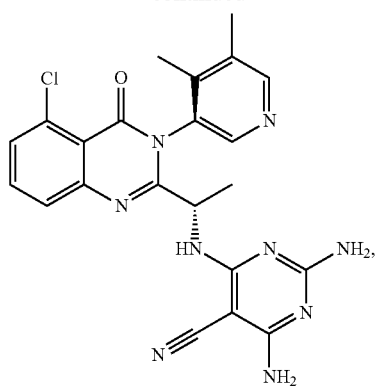
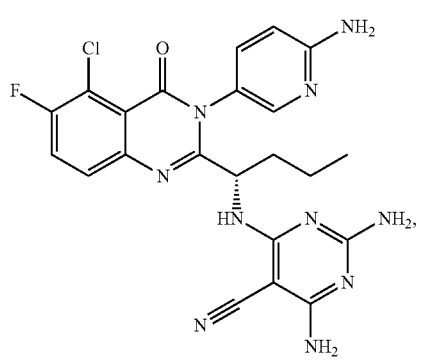
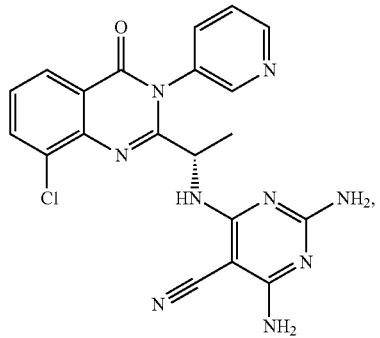
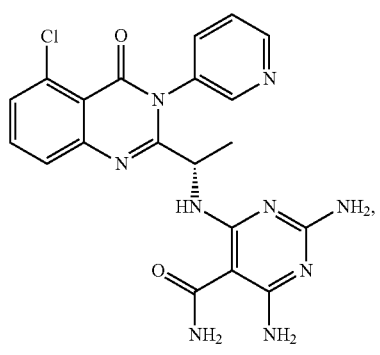
160
-continued
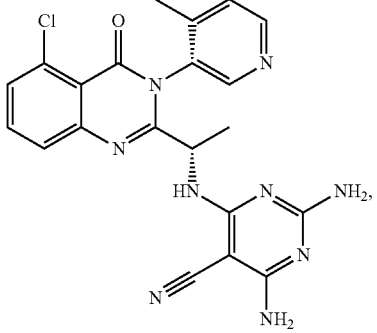
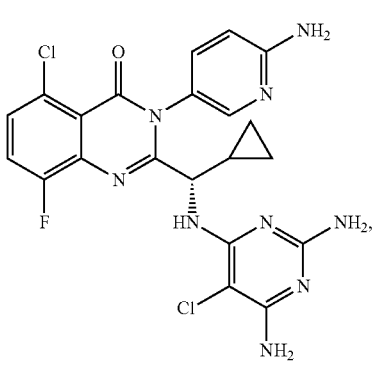
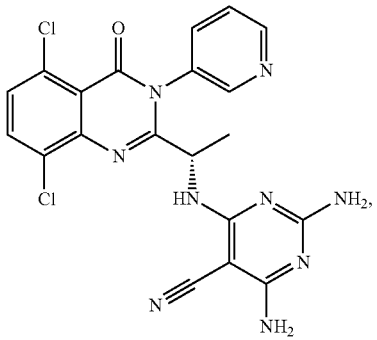
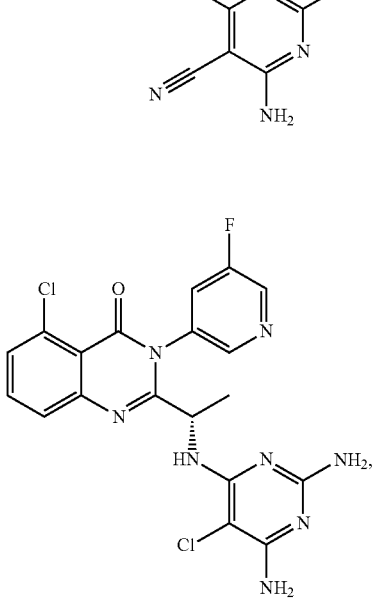

161
-continued
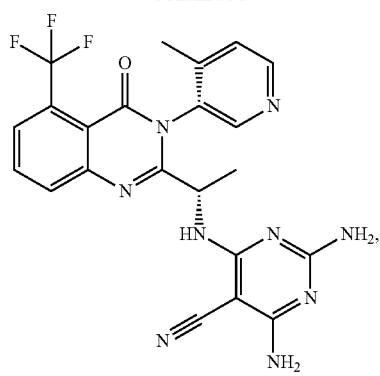
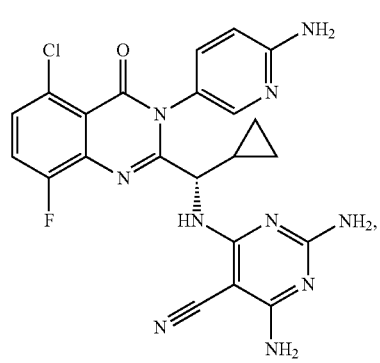
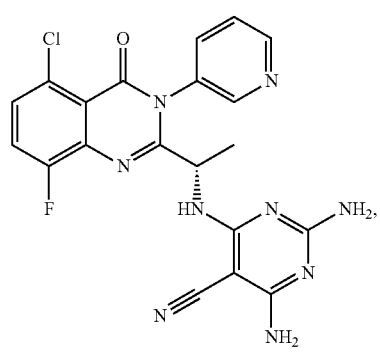
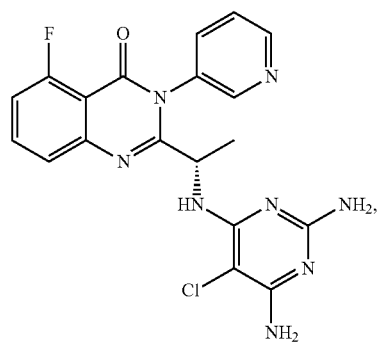
162
-continued
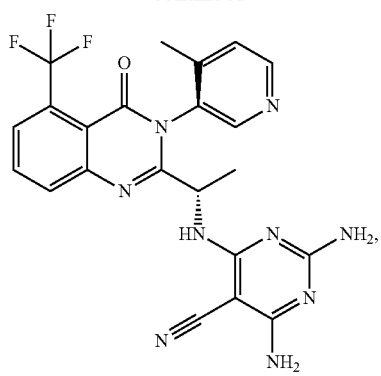
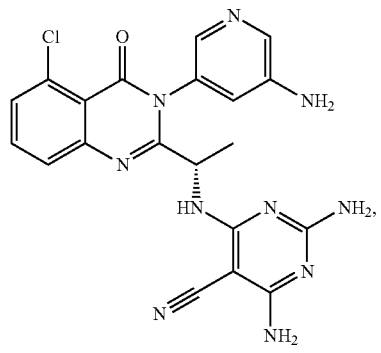
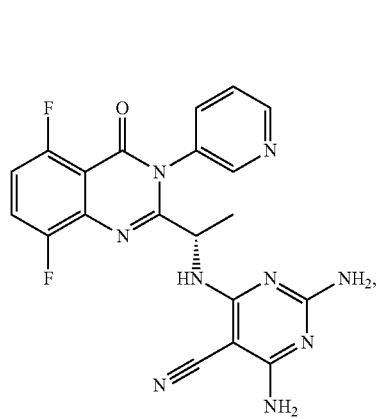
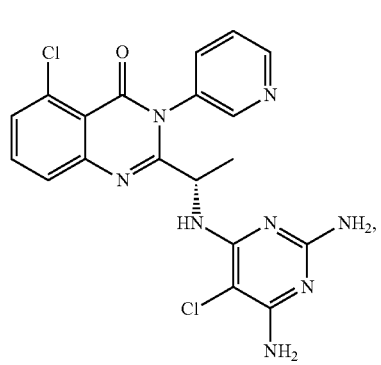

163
-continued
164
-continued
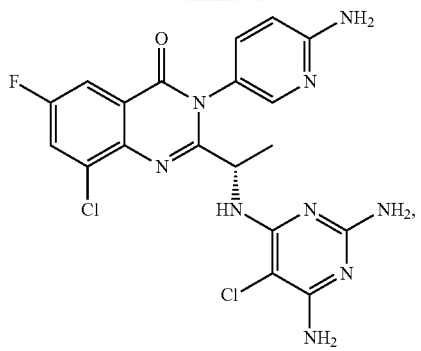
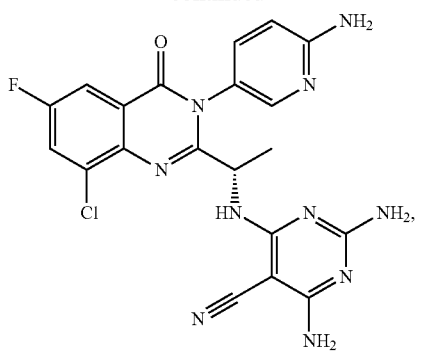
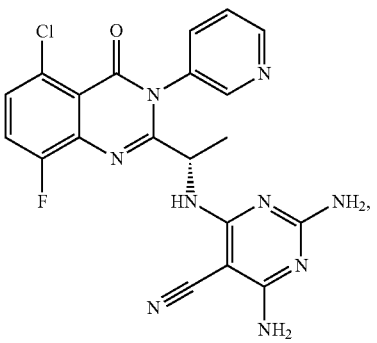
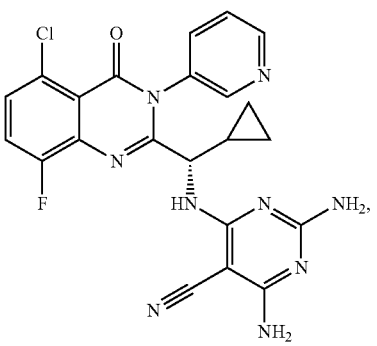

-continued

-continued

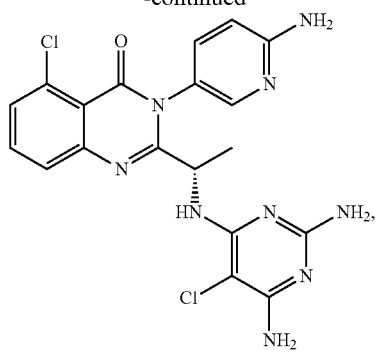

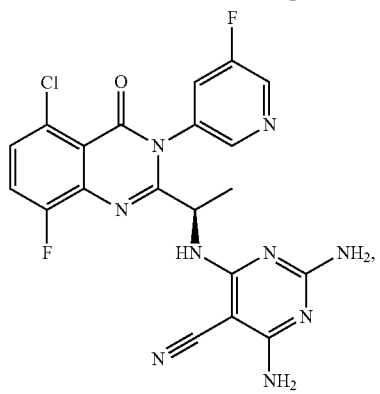

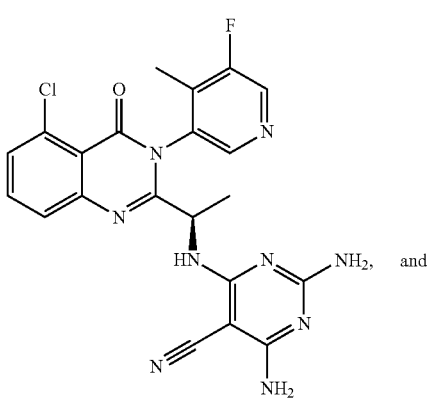

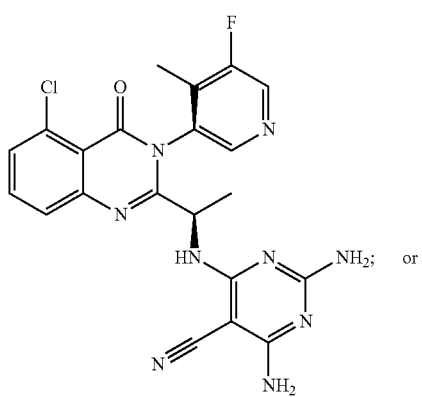

a pharmaceutically acceptable salt thereof or an atropisomer thereof.

20. A pharmaceutical composition composing: a compound having the structure of formula (I):

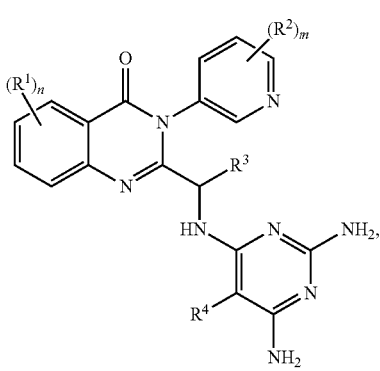

(I)

a pharmaceutically acceptable salt thereof, an isomer thereof, or a mixture thereof, wherein:

n is 0, 1, 2, 3, or 4;

each $R^1$ is independently selected from halo, cyano, alkyl, or alkylsulfonyl, wherein the alkyl moiety may be optionally substituted with 1 to 3 halogen;

m is 0, 1, 2, or 3;

each $R^2$ is independently selected from halo, —$NH_2$, alkoxy, alkyl, or cycloalkyl, wherein the alkyl moiety may be optionally substituted with 1 to 3 halogen;

$R^3$ is hydrogen, alkyl, or cycloalkyl, wherein the alkyl moiety may be optionally substituted with cycloalkyl; and $R^4$ is cyano, halo, or $CONH_2$;

and at least one pharmaceutically acceptable vehicle.

21. The compound of claim 1, wherein the compound is selected from the group consisting of:

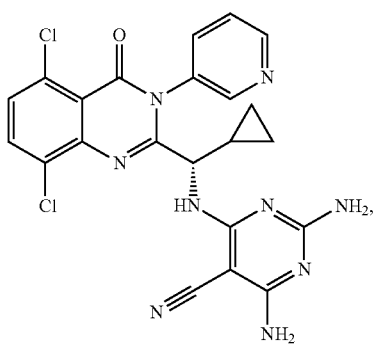

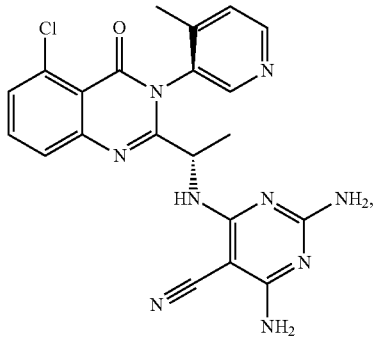

169                                      170
-continued                               -continued
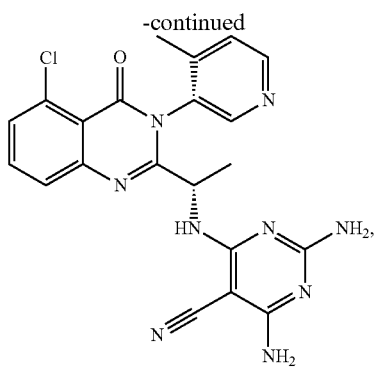
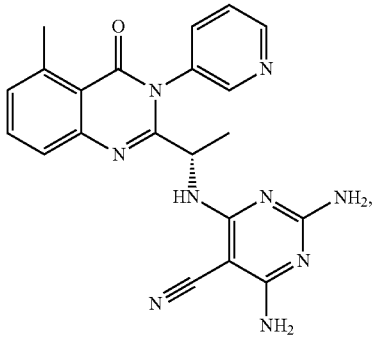
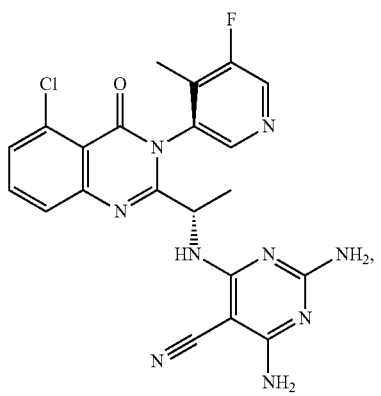
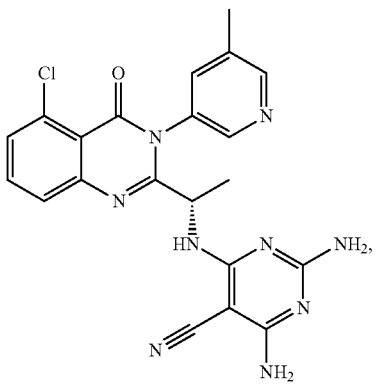
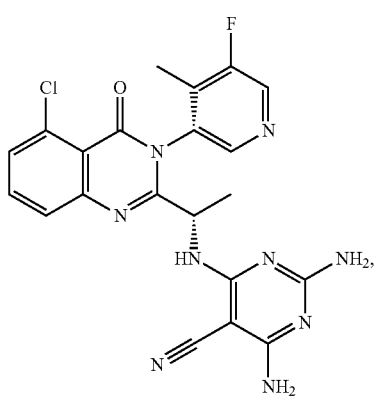
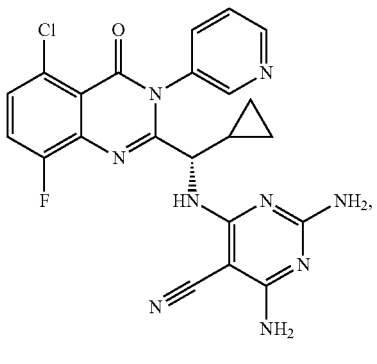
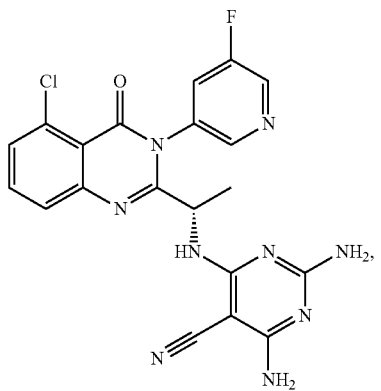
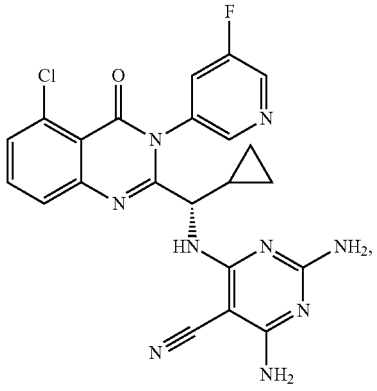

-continued
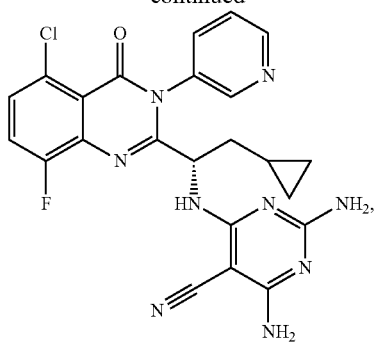
or an atropisomer thereof.
22. The compound of claim 1, wherein the compound is
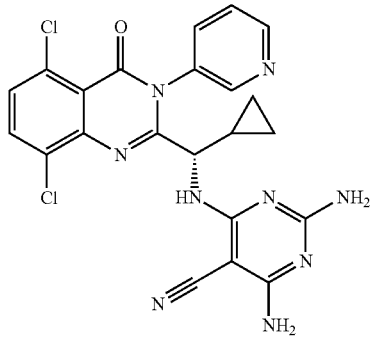
or a pharmaceutically acceptable salt thereof.
23. The compound of claim 1, wherein the compound is
or a pharmaceutically acceptable salt thereof.
24. The compound of claim 1, wherein the compound is
or a pharmaceutically acceptable salt thereof.

25. The compound of claim 1, wherein the compound is

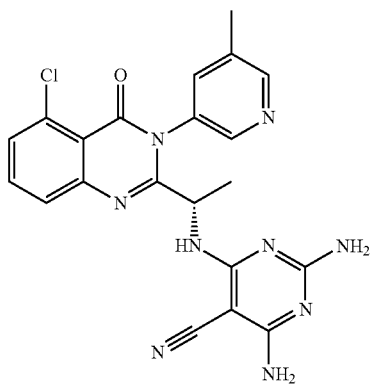 [SMILES: Cc1cncc(-n2c([C@H](C)Nc3nc(N)nc(N)c3C#N)nc3cccc(Cl)c3c2=O)c1]

or a pharmaceutically acceptable salt thereof.

26. The compound of claim 1, wherein the compound is

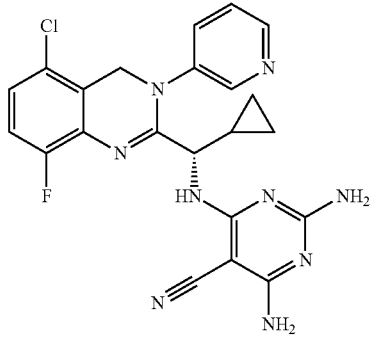 [SMILES: N#Cc1c(N)nc(N)nc1N[C@H](C1=Nc2c(F)ccc(Cl)c2CN1c1cccnc1)C1CC1]

or a pharmaceutically acceptable salt thereof.

27. The compound of claim 1, wherein the compound is

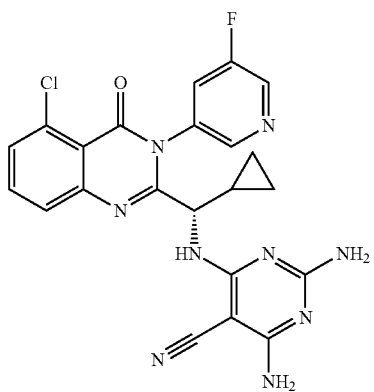 [SMILES: N#Cc1c(N)nc(N)nc1N[C@H](c1nc2cccc(Cl)c2c(=O)n1-c1cncc(F)c1)C1CC1]

or a pharmaceutically acceptable salt thereof.

28. The compound of claim 1, wherein the compound is

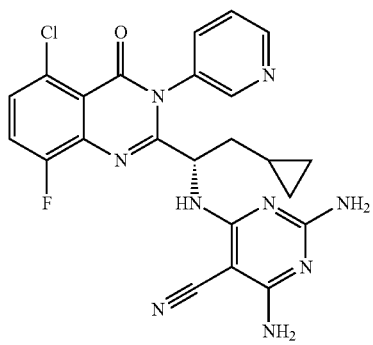

or a pharmaceutically acceptable salt thereof.

29. The compound of claim 1, wherein the compound is

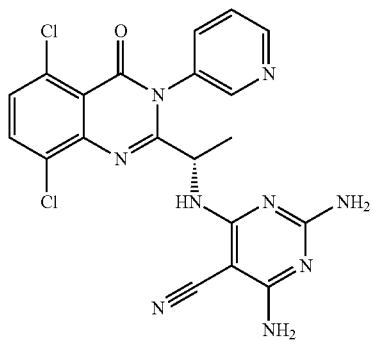

or a pharmaceutically acceptable salt thereof.

30. The compound of claim 1, wherein the compound is

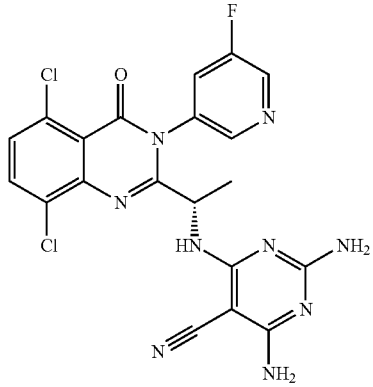

or a pharmaceutically acceptable salt thereof.

31. The compound of claim 1, wherein the compound is
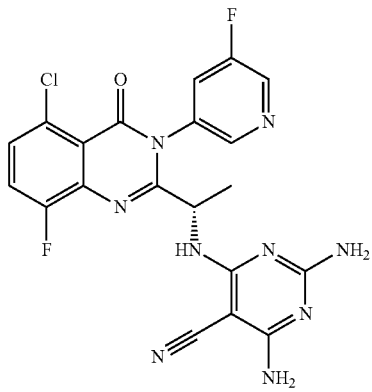
or a pharmaceutically acceptable salt thereof.
32. The pharmaceutical composition of claim 20, wherein the compound is selected from the group consisting of:
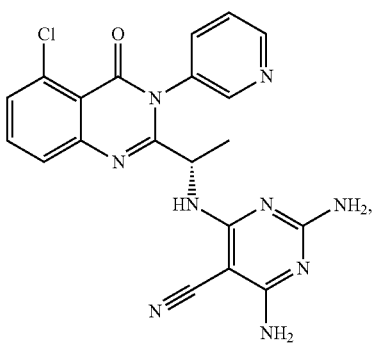
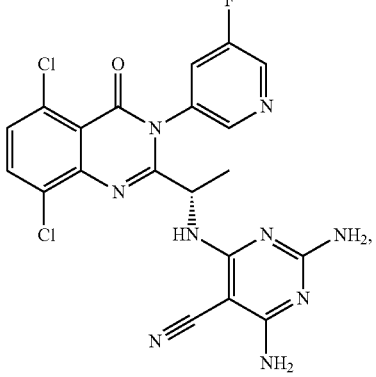
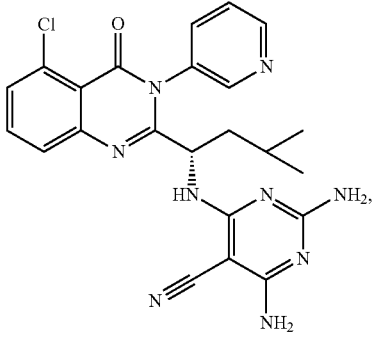
-continued
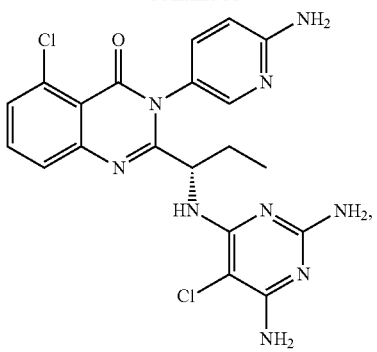
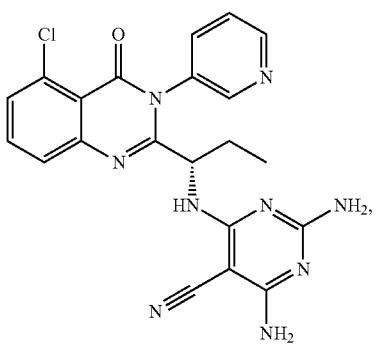
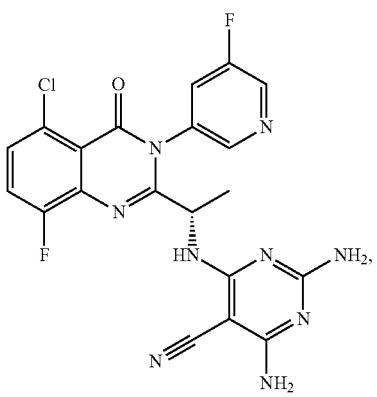
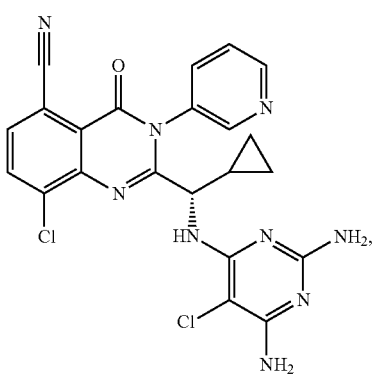

177 -continued

178 -continued

179
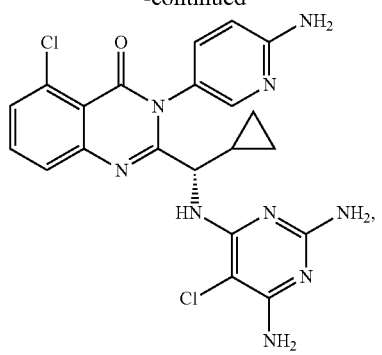
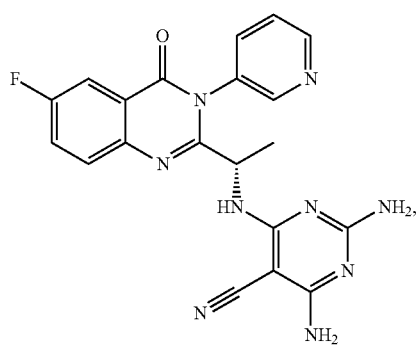
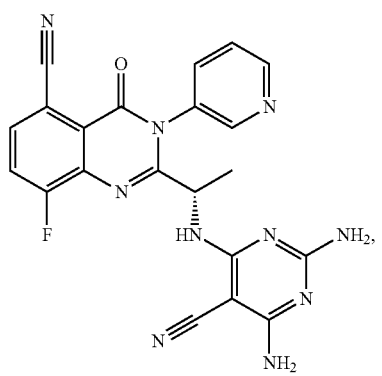
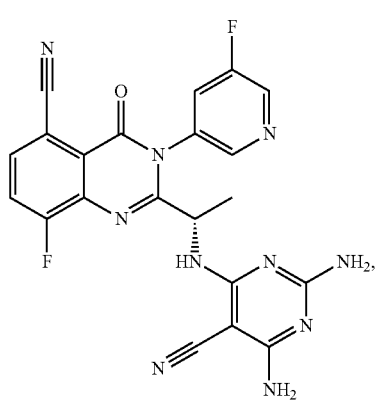
180
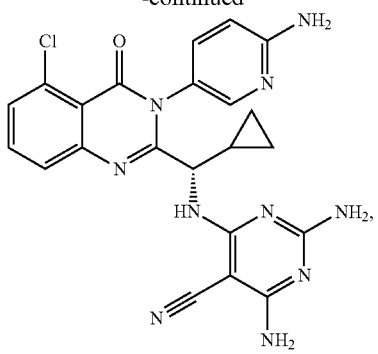
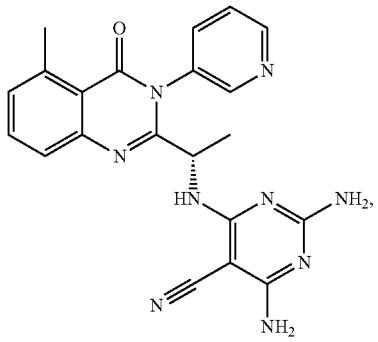
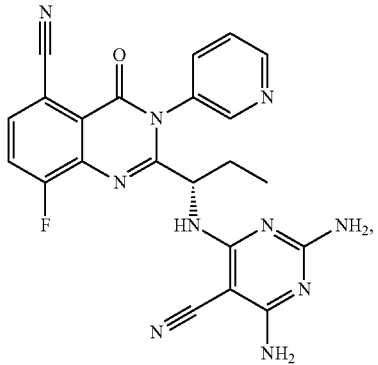
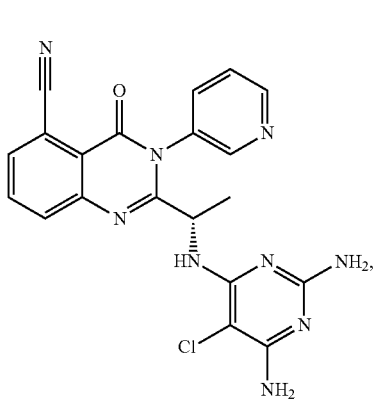

181
-continued
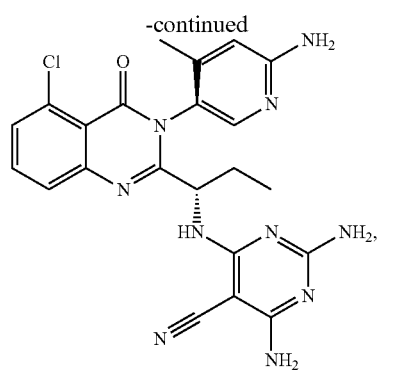
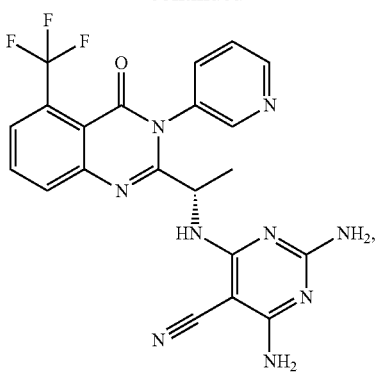
182
-continued
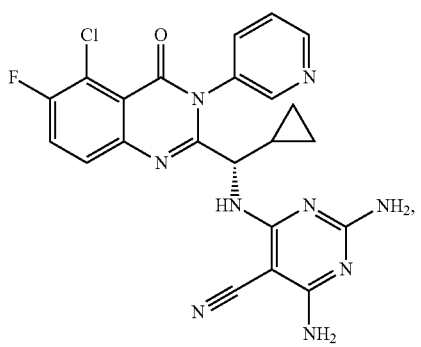
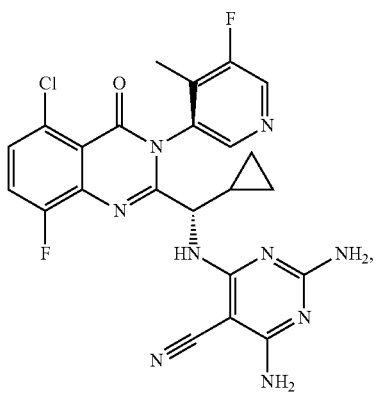
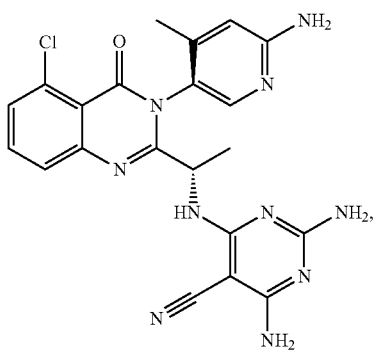

183
-continued
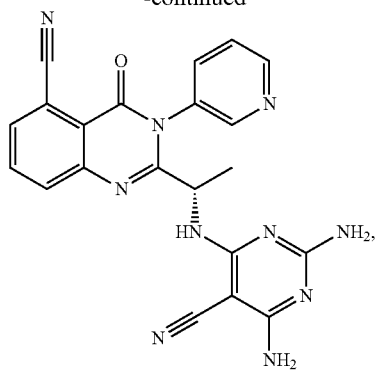
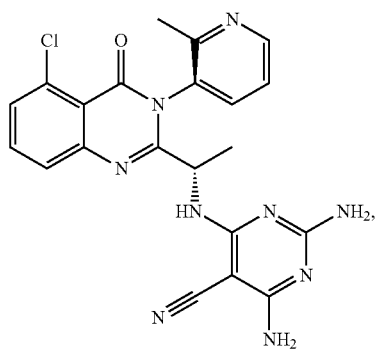
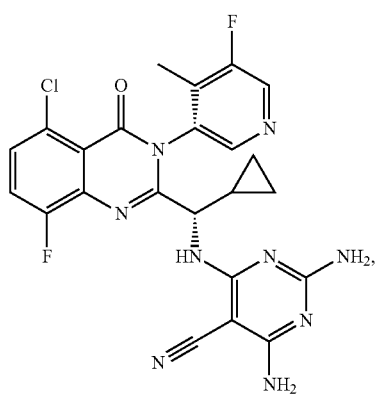
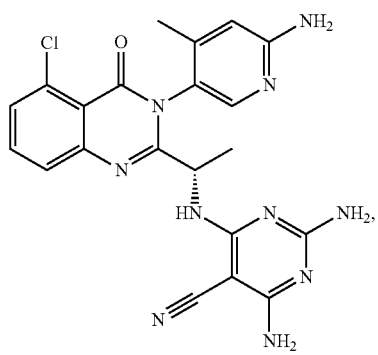
184
-continued
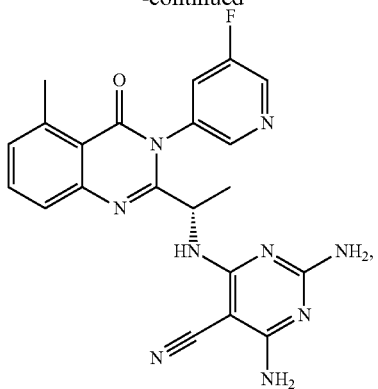
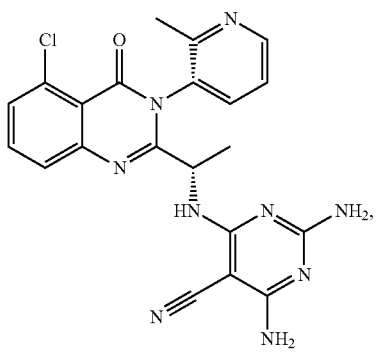
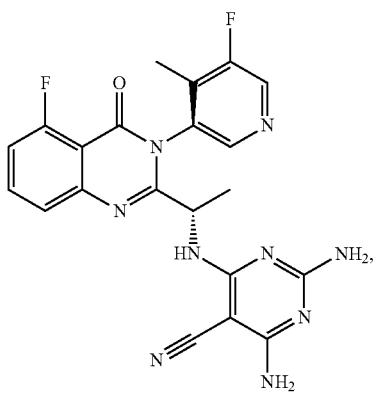
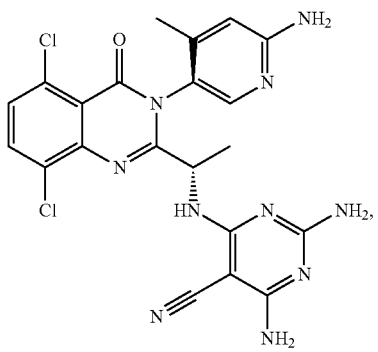

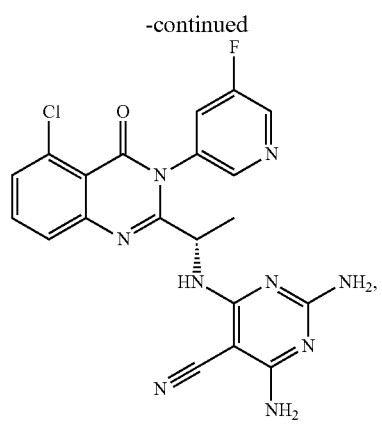
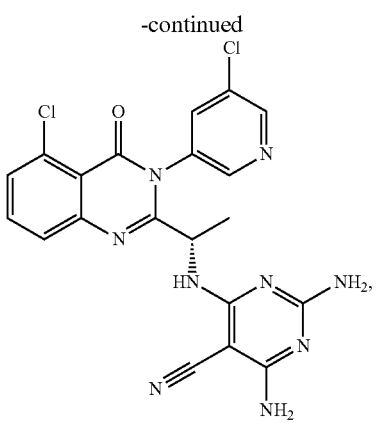
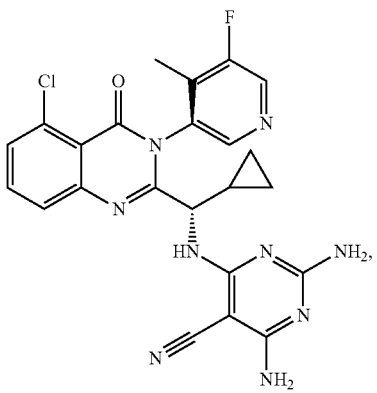
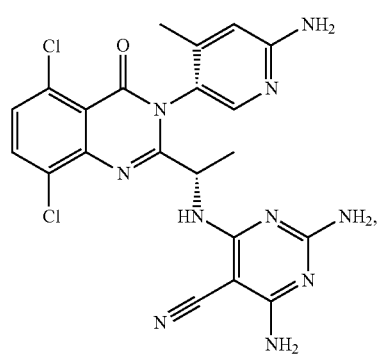

187
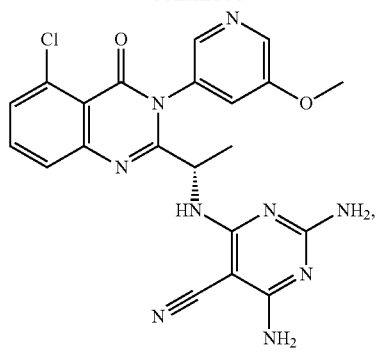
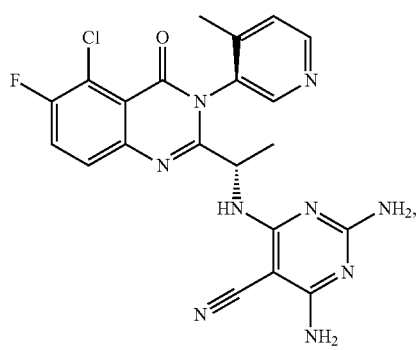
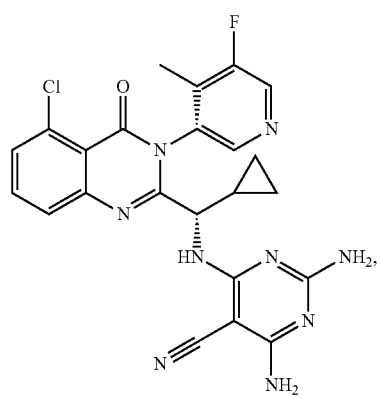
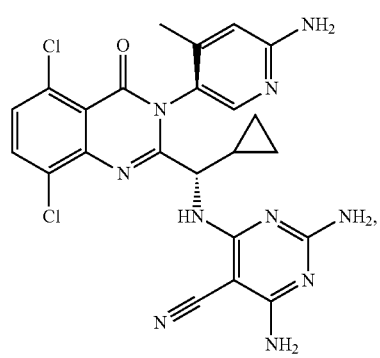
188
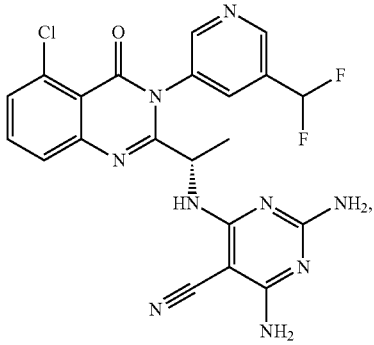
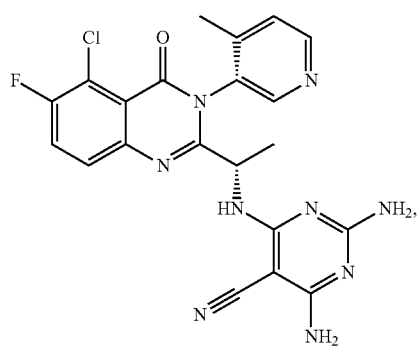
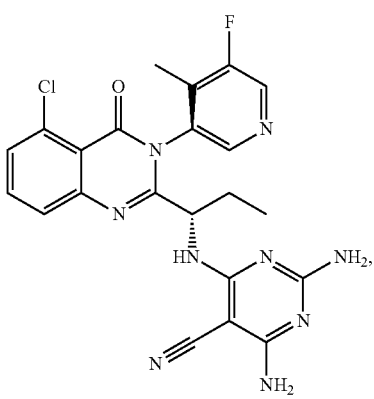
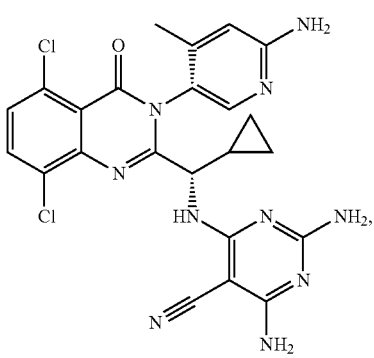

189
-continued
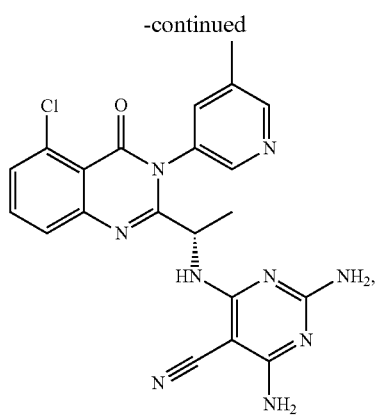
190
-continued
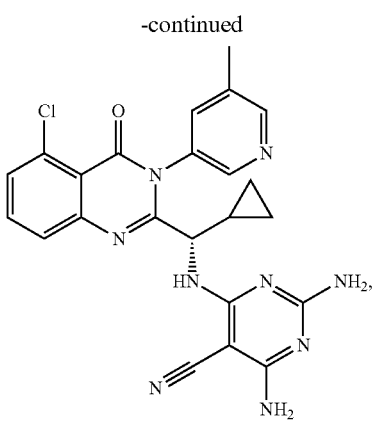
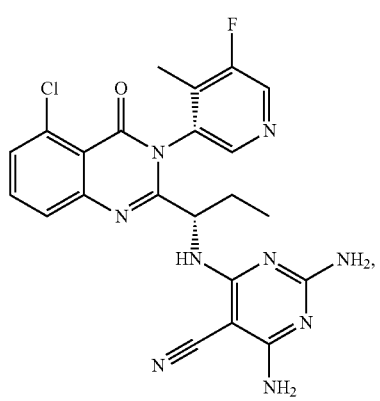
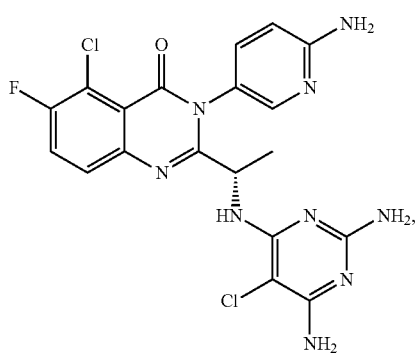
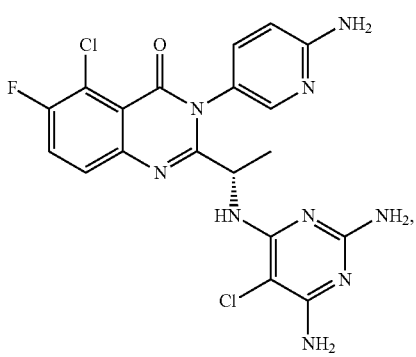

| 191 | 192 |
|---|---|
| -continued | -continued |
| 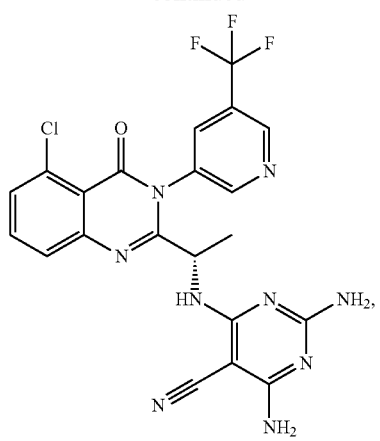 | 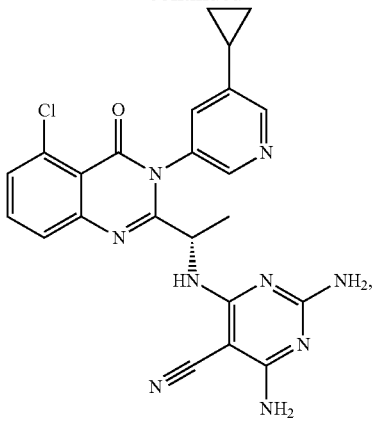 |
| 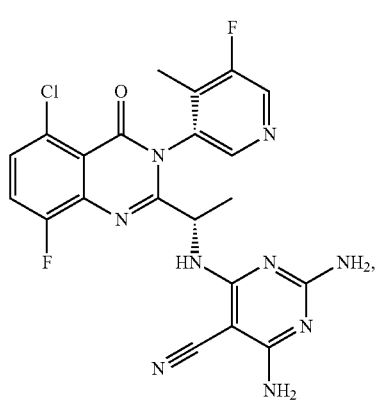 | 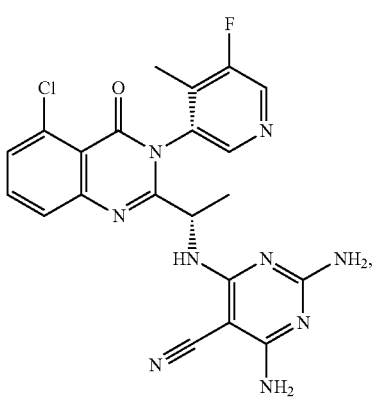 |
| | 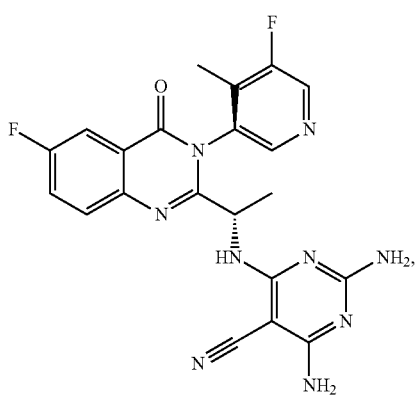 |
| 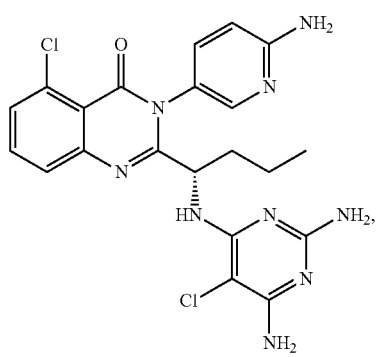 | 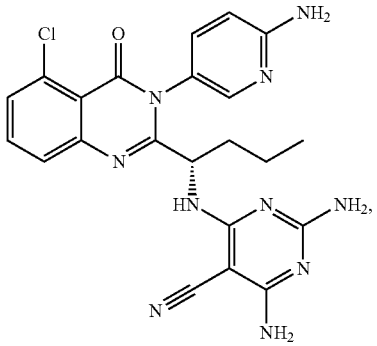 |

193
-continued
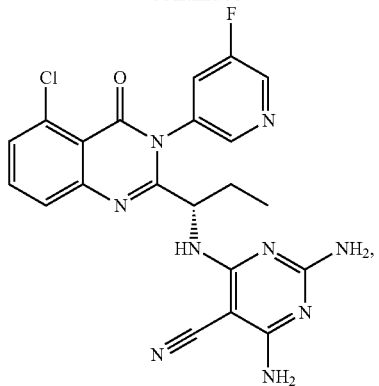
194
-continued
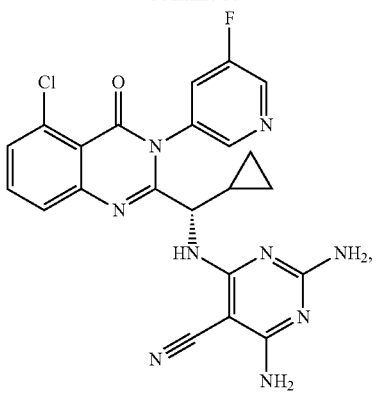
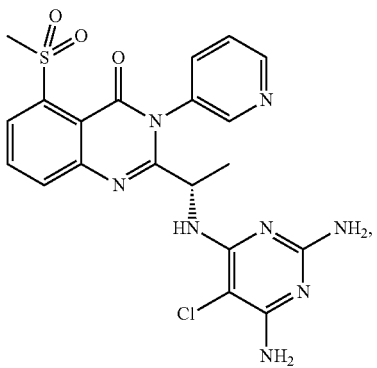
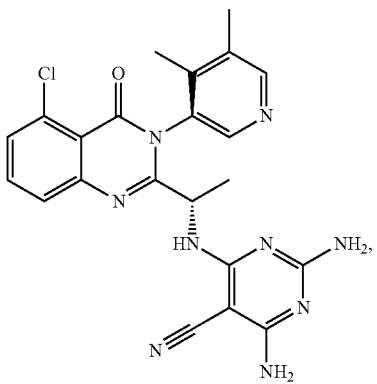
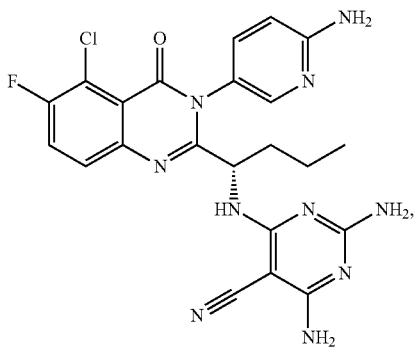

195
-continued
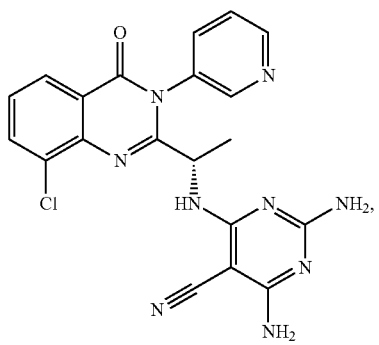
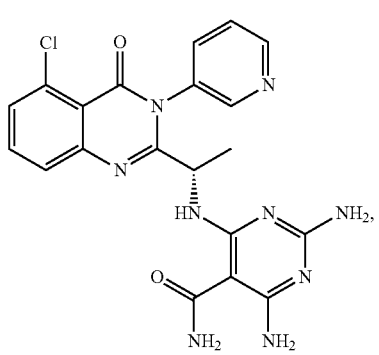
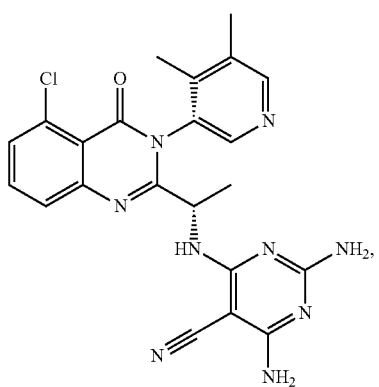
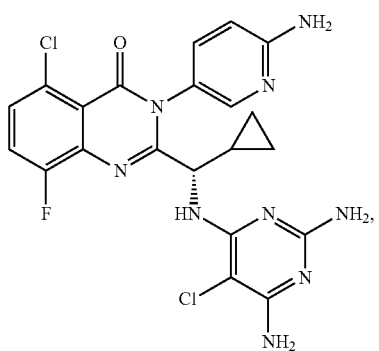
196
-continued
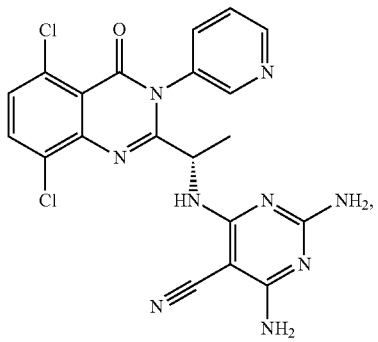
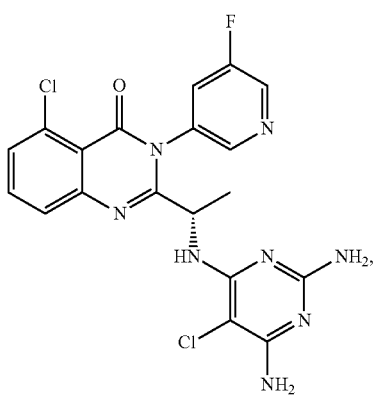
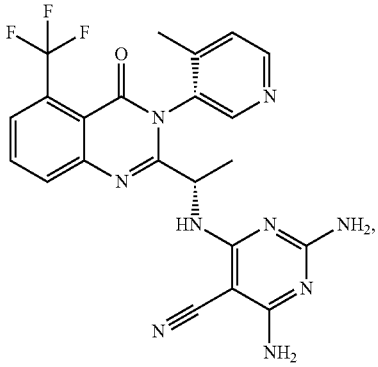
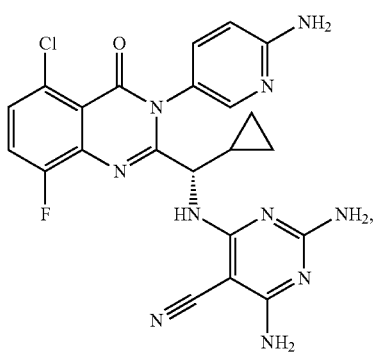

197
-continued
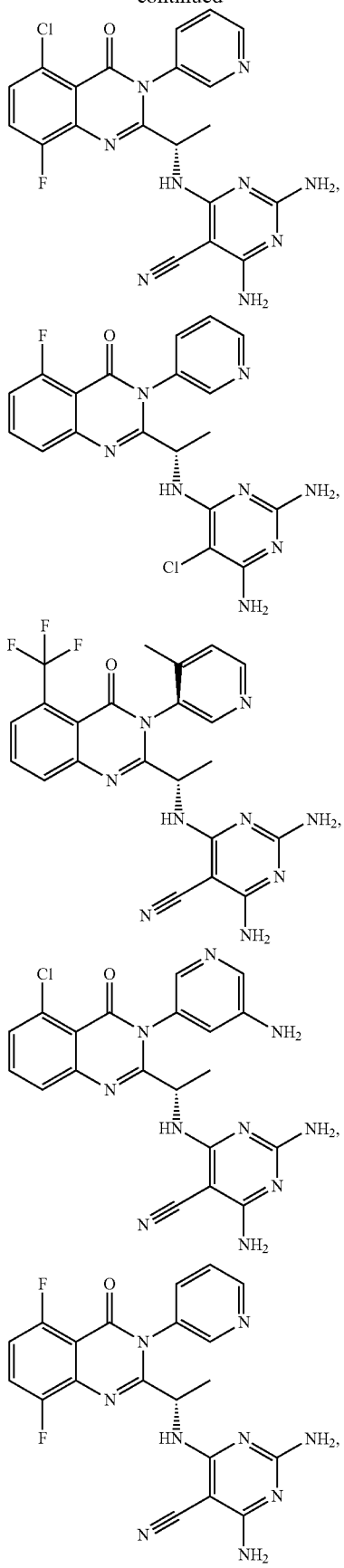
198
-continued
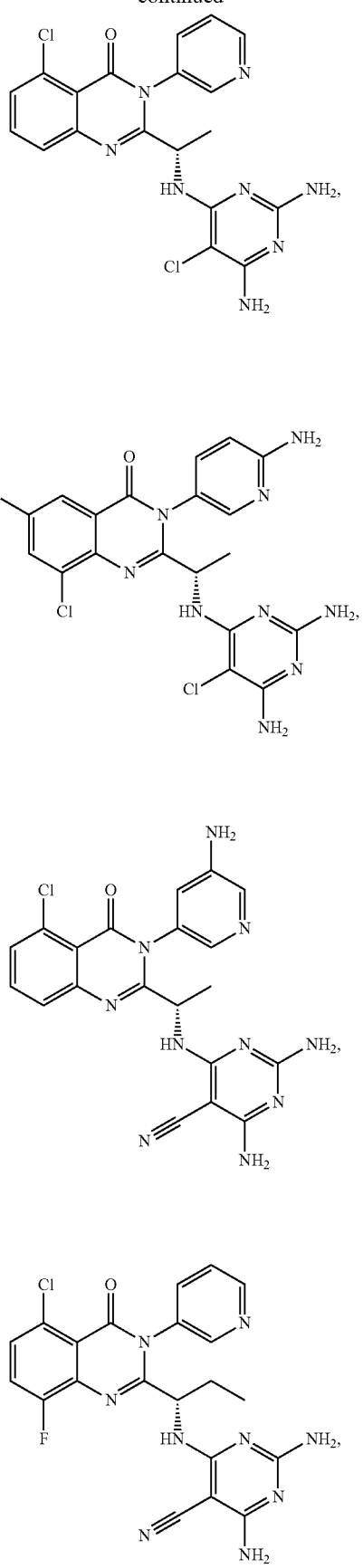

199
-continued
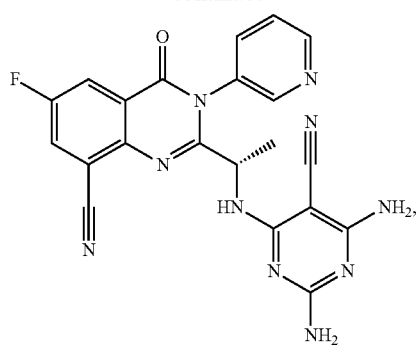
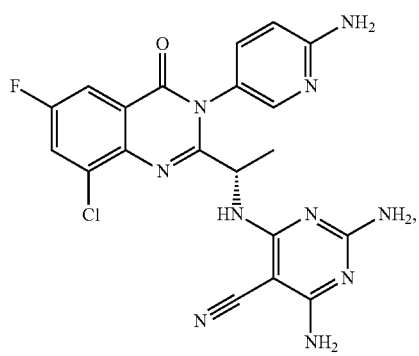
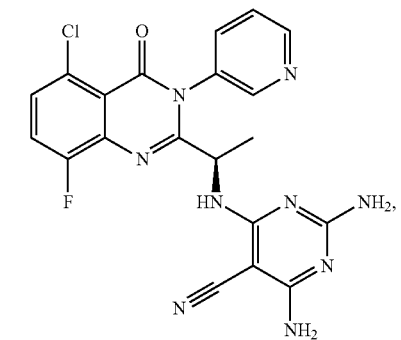
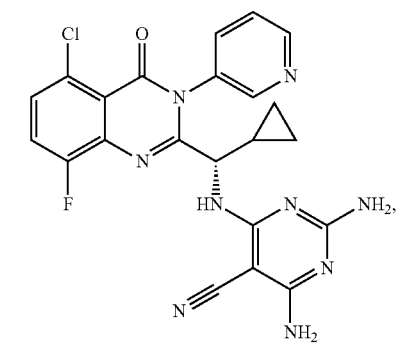
200
-continued
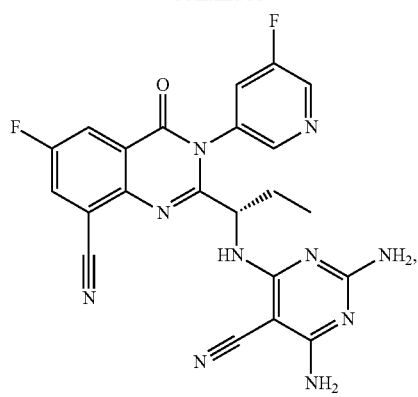
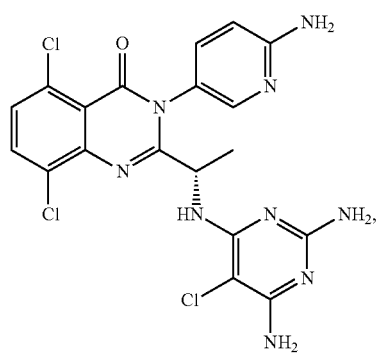
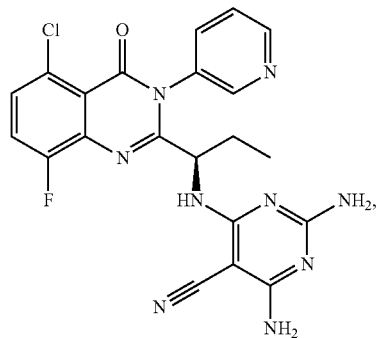
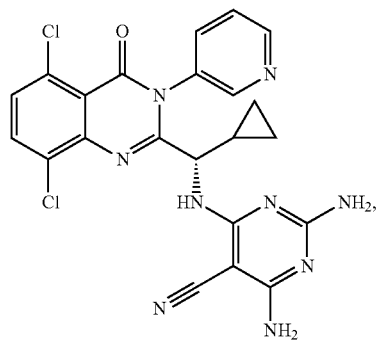

-continued
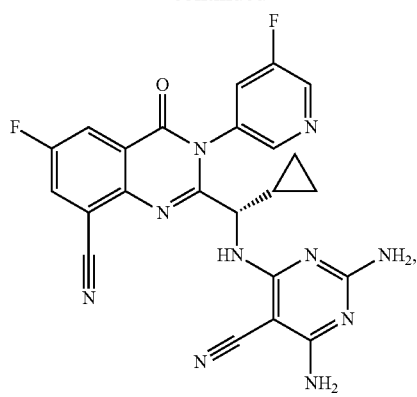
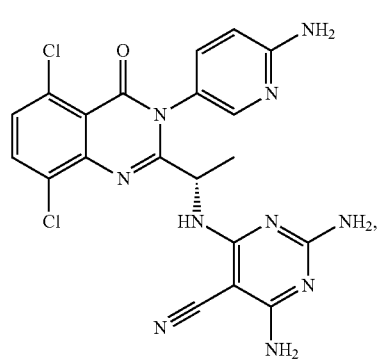
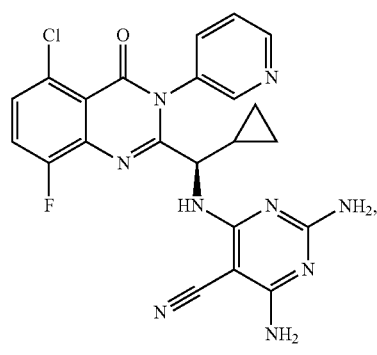
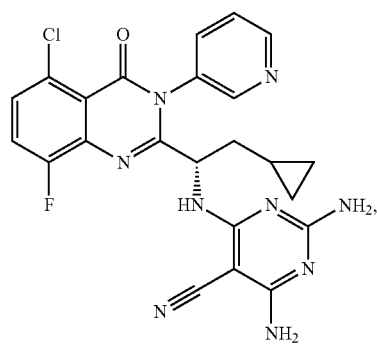
-continued
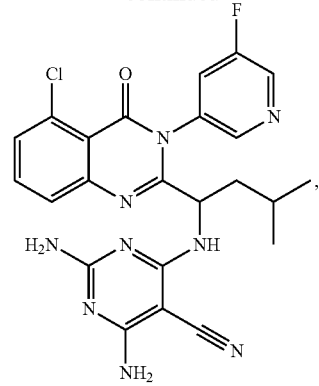
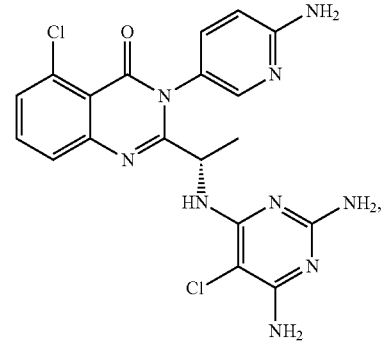
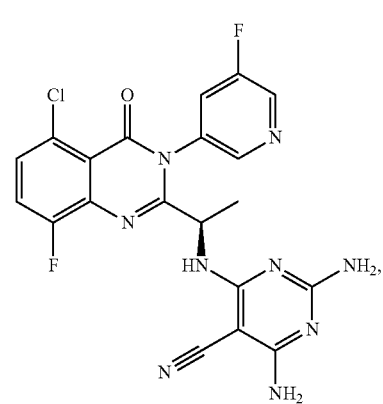
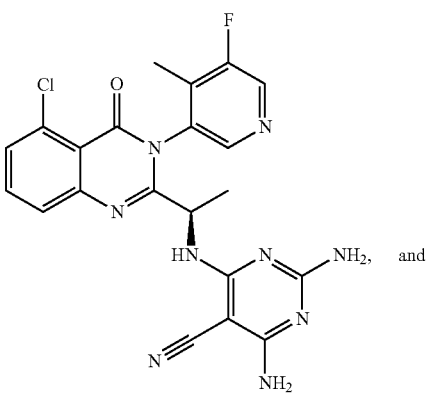
and

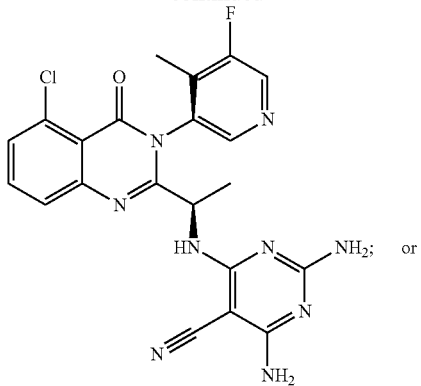
or
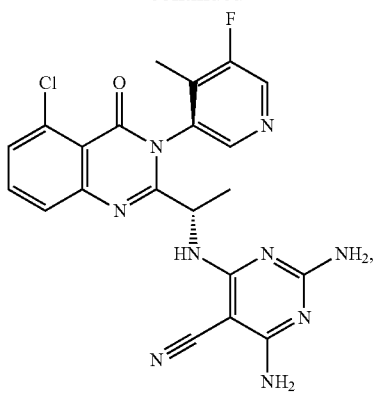
a pharmaceutically acceptable salt thereof or an atropisomer thereof.
33. The pharmaceutical composition of claim 20, wherein the compound is selected from the group consisting of:
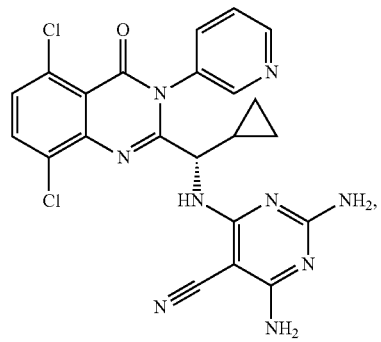
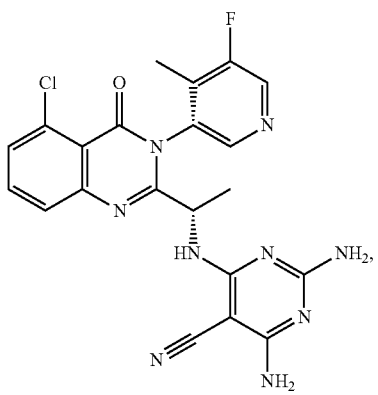
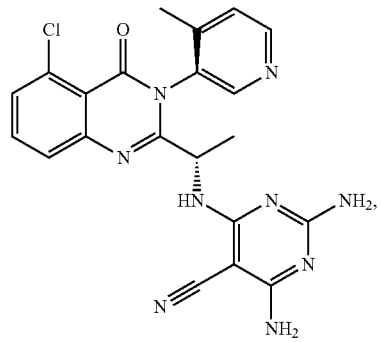
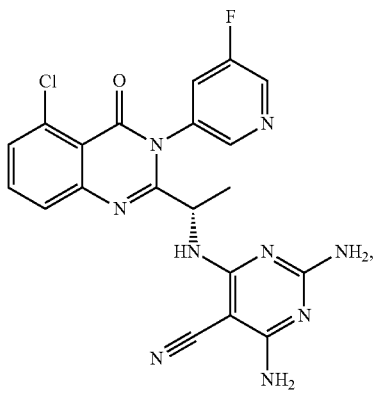
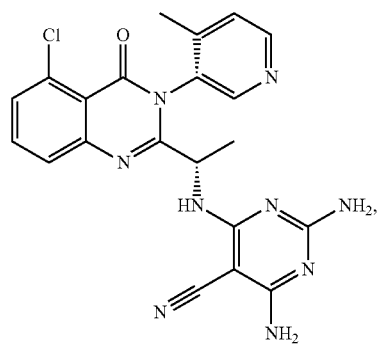
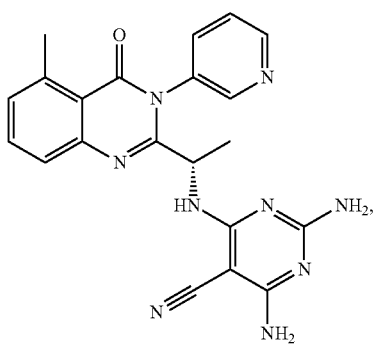

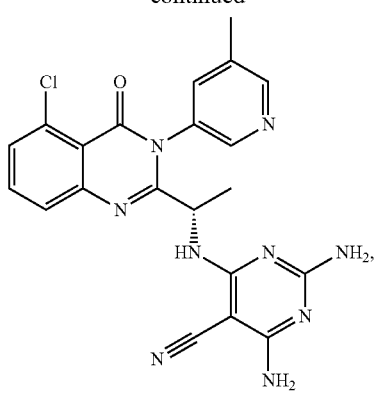
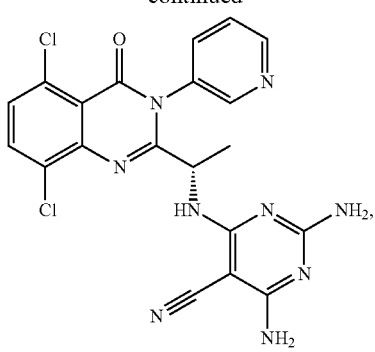
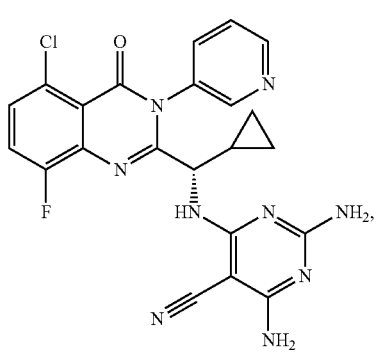
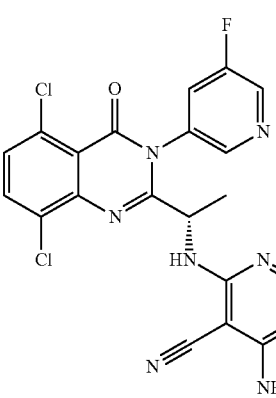
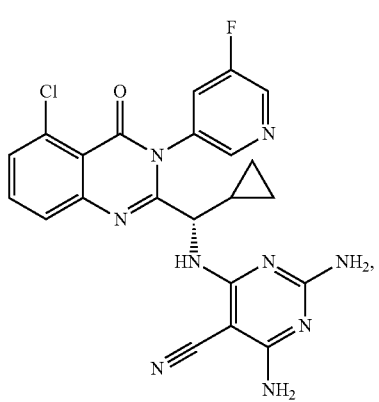
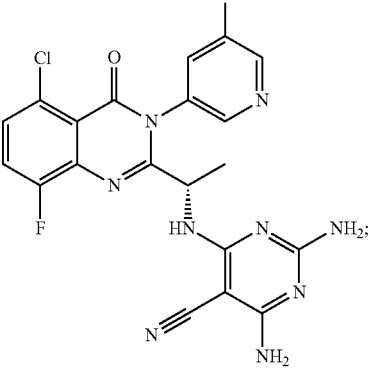
or an atropisomer thereof.
34. The pharmaceutical composition of claim 20, wherein the compound is
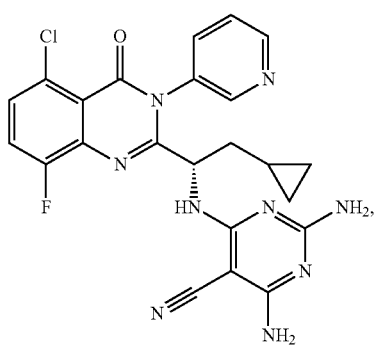
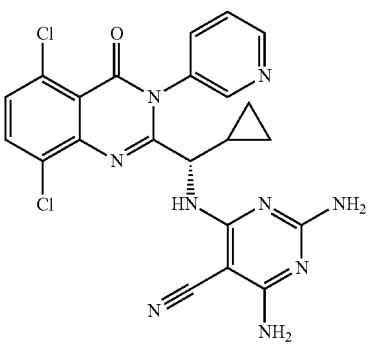
or a pharmaceutically acceptable salt thereof.

35. The pharmaceutical composition of claim 20, wherein the compound is

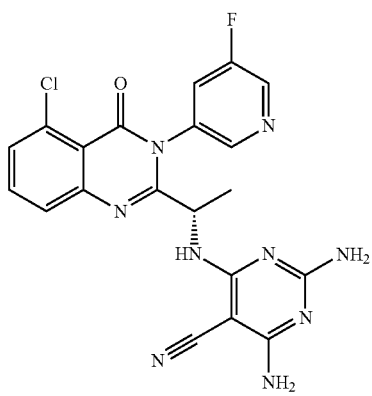

or a pharmaceutically acceptable salt thereof.

36. The pharmaceutical composition of claim 20, wherein the compound is

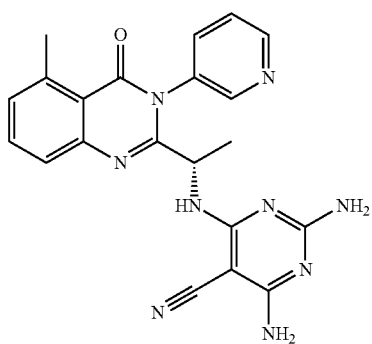 [SMILES: Cc1cccc2nc([C@H](C)Nc3nc(N)nc(N)c3C#N)n(-c3cccnc3)c(=O)c12]

or a pharmaceutically acceptable salt thereof.

37. The pharmaceutical composition of claim 20, wherein the compound is

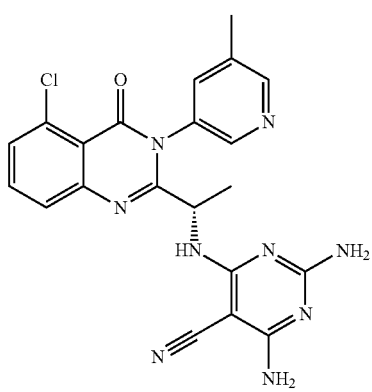 [SMILES: Cc1cncc(-n2c([C@H](C)Nc3nc(N)nc(N)c3C#N)nc3cccc(Cl)c3c2=O)c1]

or a pharmaceutically acceptable salt thereof.

38. The pharmaceutical composition of claim 20, wherein the compound is

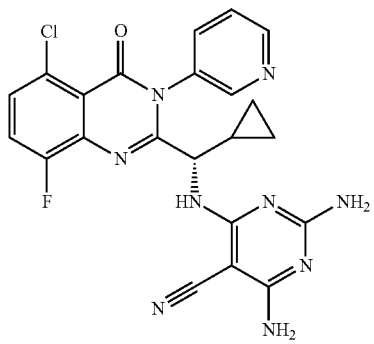

or a pharmaceutically acceptable salt thereof.

39. The pharmaceutical composition of claim 20, wherein the compound is

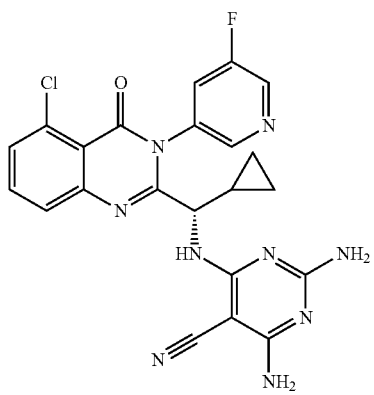 [SMILES: N#Cc1c(N)nc(N)nc1N[C@H](c1nc2cccc(Cl)c2c(=O)n1-c1cncc(F)c1)C1CC1]

or a pharmaceutically acceptable salt thereof.

40. The pharmaceutical composition of claim 20, wherein the compound is

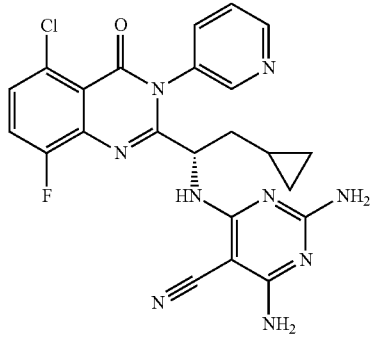

or a pharmaceutically acceptable salt thereof.

41. The pharmaceutical composition of claim 20, wherein the compound is

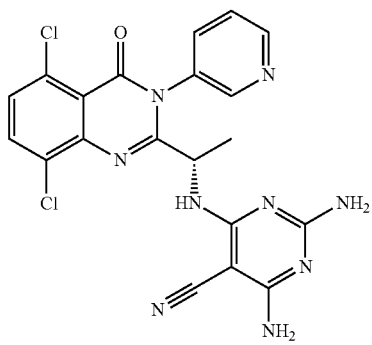 [SMILES: C[C@H](Nc1nc(N)nc(N)c1C#N)c1nc2c(Cl)ccc(Cl)c2c(=O)n1-c1cccnc1]

or a pharmaceutically acceptable salt thereof.

42. The pharmaceutical composition of claim 20, wherein the compound is

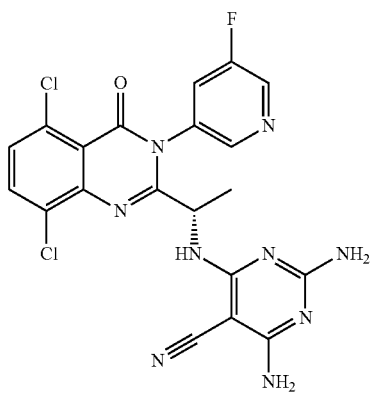 [SMILES: C[C@H](Nc1nc(N)nc(N)c1C#N)c1nc2c(Cl)ccc(Cl)c2c(=O)n1-c1cncc(F)c1]

or a pharmaceutically acceptable salt thereof.

43. The pharmaceutical composition of claim 20, wherein the compound is

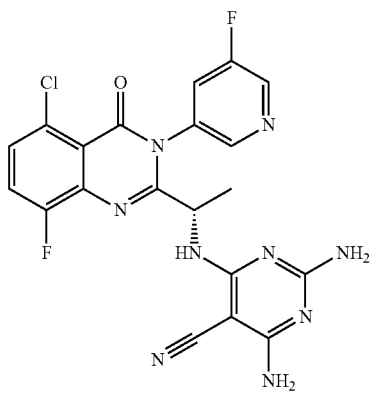

or a pharmaceutically acceptable salt thereof.

44. A composition comprising a compound having the structure of formula (1):

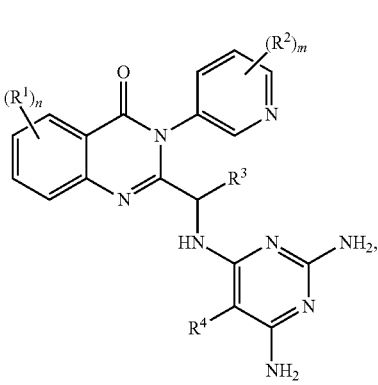

a pharmaceutically acceptable salt thereof, an isomer thereof, or a mixture thereof, wherein:

n is 0, 1, 2, 3, or 4;

each $R^1$ is independently selected from halo, cyano, alkyl, or alkylsulfonyl, wherein the alkyl moiety may be optionally substituted with 1 to 3 halogen;

in is 0, 1, 2, or 3;

each $R^2$ is independently selected from halo, $-NH_2$, alkoxy, alkyl, or cycloalkyl, wherein, the alkyl moiety may be optionally substituted with 1 to 3 halogen;

$R^3$ is hydrogen, alkyl, or cycloalkyl, wherein the alkyl moiety may be optionally substituted with cycioalkyl; and $R^4$ is cyano, halo, or $CONH_2$.

45. The composition of claim 44, wherein the mixture comprises the (S)-enantiomer and the (R)-enantiomer of the compound or a pharmaceutically acceptable salt thereof.

46. The composition of claim 45, wherein the (S)-enantiomer of the compound or a pharmaceutically acceptable salt thereof is present in excess of the corresponding (R)-enantiomer.

47. The composition of claim 45, wherein the composition comprises the (S)-enantiomer of the compound or a pharmaceutically acceptable, salt thereof and is substantially free of the corresponding (R)-enantiomer.

48. The composition of claim 44, wherein the compound is selected from the group consisting of:

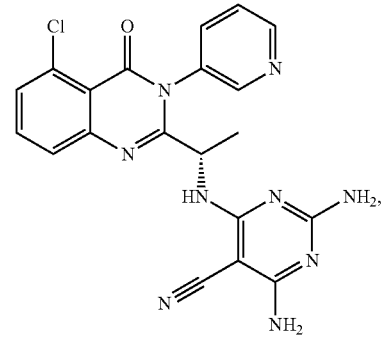

211
-continued
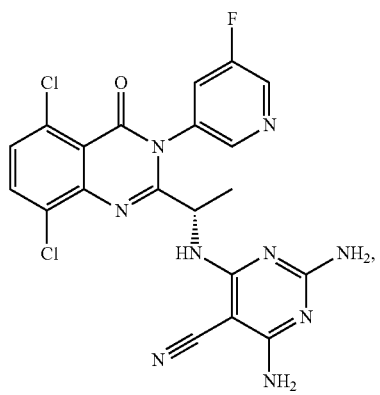
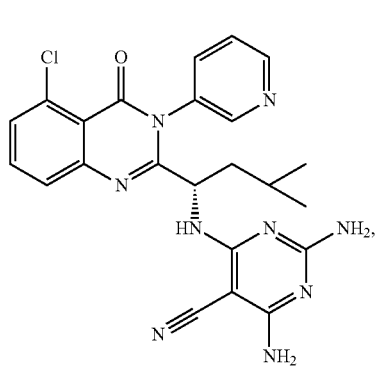
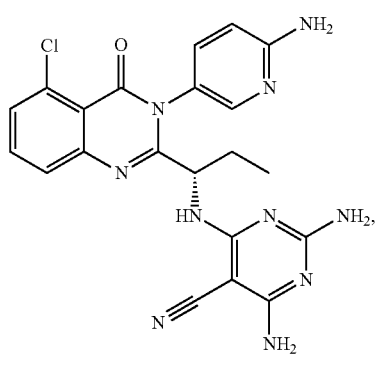
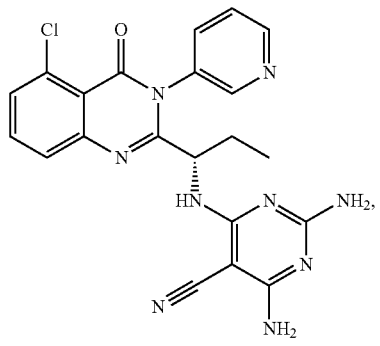
212
-continued
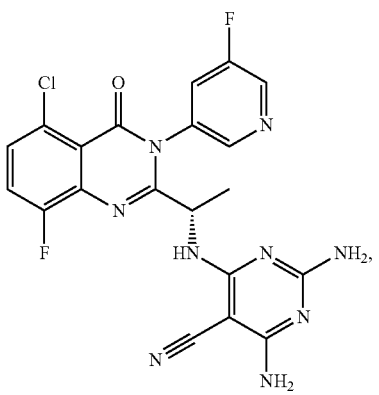
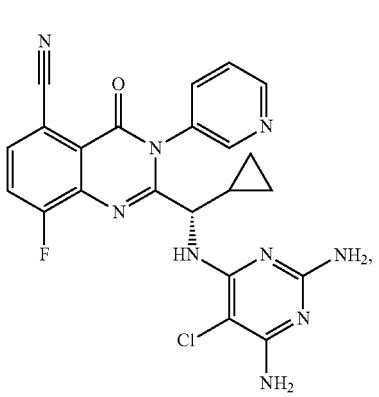
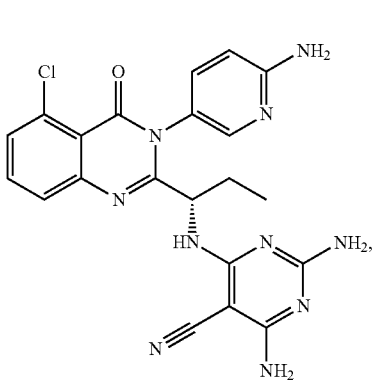
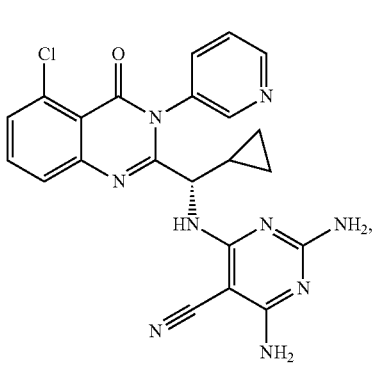

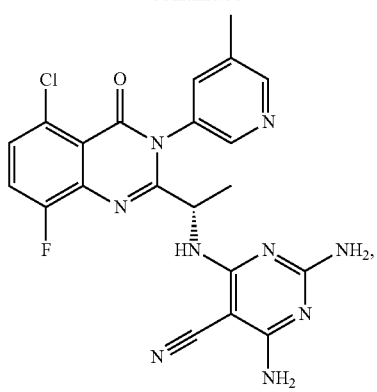
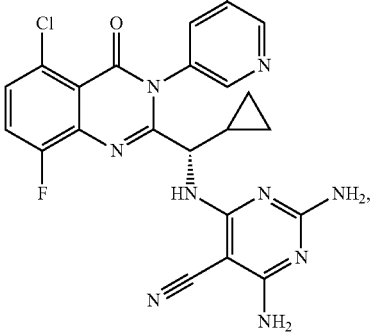
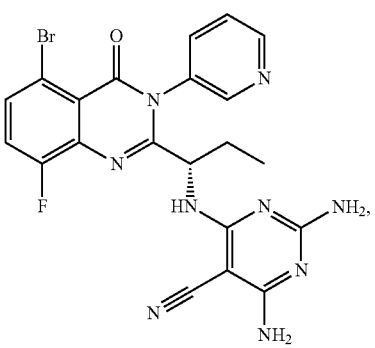
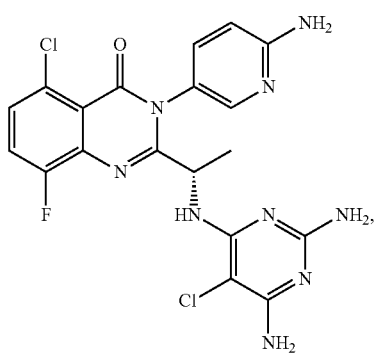
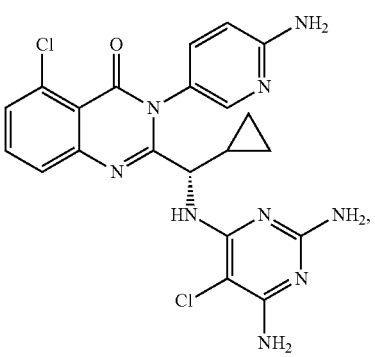
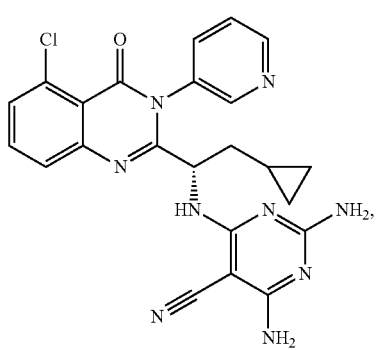

215
-continued
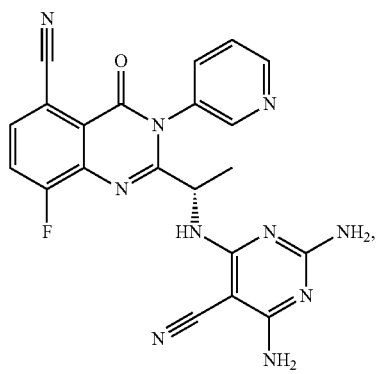
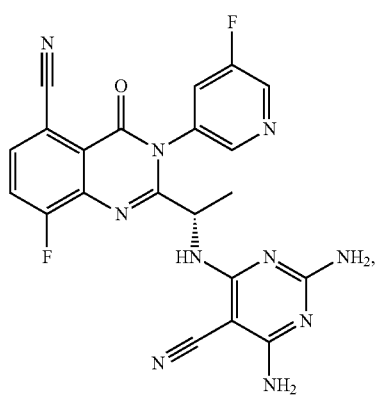
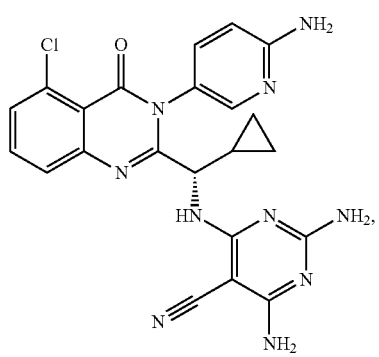
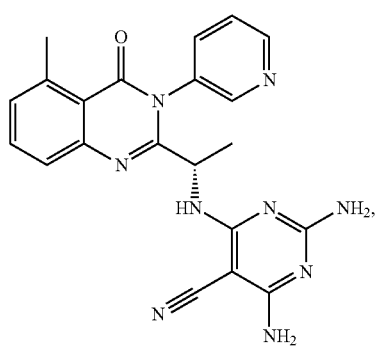
216
-continued
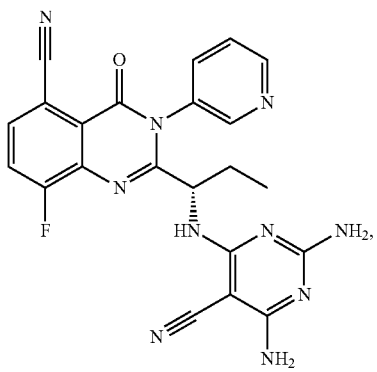
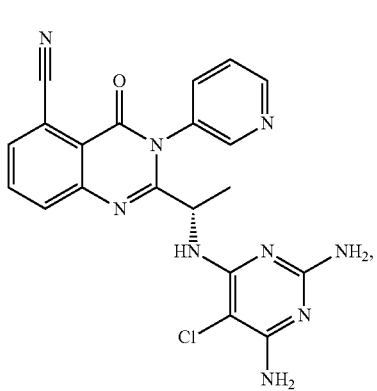
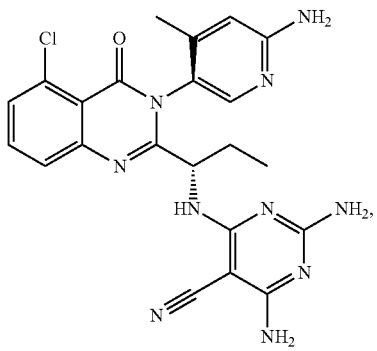
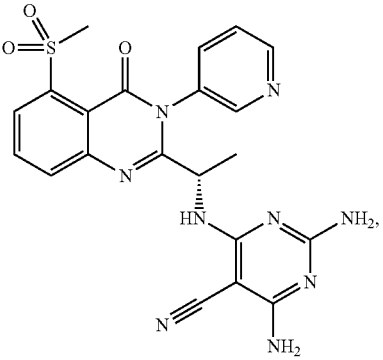

217
-continued
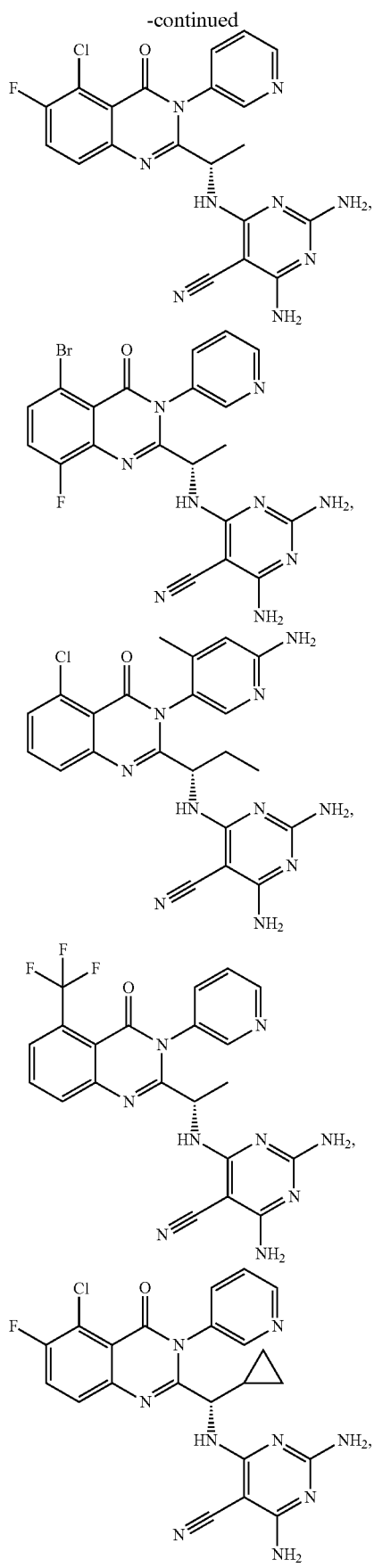
218
-continued
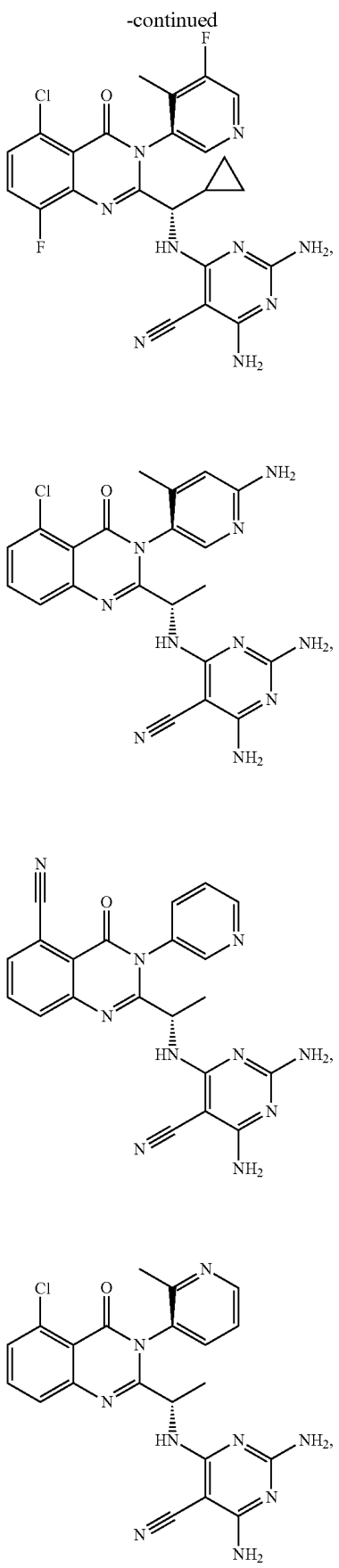

219
-continued
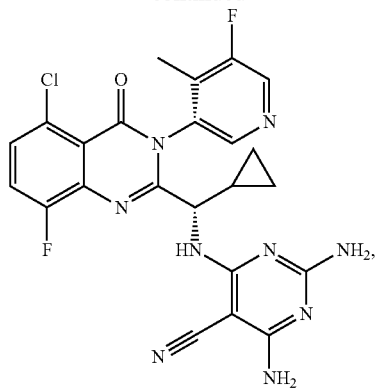
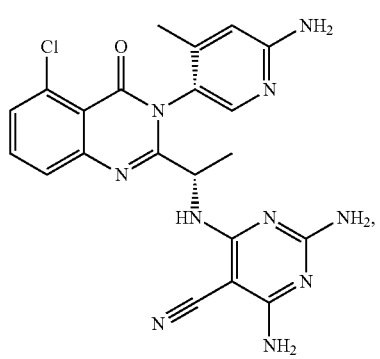
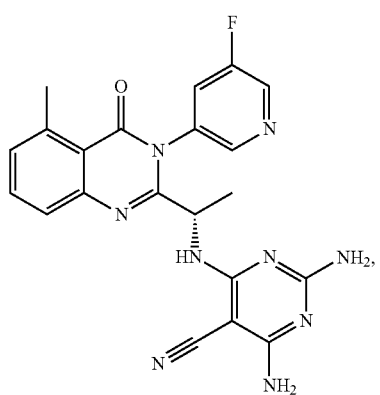
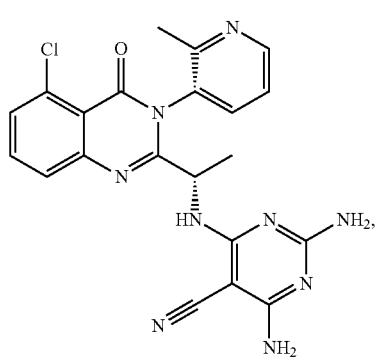
220
-continued
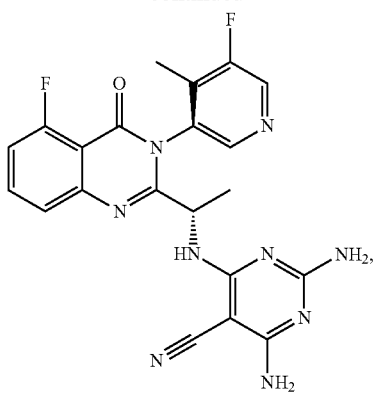
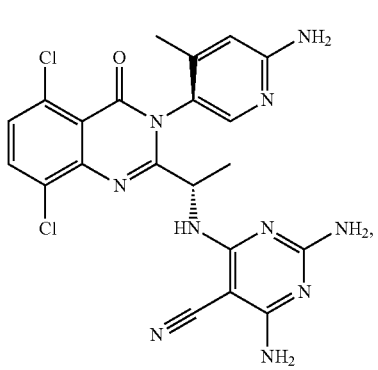
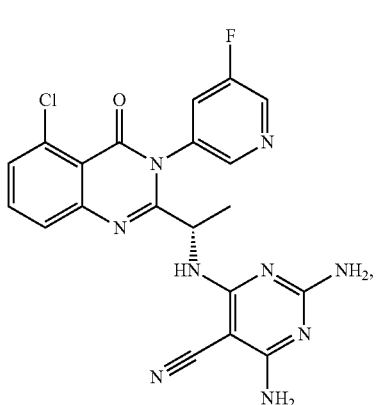
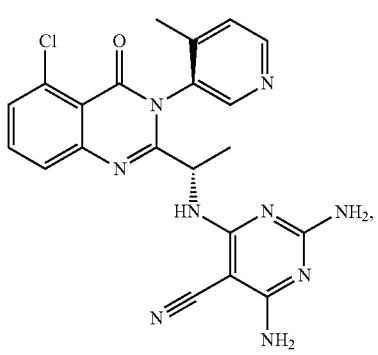

-continued
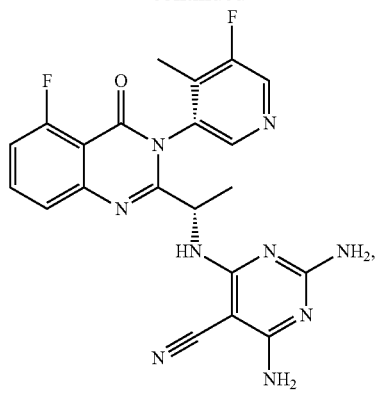
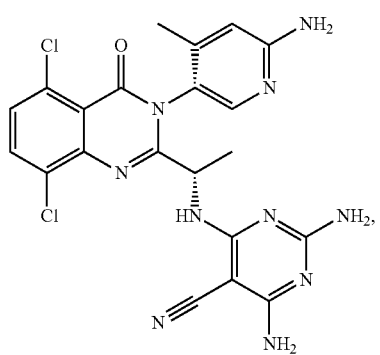
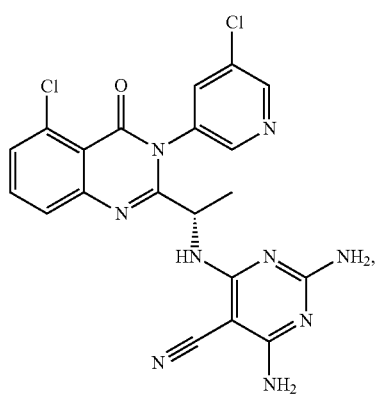
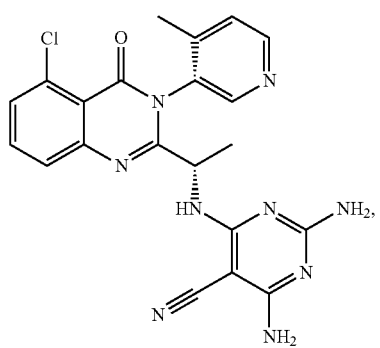
-continued
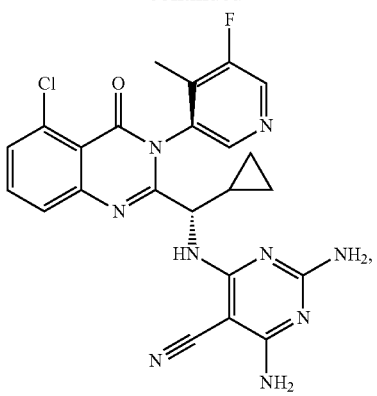
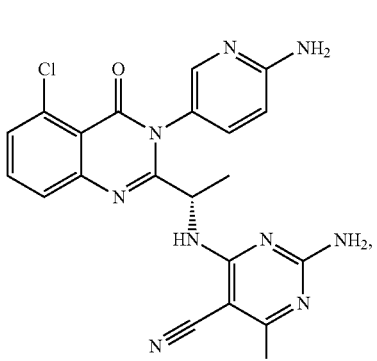
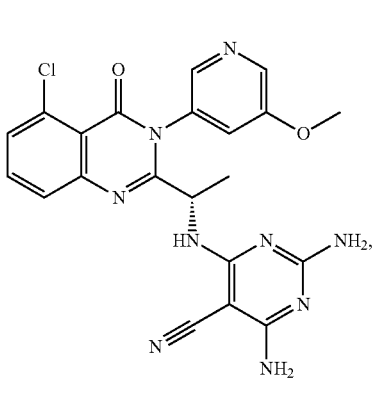
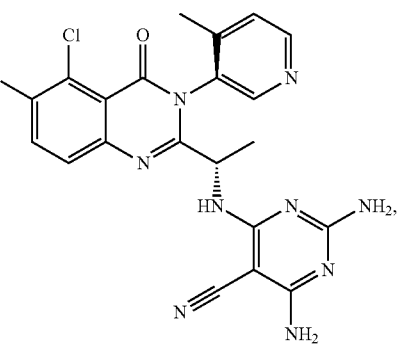

-continued
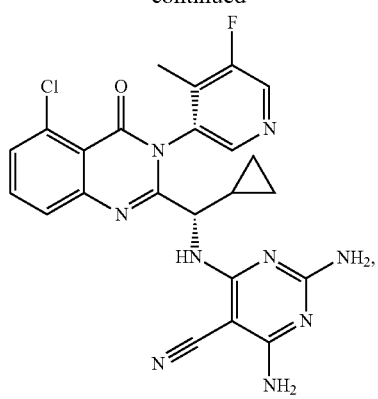
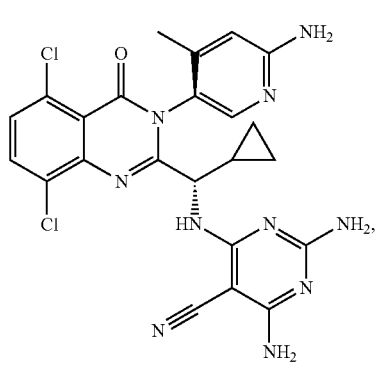
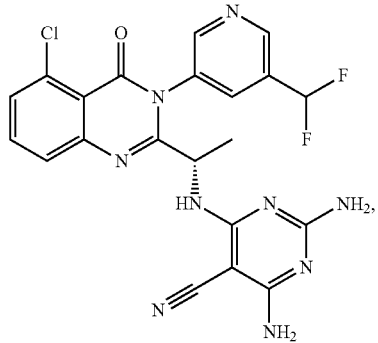
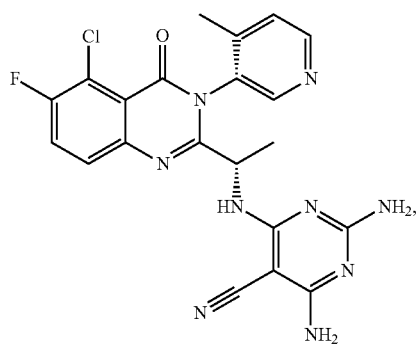
-continued
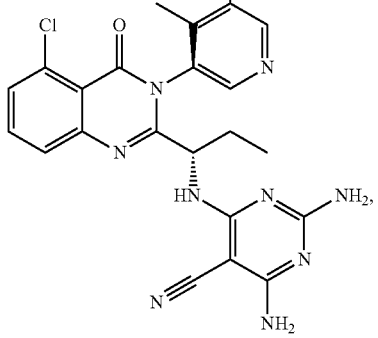
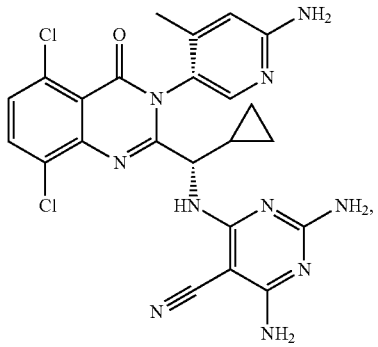
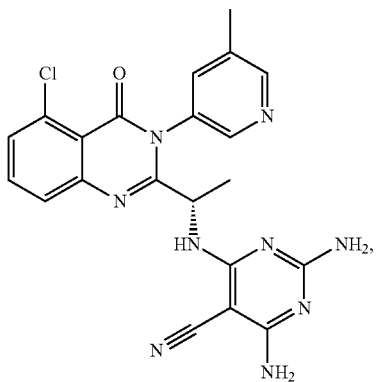
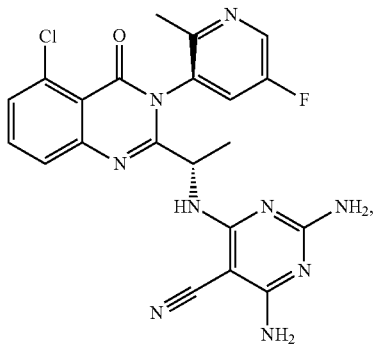

225
-continued
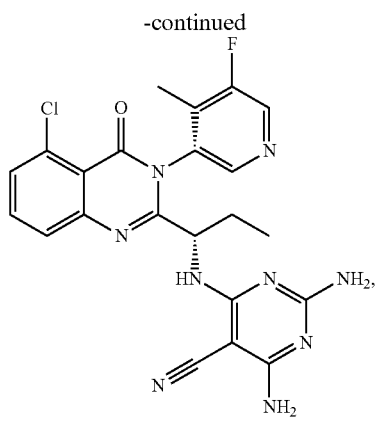
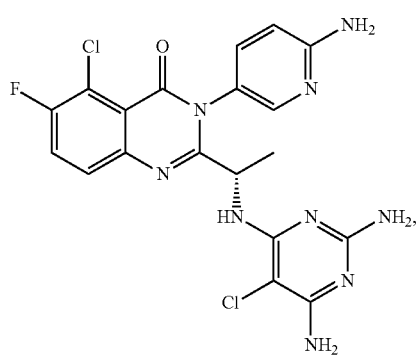
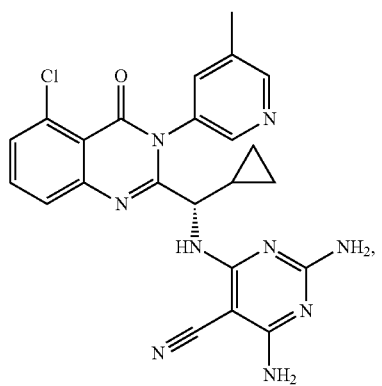
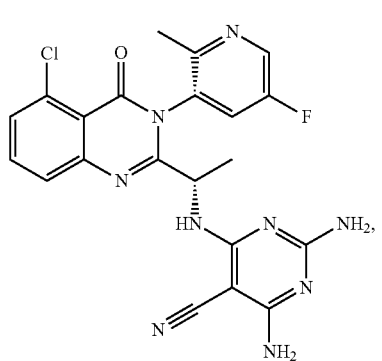
226
-continued
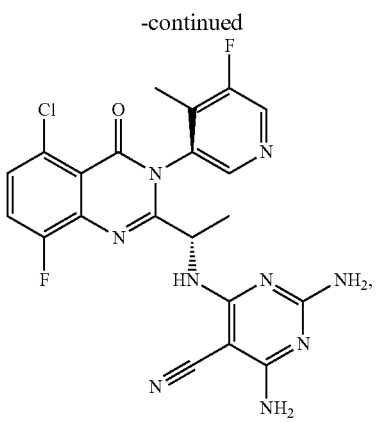
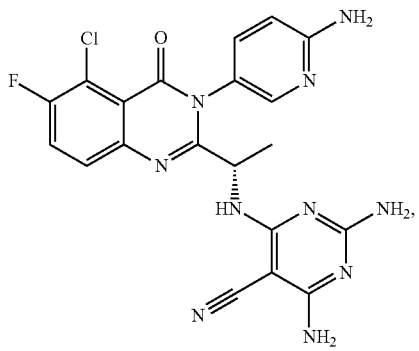
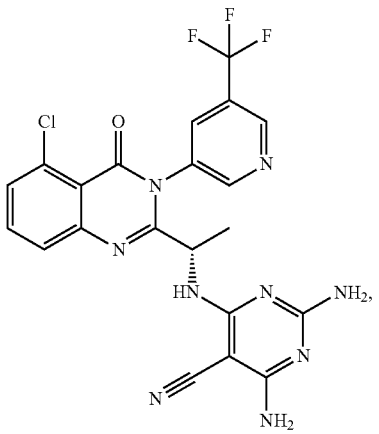
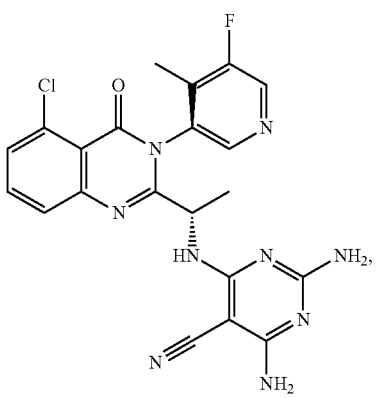

227
-continued

228
-continued

229
-continued
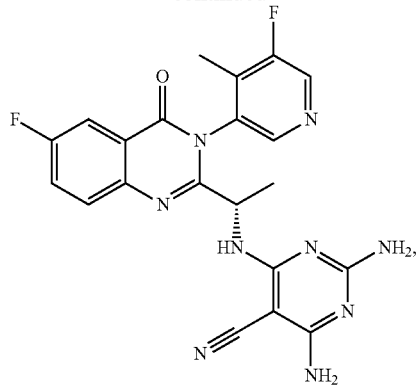
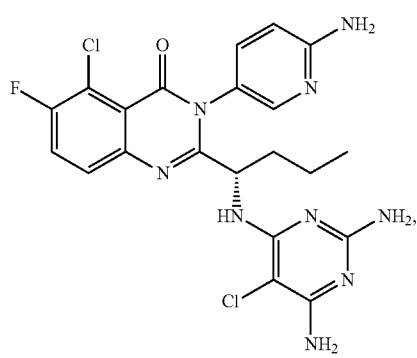
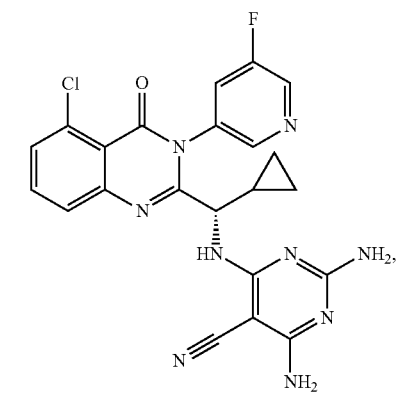
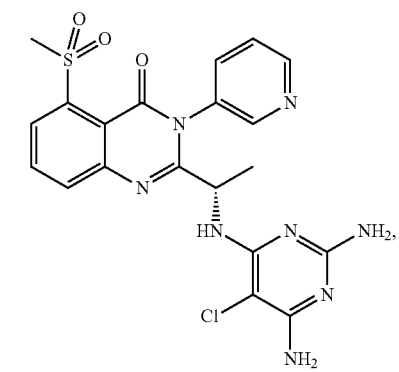
230
-continued
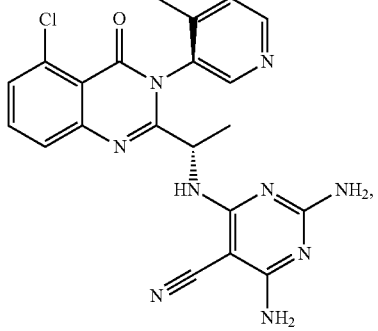
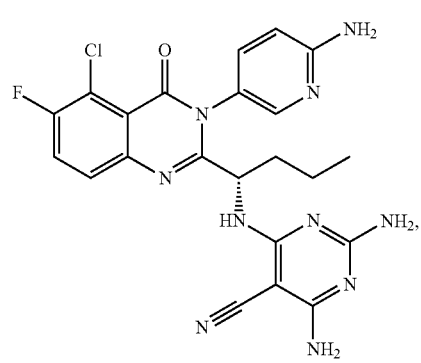
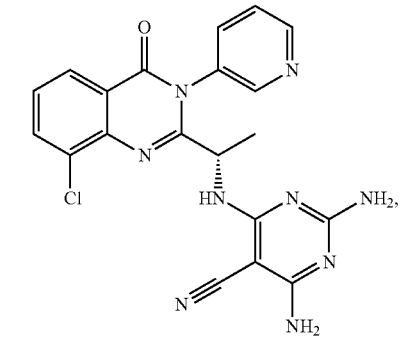
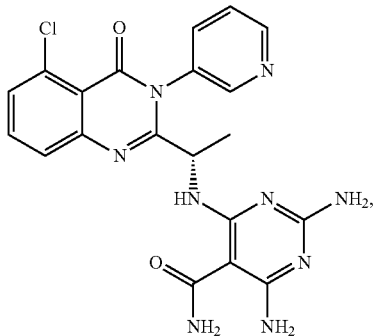

231
-continued
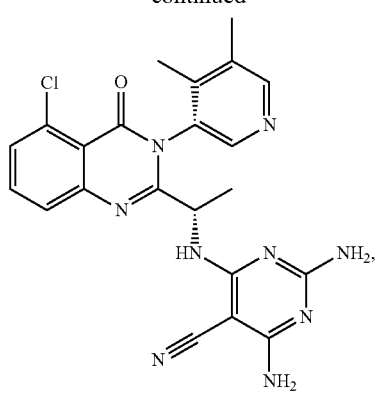
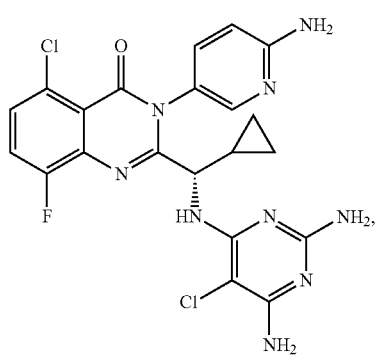
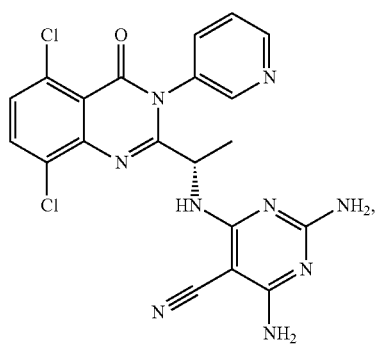
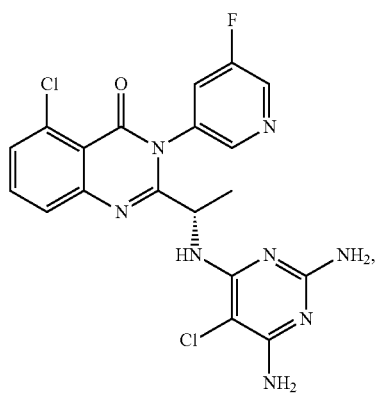
232
-continued
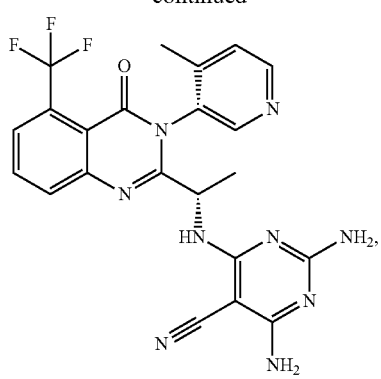
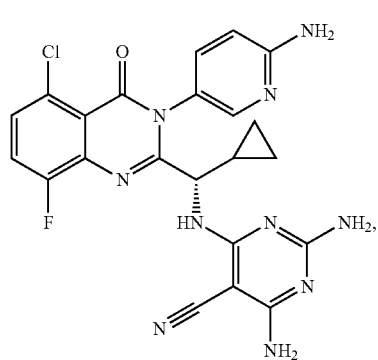
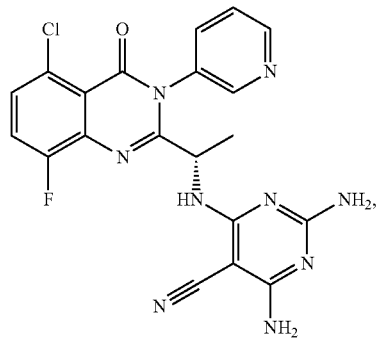
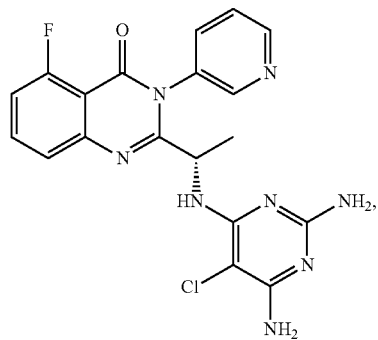

233
-continued
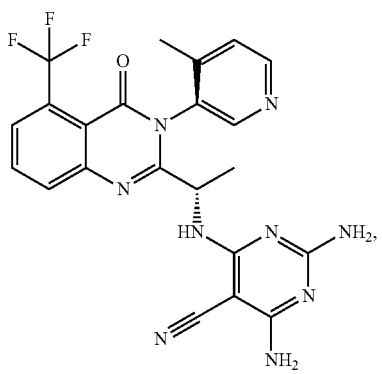
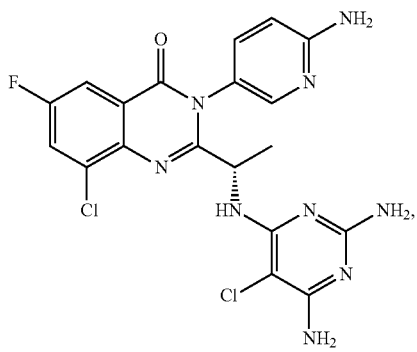
234
-continued
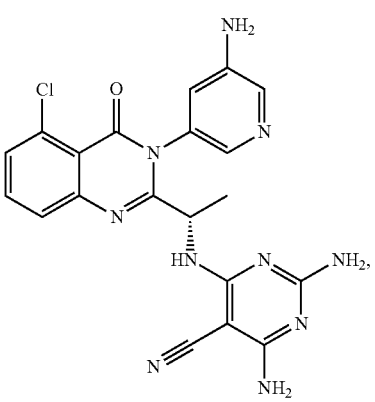
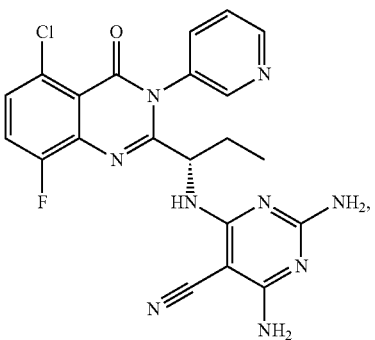
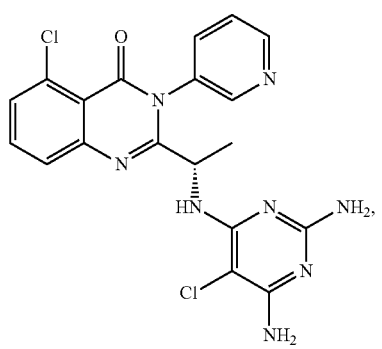
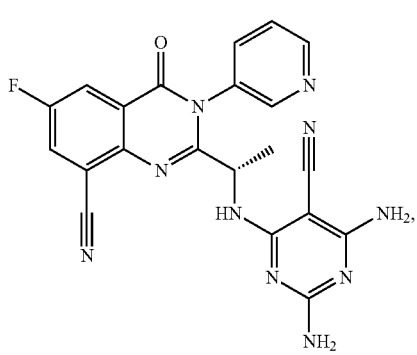

235
-continued
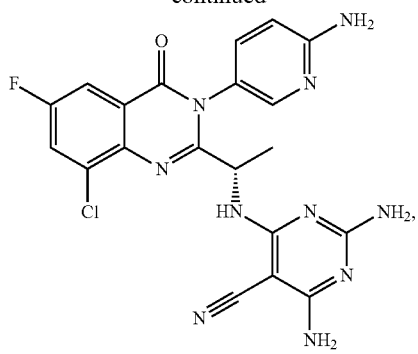
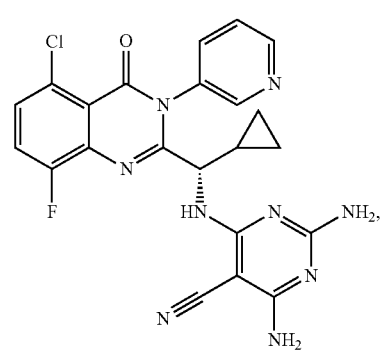
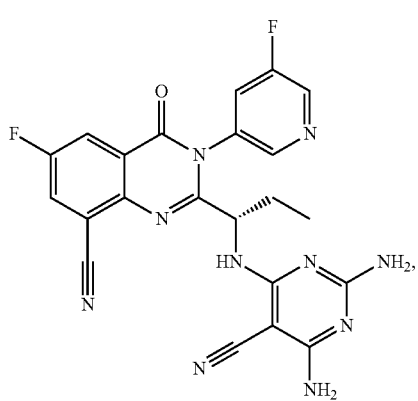
236
-continued
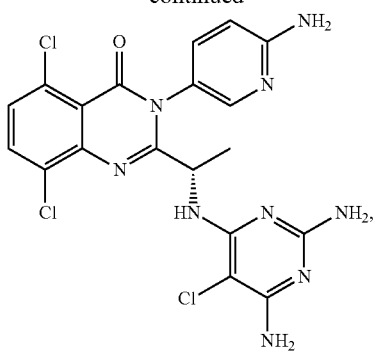
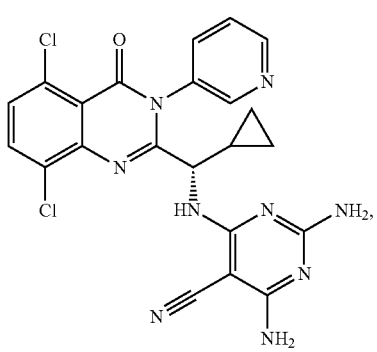
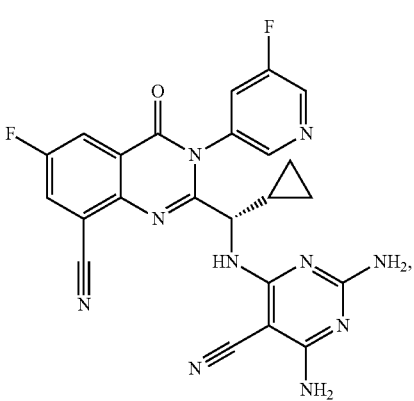

237
-continued
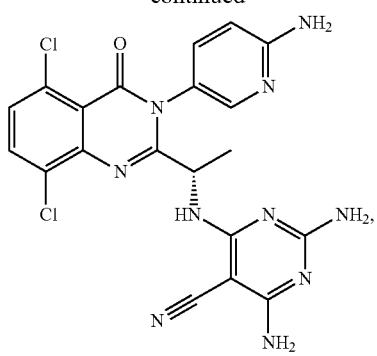
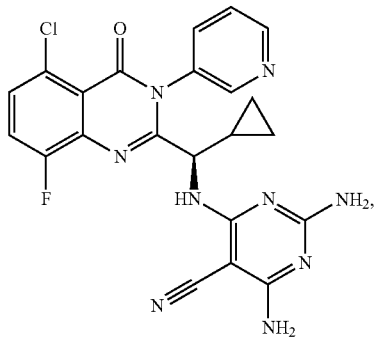
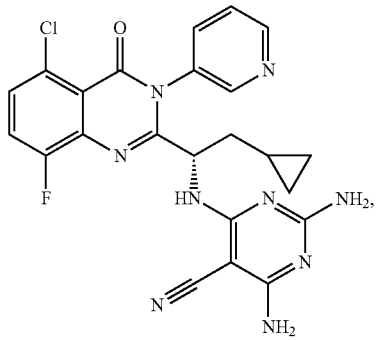
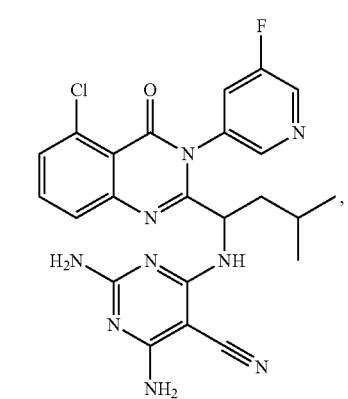
238
-continued
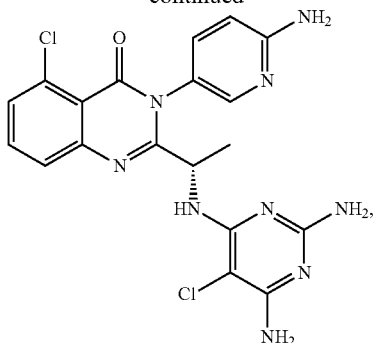
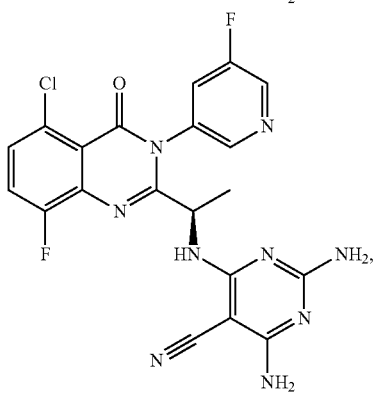
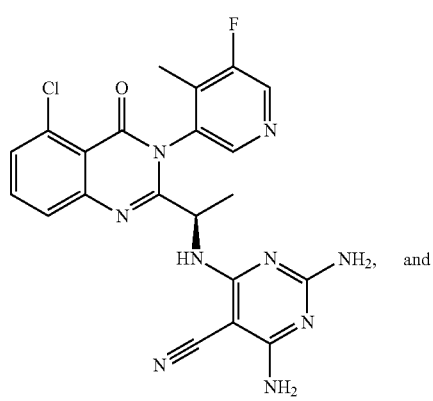
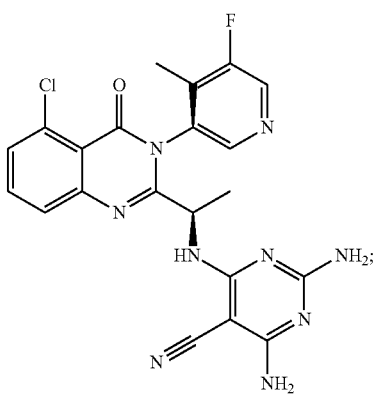
or a pharmaceutically acceptable salt thereof or an atropisomer thereof.

49. The composition of claim 44, wherein the compound is selected from the group consisting of:
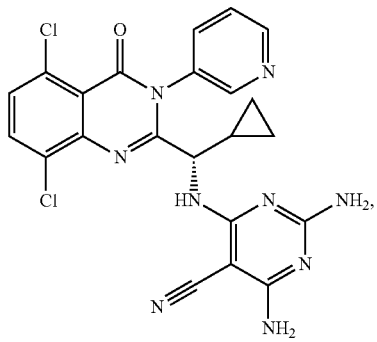
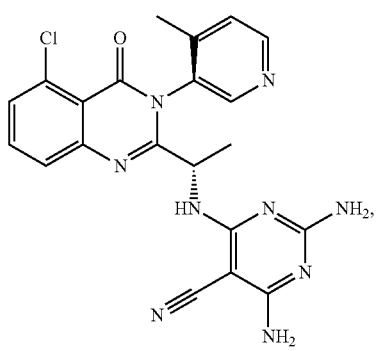
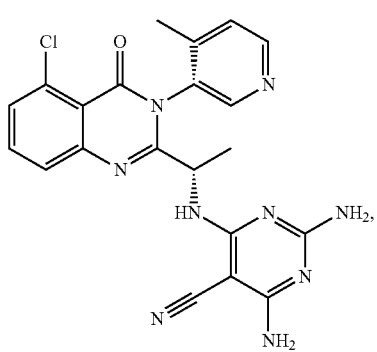
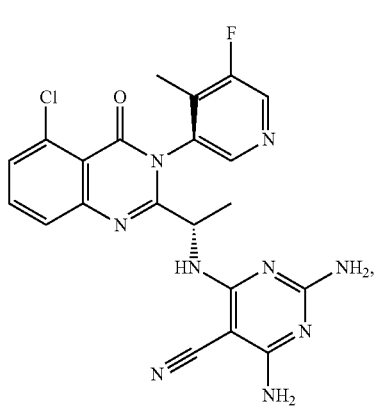
-continued
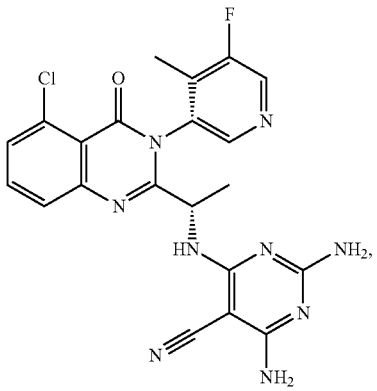
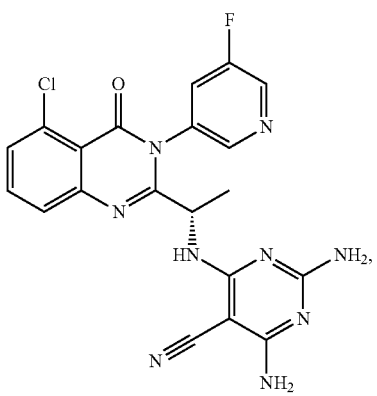
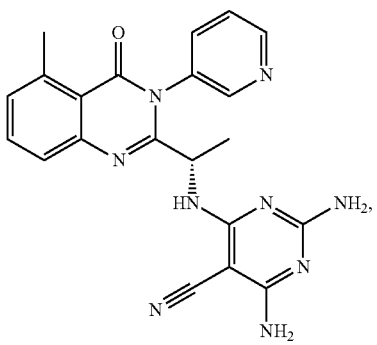
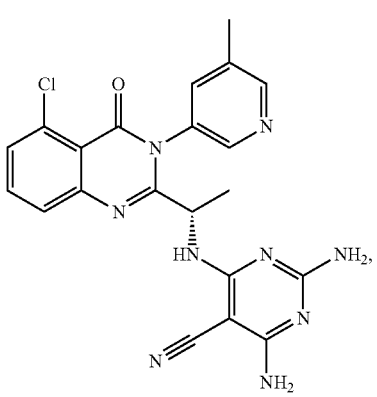

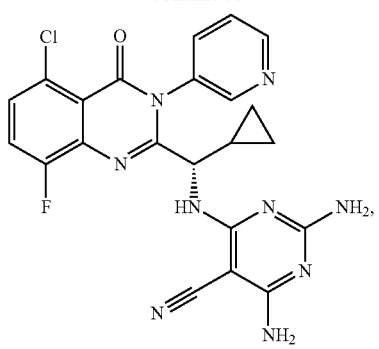
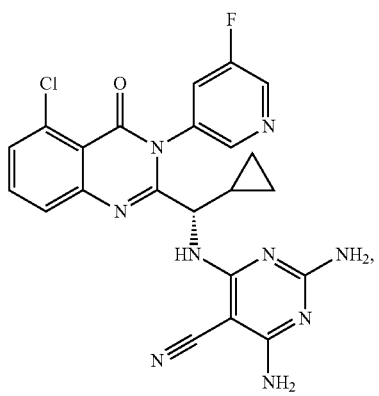
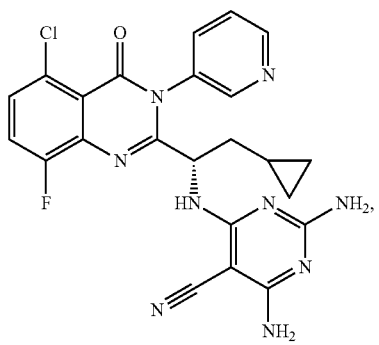
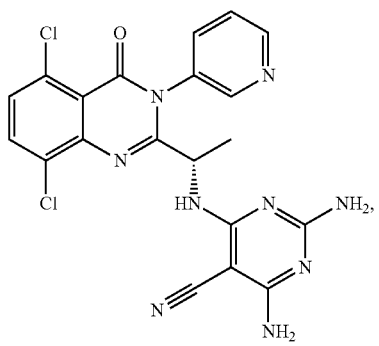
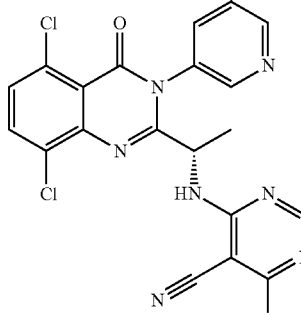
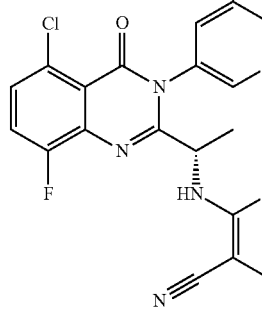
or an atropisomer thereof.
50. The composition of claim 44, wherein the compound is
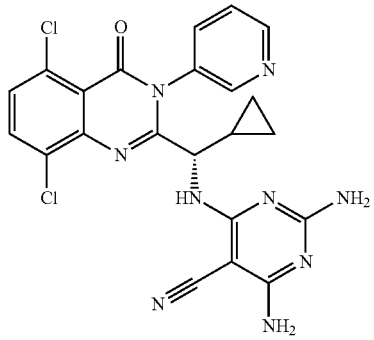
or a pharmaceutically acceptable salt thereof.
51. The composition of claim 44, wherein the compound is
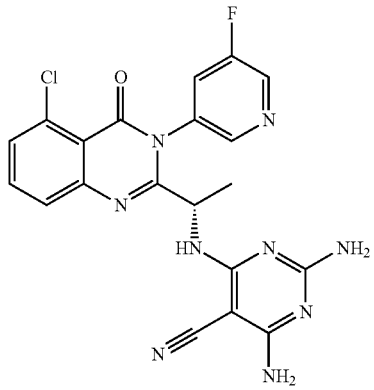
or a pharmaceutically acceptable salt thereof.

52. The composition of claim 44, wherein the compound is

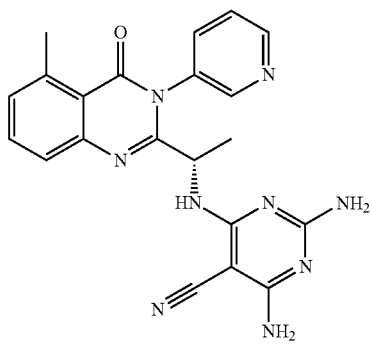 [SMILES: Cc1cccc2nc([C@H](C)Nc3nc(N)nc(N)c3C#N)n(-c3cccnc3)c(=O)c12]

or a pharmaceutically acceptable salt thereof.

53. The composition of claim 44, wherein the compound is

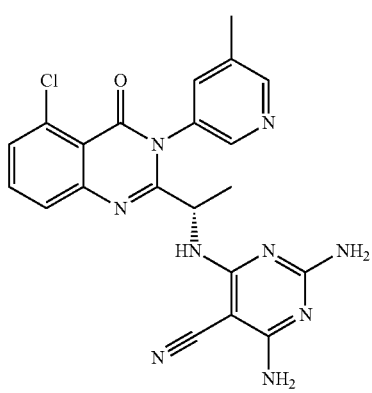 [SMILES: Cc1cncc(-n2c([C@H](C)Nc3nc(N)nc(N)c3C#N)nc3cccc(Cl)c3c2=O)c1]

or a pharmaceutically acceptable salt thereof.

54. The composition of claim 44, wherein the compound is

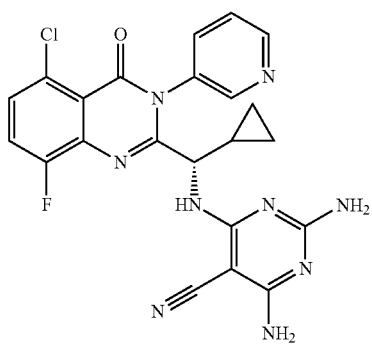 [SMILES: N#Cc1c(N)nc(N)nc1N[C@H](c1nc2c(F)ccc(Cl)c2c(=O)n1-c1cccnc1)C1CC1]

or a pharmaceutically acceptable salt thereof.

55. The composition of claim 44, wherein the compound is

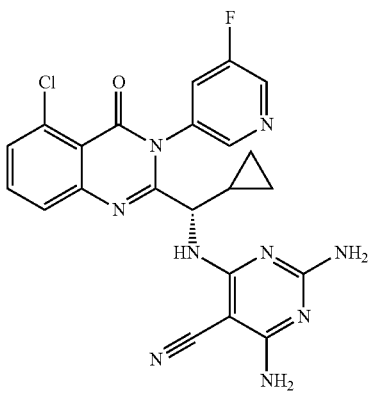 [SMILES: N#Cc1c(N)nc(N)nc1N[C@H](c1nc2cccc(Cl)c2c(=O)n1-c1cncc(F)c1)C1CC1]

or a pharmaceutically acceptable salt thereof.

56. The composition of claim 44, wherein the compound is

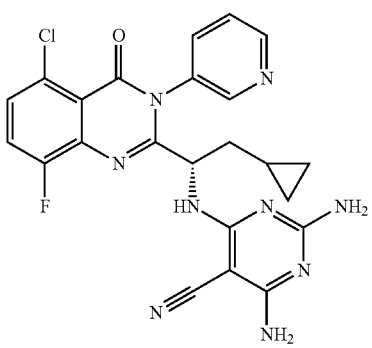

or a pharmaceutically acceptable salt thereof.

57. The composition of claim 44, wherein the compound is

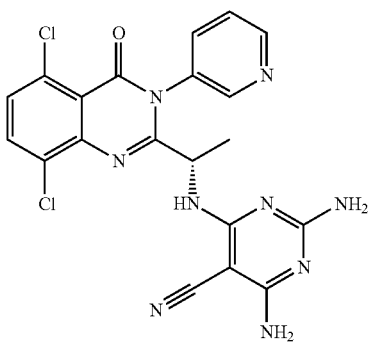

or a pharmaceutically acceptable salt thereof.

58. The composition of claim 44, wherein the compound is
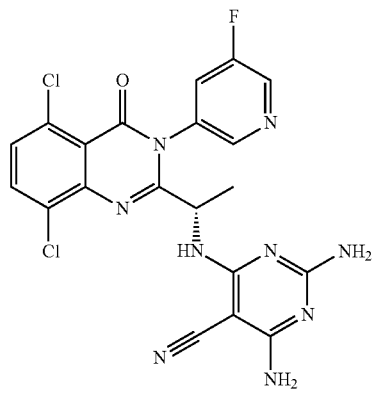 [SMILES: C[C@H](Nc1nc(N)nc(N)c1C#N)c1nc2c(Cl)ccc(Cl)c2c(=O)n1-c1cncc(F)c1]
or a pharmaceutically acceptable salt thereof.
59. The composition of claim 44, wherein the compound is
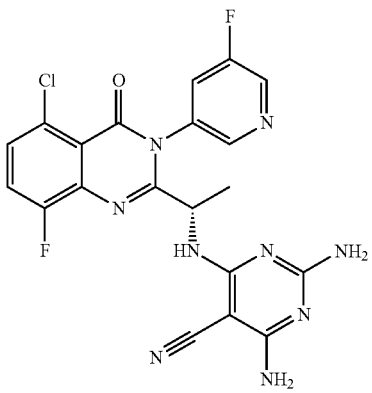 [SMILES: C[C@H](Nc1nc(N)nc(N)c1C#N)c1nc2c(F)ccc(Cl)c2c(=O)n1-c1cncc(F)c1]
or a pharmaceutically acceptable salt thereof.
* * * * *